US009388431B2

(12) United States Patent
McAuliffe et al.

(10) Patent No.: US 9,388,431 B2
(45) Date of Patent: Jul. 12, 2016

(54) **ENHANCED PRODUCTION OF ISOPRENE USING HOST CELLS HAVING DECREASED *ISPA* ACTIVITY**

(71) Applicants: Danisco US Inc., Palo Alto, CA (US); The Goodyear Tire & Rubber Company, Akron, OH (US)

(72) Inventors: Joseph C. McAuliffe, Sunnyvale, CA (US); Rachel E. Muir, Redwood City, CA (US); Alex T. Nielsen, Kokkedal (DK); Caroline M. Peres, Palo Alto, CA (US); Dmitrii V. Vaviline, Palo Alto, CA (US); Derek H. Wells, Palo Alto, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 2 days.

(21) Appl. No.: 14/593,860

(22) Filed: Jan. 9, 2015

(65) Prior Publication Data
US 2015/0218590 A1 Aug. 6, 2015

Related U.S. Application Data

(63) Continuation of application No. 13/725,929, filed on Dec. 21, 2012, now Pat. No. 8,975,051.

(60) Provisional application No. 61/639,855, filed on Apr. 27, 2012, provisional application No. 61/580,163, filed on Dec. 23, 2011.

(51) Int. Cl.
*C12N 1/20* (2006.01)
*C12P 5/00* (2006.01)
*C12N 9/10* (2006.01)
*C12N 9/88* (2006.01)

(52) U.S. Cl.
CPC .............. *C12P 5/007* (2013.01); *C12N 9/1085* (2013.01); *C12N 9/88* (2013.01); *C12Y 205/01001* (2013.01); *C12Y 402/03027* (2013.01); *Y02P 20/52* (2015.11)

(58) Field of Classification Search
CPC .............................. C12P 5/007; C12N 9/1085
USPC ................................................ 435/252.3, 167
See application file for complete search history.

(56) References Cited

U.S. PATENT DOCUMENTS

| 7,632,995 B2 | 12/2009 | Eichelberger et al. |
| 7,659,097 B2 | 2/2010 | Renninger et al. |
| 7,785,858 B2 | 8/2010 | Kozlov et al. |
| 2005/0287655 A1 | 12/2005 | Tabata et al. |
| 2008/0038805 A1 | 2/2008 | Melis |
| 2009/0203102 A1 | 8/2009 | Cervin et al. |
| 2010/0003716 A1 | 1/2010 | Cervin et al. |
| 2010/0048964 A1 | 2/2010 | Calabria et al. |
| 2010/0086978 A1 | 4/2010 | Beck et al. |
| 2010/0196977 A1 | 8/2010 | Chotani et al. |
| 2010/0285549 A1 | 11/2010 | Muramatsu et al. |
| 2010/0297749 A1 | 11/2010 | Aravanis et al. |
| 2011/0045563 A1 | 2/2011 | Melis |
| 2011/0159557 A1 | 6/2011 | Beck et al. |
| 2011/0178261 A1 | 7/2011 | Feher et al. |
| 2013/0045891 A1 | 2/2013 | Beck et al. |

FOREIGN PATENT DOCUMENTS

| JP | 2008-061506 A | 3/2008 |
| WO | WO 98/02550 A2 | 1/1998 |
| WO | WO 98/02550 A3 | 1/1998 |
| WO | WO 2004/033646 A2 | 4/2004 |
| WO | WO 2004/033646 A3 | 4/2004 |
| WO | WO 2007/140339 A2 | 12/2007 |
| WO | WO 2007/140339 A3 | 12/2007 |
| WO | WO 2007/140339 A8 | 12/2007 |
| WO | WO 2009/076676 A2 | 6/2009 |
| WO | WO 2009/076676 A3 | 6/2009 |
| WO | WO 2009/132220 A2 | 10/2009 |
| WO | WO 2009/132220 A3 | 10/2009 |
| WO | WO 2010/003007 A2 | 1/2010 |
| WO | WO 2010/003007 A3 | 1/2010 |
| WO | WO 2010/031062 A1 | 3/2010 |
| WO | WO 2010/031068 A1 | 3/2010 |
| WO | WO 2010/031076 A2 | 3/2010 |
| WO | WO 2010/031076 A3 | 3/2010 |
| WO | WO 2010/031079 A1 | 3/2010 |

(Continued)

OTHER PUBLICATIONS

Hao, H-L et al. (2002). "The Biosynthesis and Regulation of Isoprenoids," *Journal of Zhejiang University* (*Agric. & Life Sci.*) 28(2):224-230. (English translation of abstract only).
Andersen et al., (1998). Appl Environ Microbiol. 64(6):2240-2246.
Baba et al. (2006). Article No. 2006.0008, Mol. Syst. Biol. 2:1-11.
Baldini et al. (1998). Journal of Bacteriology, 180(7):1632-1641.
Becker, D. M. et al. (1990). Methods. Enzymol., 194:182-187.
Berka et al. (1989). Biotechnology Advances, 7(2):127-154.
Bhayana, V. et al. (1984). Biochemistry 23:2900-2905 (Figure 5).
Bologna, F. et al. (2007). J. Bact. 189:5937-5946.
Bunch, P. et al. (1997). Microbiol. 143:187-195.
Campbell et al. (1989). Curr. Genet. 16:53-56.
Chan E. et al. (2010). J. Exp. Microbiol Immunol., 14:127-134.

(Continued)

*Primary Examiner* — Tekchand Saidha
(74) *Attorney, Agent, or Firm* — Mintz Levin Cohn Ferris Glovsky and Popeo, P.C.

(57) ABSTRACT

This invention relates to recombinant microorganisms capable of producing isoprene and isoprene production with the use of such recombinant microorganism with good efficiency. In this invention, functional activity of the ispA gene is altered to reduce the production of isoprenoid molecules in recombinant cells engineered to produce isoprene or in cells otherwise susceptible to isoprenoid accumulation during fermentation. This decreased ispA gene functional activity enables enhanced synthesis of isoprene in a host microorganism.

43 Claims, 44 Drawing Sheets

(56) References Cited

FOREIGN PATENT DOCUMENTS

| WO | WO 2010/078457 A2 | 7/2010 |
|---|---|---|
| WO | WO 2010/078457 A3 | 7/2010 |
| WO | WO 2010/124146 A2 | 10/2010 |
| WO | WO 2010/124146 A3 | 10/2010 |
| WO | WO 2010/148150 A1 | 12/2010 |
| WO | WO 2010/148256 A1 | 12/2010 |
| WO | WO 2011/034863 A1 | 3/2011 |
| WO | WO 2011/159853 A1 | 12/2011 |
| WO | WO 2012/058494 A2 | 5/2012 |
| WO | WO 2012/058494 A3 | 5/2012 |

OTHER PUBLICATIONS

Cohen, S. N., et al. (1972). Proc. Natl. Acad. Sci., USA, 69:2110-2114.
Dawes et al. (1966). Biochem. J. 98:795-803.
Duckworth et al. (1987). Biochem Soc Symp. 54:83-92.
Egan et al. (1992). J. Bact. 174:4638-4646.
Essential Genes in *E. coli;* Mar. 2004; located at www.genome.wisc.edu/resources/essential.htm, last visited on Mar. 26, 2013, seven pages.
Fernandez, S. et al. (2000). Biochemistry, 39(50):15316-15321.
Fowler, et. al. (2009). Applied and Environmental Microbiology, 75(18):5831-5839.
Fujisaki, et al. (1989). J. Bacteriol. 171:5654-5658.
Fujisaki, et al., (1990). J. Biochem. 108:995-1000.
Fujisaki, S. et al. (Mar. 1, 2005). "Disruption of the Structural Gene for Farnesyl Diphosphate Synthase in *Escherichia coli*," Journal of Biochemistry 137(3):395-400.
Goedegebuur et al. (2002). Curr. Genet. 41:89-98.
Hedl, et al. (Apr. 2002). J Bacteriol. 184(8):2116-2122.
Hinnen, A. et al., (1978). Proc. Natl. Acad. Sci., USA, 75:1929-1933.
Innis et al. (1985). Sci. 228: 21-26.
Iwakura, M. et al. (1979). J. Biochem. 85:1355-1365.
Jobling et al. (1990). Nucleic Acids Res., 18(17):5315-5316.
Kakuda, H. et al. (1994). J. Biochem. 116:916-922.
Kazuyama et al. "Diversity of the Biosynthesis of the Isoprene Units," *Nat. Prod. Rep.* 20:171-183, 2003.
Kim J. et al. (2003). Biotech Bioeng., 83:841-853.
Kotlarz et al. (1975). Biochim. Biophys. Acta 381:257-268.
Kovach et al. (1995). Gene 166:175-176.
Koyama et al. (1993). J. Biochem., 113(3):355-363.
Krylov et al. (2010). J Mol Microbiol Biotechnol, 18:1-13.
Lindberg et al. (2010). Metab. Eng. 12(1):70-79.
Lois et al. (Mar. 3, 1998). Proc. Natl. Acad. Sci. U.S.A. 95(5):2105-2110.
Maurus, R. et al. (2003). Biochemistry. 42:5555-5565.
Meile et al. (2001). J. Bact. 183:2929-2936.
Miller et al. (2001). Planta 213:483-487.
Nakashima N. et al. (2006) Nucleic Acids Res., 34(20):e138, ten pages.
Ner, S. et al. (1983). Biochemistry 22:5243-5249.
Nichols et al. (2004). J. Bact., 186:8508-8515.
Ogasawara, H. et al. (2007). J. Bact. 189:5534-5541.
Oh, M-K. et al. (2002). J. Biol. Chem. 277:13175-13183.
Okamura et al. (2010). Proc. Natl. Acad. Sci. USA 107(25):11265-11270.
Peekhaus, N. et al. (Jul. 1998). J. Bact. 180:3495-3502.
Pitera, D.J. et al. (Feb. 16, 2007, e-pub. Nov. 23, 2006). "Balancing a Heterologous Mevalonate Pathway for Improved Isoprenoid Production in *Escherichia coli*," Metabolic Engineering 9(2):193-207.
Quant et al. (1989). Biochem J., 262:159-164.
Ranzer et al. (2009). Mar. Biotechnol, 11:62-73.
Roberts et al. (1996). Journal of Bacteriology, 178(7):1829-1841.
Rodriguez-Concepcion et al. "Elucidation of the Methylerythritol Phosphate Pathway for Isoprenoid Biosynthesis in Bacteria and Plastids. A Metabolic Milestone Achieved through Genomics," *Plant Physiology* 130:1079-1089, 2002.
Romanos et al. (1992). Yeast, 8(6):423-488.
Sánchez et al. (2005). Met. Eng. 7:229-239.
Shao Y. et al. (2006). Nucleic Acids Res., 34:5660-5669.
Sharkey, T.D. et al. (Feb. 2005). "Evolution of the Isoprene Biosynthetic Pathway in Kudzu," *Plant Physiology* 137:700-712.
Sharkey et al. (2012). "Isoprene Synthase Genes Form a Monophyletic Clade of Acyclic Terpene Synthases in the TPS-B Terpene Synthase Family," *Evolution* pp. 1-15 (available on line at DOI: 10.1111/evo.
Sheir-Neiss et al. (1984). Appl. Microbiol. Biotechnology 20:46-53.
Shimizu et al. (1969). Biochim. Biophys. Acta 191:550-558.
Shiomi, D. et al. (Dec. 1, 2011). "A Mutation of *ispA* that is Involved in Isoprenoid Biogenesis can Improve Growth of *Escherichia coli* at Low Temperatures," *Microbiology and Immunology* 55(12):885-888.
Silver et al. (1995). J. Biol. Chem. 270:13010-13016.
Song, S. et al. (1997). J. Bacterial., 179(22):7025-7032.
Sprenger, G.A. (1995). Arch. Microbiol.164:324-330.
Stokell, D.J. et al. (2003). J. Biol. Chem. 278:35435-35443.
Stülke, J. et al. (2000). Annu. Rev. Microbiol. 54:849-880.
Susin et al. (2004). Journal of Bacteriology, 186(20):6759-6767.
Underwood et al. (2002). Appl. Environ. Microbiol. 68:1071-1081.
Vienna RNA Package v.1.8.4, last modified Jan. 15, 2012, (Andreas R. Gruber, Ronny Lorenz, Stephan H. Bernhart, Richard Neuböck, and Ivo L. Hofacker (NAR, 2008)), located at http://www.tbi.univie.ac.at/~ivo/RNA/, last visited on Mar. 26, 2013, three pages.
Ward, M. et al. (1993). Appl. Microbiol. Biotechnol. 39:738-743.
Whited et al. "Development of a Gas-phase Bioprocess for Isoprene-monomer Production Using Metabolic Pathway Engineering," *Industrial Biotech* 6:152-163, Jun. 2010.
Wiegand, G. et al. (1986). Annual Rev. Biophys. Biophys. Chem. 15:97-117.
Wolfe, A. (2005). Microb. Mol. Biol. Rev. 69:12-50.

atggactttccgcaacaattggaggcgtgcgtaaagcaagcaaatcaagccctgtctctgctttatt
gcgccacttcgtttcaaaacacgcctgtggtcgaaaccatgcaatacggggctctcctggagg
gaagcggttgagaccattcttagtgtacgctaccggtcatatgtttggcgtaagtaccaacactct
ggatgcgcctgctgcgctggaatgcatccatgcgtacagtttaattcatgacgatctgcctgc
gatggatgatgatctgcgtagaggcttacctacatgtcacgtaaaatttggcgaagctaacg
caatacttgcgcgatgctctccagcgctgcttttctctatcctgtctgatcggatatgcccga
agtgagcgaccggatcggattagtatgatttcagaattgatttgatgcagagggcaaacatgtaccattagatgcaggca
tgtgcgggggacaagcactggattggatgcagagggcaaacatgtaccattagatgcattgga
acgcatacatcggcacaaaccgggcttaattagagctgccgttcggttaggagccttgtctg
ccggtgataaagggcgtgcgtcctgtattagatgctagatgccgagagtatcggtcgtctggctt
ttcaagtgcaggacgatatcctggatgtcgtaggagatacccagctctcttggtctggaacaagcagggg
tgcagatcaacagctggtaaatccacataccagctctcttggtctggaacaagcccgtaaaa
aggcaagagacctgatcgacgacgcgccagtccctgaaacagttagcggaacagtctttgga
tactagtgctttagaggccttggcagattatattatacagcgtaataagtaa

Figure 8 gcgccaatacgcaaacgcctctcccgcgcgttggccgattcattaatgcagtcggcgttcccgactggactgttccgactgaccaataatgtggttagctcactcatta
ggcacccaggctttacacttatgctccgctctggctctgtatgttgtggaattgtgagcggcagccctccgcacatgtgagcggtgctgtaaagcaagccactgtct
cgcttattgccgccactccgtttcaaaacacgcgctggtcgaaacatgcaatacgctgggggaagggctctcctggagggaaaggagcggtgagaccattcttagtgctacgccggtcatatgttggcgtaagtac
caacactctggatgcctgctcgtgccgtggaatgcatccatgcgtacagttaattcatgacgatctgcctgccgatgatgatgatcgtcgtagaggcttacttacatgtcacgtaaaatttggcg
aagctaacgcaatacttgcgggcgatgcgatctccagacgctggcttttctctatcctgtcgatgcgatatgccgaagtgagcgaccggatggattagtatgatttcagaattagcctctgcgagtgg
aattgcaggcatgtgcggggaccaagcactgatttgatgcgcagaggcaaacatgtcagtacccattagatgatgcattgaacgcatacatcggcacaaaaccgggctttaattagagctgccgttcggttag
gagccttgtcgccggtgataaagggcgtcgtcgttgcctgttattagataatatgccgagatatcgttggctttcaagtgcaggacgatatcctgatgtgtaggagataccgcaacactggg
taaacgccagggtgcagatcaacagctggtaaatcacatccagctcttcttggtctgaacagccgtaaaaggcaagagaccgatcgagacgcgccagtcctgaaacagttagcg
gaacagtctttggatactagtgcttttagaggccttgcagattatattatacagcgtaataagtaagctgagggctgcaagttgcgtaccgtcgcctcgctaaccaccacaccgcgcttaat
gcgccgtacagggcgtcaggtgcactttcggggaaatgtgcgcggaacccctatttgttatttttcggcattttgcctttcgttttgctcaccagaaacgctggtgaaagtaaaagatgctgaagatcagtt
atattgaaaaggaagagtatgagtattcaactttcgtgtcgccttatccgttcctttttgcggcattttgccccgaagacgtttcccaatgatgagcactttaaagttctgctatgtggcgcggtattatccgta
gggtgcacgagtgggttacatcgaactggatctcaacagcggtaagatcctttaattcatgacagtaaaagcatcttacggatggcatgacagtaagagaattatgcagtgctgcc
ttgacgccgggcaagagcaactcggtcgccgcataacattctcagaatgacttggttgagtactcaccagtcacagaaaagcatcttacggatggcatgacagtaagagaattatgcagtgctgcc
ataaccatgagtgataacactgcggccaacttacttctgacaacgatcggaggaccgaaggagctcaacgttgtcacaacatggggatcatgtaactgcctgtcgtgatcgttgggaaccggagctg
aatgaagccataccaaacgacgagtgacaccagtgtcaaatgccttagcaatgggcaacaacgttgcgcaaactatttaactggcgaactacttactctagcttcccggcaacaattaatagactggatgg
aggcggataaagttgcaggaccacttctgctctgctcccttcgcgctccttattgctgataaatctggagccggtgagcgtgggtatcattgcagcactgggggccagatggtaagc
cctcccgtatctagttatctacacgacgggggagtcaggcaactatgatgaacgaacgagatcacagatgctgagataggtgcctcactgattaagcattgtaactgtcagaccaagttactcatata
tactttagattgatttaaaactcattttttaaaggatcaggtaaggatcaggtaaagaatcttcaacatggggtgataatgtaaaaacatgtatgatagcgatcatagatgccggtgtatggtatgagccatatc
aacgggaaacgtcttgctctaggccgcgattaaattccaacatggccaaaggtagcgttgccaatgcttgcacaacagcagatattgctgcctcgctcggacccggaatgttatccctgactacctcct
atgcgcagagtcatgcagtcatggaaacatggccgatccgtatttcgtcctgcagccgcaatcagtgtctgatttctcactcgtcagcgcaatcacttcactcatgattcctgcgccgttgcattgattcc
gatgatgcatggttactcaccactgcgatcctttaacagcgatcgcgtattcgtcctgcagccgcaatcactgtctgatttctcacttattttcaccgaggggaaattaatagttgattatgtgacgagcttgaatgc
tgtttgaattgctctttaacagcataaactttgccattctcactccatgtaactcggtcagttttctccatgagtttctccttcattacagaaacaggggtcgcaaaaaaataggttatttattttggtgtatttggatggagatcttttattttcaaatcagttcattgatgctc
agaccgataccaggatcttgccatcctatggaactgcctcggtgagttttctccatgagtttctccttcattacagaaacaggggtcgcaaaaaaataggttatttattttgaataaattcagtttatttgatgctc
gatgagtttttctaagaattaatttcatgaccaaaatcccttaacgtgagttttcgttccactgagcgtcagaccccgtagaaaagatcaaaggatctcttttgatccttttttgcggcatcttcgcgtaatcgtgc
ttgcaaacaaaaaaaccaccgctaccagcggtggtttgtttgccggatcaagagctaccaactctttttccgaaggtaacttgggttctgctgcttgcaaacaaaaccaaatactgtccttcctagtgtagccgt
agttaggccaccacttcaagaactctgtagcaccgcctacatacctcgctctgctaatcctgttaccagtggctgctgccagtggcgataagtcgtgtcttaccgggttggactcaagacgatagttaccg
gataaggcgcagcggtcggggctgaacggggggttcgtgcacacagcccagcttggagcgaacgacctacaccgaactgagatacctacagcgtgagctatgagaaagcgccacgcttcccgaagg
gagaaaggcggacaggtatccggtaagcggcagggtcggaacaggagagcgcacgagggagcttccagggggaaacgcctggtatctttatagtcctgtcgggtttcgccacctctgacttgagcgt
cgatttttgtgatgctcgtcaggggggcggagcctatggaaaaacgccagcaacgcggcctttttacggttcctggccttttgctggccttttgctcacatgttctttcctgcgttatcccctgattctgtgga
taaccgtattaccgcctttgagtgagctgataccgctcgccgcagccgaacgaccgagcgcagcgagtcagtgagcgaggaagcggaaga

Figure 9

```
atgcataaatttactggtgtcaatgccaagtttcagcaacccgcgttgaggaacctcagcccgtggt
ggttgagaggagaggaggaggagttcgtgtgggagttcttcccgcagatcgtccgatctgaccgaggac
ggcatcggacacccggagttgggcgacgtggcgctgaaggaggtgctgcaatacaacgct
cccgtgggaaatgcaacccgtggctgacggtggctgcgtacggagctgtcggggcgggg
cagaaggatgctgagagcctgcgcgtggtgtgcgccggggttgtgcatcgagttgttccaggcctt
cttcctgtggtgggatgacatcatggatgccatcaacgactcctcctcgagtcctctgtacagagtgctga
aggaggggtcggtttgatgccatcaacgactcctcctcgagtcctctgtacagagtgctga
agaagtactgcaggcagcggccgtattacgtgcatctgttggagctcttcctgcagaccgcctaccag
actgagctcgggcagatgctgacctcatcacagctcccgtctccaaagtgattgagtcacttcagt
gaggagaggtacaaagccatcgttaagtacaagacagtaggaacacagaatgccaagcatcctgctgag
gccatgtatatggtggatcgacagtgacgatgattacctggactgtgttgggactcgctcacggga
atggggaatacttccagatccaggacaataaatgcagctgcgtggtgctcgtgcagcgtcac
aggtgggcaccgacagcagctcctggaggacaactacggccgtaaggagcccgagaaggtggcgaagg
tgaaggagctgtatgaggccgtgggatgaggcactcgaaccgctcccgaaggagatcttcctggcctggc
acagaagatctacaaacgccagaaatga
```

Figure 11 atgcataaatttactgtggtgtcaatgccaagtttcagcaacccgcgttgaggaacctcagcccgtggt
ggttgagaggagagggaggagttcgtgggttcttccgcagatcgtccgatctgaccgagga
cggcatcggacaccagaggttgggcgacgctgtggcggctgaaggagagtgctgcaatacaacg
ctcccggtgggaaatgcaacgctgggctgacggtggtgcgtaccggagctgtggggccgg
ggcagaaggatgctgagcctgagcgtgcgctgctggtgccgtggtgcatcgagttgttccaggc
cttcttcctggtgctgataatcatggatgccatgtgggactcctcctggaatcctctgtacagagtgc
gaaggagggggtcggtttggatgcagcagcgccgtattacgtgacctcatcacagtctccgttcaca
tgaagaagtactgcaggcagtgccgagatgctggaccctcgttggagctcttcctgcagaccgctac
cagactgactcgggcagcgcagatgctggacctgctcaaagtgattgagtcactt
cagtgagagaggtacaaagccatcgttaagacagtaagaagactgcttctactcctacccgtgg
ctgctgccatgtatgttggatcgacagatccaggatgattaccggactgctttgggaccgcgctac
tggagatggggaatactccagatcaggagacaataatgcagctaaggccgtaaggagccgagaaggt
gggaaggtgggcagacgcaccgagcagcaggccagctcctggagacacctacgccgtaaggagccgagaaggt
gcgtcacgccggagcagctgtgaggccgtgtatgaggcgtgcgttccagcagtgaggcccgagagga
ggcgaaggtgaagtctgcaggaactgatagagaagcactgaaccgctccgaaggagatcttcc
gcagctactacgcagcctgcgcttgaggccttgaggccgcgaaccgctccgaaggagatcttcc
tcggcctggcacagaagatctacaaacgccagaaatga

Figure 12

Codon-optimized nucleotide for *hrcA* allele expression in *E. coli*:

ATGACTCAACTTTCCCGTCCCATAGTTCGGACGACTTGCAGAACTCGATGCGCGGGCTC
GCGACATATTCAGACGTGTCGTAGAATCTTATCTGGAGACCGGTGAACCAGTGGGCTCTCGCACGAT
TAGCAAAGGTGGTGTAGCACTCAGCCCTGCGTCAATACAATGCAGGACTGGCCAGTT
GGGGTTACTTGACGCACCTCATACCAGTGCCGGCTATGCCGACACACGCTGGTTAAGAATGTTT
GTAGACGGGTCCTGGAAGTTGGGCGACGTGGGCGAGCAAGAGAAGCGGGCTATTGAAGCACGGC
TGGCAGTGAAGGGACGTTCCTTTGAAGAGCGTTCGGAGGCAAGCTCTATTTAAGCGGTCTGG
CTGGCGAGCGGGCATTGTCGTCACTCCGGTACGGGAAGGCGGGGTCAAACATGTGAGTTGTG
CCGCTGGGAGGTGTCAGTTCTCAGGTTCTCTGTCTCACCCCTTCGCTCTGCTCTACAGGAAGCCTGAATTTCTTGAATGCCCGTT
ATGCGCCAGGCCCCCGGTCACCGGAAGCCTCACGGAACCCGTACCGAAATGGGAAGCTGAACTTGATGCGGCTCGCCGC
TACGTGGACGGACACTCACGGAAGCTCGGCTGGGTGGAAGATGACTGGCAGCATGGTCAGGTGGAGAAGG
CAGCTTAATGAAACGCCGCAGTTCGTTCGGGGACAGGCGAACCTTCTTGCCGTGCGCATGCTCGATGCTCGACGAGGA
AGACGCCCGCAGTTCGTTCGGGGACAGGCGAACCTTCTTGCCGTGCGCAACTCATCGGCTCTCGATG
TATAGACCGCGTTCGTCAGTTGTTGATGATTTGAGTGCGCATTTATATTGGAGCTGAAACCCGCTGTTCTCACTTTCTGG
ATGTCCGGACGCGGGAAGGTGTGCATTTATATTGGAGCTGAAACCCGCTGTTCTCACTTTCTGG
AAGCTCGGTGATCGCTGCCCGTGCTACATGACAGGCCGTCAAAAGGTATTGGGCGCCATAGGGGTTAT
CGGACCTGCCCGCTGAATTACGCTCGGCTTATCCCACTCGTGGATTATACGGCACGCGGTTTGGGCC
GTATGATGACGGTTGA.

ENHANCED PRODUCTION OF ISOPRENE USING HOST CELLS HAVING DECREASED ISPA ACTIVITY

CROSS-REFERENCE TO RELATED APPLICATIONS

This application is a continuation of U.S. patent application Ser. No. 13/725,929, (now U.S. Pat. No. 8,975,051), filed Dec. 21, 2012, which claims priority to U.S. Provisional Application No. 61/580,163, filed Dec. 23, 2011 and U.S. Provisional Application No. 61/639,855, filed Apr. 27, 2012, the disclosures of each of which are incorporated by reference herein in their entireties.

INCORPORATION BY REFERENCE

The Sequence Listing submitted in an ASCII text file, in accordance with 37 C.F.R. §1.821(c) and (e), is incorporated herein by reference in its entirety. The text file name is 643842004201SeqList.txt, the date of creation of the text file is Apr. 14, 2015, and the size of the ASCII text file is 61 KB.

FIELD OF THE INVENTION

The present invention relates generally to methods for producing isoprene from cultured cells and compositions that include these cultured cells.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway. However, the yield of isoprene from naturally-occurring organisms is commercially unattractive. Isoprene can also be obtained by fractionating petroleum, the purification of this material is expensive and time-consuming. Petroleum cracking of the C5 stream of hydrocarbons produces only about 15% isoprene. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

During the course of metabolism in microorganisms, the mevalonate-dependent biosynthetic pathway converts acetyl-CoA to isopentenyl diphosphate (IPP) and dimethylallyl diphosphate (DMAPP). IPP and DMAPP are precursors to isoprene as well as to a class of higher molecular weight molecules known as the isoprenoids. Isoprenoids are vital to most living organisms and cells, providing a means to maintain cellular membrane fluidity and electron transport.

Recent developments in the production of isoprene disclose methods for the production of isoprene at rates, titers, and purities that can be sufficient to meet the demands of robust commercial processes (see, for example, International Patent Application Publication No. WO 2009/076676 A2); however, alternate pathways to improve production and yields of the same are still needed.

Provided herein are cultured recombinant cells, compositions of these cells, and methods of using these cells to increase production of isoprene.

Throughout this specification, various patents, patent applications and other types of publications (e.g., journal articles) are referenced. The disclosure of all patents, patent applications, and publications cited herein are hereby incorporated by reference in their entirety for all purposes.

BRIEF SUMMARY OF THE INVENTION

The invention provided herein discloses, inter alia, compositions of matter comprising recombinant cells and methods of making and using these recombinnt cells for the production of isoprene. In some aspects, the recombinant microorganisms comprise an ispA gene having decreased functional activity and one or more nucleic acids encoding one or more isoprene synthase and/or MVA pathway enzyme(s).

Accordingly, in some aspects, provided herein are recombinant cells capable of producing isoprene, wherein said cells comprise an ispA gene having decreased functional activity and one or more nucleic acids encoding: (a) an isoprene synthase polypeptide, wherein the isoprene synthase polypeptide is encoded by a heterologous nucleic acid; and (b) one or more mevalonate (MVA) pathway polypeptides, wherein culturing of said recombinant cells in a suitable media provides for the production of said polypeptides and synthesis of isoprene. In other aspects, the functional activity of the ispA gene is decreased by: deleting the ispA gene; decreasing ispA gene expression; decreasing ispA protein activity; decreasing ispA protein expression; or temporally modulating ispA expression. In another aspect, the ispA gene expression is decreased by placing the ispA gene under the control of a weak promoter. In some aspects, the ispA gene expression is decreased by placing the ispA gene under the control of an auto-regulatory promoter. In yet other aspects, the ispA protein activity is decreased by translational fusion of the ispA protein with a proteolytic tag. In other aspects, the ispA protein expression is decreased by use of antisense RNA. In some aspects, the ispA protein expression is decreased by introducing one or more mutations into a ribosomal binding site located in the ispA mRNA molecule. In other aspects, the ispA gene expression is decreased by an HrcA transcriptional repressor protein. In another aspect, the ispA protein activity is decreased by replacing the endogenous ispA gene with a gene encoding a polypeptide comprising an increased Km for DMAPP in comparison to the Km of the polypeptide encoded by the endogenous ispA gene. In another aspect, the ispA protein activity is decreased by replacing the endogenous ispA gene with another gene comprising a different temperature optimum.

In other aspects of any of the cells described herein, the isoprene synthase polypeptide is a plant isoprene synthase polypeptide or variant thereof. In some aspects, the isoprene synthase polypeptide is a polypeptide from *Pueraria* or *Populus* or a hybrid, *Populus alba*×*Populus tremula* or variant thereof. In another aspect, the isoprene synthase polypeptide is selected from the group consisting of *Pueraria montana* or *Pueraria lobata, Populus tremuloides, Populus alba, Populus nigra, Populus trichocarpa* or variant thereof. In still other aspects, the plant isoprene synthase polypeptide is a kudzu isoprene synthase polypeptide or variant thereof. In still other aspects, the plant isoprene synthase polypeptide is a *Eucalyptus* isoprene synthase polypeptide or variant thereof. In some aspects of any of the cells described herein, said one or more nucleic acids encoding one or more MVA pathway polypeptides of (b) is a heterologous nucleic acid. In some aspects, said cells comprise one or more nucleic acids encoding MVA pathway polypeptides are from the upper MVA pathway, wherein the upper MVA pathway nucleic acids are selected from the group consisting of AA-CoA thiolase or acetoacetyl-CoA synthase, HMG-CoA synthase, and HMG-CoA reductase nucleic acids. In some aspects, said cells comprise one or more nucleic acids encoding MVA pathway polypeptides are from the lower MVA pathway, wherein the lower MVA pathway nucleic acids are selected from the group consisting of MVK, PMK, and, MVD nucleic acids. In some aspects, said cells comprise one or more nucleic acids encoding MVA pathway polypeptides of the complete MVA pathway. In some aspects, said cells further comprise one or more nucleic acids encoding an isopentenyl-diphosphate delta-isomerase (IDI) polypeptide. In other aspects of any of the cells described herein, the cells further comprise a 1-Deoxyxlulose-5-phosphate synthase (DXS) polypeptide. In another aspect, said one or more nucleic acids encoding a DXS polypeptide of (b) is a heterologous nucleic acid encoding a DXS polypeptide. In yet another aspect, said one or more nucleic acids encoding a DXS polypeptide of (b) is a copy of an endogenous nucleic acid encoding a DXS polypeptide. In other aspects of any of the cells described herein, the one or more heterologous nucleic acids is placed under an inducible promoter or a constitutive promoter. In another aspect, the one or more heterologous nucleic acids are cloned into a multicopy plasmid. In other aspects, the one or more heterologous nucleic acids are integrated into a chromosome of the cells.

In still other aspects, the cells are bacterial, algal, fungal or yeast cells. In one aspect, the cells are bacterial cells. In another aspect, the bacterial cells are gram-positive bacterial cells or gram-negative bacterial cells. In some aspects, the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *Corynebacteria* sp., and *P. alcaligenes* cells. In one aspect, the bacterial cells are *E. coli*. In another aspect, the cells are algal cells. In still another aspect, the algal cells are selected from the group consisting of green algae, red algae, glaucophytes, chlorarachniophytes, euglenids, chromista, or dinoflagellates. In another aspect, the cells are fungal cells. In some aspects, the fungal cells are filamentous fungi. In another aspect, the cells are yeast cells. In one aspect, the yeast cells are selected from the group consisting of *Saccharomyces* sp., *Schizosaccharomyces* sp., *Pichia* sp., or *Candida* sp. In another aspect, the yeast cells are *Saccharomyces cerevisiae*.

Provided herein are compositions comprising any of the cells disclosed herein.

Also provided herein is a method of producing isoprene comprising: (a) culturing any of the recombinant cells described herein in conditions suitable for the synthesis of isoprene; and (b) producing isoprene. In some aspects, the method further comprises recovering the isoprene produced by said recombinant cells.

Provided herein are methods for producing isoprene comprising (a) culturing recombinant cells capable of producing of isoprene, wherein said cells comprise an ispA gene having decreased functional activity and one or more nucleic acids encoding: (i) an isoprene synthase polypeptide, wherein the isoprene synthase polypeptide is encoded by a heterologous nucleic acid; and (ii) one or more mevalonate (MVA) pathway polypeptides, wherein culturing of said recombinant cells in a suitable media provides for the production of said polypeptides and synthesis of isoprene; and (b) producing isoprene. In some aspects, the method further comprises recovering the isoprene produced by said recombinant cells. In other aspects of the methods described herein, the isoprene synthase polypeptide is a plant isoprene synthase polypeptide or variant thereof. In some aspects, the isoprene synthase polypeptide is a polypeptide from *Pueraria* or *Populus* or a hybrid, *Populus alba*×*Populus tremula* or variant thereof. In another aspect, the isoprene synthase polypeptide is selected from the group consisting of *Pueraria montana* or *Pueraria lobata*, *Populus tremuloides, Populus alba, Populus nigra, Populus trichocarpa* or variant thereof. In still other aspects, the plant isoprene synthase polypeptide is a kudzu isoprene synthase polypeptide or variant thereof. In still other aspects, the plant isoprene synthase polypeptide is a *Eucalyptus* isoprene synthase polypeptide or variant thereof. In some aspects of any of the methods described herein, said one or more nucleic acids encoding one or more MVA pathway polypeptides of (b) is a heterologous nucleic acid. In some aspects, said cells comprise one or more nucleic acids encoding MVA pathway polypeptides are from the upper MVA pathway, wherein the upper MVA pathway nucleic acids are selected from the group consisting of AA-CoA thiolase or acetoacetyl-CoA synthase, HMG-CoA synthase, and HMG-CoA reductase nucleic acids. In some aspects, said cells comprise one or more nucleic acids encoding MVA pathway polypeptides are from the lower MVA pathway, wherein the lower MVA pathway nucleic acids are selected from the group consisting of MVK, PMK, and, MVD nucleic acids. In some aspects, said cells comprise one or more nucleic acids encoding MVA pathway polypeptides of the complete MVA pathway. In some aspects, said cells further comprise one or more nucleic acids encoding an isopentenyl-diphosphate delta-isomerase (IDI) polypeptide. In other aspects of any of the cells described herein, the cells further comprise a 1-Deoxyxlulose-5-phosphate synthase (DXS) polypeptide. In another aspect, said one or more nucleic acids encoding a DXS polypeptide of (b) is a heterologous nucleic acid encoding a DXS polypeptide. In yet another aspect, said one or more nucleic acids encoding a DXS polypeptide of (b) is a copy of an endogenous nucleic acid encoding a DXS polypeptide.

BRIEF DESCRIPTION OF THE DRAWINGS

FIG. 8 depicts the nucleotide sequence of an IspA synthetic gene (SEQ ID NO: 10).

FIG. 9 depicts the nucleotide sequence of pMCM1535 (SEQ ID NO: 11).

FIG. 11 depicts the nucleotide sequence of avian farnesyl diphosphate synthase, A116W mutant (SEQ ID NO: 12).

FIG. 12 depicts the nucleotide sequence of avian farnesyl diphosphate synthase, N144'W mutant (SEQ ID NO: 13).

FIG. 18 depicts the nucleotide sequence of a codon-optimized allele of hrcA for expression in E. coli (SEQ ID NO: 14).

FIG. 25 depicts volumetric productivity achieved in each 15-L fermentation over time. All runs using the E. gallinarum or E. casseliflavus (triangles and squares, respectively) achieved a higher overall volumetric productivity than the two runs using E. faecalis upper pathway enzymes (open and closed diamonds. Volumetric Productivity was calculated using the following formula: Volumetric productivity (g/L/hr)=[Σ(ER(t)/1000*68.117)]/[t−$t_0$], where the summation is from $t_0$ to t. Tank turnaround time is not factored in.

FIG. 30 depicts the volumetric productivity achieved in each 15 L fermentation over time. The strains with the modified RBS sites, namely CMP1286 (RBS9 yddV), CMP1284 (RBS3 yddV), and CMP1275 (RBS1/3 yddV) (open circles, open squares, and open triangles, respectively) achieved a volumetric productivity of isoprene that was similar to the control strain (DW719, runs 20120526 and 20120565, closed squares and closed diamonds, respectively). Volumetric productivity was calculated using the following formula: Volumetric productivity (g/L/hr)=[Σ(HGER(t)/1000*68.117)]/[t−$t_0$], where the summation is from $t_0$ to t. Tank turnaround time is not factored in.

FIG. 38 depicts the nucleotide sequence of pCHL426 (SEQ ID NO: 104).

FIG. 40 depicts the nucleotide sequence of pCHL427 (SEQ ID NO: 105).

DETAILED DESCRIPTION

Figure 1A:
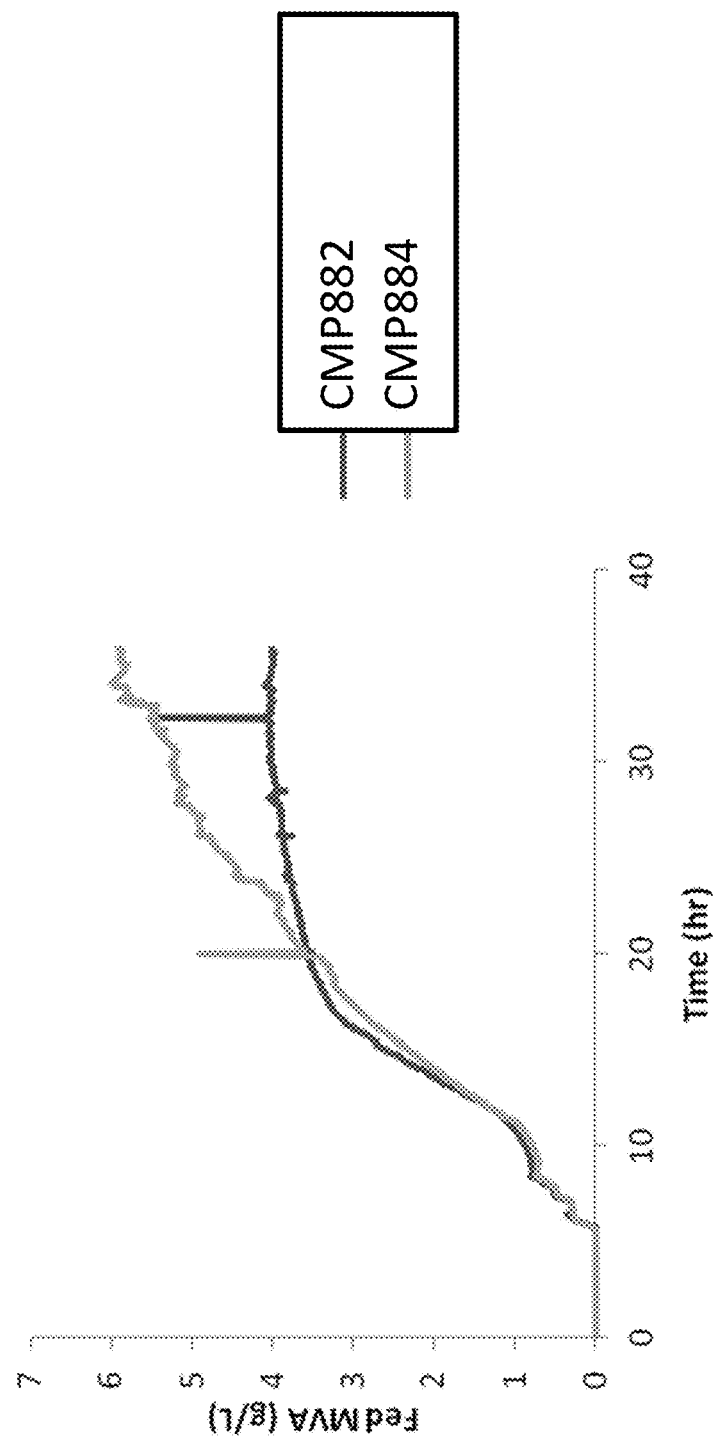
FIG. 1a depicts mevalonate feed concentrations during fermentations of CMP882 and CMP884.
Figure 1B:
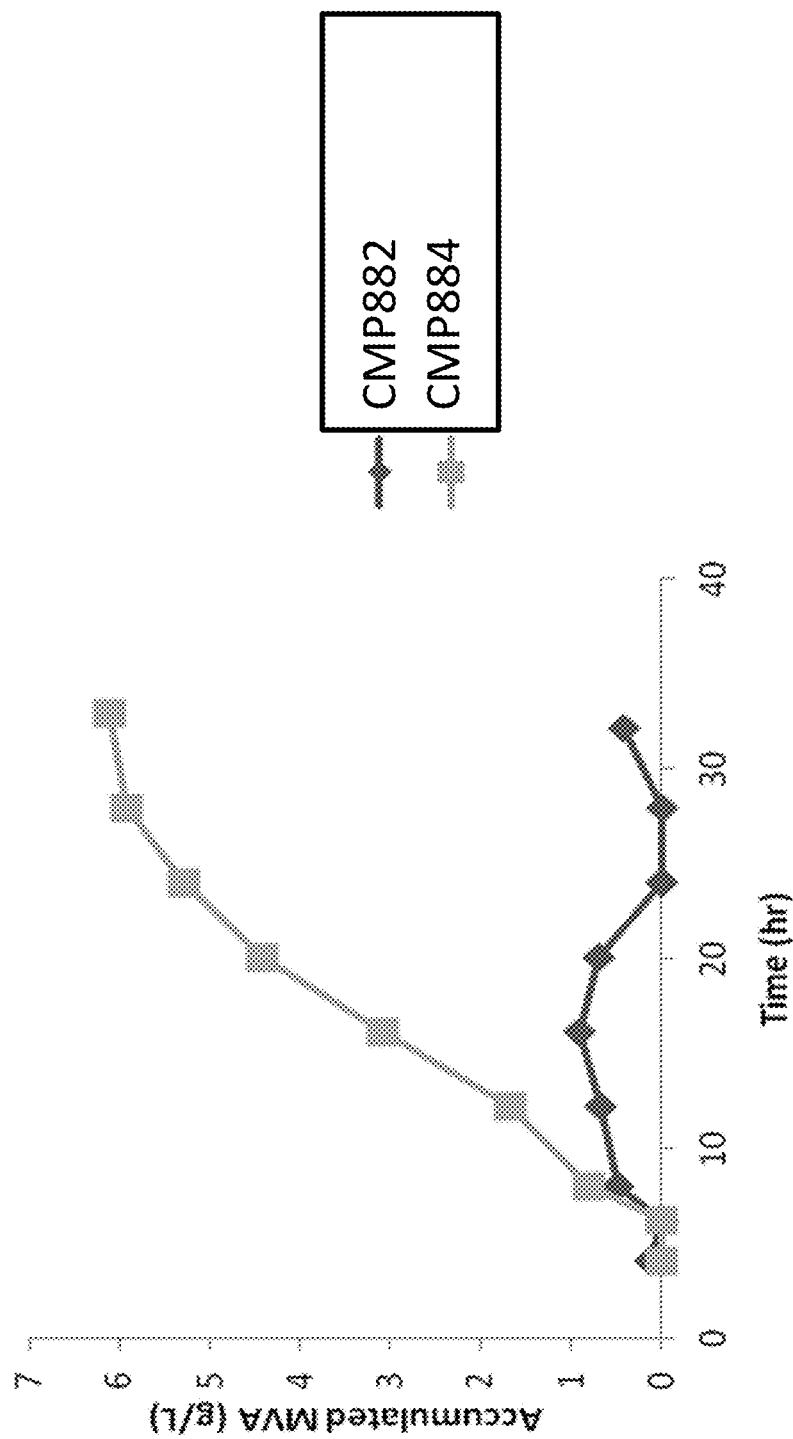
FIG. 1b depicts mevalonate accumulation in the media during fermentations of strains CMP882 and CMP884.
Figure 2:
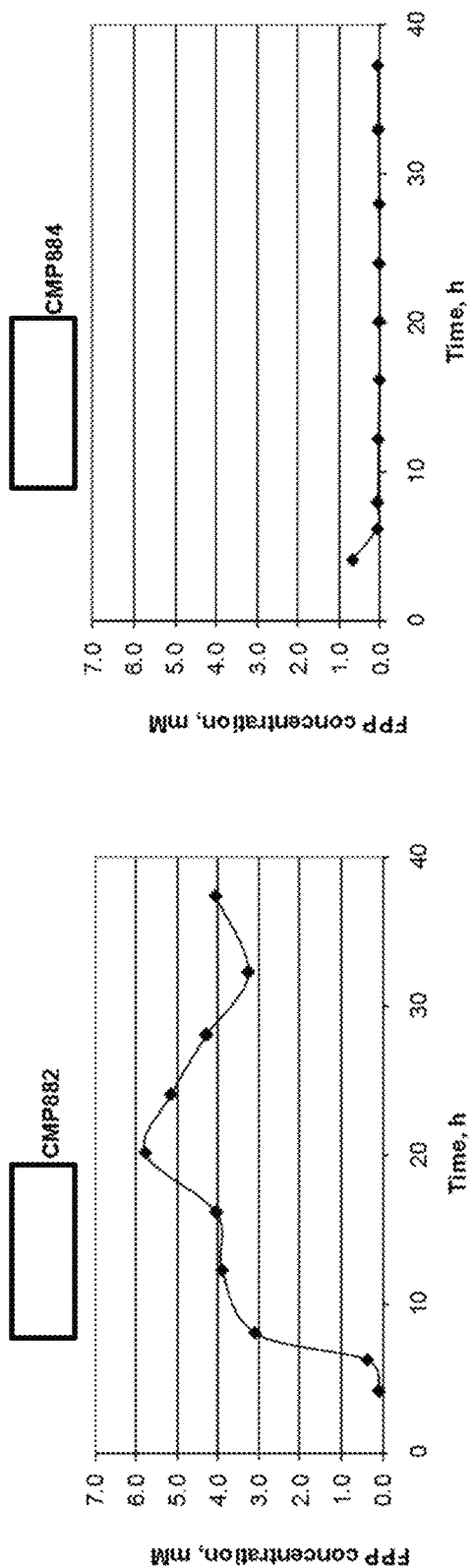
FIG. 2 depicts farnesyl pyrophosphate (FPP) concentration during fermentation of CMP882 and CMP884.

The invention provided herein discloses, inter alia, compositions and methods for the production of isoprene in recombinant cells that have been engineered to downregulate the expression or functional activity of the ispA gene during precise time periods during fermentation. The invention is based on the discovery that decreased expression of the ispA gene of recombinant cells during fermentation results in higher levels of isoprene production in comparison to cells that do not possess decreased ispA gene functional activity. Without being bound to theory, it is believed that decreasing ispA gene expression and/or functional activity improves isoprene yields by decreasing the production and accumulation of higher molecular weight isoprenoid molecules thereby resulting in higher carbon availability for isoprene synthesis as well as improved cell viability. However, because the ispA gene produces an enzyme that is essential for the robust growth of bacteria and other microorganisms, total elimination of this gene, such as through a gene knock out, is not a practical option for improving isoprene yields as it has been reported to result in either impaired growth (Fukisaki et al., 2005, *J. Biochem.*, 137(3):395-400) or in the death (worldwide web.genome.wisc.edu/resources/essential.htm; Baba et al., 2006, *Mol. Syst. Biol.*, 2006.0008) of the cells. The inventors have solved this technical problem based on their discovery that specific and temporally-precise decreased expression and/or functional activity of the ispA gene during isoprene production (e.g. subsequent to the linear growth phase of fermentation) results in higher isoprene yield, titer, cell productivity, volumetric productivity, specific productivity, and cell viability by the recombinant cells.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", third edition (Sambrook et al., 2001); "*Oligonucleotide Synthesis*" (M. J. Gait, ed., 1984); "*Animal Cell Culture: A practical approach*", third edition (J. R. Masters, ed., 2000); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 3rd revised ed., J. Wiley & Sons (New York, N.Y. 2006), and March's Advanced Organic Chemistry Reactions, Mechanisms and Structure 6th ed., John Wiley & Sons (New York, N.Y. 2007), provide one skilled in the art with a general guide to many of the terms used in the present application.

Definitions

The term "ispA" can refer to any geranyltranstransferase or farnesyl diphosphate (FPP) synthase enzyme or any member of the prenyl transferase family of enzymes that can catalyze the condensation of isopentenyl diphosphate (IPP) with 3,3-dimethylallyl diphosphate (DMAPP) or geranyl diphosphate (GPP) to yield FPP in any organism. In some embodiments, ispA is encoded by an ispA gene.

The term "isoprene" refers to 2-methyl-1,3-butadiene (CAS#78-79-5). It can be the direct and final volatile C5 hydrocarbon product from the elimination of pyrophosphate from DMAPP. It may not involve the linking or polymerization of IPP molecules to DMAPP molecules. The term "isoprene" is not generally intended to be limited to its method of production unless indicated otherwise herein.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the terms "minimal medium" or "minimal media" refer to growth medium containing the minimum nutrients possible for cell growth, generally without the presence of amino acids. Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "isoprenoid" refers to a large and diverse class of naturally-occurring class of organic compounds composed of two or more units of hydrocarbons, with each unit consisting of five carbon atoms arranged in a specific pattern. Isoprenoids can include, but are not limited to, terpenoids (for example, hemiterpenoids, monoterpenoids, sesquiterpenoids, diterpenoids, sesterterpenoids, triterpenoids, tetraterpenoids, and/or polyterpenoids). As used herein, "isoprene" is expressly excluded from the definition of "isoprenoid."

As used herein, the term "mass yield" refers to the mass of the product produced by the recombinant (e.g., bacterial) cells divided by the mass of the glucose consumed by the recombinant cells multiplied by 100.

By "specific productivity," it is meant the mass of the product produced by the bacterial cell divided by the product of the time for production, the cell density, and the volume of the culture.

By "titer," it is meant the mass of the product produced by the recombinant (e.g., bacterial) cells divided by the volume of the culture.

As used herein, the term "cell productivity index (CPI)" refers to the mass of the product produced by the recombinant (e.g., bacterial) cells divided by the mass of the recombinant cells produced in the culture.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Recombinant Microorganisms Capable of Enhanced Production of Isoprene

Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals. The mevalonate-dependent biosynthetic pathway (MVA pathway) is a key metabolic pathway present in all higher eukaryotes and certain bacteria. In addition to being important for the production of molecules used in processes as diverse as protein prenylation, cell membrane maintenance, protein anchoring, and N-glycosylation, the mevalonate pathway provides a major source of dimethylallyl diphosphate (DMAPP) and isopentenyl diphosphate (IPP), which serve as the basis for the biosynthesis of both isoprenoids and isoprene.

Isoprenoid compounds such as isopentenyl tRNA, isoprenoid quinones, and sugar carrier lipids are synthesized as part of normal metabolism by many microorganisms, including *E. coli* (Fujisaki, et al. (1989) *J. Bacteriol.* 171:5654-5658). A branch point in the synthetic pathway for the production of isoprenoid compounds involves a reaction catalyzed by the enzyme farnesyl diphosphate (FPP) synthase which condenses IPP with DMAPP or geranyl diphosphate (GPP) to yield FPP. FPP synthase (EC: 2.5.1.10) belongs to the transferase family of enzymes, specifically those enzymes capable of transferring aryl or alkyl groups other than methyl groups in metabolic reactions. Other names in common use for FPP synthase include geranyltranstransferase, geranyl transferase I, prenyltransferase, farnesyl pyrophosphate synthetase, and farnesylpyrophosphate synthetase.

As described above, DMAPP and IPP provide the initial carbon source input for the biosynthesis of both isoprenoids and isoprene. The enzyme isoprene synthase uses these molecules to catalyze the production of isoprene while FPP synthase utilizes them to produce GPP and FPP—which are then further synthesized into larger molecular weight isoprenoid molecules. Therefore, without being bound to theory, it is believed that for recombinant cells engineered to produce isoprene, the enzymatic activity of FPP synthase results in reduced carbon availability for isoprene production by making less DMAPP and IPP molecules available for conversion into isoprene by isoprene synthase. Furthermore, increased isoprenoid production in recombinant cells or in cells otherwise susceptible to isoprenoid accumulation is associated with poor morphology and decreased cell viability In microorganisms such as *E. coli*, FPP synthase is encoded by the ispA gene (Fukisaki, et al., (1990), *J. Biochem.* 108: 995-1000). The ispA gene is located in an operon along two other genes: the dxs gene, which encodes the enzyme deoxyxylulose-5-phosphate synthase (DXS), as well as the xseB gene that produces the exonuclease VII small subunit (Lois et al., (Mar. 3, 1998) *Proc. Natl. Acad. Sci. U.S.A.* 95(5):2105-2110). IspA gene expression has been reported to be required for robust growth of microorganisms, since complete removal of this gene produces cells with growth rates lower than those of wild type strains (Fukisaki et al., 2005, *J. Biochem.*, 137

(3):395-400) or results in cell lethality (worldwide web.genome.wisc.edu/resources/essential.htm; Baba et al., 2006, *Mol. Syst. Biol.,* 2006.0008).

Recombinant cells that have been engineered to produce isoprene can exhibit two phases in culture: 1) a growth phase wherein the recombinant cells divide in a linear fashion and 2) a fermentation phase wherein the cells utilize a carbon source (e.g., glucose) to produce isoprene. Thus, in some embodiments, the recombinant cells comprise an ispA having decreased functional activity. In one aspect, the functional activity of ispA is decreased only during the fermentation phase of cell culture. In another aspect, the functional activity of ispA is not decreased during the linear growth phase during cell culture. In some aspects, the functional activity of ispA is decreased in both the growth and fermentation phases of cell culture. In yet another aspect, the functional activity of ispA is decreased in both the growth and fermentation phases of cell culture, but the decrease is larger in the fermentation phase.

Any method can be used to decrease the functional activity of ispA, such as, but not limited to, deleting the ispA gene, decreasing ispA gene expression, or decreasing the activity or availability of the polypeptide encoded by the ispA gene. In other aspects, the recombinant cells of the present invention comprise an ispA having decreased functional activity and one or more of a group of genes involved in isoprene biosynthesis that enables the synthesis of isoprene in the host microorganism. In another aspect, the recombinant host cells of the present invention comprise a recombinant ispA gene that has been codon optimized for expression in host cells. In some aspects, the codon optimized ispA gene is integrated into the host cell genome. In other aspects, the codon optimized ispA gene is expressed on a piece of extrachromosomal DNA (such as a plasmid). In another aspect, the codon optimized ispA gene is integrated into the host cell genome at the yhfS locus and the endogenous ispA gene is deleted.

In some aspects, the recombinant host cells of the present invention comprise a recombinant ispA gene that encodes a FPP synthase with an increased Km value (for example, an avian FPP synthase) for DMAPP in comparison to the Km value for DMAPP exhibited by the endogenously encoded FPP synthase. Such high Km FPP synthases have been described, for example, in Fernandez et al., *Biochemistry,* 2000, 39(50):15316-21. In other aspects, the recombinant host cells of the present invention can comprise an FPP synthase with a different temperature optimum (such as, but not limited to, the thermophilic FPP synthase described in Koyama et al., 1993, *J. Biochem.,* 113(3):355-363), a psychrophilic FPP synthase (such as the FPP synthase described in Nichols et al., 2004, *J. Bact.,* 186:8508-8515, the contents of which is incorporated by reference herein in its entirety), or an FPP synthase from a marine prokaryote (such as the FPP synthase described in Ranzer et al., 2009, *Mar. Biotechnol,* 11:62-73). In some aspects, the endogenous host cell ispA gene in any of the recombinant cells described herein is replaced by any of the alternative genes encoding an FPP synthase described herein. In other aspects, the recombinant ispA gene is placed under the control of an inducible or a constitutive promoter. In another aspect, the recombinant ispA gene is expressed on a multicopy plasmid. In still another aspect, the recombinant ispA gene is integrated into a chromosome of the host cells.

In some aspects, the recombinant host cells of the present invention comprise an ispA gene under the control of a weak promoter (i.e., a promoter driving the expression of an ispA gene, wherein the amount of expression is less than what is observed by the endogenous or wild type ispA promoter). In some aspects, the promoter controlling the expression of the ispA gene expresses the ispA gene at a higher level during the linear growth phase during cell culture in comparison to the expression of the ispA gene during the fermentation phase.

Decreased Functional Activity of ispA

In some aspects, the recombinant cells described herein comprise an ispA having decreased functional activity. "Decreased functional activity" in this context refers to the ability of an ispA polypeptide (for example, a polypeptide encoded by an ispA gene) to convert IPP and DMAPP to GPP and/or FPP (i.e., the molecules necessary for subsequent production of isoprenoids). In some aspects, any of the recombinant cells disclosed herein can comprise an ispA gene wherein functional activity of ispA is decreased such that the cells produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an ispA having decreased functional activity. In another aspect, recombinant cells that have been engineered to produce isoprene comprising one or more heterologous nucleic acids encoding a polypeptide having isoprene synthase activity, one or more heterologous nucleic acids encoding one or members of the MVA pathway and an ispA having decreased functional activity produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but that do not comprise an ispA having decreased functional activity.

In other aspects, any of the recombinant cells disclosed herein can comprise ispA wherein functional activity of ispA is decreased such that the cells produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise ispA having decreased functional activity. In other aspects, any of the recombinant cells disclosed herein can comprise ispA wherein functional activity of the ispA gene is decreased such that the cells exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise ispA having decreased functional activity. In another aspect, recombinant cells that have been engineered to produce isoprene comprising one or more heterologous nucleic acids encoding one or members of the MVA pathway and an ispA having decreased functional activity can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an ispA having decreased functional activity. As used herein, "improved viability" means there are less dead, dying, or otherwise morphologically abnormal cells produced during the course of fermentation. Morphological abnormalities can include, but are not limited to, elongated cells and/or cellular debris from dead or dying cells. In some embodiments, "improved viability" can mean that a greater number of cells are determined to be alive through a cell biological, molecular biological, or biochemical technique that is known in the art (such as, but not limited to, Fluorescent Activated Cell Sorting (FACS) or DiBAC4(3) staining). In some aspects, ispA functional activity is decreased during the peak isoprene production phase of fermentation. In other aspects, ispA functional activity is not decreased during the linear growth phase of fermentation.

Methods to measure decreased functional activity of ispA are many and well known in the art. For example, standard methods can be used to determine the production of metabolites (for example, FPP and GPP) in cells, such as by the chemical extraction of metabolites from whole cells followed by identification via mass spectrometry. Similarly, standard methods can be used to assay viability of cells with decreased ispA functional activity such as morphological analysis by microscopy or by assessing membrane potential. Cells with intact membrane potential are assumed to be alive and metabolically active, while cells with no membrane potential were assumed to be dead and metabolically inactive.

Decreased Expression of the ispA Gene

In some aspects, the functional activity of the ispA gene is decreased by decreasing the expression of the ispA gene. This can include deleting the ispA gene itself, either in whole or in part, or by decreasing its expression through any number of methods as described herein or known to one of skill in the art. In some aspects, promoters may be engineered into the cell to control the expression of the ispA gene. In one aspect, a promoter driving the expression of the ispA gene can be repressed due to increased accumulation of isoprenoid compounds. When such promoters are introduced to control the expression of ispA, ispA can be repressed at time periods which correspond to flux through the isoprenoid pathway. However, at time periods where the flux is low, the promoter remains induced and thereby permits expression of ispA.

Temporally-regulated Decreased Expression Via Auto-regulatory Promoters

In some aspects, ispA gene expression is decreased by placing the ispA gene under the control of an auto-regulatory promoter. In certain embodiments, promoters which are repressed only during late stage fermentation of recombinant cells that have been engineered to produce increased levels of isoprene can be used to decrease the functional activity of the ispA gene. Without being bound to theory, it is hypothesized that such promoters are repressed during periods of increased accumulation of isoprenoid compounds as fermentation progresses. Therefore, placing the ispA gene under the control of these promoters can be used to temporally modulate the expression of ispA, such that ispA repression occurs at time periods which correspond to increased flux through the isoprenoid pathway. However, at time periods where the isoprenoid pathway flux is low, such as during the linear growth phase of fermentation, then the promoter will remain induced and thereby permit expression of the ispA gene. This signature activity profile constitutes an auto-regulatory ispA expression control system.

Accordingly, in some aspects, any of the recombinant cells described herein can comprise an ispA gene having decreased functional activity, wherein the functional activity of the ispA gene is decreased by placing the ispA gene under the control of an auto-regulatory promoter. In some aspects, the auto-regulatory promoter is selected from the group consisting of: efeO, kpsC, kpsD, kpsD, kpsE, kpsF, kpsS, kpsU, nmpC, sodA, ybl129, ybl130, ybl131, yddV, and ydiU. In one aspect, the ispA gene is placed under control of the yddV promoter.

In other aspects, the endogenous ispA gene can be deleted from the genome of the recombinant cell (for example, a recombinant *E. coli* cell) and a new ispA gene can be substituted into the genome at a different locus. In one aspect, a heterologous ispA gene is inserted into the genome of the recombinant cell (for example, a recombinant *E. coli* cell) at the yhfS locus. The heterologous ispA gene can be identical to the deleted endogenous ispA gene or be an ispA gene from another source. In other aspects, the heterologous ispA gene under control of an auto-regulatory promoter is expressed extrachromosomally. In another aspect, the recombinant host cells of the present invention comprise a recombinant ispA gene that has been codon optimized for expression in host cells. In some aspects, the codon optimized ispA gene is integrated into the host cell genome. In another aspect, the codon optimized ispA gene is under the control of an auto-regulatory promoter selected from the group consisting of: efeO, kpsC, kpsD, kpsD, kpsE, kpsF, kpsS, kpsU, nmpC, sodA, ybl129, ybl130, ybl131, yddV, and ydiU. In some aspects, the codon optimized ispA gene is under the control of the yddV promoter. In yet another aspect, any of the auto-regulatory promoters described herein can drive the expression of an ispA gene selected from the group consisting of: a codon-optimized ispA, an ispA allele (for example, an avian ispA allele) encoding an enzyme comprising a Km that is higher in comparison to ispA-encoded enzymes from microorganisms, and an endogenous ispA allele.

In some aspects, recombinant cells (such as any of the recombinant cells disclosed herein) expressing an ispA gene under the control of an auto-regulatory promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an ispA gene under the control of an auto-regulatory promoter. In another aspect, recombinant cells that have been engineered to produce isoprene comprising one or more heterologous nucleic acids encoding one or members of the MVA pathway and an ispA gene under the control of an auto-regulatory promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but that do not comprise an ispA gene under the control of an auto-regulatory promoter. In some aspects, recombinant cells (such as any of the recombinant cells disclosed herein) expressing an ispA gene under the control of an auto-regulatory promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise an ispA gene under the control of an auto-regulatory promoter. In other aspects, recombinant cells (such as any of the recombinant cells disclosed herein) expressing an ispA gene under the control of an auto-regulatory promoter exhibit any of 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise an ispA gene under the control of an auto-regulatory promoter. In another aspect, recombinant cells that have been engineered to produce isoprene comprising one or more heterologous nucleic acids encoding one or members of the MVA pathway and an ispA gene under the control of an auto-regulatory promoter can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an ispA gene under the control of an auto-regulatory promoter.

Temporally-regulated Decreased Expression Via the Heterologous Repressor Protein HrcA An alternate method to control expression of ispA utilizes the transcriptional repressor protein HrcA of *Caulobacter crescentus* (Roberts et al., 1996, *Journal of Bacteriology*, 178(7):1829-1841; Susin et al., 2004, *Journal of Bacteriology*, 186(20): 6759-6767). The gene encoding HrcA is not naturally found in *E. coli* and there is no known information suggesting that the CIRCE element, which is recognized by HrcA, is involved in governing *E. coli* gene expression. Therefore, incorporating the CIRCE element within the regulatory sequence governing ispA expression within an *E. coli* isoprene producing system would permit HrcA-mediated repression of ispA. In addition, the heterologous hrcA gene can be introduced into an *E. coli* isoprene-producing host where its expression can be governed by at least one of a number of tightly regulated means.

Therefore, in some aspects, any of the recombinant cells described herein can comprise an ispA gene having decreased functional activity, wherein the functional activity of the ispA gene is decreased by an HrcA transcriptional repressor protein encoded by an hrcA gene and wherein a CIRCE element is engineered into a regulatory sequence governing ispA expression. In some aspects, hrcA expression is controlled by a linear growth phase regulated promoter identified within the transcriptional profile of cells across a large scale isoprene-generating fermentation. In some aspects, the linear growth phase regulated promoter is selected from the group consisting of otsA, amiB, and deoC.

In other aspects, hrcA expression may be controlled by a positive regulatory-loop that is itself turned on during the desired slow growth phase of fermentation via an inducing signal, such as acute nutrient limitation or altered temperature. In this aspect, a transactivator peptide, such as transactivator T, is functionally linked to a particular signal-sensing promoter. Introduction of the inducing signal will induce activity of the signal-sensing promoter, which, in turn, upregulates the expression of transactivator T. By linking further copies of transactivator T genes to transactivator T-dependent promoters a positive feedback loop is initiated and sustained once the inducing signal is removed. In other aspects, the hrcA gene is linked to at least one transactivator T-dependent promoter resulting in HrcA being continually expressed during periods subsequent to activation of the positive regulatory loop. In certain aspects, the transactivator T gene driven by transactivator T dependent promoter is located on the same operon as the hrcA gene. In other aspects, the transactivator T gene driven by transactivator T dependent promoters is located in an independent locus not containing the hrcA gene.

In some aspects, recombinant cells (such as any of the recombinant cells disclosed herein) expressing an ispA gene under the control of an HrcA repressor protein produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an ispA gene under the control of an HrcA repressor protein. In another aspect, recombinant cells that have been engineered to produce isoprene comprising one or more heterologous nucleic acids encoding one or members of the MVA pathway and an ispA gene under the control of an HrcA repressor protein produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but that do not comprise an ispA gene under the control of an HrcA repressor protein. In some aspects, recombinant cells (such as any of the recombinant cells disclosed herein) expressing an ispA gene under the control of an HrcA repressor protein produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise an ispA gene under the control of an HrcA repressor protein. In other aspects, recombinant cells (such as any of the recombinant cells disclosed herein) expressing an ispA gene under the control of an HrcA repressor protein exhibit any of 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise an ispA gene under the control of an HrcA repressor protein. In another aspect, recombinant cells that have been engineered to produce isoprene comprising one or more heterologous nucleic acids encoding one or members of the MVA pathway and an ispA gene under the control of an HrcA repressor protein can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an ispA gene under the control of an HrcA repressor protein.

Temporally-regulated Decreased Expression Via Xylose-regulated Expression of ispA Regulated gene expression mediated by carbon source availability is another scalable alternative to controlling ispA gene expression within a production host (for example, an *E. coli* production host). Such a method offers the ability to provide relatively normal and/or sufficient levels of ispA gene expression required for healthy robust fast growing cells, allowing quick biomass placement. In addition, such a method offers the ability to restrict expression of ispA during glucose-supported isoprene production when FPP synthase activity is believed to be detrimental to cell viability, resulting in reduced yield of isoprene produced from glucose.

Consequently, in some aspects, any of the recombinant cells described herein can comprise an ispA gene having decreased functional activity, wherein the functional activity of the ispA gene is decreased by placing the ispA gene under direct control of a xylose-regulated promoter. In some aspects, ispA expression in recombinant cell (such as a recombinant *E. coli* cell) is placed under the direct control of an endogenous xylA or xylF promoters or under control of any promoter that is positively influence by D-xylose and negatively influenced by glucose within the recombinant cell. This is accomplished by deleting the endogenous ispA gene and substituting a heterologous ispA under the control of either the xylA or xylF D-xylose-responsive promoters. The divergent xylA-xylF promoters of E. coli and their positive regulation via D-xylose and the transcriptional activator XylR as well as their negative regulation by glucose and catabolite repression have been described (S. Song and C. Park, 1997, J. Bacterial., 179(22):7025-7032). In some aspects, ispA gene expression is governed positively by the availability of xylose in the absence of glucose and negatively by the presence of glucose. In some aspects, the xylose-inducible ispA locus is present within the chromosome of the recombinant cell (such as a recombinant E. coli cell), but, alternatively, may also be encoded on an extrachromosomal nucleotide sequence such as a plasmid. Construction of the xylose-inducible ispA construct and its introduction into the isoprene producing E. coli host can be performed using standard molecular and microbiology techniques (J. Sambrook, E. F. Fritsch, and T. Maniatis Cold Spring Harbor Laboratory Press, NY. 1989).

In some aspects, recombinant cells (such as any of the recombinant cells disclosed herein) expressing an ispA gene under the control of an xylose-inducible promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an ispA gene under the control of an xylose-inducible promoter. In another aspect, recombinant cells that have been engineered to produce isoprene comprising one or more heterologous nucleic acids encoding one or members of the MVA pathway and an ispA gene under the control of an xylose-inducible promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but that do not comprise an ispA gene under the control of an xylose-inducible promoter. In some aspects, recombinant cells (such as any of the recombinant cells disclosed herein) expressing an ispA gene under the control of an xylose-inducible promoter produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise an ispA gene under the control of an xylose-inducible promoter. In other aspects, recombinant cells (such as any of the recombinant cells disclosed herein) expressing an ispA gene under the control of an xylose-inducible promoter exhibit any of 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise an ispA gene under the control of an xylose-inducible promoter. In another aspect, recombinant cells that have been engineered to produce isoprene comprising one or more heterologous nucleic acids encoding one or members of the MVA pathway and an ispA gene under the control of an xylose-inducible promoter can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an ispA gene under the control of an xylose-inducible promoter.

Decreased FPP Synthase Activity

In some aspects, the functional activity of the ispA gene is decreased by decreasing the activity of the IspA protein, FPP synthase. This can include inhibiting the translation of the IspA mRNA or by degrading FPP synthase itself through any number of methods as described herein.

Translational Fusion of the IspA Protein with a Proteolytic Tag to Decrease Protein Activity In some aspects of any of the recombinant cells described herein, FPP synthase is targeted for proteolytic degradation by engineering a DNA sequence into the ispA gene which encodes an 11 amino acid protein tag (Andersen et al., 1998, Appl Environ Microbiol., 64(6):2240-2246). The proteolytic tmRNA tag then targets FPP synthase for degradation in host cells, thus decreasing FPP synthase activity. In some aspects, the proteolytic tag is fused to the C-terminus of the FPP synthase protein. In other aspects, the proteolytic tag is fused to the N-terminus of the FPP synthase protein.

In some aspects, recombinant cells (such as any of the recombinant cells disclosed herein) expressing an FPP synthase protein fused to a proteolytic tag produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in cells that do not comprise an FPP synthase protein fused to a proteolytic tag. In another aspect, recombinant cells (such as any of the recombinant cells disclosed herein) expressing an FPP synthase protein fused to a proteolytic tag that have been engineered to produce isoprene comprising one or more heterologous nucleic acids encoding one or members of the MVA pathway produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of GPP and/or FPP in comparison to the concentration of these molecules in recombinant cells that comprise one or more heterologous nucleic acids encoding one or more members of the MVA pathway but do not comprise an FPP synthase protein fused to a proteolytic tag. In some aspects, recombinant cells (such as any of the recombinant cells disclosed herein) expressing an FPP synthase protein fused to a proteolytic tag produce less than about 1%, 2%, 3%, 4%, 5%, 6%, 7%, 8%, 9%, 10%, 15%, 20%, 25%, 30%, 35%, 40%, 45%, 50%, 60%, 70%, 80%, 90%, or 100%, inclusive, including any percentages in between these values, of the concentration of isoprenoids in comparison to the concentration of these molecules in cells that do not comprise an FPP synthase protein fused to a proteolytic tag. In other aspects, recombinant cells (such as any of the recombinant cells disclosed herein) expressing an FPP synthase protein fused to a proteolytic tag exhibit any of 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that do not comprise an IspA protein fused to a proteolytic tag. In another aspect, recombinant cells (such as any of the recombinant cells disclosed herein) expressing an FPP synthase protein fused to a proteolytic tag comprising one or more heterologous nucleic acids encoding one or members of the MVA pathway and an ispA gene can exhibit any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, improved viability in comparison to the viability of cells that comprise one or more heterologous nucleic acids encoding one or more members of the MVA pathway but that do not comprise an FPP synthase protein fused to a proteolytic tag.

Decreased IspA Protein Expression Via the Use of Antisense mRNA and Ribosomal Binding Mutations In some aspects, antisense mRNA directed towards ispA mRNA is used to prevent the translation of ispA mRNA into IspA protein and result in decreased IspA protein expression. Antisense is well known in the art and has been used in *E. coli*, among other organisms, to reduce the production of molecules such as acetate (Kim J. and Cha H.J., 2003, *Biotech Bioeng.*, 83:841-853) or to engineer a catalase knockout phenotype (Chan E. et al., 2010, *J. Exp. Microbiol Immunol.*, 14:127-134). Design of antisense constructs targeted to the ispA gene of *E. coli* can be prepared using methods described by Shao Y. et al., 2006, *Nucleic Acids Res.*, 34:5660-5669. The antisense RNA molecules can be stabilized using paired termini (Nakashima N. et al., 2006, *Nucleic Acids Res.*, 34:e138). In some aspects, the antisense oligonucleotide is about 150 bp long. Decreased translation of ispA mRNA due to antisense mRNA treatment can be measured by any means known in the art including, but not limited to, enzyme activity assays, Western Blot, Northern Blot, or RT-PCR.

In other aspects, IspA protein expression is decreased through the introduction of one or more mutations into one or more ribosomal binding sites located in the ispA mRNA molecule. Introduction of ribosomal-binding mutations interferes or abolishes the translation of the IspA mRNA leading to decreased IspA protein expression. Decreased translation of ispA mRNA due to the introduction of one or more mutations into one or more ribosomal binding sites located in the ispA mRNA molecule can be measured by any means known in the art including, but not limited to, enzyme activity assays or Western Blot.

The location of ribosomal binding sites (RBSs) in a particular mRNA can be identified using optimization software known in the art. For example, RBS calculator optimization software using RNA thermodynamic parameters can be used in conjunction with Vienna RNA Package v.1.8.4 (available at world.wide.web.tbi.univie.ac.at/~ivo/RNA/, Gruber et al., (NAR, 2008) and the Vienna RNA model for the RBS calculator. Such RBS calculator optimization software can be used to identify RBSs with a predicted effect on protein expression. For example, RBSs that should provide for decreased expression of a target protein (e.g. ispA) can be identified using RBS calculator optimization software.

Isoprene Synthase Nucleic Acids and Polypeptides

In some aspects of the invention, the recombinant cells described in any of the compositions or methods described herein further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In some aspects, more than one endogenous nucleic acid encoding an isoprene synthase polypeptide is used (e.g., 2, 3, 4, or more copies of an endogenous nucleic acid encoding an isoprene synthase polypeptide). In a particular aspect, the cells are engineered to over-express the endogenous isoprene synthase pathway polypeptide relative to wild-type cells. In some aspects, the endogenous nucleic acid encoding an isoprene synthase polypeptide is operably linked to a weak promoter. In some aspects, the isoprene synthase polypeptide is a polypeptide from *Pueraria* or *Populus* or a hybrid such as *Populus albax × Populus tremula*. In some aspects, the isoprene synthase polypeptide is from *Eucalyptus*.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., 1995, *J. Biol. Chem.* 270:13010-13016. In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 µL of 1M $MgCl_2$, 1 mM (250 µg/ml) DMAPP, 65 µL of Plant Extract Buffer (PEB) (50 mM Tris-HCl, pH 8.0, 20 mM $MgCl_2$, 5% glycerol, and 2 mM DTT) can be added to 25 µL of cell extract in a 20 ml Headspace vial with a metal screw cap and teflon coated silicon septum (Agilent Technologies) and cultured at 370 C for 15 minutes with shaking. The reaction can be quenched by adding 200 µL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba*×*Populus tremula*, or a variant thereof.

In some aspects, the isoprene synthase polypeptide or nucleic acid is from the family Faboideae, such as the Faboideae subfamily. In some aspects, the isoprene synthase polypeptide or nucleic acid is a polypeptide or nucleic acid from *Pueraria montana* (kudzu) (Sharkey et al., 2005, *Plant Physiology* 137: 700-712), *Pueraria lobata*, poplar (such as *Populus alba, Populus nigra, Populus trichocarpa*, or *Populus alba*×*tremula* (CAC35696) (Miller et al., 2001, *Planta* 213: 483-487), aspen (such as *Populus tremuloides*) (Silver et al., 1995, JBC 270(22): 13010-1316), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra*, or *Populus trichocarpa* or a variant thereof. In some aspects, the isoprene synthase polypeptide is an isoprene synthase from *Populus alba* or a variant thereof. In some aspects, the isoprene synthase is *Populus balsamifera* (Genbank JN173037), *Populus deltoides* (Genbank JN173039), *Populus fremontii* (Genbank JN173040), *Populus granididenta* (Genbank JN173038), *Salix* (Genbank JN173043), *Robinia pseudoacacia* (Genbank JN173041), *Wisteria* (Genbank JN173042), *Eucalyptus globulus* (Genbank AB266390) or *Melaleuca alterniflora* (Genbank AY279379) or variant thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase. In some aspects, the isoprene synthase polypeptide is from *Eucalyptus*, or variant thereof. In other aspects, the isoprene synthase is from *Robinia, Salix*, or *Melaleuca*, or variants thereof.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed). In some aspects, the isoprene synthase polypeptide is from *Eucalyptus*, or variant thereof. In other aspects, the isoprene synthase is from *Robinia, Salix*, or *Melaleuca*, or variants thereof.

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making microorganisms encoding isoprene synthase described herein are also described in International Patent Application Publication Nos. WO 2009/076676, WO 2010/003007, WO 2009/132220, WO 2010/031062, WO 2010/031068, WO 2010/031076, WO 2010/013077, WO 2010/031079, WO 2010/148150, WO 2010/124146, WO 2010/078457, WO 2010/148256, and Sharkey et al., "*Isoprene Synthase Genes Form A Monophyletic Clade Of Acyclic Terpene Synthases In The Tps-B Terpene Synthase Family*", Evolution (2012) (available on line at DOI: 10.1111/evo.12013), the contents of each of which are incorporated by reference herein.

Various isoprene synthase variants can be made with substitutions at the residue locations shown in Table A. Any of the variants described herein (including in Tables A, the claims, or the Examples) may be used in the compositions and methods of the invention. In some aspects, the variant comprises one or more (i.e. 2, 3, 4, 5, 6, etc.) mutations from Table A corresponding to the amino acid sequence of P. alba

TABLE A

| Isoprene Synthase Variants of P. Alba (MEA) | | | | |
|---|---|---|---|---|
| A118E | E472R | S510V | K161K | A118P |
| S22K | K463F | I342I | W392A | A118Q |
| S21R | K463T | K348F | W392C | A118A |
| S22K | R71K | K348Y | W392F | E41M |
| S22R | R71L | K348K | S288Y | G111S |
| E58L | R71M | C437L | M228Y | S74Q |
| T481V | R71V | T240C | A3T | S74S |
| T481Y | R71R | M460M | W392Y | K36D |
| T502F | K393L | R461A | W392W | S282H |
| T381L | F542L | H424P | F89D | S282I |
| T381M | P538K | H424H | F89E | S282W |
| T381Y | P538R | A448L | F89F | S282Y |
| T383H | P538P | A448Q | E41Y | S282S |
| T383L | A503A | A448V | E41E | K36S |
| E480I | L436I | G389D | R43E | K36T |
| E480R | L436Y | S444E | R43L | K36W |
| K393V | L436F | S444S | K36E | K36Y |
| K393I | E488L | H511Y | K36H | K36K |
| E415H | E488M | H511H | K36N | |
| E415V | E488T | R071I | K36P | |
| E415Y | E488W | R071K | K36Q | |
| R71H | E488E | R071L | A453I | |
| R71I | I342Y | K374Y | A453V | |
| E58Y | C437M | K374K | A453A | |
| E135G | C437W | L526E | V409I | |
| A363L | C437Y | L526Q | V409T | |
| K374Y | C437C | L526L | K161C | |
| T381I | M460A | R242G | K161E | |
| L436L | I447T | R242R | K161N | |
| H254R | I447V | A443G | K161Q | |
| H254C | I447Y | A443Q | G99E | |
| E488C | S444D | A443R | G99G | |
| E488F | G389E | A443S | S288A | |
| T383Y | L376I | S13S | S288C | |
| K414I | L376M | V268I | S288T | |
| K414R | L376L | V268V | W392I | |
| K414S | I504F | K161A | W392M | |
| K414W | I504I | V409V | W392S | |

TABLE A-continued

| Isoprene Synthase Variants of P. Alba (MEA) | | | |
|---|---|---|---|
| E472C | E467W | D323F | W392T |
| E472L | S510C | G99D | W392V |

Table A describes specific substitutions in MEA P. alba isoprene synthase. Corresponding residues in other parent isoprene synthases may be similarly mutated to generate isoprene synthase variants of the invention.

MVA Pathway Nucleic Acids and Polypeptides

The complete MVA pathway can be subdivided into two groups: an upper and lower pathway. In the upper portion of the MVA pathway, acetyl Co-A produced during cellular metabolism is converted to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. In the lower MVA pathway, mevalonate is then converted into mevalonate-5-phosphate via the action of mevalonate kinase which is subsequently transformed into 5-diphosphomevalonate by the enzymatic activity of phosphomevalonate kinase. Finally, IPP is formed from 5-diphosphomevalonate by the activity of the enzyme mevalonate-5-pyrophosphate decarboxylase.

Exemplary MVA pathway polypeptides that can be used in conjunction with an ispA gene having decreased functional activity include, but are not limited to: 3-hydroxy-3-methylglutaryl-CoA synthase (HMG-CoA synthase) polypeptides (e.g., an enzyme encoded by mvaS), 3-hydroxy-3-methylglutaryl-CoA reductase (HMG-CoA reductase) polypeptides (e.g., enzyme encoded by mvaR or enzyme encoded by mvaE that has been modified to be thiolase-deficient but still retains its reductase activity), mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IPP isomerase polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better isoprene production can also be used as well.

Non-limiting examples of MVA pathway polypeptides which can be used are described in International Patent Application Publication No. WO 2009/076676; WO 2010/003007 and WO 2010/148150.

Acetoacetyl-CoA Synthase Nucleic Acids and Polypeptides

The acetoacetyl-CoA synthase gene (aka nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., 2010, *Proc. Natl. Acad. Sci. USA* 107(25): 11265-11270, the contents of which are expressly incorporated herein for teaching about nphT7. An acetoacetyl-CoA synthase gene from an actinomycete of the genus *Streptomyces* CL190 strain was described in JP Patent Publication (Kokai) No. 2008-61506 A and US Patent Application Publication No. 2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In one embodiment, acetoacetyl-CoA synthase of the present invention synthesizes acetoacetyl-CoA from malonyl-CoA and acetyl-CoA via an irreversible reaction. The use of acetoacetyl-CoA synthase to generate acetyl-CoA provides an additional advantage in that this reaction is irreversible while acetoacetyl-CoA thiolase enzyme's action of synthesizing acetoacetyl-CoA from two acetyl-CoA molecules is reversible. Consequently, the use of acetoacetyl-CoA synthase to synthesize acetoacetyl-CoA from malonyl-CoA and acetyl-CoA can result in significant improvement in productivity for isoprene compared with using thiolase to generate the end same product.

Furthermore, the use of acetoacetyl-CoA synthase to produce isoprene provides another advantage in that acetoacetyl-CoA synthase can convert malonyl CoA to acetyl CoA via decarboxylation of the malonyl CoA. Thus, stores of starting substrate are not limited by the starting amounts of acetyl CoA. The synthesis of acetoacetyl-CoA by acetoacetyl-CoA synthase can still occur when the starting substrate is only malonyl-CoA. In one embodiment, the pool of starting malonyl-CoA is increased by using host strains that have more malonyl-CoA. Such increased pools can be naturally occurring or be engineered by molecular manipulation. See, for example Fowler, et. al, 2009, *Applied and Environmental Microbiology*, 75(18):5831-5839.

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used.

An example of such an acetoacetyl-CoA synthase gene is the gene encoding a protein having the amino acid sequence of SEQ ID NO: 1. Such a protein having the amino acid sequence of SEQ ID NO: 1 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules.

In one embodiment, the gene encoding a protein having the amino acid sequence of SEQ ID NO: 1 can be obtained by a nucleic acid amplification method (e.g., PCR) with the use of genomic DNA obtained from an actinomycete of the *Streptomyces* sp. CL190 strain as a template and a pair of primers that can be designed with reference to JP Patent Publication (Kokai) No. 2008-61506 A.

As described herein, an acetoacetyl-CoA synthase gene for use in the present invention is not limited to a gene encoding a protein having the amino acid sequence of SEQ ID NO: 1 from an actinomycete of the *Streptomyces* sp. CL190 strain. Any gene encoding a protein having the ability to synthesize acetoacetyl-CoA from malonyl-CoA and acetyl-CoA and which does not synthesize acetoacetyl-CoA from two acetyl-CoA molecules can be used in the presently described methods. In certain embodiments, the acetoacetyl-CoA synthase gene can be a gene encoding a protein having an amino acid sequence with high similarity or substantially identical to the amino acid sequence of SEQ ID NO: 1 and having the function of synthesizing acetoacetyl-CoA from malonyl-CoA and acetyl-CoA. The expression "highly similar" or "substantially identical" refers to, for example, at least about 80% identity, at least about 85%, at least about 90%, at least about 91%, at least about 92%, at least about 93%, at least about 94%, at least about 95%, at least about 96%, at least about 97%, at least about 98%, and at least about 99% identity. As used above, the identity value corresponds to the percentage of identity between amino acid residues in a different amino acid sequence and the amino acid sequence of SEQ ID NO: 1, which is calculated by performing alignment of the amino acid sequence of SEQ ID NO: 1 and the different amino acid sequence with the use of a program for searching for a sequence similarity.

In other embodiments, the acetoacetyl-CoA synthase gene may be a gene encoding a protein having an amino acid sequence derived from the amino acid sequence of SEQ ID NO: 1 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

In still other embodiments, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO: 1 under stringent conditions and capable of encoding a protein having the function of synthesizing acetoacetyl-CoA from malonyl-CoA and acetyl-CoA. Herein, hybridization under stringent conditions corresponds to maintenance of binding under conditions of washing at 60.degree. C. 2.times.SSC. Hybridization can be carried out by conventionally known methods such as the method described in J. Sambrook et al. Molecular Cloning, A Laboratory Manual, 3rd Ed., Cold Spring Harbor Laboratory (2001).

As described herein, a gene encoding an acetoacetyl-CoA synthase having an amino acid sequence that differs from the amino acid sequence of SEQ ID NO: 1 can be isolated from potentially any organism, for example, an actinomycete that is not obtained from the *Streptomyces* sp. CL190 strain. In addition, acetoacetyl-CoA synthase genes for use herein can be obtained by modifying a polynucleotide encoding the amino acid sequence of SEQ ID NO: 1 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO: 1 can be evaluated as described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

Nucleic Acids Encoding Polypeptides of the Upper MVA Pathway

The upper portion of the MVA pathway uses acetyl Co-A produced during cellular metabolism as the initial substrate for conversion to mevalonate via the actions of polypeptides having either: (a) (i) thiolase activity or (ii) acetoacetyl-CoA activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production.

Non-limiting examples of upper MVA pathway polypeptides that can be used in conjunction with an ispA gene having decreased functional activity include: acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention.

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides. Thus, in certain aspects, any of the combinations of genes contemplated can be expressed in recombinant cells in conjunction with an ispA gene having decreased functional activity in any of the ways described herein.

Additional non-limiting examples of upper MVA pathway polypeptides which can be used herein are described in International Patent Application Publication No. WO 2009/076676; WO 2010/003007 and WO 2010/148150.

Genes Encoding mvaE and mvaS Polypeptides

In certain embodiments, various options of mvaE and mvaS genes (such as, but not limited to, mvaE and mvaS genes from *L. grayi, E. faecium, E. gallinarum, E. casseliflavus* and/or *E. faecalis*) alone or in combination with one or more other mvaE and mvaS genes encoding proteins from the upper MVA pathway are contemplated within the scope of the invention in conjunction with an IspA having decreased functional activity in recombinant cells. In many organisms (for eample, *L. grayi, E. faecium, E. gallinarum, E. casseliflavus*, and *E. faecalis*), the mvaE gene encodes a polypeptide that possesses both thiolase and HMG-CoA reductase activities (Hedl, et al., April 2002, *J Bacteriol.* 184(8): 2116-2122). The mvaS gene, on the other hand, encodes a polypeptide having an HMG-CoA synthase activity.

Accordingly, recombinant cells (e.g., *E. coli*) can be engineered to express one or more mvaE and mvaS genes (such as, but not limited to, mvaE and mvaS genes from *L. grayi, E. faecium, E. gallinarum, E. casseliflavus* and/or *E. faecalis*), to produce isoprene in conjunction with an ispA gene having decreased functional activity. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or cannot be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl-CoA to mevalonate can be introduced into the mvaE polypeptide. In some aspects, the mutant mvaE polypeptides contain one or more conservative amino acid substitutions.

In one aspect, mvaE proteins that are not degraded or less prone to degradation can be used for the production of isoprene. Examples of gene products of mvaEs that are not degraded or less prone to degradation which can be used include, but are not limited to, those from the organisms *E. faecium, E. gallinarum, E. casseliflavus, E. faecalis*, and *L. grayi*. One of skill in the art can express mvaE protein in *E. coli* BL21 (DE3) and look for absence of fragments by any standard molecular biology techniques. For example, absence of fragments can be identified on Safestain stained SDS-PAGE gels following His-tag mediated purification or when expressed in mevalonate, isoprene or isoprenoid producing *E. coli* BL21 using the methods of detection described herein.

Standard methods, such as those described in Hedl et al., (Hedl, et al., *J Bacteriol*. April 2002, 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 200 μl. For the assay, 1 enzyme unit (eu) represents the synthesis or thiolysis in 1 min of 1 μmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 200 μl. Reactions are initiated by adding the enzyme. For the assay, 1 eu represents the turnover, in 1 min, of 1 μmol of NADP(H). This corresponds to the turnover of 0.5 μmol of HMG-CoA or mevalonate.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi*_DSM 20601, *Enterococcus-faecium, Enterococcus gallinarum* EG2, *Enterococcus faecalis*, and/or *Enterococcus casseliflavus*. The mvaE nucleic acid encoded by the *Listeria grayi*_DSM 20601 mvaE gene can have a 99%, 98%, 97%, 96%, 95%, 95%, 93%, 92%, 91%, 90%, 89%, 88%, 87%, 86%, or 85% sequence identity to SEQ ID NO: 2. The mvaE nucleic acid encoded by the *Enterococcus faecium* mvaE gene can have a 99%, 98%, 97%, 96%, 95%, 95%, 93%, 92%, 91%, 90%, 89%, 88%, 87%, 86%, or 85% sequence identity to SEQ ID NO: 3. The mvaE nucleic acid encoded by the *Enterococcus gallinarum* EG2 mvaE gene can have a 99%, 98%, 97%, 96%, 95%, 95%, 93%, 92%, 91%, 90%, 89%, 88%, 87%, 86%, or 85% sequence identity to SEQ ID NO: 4. The mvaE nucleic acid encoded by the *Enterococcus casseliflavus* mvaE gene can have a 99%, 98%, 97%, 96%, 95%, 95%, 93%, 92%, 91%, 90%, 89%, 88%, 87%, 86%, or 85% sequence identity to SEQ ID NO: 5. The mvaE nucleic acid encoded by the *Enterococcus faecalis* mvaE gene can have a 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. 2004, *Biotechnology Letters* 26:1487-1491).

The mvaE nucleic acid can be expressed in a recombinant cell on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA). Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (1989, *Biochem J.*, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-MgCl2 and 0.2 mM-dithiothreitol at 30° C.; 5 mM-acetyl phosphate, 10 mM-acetoacetyl-CoA and 5 µl samples of extracts can be added, followed by simultaneous addition of acetyl-CoA (100 µM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-MgCl$_2$), is 12.2×10$^3$ M$^{-1}$ cm$^{-1}$. By definition, 1 unit of enzyme activity causes 1 µmol of acetoacetyl-CoA to be transformed per minute.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria gray_DSM 20601*, *Enterococcus faecium*, *Enterococcus gallinarum* EG2, *Enterococcus faecalis*, and/or *Enterococcus casseliflavus*. The mvaS nucleic acid encoded by the *Listeria grayi_DSM 20601* mvaS gene can have a 99%, 98%, 97%, 96%, 95%, 95%, 93%, 92%, 91%, 90%, 89%, 88%, 87%, 86%, or 85% sequence identity to SEQ ID NO: 6. The mvaS nucleic acid encoded by the *Enterococcus faecium* mvaS gene can have a 99%, 98%, 97%, 96%, 95%, 95%, 93%, 92%, 91%, 90%, 89%, 88%, 87%, 86%, or 85% sequence identity to SEQ ID NO: 7. The mvaS nucleic acid encoded by the *Enterococcus gallinarum* EG2 mvaS gene can have a 99%, 98%, 97%, 96%, 95%, 95%, 93%, 92%, 91%, 90%, 89%, 88%, 87%, 86%, or 85% sequence identity to SEQ ID NO: 8. The mvaS nucleic acid encoded by the *Enterococcus casseliflavus* mvaS gene can have a 99%, 98%, 97%, 96%, 95%, 95%, 93%, 92%, 91%, 90%, 89%, 88%, 87%, 86%, or 85% sequence identity to SEQ ID NO: 9. The mvaS nucleic acid encoded by the *Enterococcus faecalis* mvaS gene can have a 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. 2004, *Biotechnology Letters* 26:1487-1491).

The mvaS nucleic acid can be expressed in a recombinant cell on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Compositions of recombinant cells as described herein are contemplated within the scope of the invention as well. It is understood that recombinant cells also encompass progeny cells as well.

Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase, *M. burtonii* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae*, *Enterococcus faecalis*, *Methanococcoides burtonii*, or *Methanosarcina mazei*.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from Methanosarcina mazei. Additionally, the lower MVK polypeptide can be from the genus *Methanococcoides*, and, more specifically, can be from *M. Burtonii*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variants.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis, Methanococcoides burtonii*, or *Methanosarcina mazei*. In some aspects, the MVK polypeptide is selected from the group consisting of *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, and *Methanosarcina mazei* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

DXP Pathway Nucleic Acids and Polypeptides

In some aspects of the invention, the recombinant cells described in any of the compositions or methods described herein further comprise one or more heterologous nucleic acids encoding a DXS polypeptide or other DXP pathway polypeptides. In some aspects, the cells further comprise a chromosomal copy of an endogenous nucleic acid encoding a DXS polypeptide or other DXP pathway polypeptides. In some aspects, the *E. coli* cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide or other DXP pathway polypeptides. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No.: WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). In one embodiment, the ispH gene can be used to encode for HDR polypeptides. IspH is also known as 1-hydroxy-2-methyl-2-(E)-butenyl 4-diphosphate reductase, 4Fe-4S protein, ECK0030, JW0027, lytB, yaaE, and b0029. Standard methods can be used to determine whether a polypeptide has HDR polypeptides activity by measuring the ability of the polypeptide to convert HMBPP in vitro, in a cell extract, or in vivo.

Source Organisms for MVA Pathway, Isoprene Synthase, IDI, and DXP Pathway Polypeptides Isoprene synthase, IDI, DXP pathway, and/or MVA pathway nucleic acids can be obtained from any organism that naturally contains isoprene synthase, IDI, DXP pathway, and/or MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., Methanosarcina mazei) or species of *Methanococcoides* (e.g., *M. Burtonii*), plants, such as kudzu or poplar (e.g., *Populus alba* or *Populus albax tremula* CAC35696) or aspen (e.g., *Populus tremuloides*). Exemplary sources for isoprene synthases, IDI, and/or MVA pathway polypeptides which can be used are also described in International Patent Application Publication Nos. WO 2009/076676, WO 2010/003007, WO 2009/132220, WO 2010/031062, WO 2010/031068, WO 2010/031076, WO 2010/013077, WO 2010/031079, WO 2010/148150, WO 2010/078457, and WO 2010/148256.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., 1984, *Appl. Microbiol. Biotechnol.* 20: 46-53; ATCC No. 56765 and ATCC No. 26921); *Penicillium* sp., *Humicola* sp. (e.g., *H. insolens*, *H. lanuginose*, or *H. grisea*); *Chrysosporium* sp. (e.g., *C. lucknowense*), *Gliocladium* sp., *Aspergillus* sp. (e.g., *A. oryzae*, *A. niger*, *A sojae*, *A. japonicus*, *A. nidulans*, or *A. awamori*) (Ward, M. et al., 1993, *Appl. Microbiol. Biotechnol.* 39:738-743, and Goedegebuur et al., 2002, Genet 41: 89-98), *Fusarium* sp., (e.g., *F. roseum*, *F. graminum F. cerealis*, *F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., 1985, Sci. 228: 21-26). The term "*Trichoderma*" or "*Trichoderma* sp." or "*Trichoderma* spp." refer to any fungal genus previously or currently classified as *Trichoderma*.

In some embodiments, the fungus is *A. nidulans*, *A. awamori*, *A. oryzae*, *A. aculeatus*, *A. niger*, *A. japonicus*, *T. reesei*, *T. viride*, *F. oxysporum*, or *F. solani*. *Aspergillus* strains are disclosed in Ward, M. et al., *Appl. Microbiol. Biotechnol.* 39:738-743 and Goedegebuur et al., 2002, *Curr Gene* 41:89-98, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., 1984, *Appl. Microbiol. Biotechnology* 20:46-53, which is hereby incorporated by reference in its entirety, particularly with respect to strains of *T. reesei*.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E.* coli, strains of *Enterobacter*, strains of *Streptococcus*, or strains of Archaea such as Methanosarcina mazei.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some aspects, the source organism is a gram-positive bacterium. Non-limiting examples include strains of *Streptomyces* (e.g., *S. lividans, S. coelicolor*, or *S. griseus*) and *Bacillus*. In some aspects, the source organism is a gram-negative bacterium, such as *E. coli* or *Pseudomonas* sp. In some aspects, the source organism is *L. acidophilus*.

In some aspects, the source organism is a plant, such as a plant from the family Fabaceae, such as the Faboideae subfamily. In some aspects, the source organism is kudzu, poplar (such as *Populus alba×tremula* CAC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: *Chroococcales, Pleurocapsales, Oscillatoriales, Nostocales*, or *Stigonematales*.

Phosphoketolase Nucleic Acids and Polypeptides

In some aspects of the invention, the recombinant cells described in any of the compositions or methods described herein further comprise one or more nucleic acids encoding an phosphoketolase polypeptide or a polypeptide having phosphoketolase activity. In some aspects, the phosphoketolase polypeptide is an endogenous polypeptide. In some aspects, the endogenous nucleic acid encoding a phosphoketolase polypeptide is operably linked to a constitutive promoter. In some aspects, the endogenous nucleic acid encoding a phosphoketolase polypeptide is operably linked to an inducible promoter. In some aspects, the endogenous nucleic acid encoding a phosphoketolase polypeptide is operably linked to a strong promoter. In some aspects, more than one endogenous nucleic acid encoding a phosphoketolase polypeptide is used (e.g, 2, 3, 4, or more copies of an endogenous nucleic acid encoding a phosphoketolase polypeptide). In a particular aspect, the cells are engineered to overexpress the endogenous phosphoketolase polypeptide relative to wild-type cells. In some aspects, the endogenous nucleic acid encoding a phosphoketolase polypeptide is operably linked to a weak promoter.

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produces mevalonate, isoprenoid precursor molecules, isoprene and/or isoprenoids. Thus the amount of these compounds produced from a carbohydrate substrate may be increased. Alternatively, production of Acetyl-P and AcCoA can be increased without the increase being reflected in higher intracellular concentration. In certain embodiments, intracellular acetyl-P or acetyl-CoA concentrations will remain unchanged or even decrease, even though the phosphoketolase reaction is taking place.

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., 2001, *J. Bact*. 183:2929-2936). Any polypeptide identified as having phosphoketolase peptide activity as described herein is suitable for use in the present invention.

In other aspects, exemplary phosphoketolase nucleic acids include, for example, a phosphoketolase isolated from *Lactobacillus reuteri, Bifidobacterium longum, Ferrimonas balearica, Pedobactor saltans, Streptomyces griseus*, and/or *Nocardiopsis dassonvillei*. Additional examples of phosphoketolase enzymes which can be used herein are described in U.S. Pat. No. 7,785,858 and International Patent Application Publication No. WO 2011/159853 which are incorporated by reference herein.

Pathways Involving the Entner-Doudoroff Pathway

The Entner-Doudoroff (ED) pathway is an alternative to the Emden-Meyerhoff-Parnass (EMP—glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway, 1998, *J. Bact*. 180:3495-3502; Stulke and Hillen, 2000, *Annu. Rev. Microbiol*. 54:849-880; Dawes et al. 1966. *Biochem. J*. 98:795-803).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. *J. Bact*. 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or an 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of mevalonate, isoprene or isoprenoids.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

Pathways Involving the Oxidative Branch of the Pentose Phosphate Pathway

E. coli uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pg1) or 6-phosphogluconate dehydrogenase (gnd)) and a non-oxidative branch (with enzymes such as transketolase (tktA), transaldolase (talA or talB), ribulose-5-phosphate-epimerase and (or) ribose-5-phosphate epimerase) (Sprenger, 1995, *Arch. Microbiol.* 164:324-330).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase) expression can be modulated (e.g., increase enzyme activity) to allow more carbon to flux towards fructose 6-phosphate and xylulose 5-phosphate, thereby increasing the eventual production of mevalonate, isoprene and isoprenoids. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epi-merase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

Pathways Involving Phosphofructokinase

Phosphofructokinase is a crucial enzyme of glycolysis which catalyzes the phosphorylation of fructose 6-phosphate. *E. coli* has two isozymes encoded by pfkA and pfkB. Most of the phosphofructokinase activity in the cell is due to pfkA (Kotlarz et al., 1975, *Biochim. Biophys. Acta* 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of mevalonate, isoprene and isoprenoids. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

Additional Host Cell Mutations

The invention also contemplates additional host cell mutations that increase carbon flux through the MVA pathway. By increasing the carbon flow, more isoprene can be produced. The recombinant cells comprising any of the heterologously expressed nucleic acids (e.g., a heterologously expressed acetoacetyl-CoA synthase nucleic acid) as described herein can also be engineered for increased carbon flux towards mevalonate production wherein the activity of one or more enzymes from the group consisting of: (a) citrate synthase, (b) phosphotransacetylase; (c) acetate kinase; (d) lactate dehydrogenase; (e) NADP-dependent malic enzyme, and; (f) pyruvate dehydrogenase is modulated.

Citrate Synthase Pathway

Figure 5:
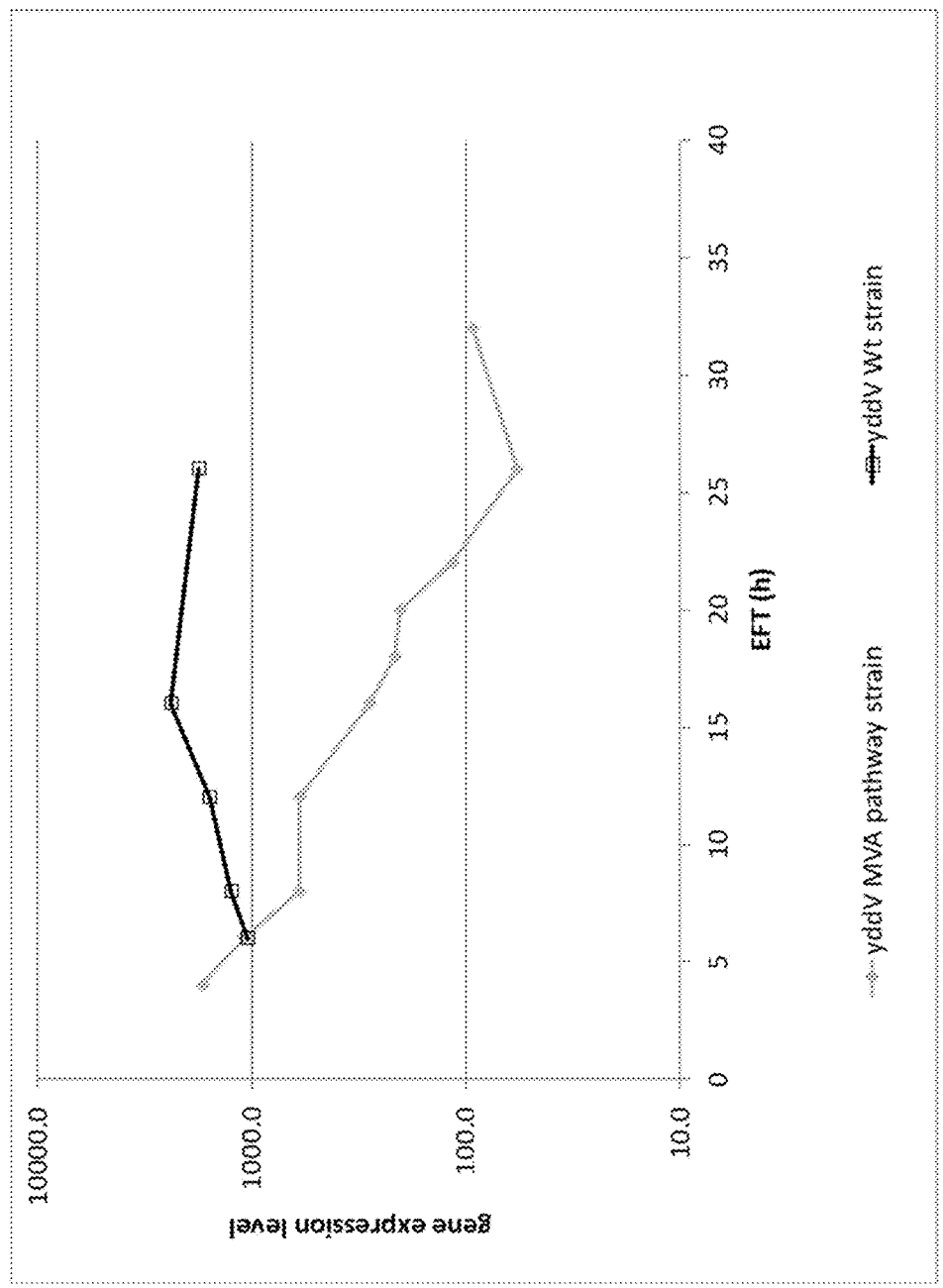
FIG. 5 depicts the expression of yddV during fermentation in MVA pathway strain (CMP457) versus wild type control strain (MCM1020).

Citrate synthase catalyzes the condensation of oxaloacetate and acetyl-CoA to form citrate, a metabolite of the Tricarboxylic acid (TCA) cycle (Ner, S. et al. 1983. *Biochemistry* 22: 5243-5249; Bhayana, V. and Duckworth, H. 1984. *Biochemistry* 23: 2900-2905) (FIG. 5). In *E. coli*, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. *Annual Rev. Biophysics Biophys. Chem.*15: 97-117; Duckworth et al. 1987. *Biochem Soc Symp.* 54:83-92; Stockell, D. et al. 2003. *J. Biol. Chem.* 278: 35435-43; Maurus, R. et al. 2003. *Biochemistry*. 42:5555-5565). To avoid allosteric inhibition by NADH, replacement by or supplementation with the *Bacillus subtilis* NADH-insensitive citrate synthase has been considered (Underwood et al. 2002. *Appl. Environ. Microbiol.* 68:1071-1081; Sanchez et al. 2005. *Met. Eng.* 7:229-239).

The reaction catalyzed by citrate synthase is directly competing with the thiolase catalyzing the first step of the mevalonate pathway, as they both have acetyl-CoA as a substrate (Hedl et al. 2002. *J. Bact.* 184:2116-2122). Therefore, one of skill in the art can modulate citrate synthase expression (e.g., decrease enzyme activity) to allow more carbon to flux into the mevalonate pathway, thereby increasing the eventual production of mevalonate and isoprene. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The decrease of the activity of citrate synthase can result in more carbon flux into the mevalonate dependent biosynthetic pathway in comparison to microorganisms that do not have decreased expression of citrate synthase.

Pathways Involving Phosphotransacetylase and/or Acetate Kinase

Phosphotransacetylase (pta) (Shimizu et al. 1969. *Biochim. Biophys. Acta* 191: 550-558) catalyzes the reversible conversion between acetyl-CoA and acetylphosphate (acetyl-P), while acetate kinase (ackA) (Kakuda, H. et al. 1994. *J. Biochem.* 11:916-922) uses acetyl-P to form acetate. These genes can be transcribed as an operon in *E. coli*. Together, they catalyze the dissimilation of acetate, with the release of ATP. Thus, one of skill in the art can increase the amount of available acetyl Co-A by attenuating the activity of phosphotransacetylase gene (e.g., the endogenous phosphotransacetylase gene) and/or an acetate kinase gene (e.g., the endogenous acetate kinase gene). One way of achieving attenuation is by deleting phosphotransacetylase (pta) and/or acetate kinase (ackA). This can be accomplished by replacing one or both genes with a chloramphenicol cassette followed by looping out of the cassette. Acetate is produced by *E. coli* for a variety of reasons (Wolfe, A. 2005. *Microb. Mol. Biol. Rev.* 69:12-50). Without being bound by theory, since ackA-pta use acetyl-CoA, deleting those genes might allow carbon not to be diverted into acetate and to increase the yield of mevalonate and/or isoprene.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of phosphotransacetylase (pta) and/or acetate kinase (ackA) can also be decreased by other molecular manipulation of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

Pathways Involving Lactate Dehydrogenase

In *E. coli*, D-Lactate is produced from pyruvate through the enzyme lactate dehydrogenase (ldhA—FIG. 5) (Bunch, P. et al. 1997. *Microbiol.* 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevolnate production (and isopren production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

Pathways Involving Malic Enzyme

Malic enzyme (in *E. coli* sfcA and maeB) is an anaplerotic enzyme that catalyzes the conversion of malate into pyruvate (using NAD+ or NADP+) by the equation below:

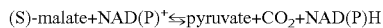

(S)-malate+NAD(P)$^+$⇌pyruvate+$CO_2$+NAD(P)H

Thus, the two substrates of this enzyme are (S)-malate and NAD(P)$^+$, whereas its 3 products are pyruvate, $CO_2$, and NADPH.

Expression of the NADP-dependent malic enzyme (maeB—FIG. 5) (Iwikura, M. et al. 1979. *J. Biochem.* 85: 1355-1365) can help increase mevalonate and/or isoprene yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M K et al. (2002) *J. Biol. Chem.* 277: 13175-13183; Bologna, F. et al. (2007) *J. Bact.* 189:5937-5946).

As such, more starting substrate (pyruvate or acetyl-CoA) for the downstream production of mevalonate and/or isoprene can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataac-catctgcggtgataaattatctctggcg-gtgttgacataaataccactggcggtgatactgagcacatca gcaggacgcact-gaccaccatgaaggtg—lambda promoter, GenBank NC_001416 (SEQ ID NO: 15), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl Co-A in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

Combinations of Mutations

It is understood that for any of the enzymes and/or enzyme pathways described herein, molecular manipulations that modulate any combination (two, three, four, five or six) of the enzymes and/or enzyme pathways described herein is expressly contemplated. For ease of the recitation of the combinations, citrate synthase (gltA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, and pyruvate decarboxylase (aceE, aceF, and/or lpdA) is designated as F. As discussed above, aceE, aceF, and/or lpdA enzymes of the pyruvate decarboxylase complex can be used singly, or two of three enzymes, or three of three enzymes for increasing pyruvate decarboxylase activity.

Accordingly, for combinations of any two of the enzymes A-F, non-limiting combinations that can be used are: AB, AC, AD, AE, AF, BC, BD, BE, BF, CD, CE, CF, DE, DF and EF. For combinations of any three of the enzymes A-F, non-limiting combinations that can be used are: ABC, ABD, ABE, ABF, BCD, BCE, BCF, CDE, CDF, DEF, ACD, ACE, ACF, ADE, ADF, AEF, BDE, BDF, BEF, and CEF. For combinations of any four of the enzymes A-F, non-limiting combinations that can be used are: ABCD, ABCE, ABCF, ABDE, ABDF, ABEF, BCDE, BCDF, CDEF, ACDE, ACDF, ACEF, BCEF, BDEF, and ADEF. For combinations of any five of the enzymes A-F, non-limiting combinations that can be used are: ABCDE, ABCDF, ABDEF, BCDEF, ACDEF, and ABCEF. In another aspect, all six enzyme combinations are used: ABCDEF.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase and/or acetate kinase, (c) lactate dehydrogenase, (d) malic enzyme, and (e) pyruvate decarboxylase complex.

Other Regulators and Factors for Increased Isoprene Production

Other molecular manipulations can be used to increase the flow of carbon towards isoprene production. One method is to reduce, decrease or eliminate the effects of negative regulators for pathways that feed into the mevalonate pathway. For example, in some cases, the genes aceEF-lpdA are in an operon, with a fourth gene upstream pdhR. pdhR is a negative regulator of the transcription of its operon. In the absence of pyruvate, it binds its target promoter and represses transcription. It also regulates ndh and cyoABCD in the same way (Ogasawara, H. et al. 2007. *J. Bact.* 189:5534-5541). In one aspect, deletion of pdhR regulator can improve the supply of pyruvate, and hence the production mevalonate and/or isoprene.

In other aspects, the introduction of 6-phosphogluconolactonase (PGL) into microorganisms (such as various *E. coli* strains) which lack PGL can be used to improve production of mevalonate and/or isoprene. PGL may be introduced using chromosomal integration or extrachromosomal vehicles, such as plasmids. In other aspects, PGL may be deleted from the genome of microorganisms (such as various *E. coli* strains) which express an endogenous PGL to improve production of mevalonate and/or isoprene. In some aspects, deletion of PGL results in any of about 10%, 20%, 30%, 40%, 50%, 60%, 70%, 80%, 90%, or 100%, inclusive, including any values in between these percentages, higher percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher instantaneous percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher cell productivity index for isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher volumetric productivity of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher peak specific productivity of isoprene in comparison to microorganisms that express PGL. In some aspects the deletion of PGL results in peak specific productivity being maintained for a longer period of time in comparison to microorganisms that express PGL.

Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any microorganism or progeny thereof can be used to express any of the genes (heterologous or endogenous) described herein. Bacteria cells, including gram positive or gram negative bacteria can be used to express any of the genes described herein. In particular, the genes described herein can be expressed in any one of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes*, and *L. acidophilus* cells. In some aspects, the bacterial cells for use in any of the compositions or methods described herein are from a *Corynebacterium* spp. In some aspects, the bacterial cells for use in any of the compositions or methods described herein are from a *Lactobacilus* spp., such as *Lactobacilus lactis*.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce isoprene can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce isoprene. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances*, (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans*, or *A. awamori, Fusarium* sp., such as *F. roseum, F. graminum F. cerealis, F. oxysporuim*, or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum*, or *F. solani*. In certain embodiments, plasmids or plasmid components for use herein include those described in U.S. Patent Pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., 1992, *Yeast*, 8(6):423-488). In certain embodiments, plasmids or plasmid components for use herein include those described in U.S. Pat. No. 7,659,097 and U.S. Patent Pub. No. US 2011/0045563.

The host cell can additionally be a species of algae, such as a green algae, red algae, glaucophytes, chlorarachniophytes, euglenids, chromista, or dinoflagellates. (See, e.g., Saunders & Warmbrodt, 1993, "Gene Expression in Algae and Fungi, Including Yeast," National Agricultural Library, Beltsville, Md.). In certain embodiments, plasmids or plasmid components for use herein include those described in U.S. Patent Pub. No. US 2011/0045563. In some aspects, the host cell is a *cyanobacterium*, such as *cyanobacterium* classified into any of the following groups based on morphology: *Chlorococcales, Pleurocapsales, Oscillatoriales, Nostocales*, or *Stigonematales* (See, e.g., Lindberg et al., 2010, *Metab. Eng.* 12(1):70-79). In certain embodiments, plasmids or plasmid components for use herein include those described in U.S. Patent Pub. Nos. US 2010/0297749; US 2009/0282545 and Intl. Pat. Appl. No. WO 2011/034863.

In some aspects, *E. coli* host cells can be used to express one or more of an HMG-CoA reductase, an isoprene synthase, an MVA pathway (including, e.g., a non-thiolase MVA pathway), and/or DXP pathway nucleic acid in the compositions and methods described herein. In one aspect, the host cell is a recombinant cell of an *Escherichia coli* (*E. coli*) strain, or progeny thereof, capable of producing mevalonate or isoprene that expresses one or more nucleic acids encoding HMG-CoA reductase, isoprene synthase, an MVA pathway (including, e.g., a non-thiolase MVA pathway), and/or a DXP pathway nucleic acid. The *E. coli* host cells can produce mevalonate or isoprene in amounts, peak titers, and cell productivities greater than that of the same cells lacking one or more heterologously expressed nucleic acids encoding HMG-CoA reductase, isoprene synthase, one or more MVA pathway (including, e.g., a non-thiolase MVA pathway), and/ or one or more DXP pathway nucleic acids. In addition, the one or more heterologously expressed nucleic acids encoding HMG-CoA reductase, isoprene synthase, one or more MVA pathway (including, e.g., a non-thiolase MVA pathway), and/ or one or more DXP pathway nucleic acids in *E. coli* can be chromosomal copies (e.g., integrated into the *E. coli* chromosome). In other aspects, the *E. coli* cells are in culture.

Vectors

Suitable vectors can be used for any of the compositions and methods described herein. For example, suitable vectors can be used to optimize the expression of one or more copies of a gene encoding a HMG-CoA reductase, an isoprene synthase, and/or one or more non-thiolase MVA pathway polypeptides. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/ or nucleic acids that confer a metabolic advantage, such as a nutritional advantage on the host cell. In some aspects, one or more copies of HMG-CoA reductase, an isoprene synthase, and/or one or more non-thiolase MVA pathway polypeptides nucleic acid(s) integrate into the genome of host cells without a selective marker. Any one of the vectors characterized or used in the Examples of the present disclosure can be used.

Transformation Methods

Nucleic acids encoding acetoacetyl-CoA synthase, an enzyme that produces acetoacetyl-CoA synthase from malonyl-CoA and acetyl-CoA, non-thiolase MVA pathway polypeptides, MVA pathway polypeptide (including acetyl-CoA acetyltransferase (AA-CoA thiolase), 3-hydroxy-3-methylglutaryl-CoA synthase (HMG-CoA synthase), 3-hydroxy-3-methylglutaryl-CoA reductase (HMG-CoA reductase), mevalonate kinase (MVK), phosphomevalonate kinase (PMK), diphosphomevalonte decarboxylase (MVD), phosphomevalonate decarboxylase (PMDC) and/or isopentenyl phosphate kinase (IPK)), DXP pathway polypeptides, isoprene synthase polypeptides, IDI, and any other enzyme needed to produce isoprene can be introduced into host cells (e.g., a plant cell, a fungal cell, a yeast cell, or a bacterial cell) by any technique known to one of the skill in the art.

Standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion can be used. General transformation techniques are known in the art (See, e.g., *Current Protocols in Molecular Biology* (F. M. Ausubel et al. (eds.) Chapter 9, 1987; Sambrook et al., *Molecular Cloning: A Laboratory Manual*, 3$^{rd}$ ed., Cold Spring Harbor, 2001; and Campbell et al., 1989, *Curr. Genet.* 16:53-56). The introduced nucleic acids can be integrated into chromosomal DNA or maintained as extrachromosomal replicating sequences. Transformants can be selected by any method known in the art. Suitable methods for selecting transformants are described in International Publication No. WO 2009/076676, U.S. patent application Ser. No. 12/335,071 (US Patent Appl. Publ. No. 2009/0203102), WO 2010/003007, U.S. Patent Appl. Publ. No. 2010/0048964, WO 2009/132220, and U.S. Patent Appl. Publ. No. 2010/0003716.

In one embodiment, a bacterium such as *Escherichia coli* is used as a host. In this embodiment, an expression vector can be selected and/or engineered to be able to autonomously replicate in such bacterium. Promoters, a ribosome binding sequence, transcription termination sequence(s) can also be included in the expression vector, in addition to the genes listed herein. Optionally, an expression vector may contain a gene that controls promoter activity.

Any promoter may be used as long as it can be expressed in a host such as *Escherichia coli*. Examples of such promoter that can be used include a trp promoter, an lac promoter, a PL promoter, a PR promoter, and the like from *Escherichia coli*, and a T7 promoter from a phage. Further, an artificially designed or modified promoter such as a tac promoter may be used.

A method for introduction of an expression vector is not particularly limited as long as DNA is introduced into a bacterium thereby. Examples thereof include a method using calcium ions (Cohen, S. N., et al., 1972, *Proc. Natl. Acad. Sci.*, USA, 69:2110-2114) and an electroporation method.

When a yeast is used as a host, *Saccharomyces cerevisiae, Schizosaccharomyces pombe, Pichia pastoris*, or the like can be used. In this case, a promoter is not particularly limited as long as it can be expressed in yeast. Examples thereof include a gall promoter, a gall° promoter, a heat-shock protein promoter, an MF.alpha.1 promoter, a PHO5 promoter, a PGK promoter, a GAP promoter, an ADH promoter, and an AOX1 promoter.

A method for introducing a recombinant vector into yeast is not particularly limited as long as DNA is introduced into yeast thereby. Examples thereof include the electroporation method (Becker, D. M., et al. (1990) *Methods. Enzymol.*, 194:182-187), the spheroplast method (Hinnen, A. et al., (1978) *Proc. Natl. Acad. Sci.*, USA, 75: 1929-1933), and the lithium acetate method (Itoh, H.: (1983) *J. Bacteriol.*, 153: 163-168).

Exemplary Cell Culture Media

As used herein, the terms "minimal medium" or "minimal media" refer to growth medium containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 100 µl of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4$*$H_2O$; (3) 10 g NaCl; (4) 1 g $FeSO_4$*$7H_2O$; (4) 1 g $CoCl_2$*$6H_2O$; (5) 1 g $ZnSO_4$*$7H_2O$; (6) 100 mg $CuSO_4$*$5H_2O$; (7) 100 mg $H_3BO_3$; and (8) 100 mg $NaMoO_4$*$2H_2O$; pH is adjusted to ~3.0.

An additional exemplary minimal media includes (1) potassium phosphate $K_2HPO_4$, (2) Magnesium Sulfate $MgSO_4$*$7H_2O$, (3) citric acid monohydrate $C_6H_8O_7$*$H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml. All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells can include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup). In one aspect, the host cells are initially cultured in a medium (such as a TM3 medium) containing D-xylose as a carbon source during the linear growth phase of fermentation. In another aspect, the carbon source is changed from D-xylose to glucose once the host cells reach the isoprene-production phase of fermentation.

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

In some aspects, the cells described herein are capable of using syngas as a source of energy and/or carbon. In some embodiments, the syngas includes at least carbon monoxide and hydrogen. In some embodiments, the syngas further additionally includes one or more of carbon dioxide, water, or nitrogen. In some embodiments, the molar ratio of hydrogen to carbon monoxide in the syngas is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, or 10.0. In some embodiments, the syngas comprises 10, 20, 30, 40, 50, 60, 70, 80, or 90% by volume carbon monoxide. In some embodiments, the syngas comprises 10, 20, 30, 40, 50, 60, 70, 80, or 90% by volume hydrogen. In some embodiments, the syngas comprises 10, 20, 30, 40, 50, 60, 70, 80, or 90% by volume carbon dioxide. In some embodiments, the syngas comprises 10, 20, 30, 40, 50, 60, 70, 80, or 90% by volume water. In some embodiments, the syngas comprises 10, 20, 30, 40, 50, 60, 70, 80, or 90% by volume nitrogen.

Synthesis gas may be derived from natural or synthetic sources. The source from which the syngas is derived is referred to as a "feedstock." In some embodiments, the syngas is derived from biomass (e.g., wood, switch grass, agriculture waste, municipal waste) or carbohydrates (e.g., sugars). In other embodiments, the syngas is derived from coal, petroleum, kerogen, tar sands, oil shale, or natural gas. In other embodiments, the syngas is derived from rubber, such as from rubber tires.

Syngas can be derived from a feedstock by a variety of processes, including methane reforming, coal liquefaction, co-firing, fermentative reactions, enzymatic reactions, and biomass gasification. Biomass gasification is accomplished by subjecting biomass to partial oxidation in a reactor at temperatures above about 700° C. in the presence of less than a stoichiometric amount of oxygen. The oxygen is introduced into the bioreactor in the form of air, pure oxygen, or steam. Gasification can occur in three main steps: 1) initial heating to dry out any moisture embedded in the biomass; 2) pyrolysis, in which the biomass is heated to 300-500° C. in the absence of oxidizing agents to yield gas, tars, oils and solid char residue; and 3) gasification of solid char, tars and gas to yield the primary components of syngas. Co-firing is accomplished by gasification of a coal/biomass mixture. The composition of the syngas, such as the identity and molar ratios of the components of the syngas, can vary depending on the feedstock from which it is derived and the method by which the feedstock is converted to syngas.

Synthesis gas can contain impurities, the nature and amount of which vary according to both the feedstock and the process used in production. Fermentations may be tolerant to some impurities, but there remains the need to remove from the syngas materials such as tars and particulates that might foul the fermentor and associated equipment. It is also advisable to remove compounds that might contaminate the isoprene product such as volatile organic compounds, acid gases, methane, benzene, toluene, ethylbenzene, xylenes, $H_2S$, COS, $CS_2$, HCl, $O_3$, organosulfur compounds, ammonia, nitrogen oxides, nitrogen-containing organic compounds, and heavy metal vapors. Removal of impurities from syngas can be achieved by one of several means, including gas scrubbing, treatment with solid-phase adsorbents, and purification using gas-permeable membranes.

Exemplary Cell Culture Conditions

Materials and methods suitable for the maintenance and growth of the recombinant cells of the invention are described infra, e.g., in the Examples section. Other materials and methods suitable for the maintenance and growth of bacterial cultures are well known in the art. Exemplary techniques can be found in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of one or more isoprene synthase, one or more DXP pathway polypeptides, one or more MVA pathway polypeptides, IDI, or PGL polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the host cells. In addition, more specific cell culture conditions can be used to culture the cells. For example, in some embodiments, the recombinant (e.g., bacterial) cells express one or more heterologous nucleic acids encoding any of the nucleic acids described herein (e.g., a HMG-CoA reductase, an isoprene synthase, an MVA pathway enzyme, and/or a DXP pathway enzyme) under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716. Batch and Fed-Batch fermentations are common and well known in the art and examples can be found in Brock, Biotechnology: *A Textbook of Industrial Microbiology*, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions can allow more favorable regulation of the cells.

In some aspects, the recombinant (e.g., bacterial) cells are grown in batch culture. The recombinant cells can also be grown in fed-batch culture or in continuous culture. Additionally, the recombinant cells can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

In some aspects, the recombinant cells are grown under low oxygen conditions. In other aspects, the recombinant (e.g., bacterial) cells are grown under atmospheric conditions comprising any of about 4%, 5%, 6%, 7%, 8%, 9%, 10%, 11%, 12%, 13%, 14%, or 15%, inclusive, including any values in between these percentages, oxygen. In other aspects, the recombinant cells are grown under atmospheric conditions comprising any of about 3-8%, 3.5-8.5%, 4-9%, 4.5-9.5%, 5-10%, 5.5-10.5%, 6-11%, or 6.5-11.5% oxygen.

Methods of Using the Recombinant Cells to Produce Isoprene

Provided herein are methods of producing isoprene by culturing any of the recombinant cells described herein under conditions such as those disclosed herein. In one aspect, isoprene can be produced by culturing recombinant cells comprising an ispA gene having decreased functional activity and one or more nucleic acids encoding: (a) an isoprene synthase polypeptide, wherein the isoprene synthase polypeptide is encoded by a heterologous nucleic acid; and (b) one or more mevalonate (MVA) pathway polypeptides. In one aspect, one or more heterologous nucleic acids encoding a HMG-CoA reductase, a lower MVA pathway polypeptide, and an isoprene synthase polypeptide can be used. In another aspect, isoprene can be produced by culturing recombinant cells comprising one or more heterologous nucleic acids encoding a HMG-CoA reductase and HMG-CoA synthase, a lower MVA pathway polypeptide, and an isoprene synthase polypeptide. In yet another aspect, one or more heterologous nucleic acids encoding one or more upper MVA pathway polypeptides, one or more lower MVA pathway polypeptides, and/or one or more DXP pathway polypeptides can be used. In some aspects, the recombinant cells described herein exhibit any of about 10%, 15%, 20%, 25%, 30%, 35%, 40%, 45%, 50%, 55%, 60%, 65%, 70%, 75%, 80%, 95%, or 100%, inclusive, including any value in between these percentages, increased isoprene production in comparison to cells which do not comprise an IspA having decreased functional activity. The isoprene can be produced from any of the cells described herein and according to any of the methods described herein. Any of the cells can be used for the purpose of producing isoprene from carbohydrates, including six carbon sugars such as glucose.

The cells can further comprise one or more nucleic acid molecules encoding the lower MVA pathway polypeptide(s) described above (e.g., MVK, PMK, MVD, and/or IDI), any of the upper MVA pathways polypeptide(s) described above (e.g., a thiolase, an acetoacetyl-CoA synthase, an HMG-CoA reductase, and/or an HMG-CoA synthase) and/or any of the isoprene synthase polypeptide(s) described above (e.g. *P. alba* isoprene synthase). In some aspects, the recombinant (e.g., bacterial) cells can be any of the cells described herein. Any of the isoprene synthases or variants thereof described herein, any of the bacterial strains described herein, any of the promoters described herein, and/or any of the vectors described herein can also be used to produce isoprene using any of the energy sources (e.g. glucose or any other six carbon sugar) described herein. In some aspects, the method of producing isoprene further comprises a step of recovering the isoprene.

In some aspects, the amount of isoprene produced is measured at a productivity time point. In some aspects, the productivity for the cells is about any of the amounts of isoprene disclosed herein. In some aspects, the cumulative, total amount of isoprene produced is measured. In some aspects, the cumulative total productivity for the cells is about any of the amounts of isoprene disclosed herein.

In some aspects, any of the cells described herein (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the isoprene produced by the cells in culture (such as any of the recombinant cells described herein) comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

In some aspects, the cells in culture (such as any of the recombinant cells described herein) produce any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, higher cumulative isoprene yield on glucose in comparison to cells that do not comprise decreased IspA functional activity. In another aspect, the cells in culture (such as any of the recombinant cells described herein) produce any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, greater isoprene productivity in comparison to cells that do not comprise decreased IspA functional activity. In other aspects, the cells in culture (such as any of the recombinant cells described herein) produce any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, greater isoprene peak specific productivity in comparison to cells that do not comprise decreased IspA functional activity. In some aspects, the cells in culture (such as any of the recombinant cells described herein) produce any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentages in between these values, greater cell isoprene productivity index in comparison to cells that do not comprise decreased IspA functional activity.

Exemplary Purification Methods

In some aspects, any of the methods described herein further include a step of recovering isoprene produced by any of the recombinant cells disclosed herein. In some aspects, the isoprene is recovered by absorption stripping (See, e.g., U.S. Publication No. 2011/0178261 A1). In some aspects, any of the methods described herein further include a step of recovering the heterologous polypeptide.

Suitable purification methods are described in more detail in U.S. Publication No. US2010/0196977 A1.

Throughout this specification, various patents, patent applications and other types of publications (e.g., journal articles) are referenced. The disclosure of all patents, patent applications, and publications cited herein are hereby incorporated by reference in their entirety for all purposes.

The invention can be further understood by reference to the following examples, which are provided by way of illustration and are not meant to be limiting.

EXAMPLES

General Information

TABLE 1

Strains used

| Strain name | Genotype | Parent | Plasmids |
|---|---|---|---|
| CMP451 | BL21 pgl PL.2mKKDyI GI 1.2 gltA | | None |
| CMP457 | BL21 pgl + PL.2 mKKDyI GI1.2 gltA, pTrc(MEA)alba_mMVK, pCLPtrcUpper_Efaecalis | CMP451 | pDW34, MCM82 |
| CMP596 | BL21 pgl PL.2mKKDyI GI 1.2 gltA ldhA::Kan | CMP451 | None |
| CMP722 | BL21 pgl PL.2mKKDyI GI 1.2 gltA ldhA | CMP596 | None |
| CMP876 | BL21 pgl PL.2mK*KDyI GI 1.2 gltA ldhA | CMP451 | None |
| CMP882 | BL21 pgl PL.2mKKDyI GI 1.2 gltA, pTrcHis2B, pCL1920 | CMP451 | pTrcHis2B, pCL1920 |
| CMP884 | BL21 pgl PL.2mK*KDyI GI 1.2 gltA, pTrcHis2B, pCL1920 | CMP451 | pTrcHis2B, pCL1920 |
| CMP981 | BL21 pgl PL.2mKKDyI GI1.2gltA yhfSpKD3IspAyhfS | CMP451 | None |
| CMP992 | BL21 pgl PL.2mKKDyI GI1.2gltA yhfSFRTIspAyhfS | CMP981 | None |
| CMP1018 | BL21 pgl PL.2mKKDyI GI1.2gltA yhfSFRTIspAyhfS thipKD3truncIspA | CMP992 | None |
| CMP1024 | BL21 pgl PL.2mKKDyI GI 1.2 gltA ldhA Cm::ispA-proteolytic tag | CMP722 | None |
| CMP1030 | BL21 pgl PL.2mKKDyI GI1.2gltA yhfSFRTIspAyhfS thiFRTtruncIspA | CMP1018 | None |
| CMP1034 | BL21 pgl PL.2mKKDyI GI 1.2 gltA ldhA ispA-proteolytic tag | CMP1024 | None |
| CMP1059 | BL21 pgl PL.2mKKDyI GI 1.2 gltA ldhA ispA-proteolytic tag, pCLPtrcUpper, pTrc(MEA variant)alba mMVK | CMP1034 | MCM82, pCHL243 |
| CMP1061 | BL21 pgl PL.2mKKDyI GI1.2gltA yhfSFRTIspAyhfS thiFRT3truncIspA, pCLPtrcUpper, pTrc(MEA variant)alba mMVK | CMP1030 | MCM82, pCHL243 |
| CMP1067 | BL21 pgl PL.2mKKDyI GI1.2gltA yhfSpKD4PyddVIspAyhfS thipKD3truncIspA | CMP1018 | None |
| CMP1075 | BL21 pgl PL.2mKKDyI GI1.2gltA yhfSFRTPyddVIspAyhfS thiFRTtruncIspA | CMP1067 | None |
| CMP1082 | BL21 pgl PL.2mKKDyI GI1.2gltA yhfSFRTPyddVIspAyhfS thiFRTtruncIspA, pCLPtrcUpper_Efaecalis, pTrc(MEA variant)alba mMVK | CMP1075 | MCM82, pCHL243 |
| CMP1101 | BL21 pgl PL.2mKKDyI GI1.2gltA yhfSFRTIspAyhfS thipKD3truncIspA yhfS-pKD4-PispA_avianA166W | CMP1018 | None |
| CMP1102 | BL21 pgl PL.2mKKDyI GI1.2gltA yhfSFRTIspAyhfS thipKD3truncIspA yhfS-pKD4-PispA_avianN144'W | CMP1018 | None |
| CMP1107 | BL21 pgl PL.2mKKDyI GI1.2gltA yhfSFRTIspAyhfS thipKD3truncIspA yhfS-FRT-PispA_avianA166W | CMP1101 | None |
| CMP1108 | BL21 pgl PL.2mKKDyI GI1.2gltA yhfSFRTIspAyhfS thipKD3truncIspA yhfS-FRT-PispA_avianN144'W | CMP1102 | None |
| CMP1112 | BL21 pgl PL.2mKKDyI GI1.2gltA yhfSFRTIspAyhfS thipKD3truncIspA yhfS-FRT-PispA_avianA166W, pCLPtrcUpper_Efaecalis, pTrc(MEA variant)alba mMVK | CMP1107 | MCM82, pCHL243 |
| CMP1113 | BL21 pgl PL.2mKKDyI GI1.2gltA yhfSFRTIspAyhfS thipKD3truncIspA yhfS-FRT-PispA_avianN144'W, pCLPtrcUpper_Efaecalis, pTrc(MEA variant)alba mMVK | CMP1108 | MCM82, pCHL243 |
| CMP1125 | BL21 pgl::Kan PL.2mKKDyI GI1.2gltA yhfSFRTPyddVIspAyhfS thiFRTtruncIspA | CMP1075 | None |
| CMP1133 | BL21 Δpgl PL.2mKKDyI GI1.2gltA yhfSFRTPyddVIspAyhfS thiFRTtruncIspA | CMP1125 | None |
| CMP1136 | BL21 Δpgl PL.2mKKDyI GI1.2gltA yhfSFRTPyddVIspAyhfS thiFRTtruncIspA, pCLPtrcUpper_Efaecalis, pTrc(MEA variant)alba mMVK | CMP1133 | MCM82, pCHL243 |
| MCM1020 | BL21 t pgl, pTrcHis2B, pCL1920 | CMP258 | pTrcHis2B, pCL1920 |

Example 1

Increased Carbon Flux into the Isoprenoid Pathway Affects Cellular Viability

In order to investigate the effects of increased carbon flux through the isoprenoid pathway in *E. coli*, two strains carrying the lower MVA pathway integrated on the chromosome, CMP882 (HMB gi1.2 gltA+pTrcHis2B+pCL1920) and CMP884 (HMB GI1.2 gltA evolved, pTrcHis2B, pCL1920 (inactive MVK)) were grown under fed batch conditions. The CMP884 strain contained a point mutation in the mevalonate kinase (MVK) gene causing the enzyme to be inactive, which, in effect, prevents carbon flux through the lower MVA pathway. Mevalonate was fed to the fermentors and the concentration of mevalonate was measured in the media.

Methods

Medium Recipe (Per Liter Fermentation Medium): K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter): Citric Acids*$H_2O$ 40 g, MnSO4*H2O 30 g, NaCl 10 g, FeSO4*7H2O 1 g, CoCl2*6H2O 1 g, ZnSO4*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter): Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter): MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram): Glucose 0.590 kg, Di $H_2O$ 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

Mevalonic Acid Feed: A purified and concentrated source of mevalonic acid was diluted with deionized water to yield a final concentration of approximately 60 g/L. The solution was filter sterilized with a 0.22 micron filter and poured into a feed bottle.

This experiment was carried out to monitor isoprene formation from glucose at the desired fermentation pH (7.0) and temperature (34° C.). A frozen vial of the *E. coli* strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L.

The batched media had glucose batched in at 9.7 g/L. Induction was achieved by adding isopropyl-beta-D-1-thiogalactopyranoside (IPTG). IPTG was added to the tank to bring the concentration to 200 uM when the cells were at an $OD_{550}$ of 6. The mevalonic acid feed was delivered to the fermentor in a continuous manner at a rate equal to the TCER (total carbon dioxide evolution rate, mmol $CO_2$/h) divided my 3000 with final units of g feed/min. Glucose exhaustion, as signaled by a rise in pH, was used for feeding supplemental glucose feed solution to meet metabolic demands at rates less than or equal to 10 g/min.

CMP882 was constructed by concomitant electroporation of pTrcHis2B (Invitrogen, Carlsbad, Calif.) and pCL1920 (see U.S. Publ. No. US2009/0203102) into CMP451. A colony growing on LB+carbenicilin 50 mg/L and spectinomycin 50 mg/L was selected and named CMP882. CMP876 is homologous to CMP451 except for one mutation in the chromosomal mevalonate kinase which renders the enzyme inactive. Plasmids pTrcHis2B and pCL1920 were concomitantly electroporated in CMP876. A colony growing on LB+carbenicilin 50 mg/L and spectinomycin 50 mg/L was selected and named CMP884.

Membrane potential analysis was used to assess viability of the bacteria during fermentation. Broth from the fermentor was collected and immediately diluted 150-fold into PBS buffer. The cells were then further diluted 150-fold into PBS buffer containing 1 μM bis-(1,3-dibutylbarbituric acid)trimethine oxonol, $DiBAC_4(3)$ (Invitrogen, Cat. No. B-438). Samples were allowed to stain for 10 minutes before quantification of green fluorescence at the single cell level using flow cytometry (FACSCalibur, Becton Dickinson). An excitation wave length of 488 nm and an emission wave length of 530 nm were used. Initially, an exponentially growing culture and a heat killed culture of *E. coli* BL21 were stained with $DiBAC_4(3)$ to determine green fluorescence levels from healthy and dead cells respectively. This information was used to create gates for analyzing the flow cytometry data to determine the fraction of cells with intact membrane potential and the fraction of cells without membrane potential. The data was also gated on appropriate cell size (forward scatter versus side scatter measured at 488 nm) to identify only intact bacteria. The level of green fluorescence from the cells passing these criteria was then used to determine the fraction of cells with a healthy membrane potential and the fraction of cells with no membrane potential in the fermentation samples. Cells with intact membrane potential were assumed to be alive and metabolically active, while cells with no membrane potential were assumed to be dead and metabolically inactive.

Results

Figure 3:
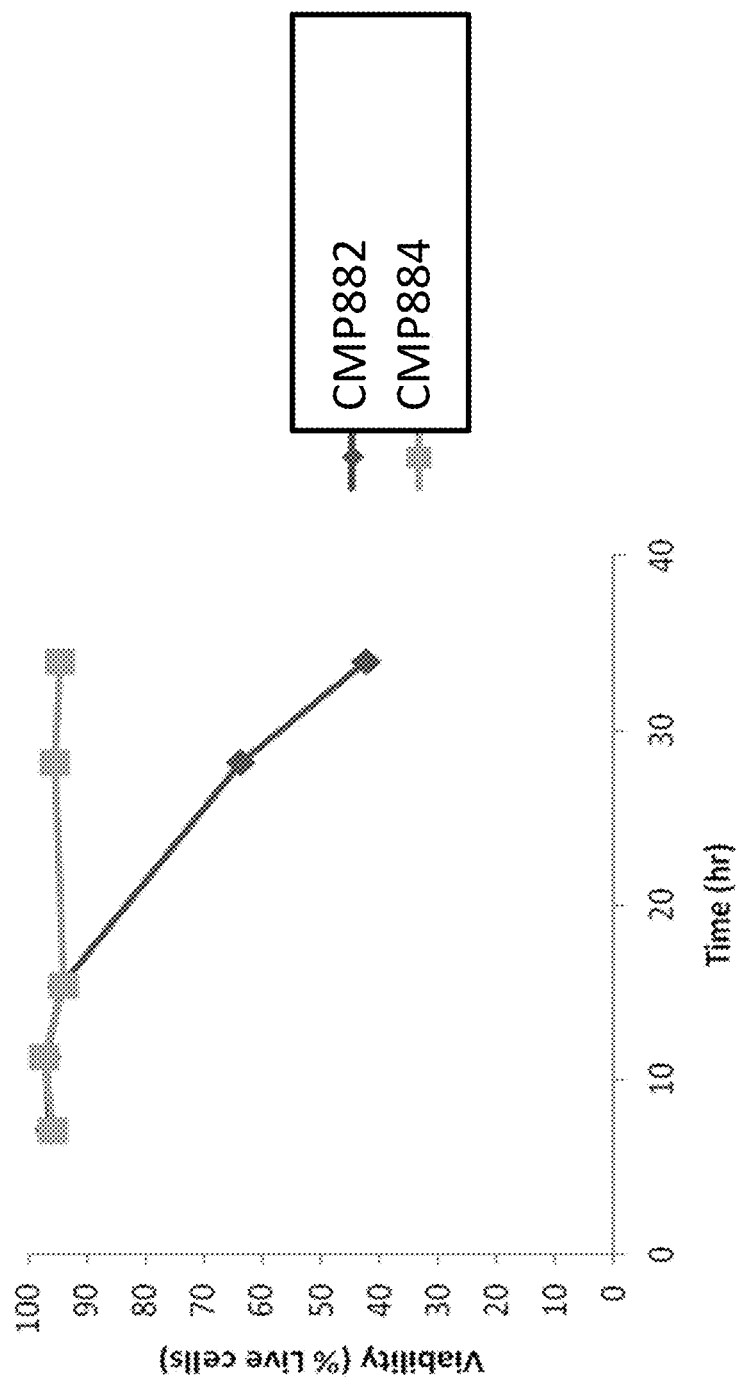
FIG. 3 depicts cell viability of CMP882 and CMP884 during fermentations.
Figure 4:
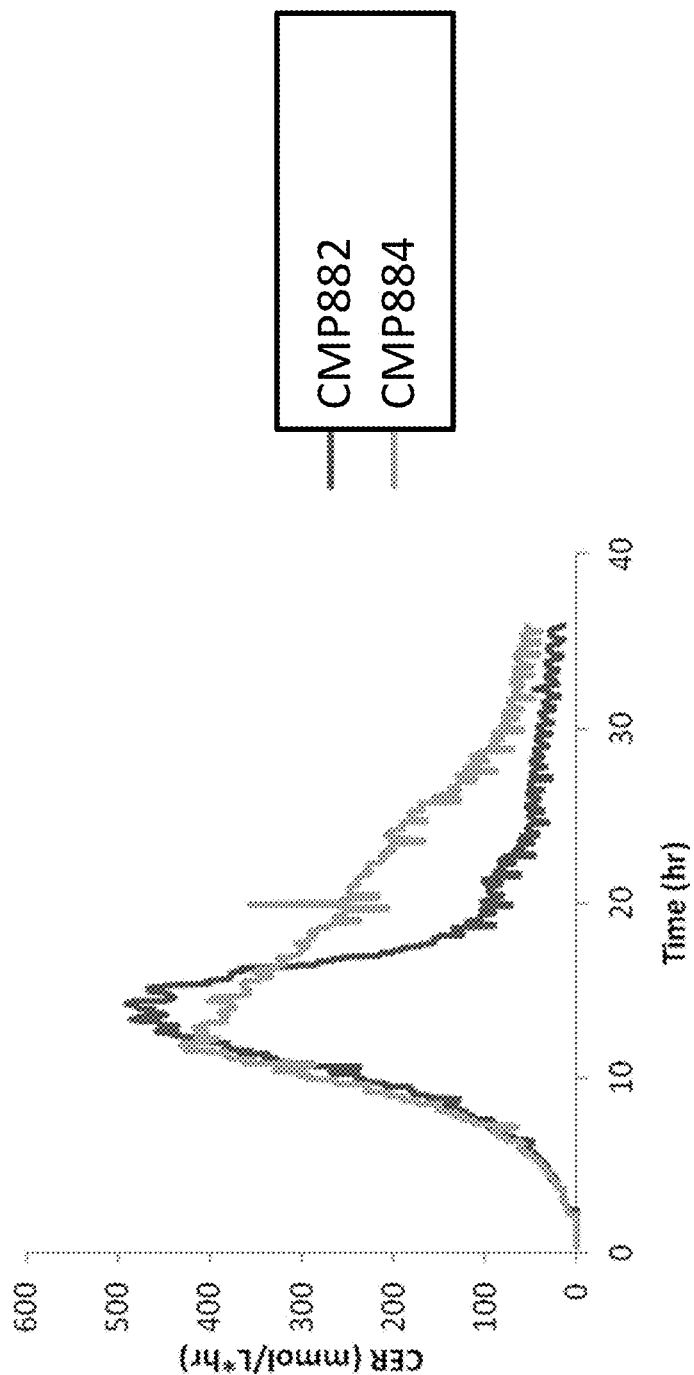
FIG. 4 depicts the respiration rate (CER) during of fermentation of strains CMP882 and CMP884.

Results of the present experiment are shown in FIG. 1 through FIG. 4. The presence of an inactive MVK enzyme in cells fed mevalonate showed significant affects to the organism's viability. As shown in FIG. 1*b*, mevalonate was successfully taken up by the cells containing the active MVK while accumulation of mevalonate in the media occurred in the MVK inactive cell line CMP884. This uptake results in an increase of the carbon flux through IspA into the isoprenoid pathway, as indicated by the increased levels of farnesyl pyrophosphate shown in FIG. 2. The strain with an inactive mevalonate kinase enzyme did not accumulate farnesyl pyrophosphate. Membrane potential analysis showed the MVK inactive cell lines maintaining a high percent cell viability during mevalonate feeding whereas MVK active cells showed a decline in cell viability (FIG. 3). The carbon evolution rate (CER) of the two cell lines was also altered, see FIG. 4. When the fermentations reached stationary phase, the respiration rate (i.e. $CO_2$ emission) of the strain with the active MVK decreased rapidly. By contrast, the strain with the inactive MVA pathway showed a much slower decline in respiration rate. These results indicate that increased isoprenoid flux may be detrimental to *E. coli*, and suggests that decreased activity of ispA may be beneficial to the viability of *E. coli* strains having increased flux to DMAPP and IPP.

Example 2

Utilization of a Proteolytic Tag to Control IspA Protein Activity

To optimize intracellular levels of FPP and DMAPP in isoprene production strains, a translational fusion between FPP synthase (IspA) and a proteolytic tag was generated. The proteolytic tmRNA tag (Andersen et al., 1998, *Appl Environ Microbiol.*, 64(6), 2240-2246) targets IspA for degradation in host cells.

Methods

An 11 amino acid tmRNA proteolytic tag was fused to the C-terminus of IspA using the Red/ET recombination system according to the manufacturer's recommended protocol (Gene Bridges). Briefly, the Gene Bridges insertion cassette encoding chloramphenicol resistance was amplified by PCR using primers "GBIspACtmRNA-ASV-For" and "GBisp2" (see Table 2). The cassette was then introduced into *E. coli* BL21 DE3 (Invitrogen, Carlsbad, Calif.) according to the manufacturer's recommended protocol, and colonies resistant to chloramphenicol were selected for validation. Correct integration of the insertion cassette was verified by PCR using the primers "ispTest1" and "GBprimer2" (see Table 2). A validated strain, MD08-97, which displayed a PCR product of the appropriate size, was selected for further analysis.

The lower mevalonic acid pathway in the vector pTrcK-anKKDIy (see U.S. Pub. No. 2009/0203102) was transformed using standard molecular biology practices into both BL21 DE3, as a control, and MD08-97, to yield strains DW141 and DW142, respectively. Strains were grown in the appropriate antibiotics in TM3 medium to early exponential phase, and then induced with 500 uM IPTG and treated with 5 mM mevalonic acid for approximately 2-3 hours. Cultures were harvested in an equal volume of cold methanol prior to metabolite analysis. Metabolite analysis was carried out using methods analogous to those described below. Metabolite values shown in Table 4 were corrected for $OD_{600}$. Two independent, identical experiments (exp. 1 and 2, see Table 4) were carried out to confirm the effects of the proteolytically tagged IspA enzyme on metabolite distributions.

Results

In comparison to the control strain DW141, strain DW142 containing the proteolytically tagged IspA enzyme displayed significantly higher DMAPP, IPP, and GPP levels in both experiments. DW142 also displayed significantly decreased intracellular levels of FPP compared to the control. These results indicate that the tmRNA tag increases the degradation or turnover of IspA within the cell, and thereby decreases the activity of IspA within these strains. Without being bound to theory, it is believed that the decrease in FPP synthase activity may generate an intracellular environment better suited for isoprene production, where more substrate is available for isoprene synthase, and less carbon is lost to higher molecular weight isoprenoids.

TABLE 2

Primers

| Primer | Description |
|---|---|
| GBIspAC tmRNA-ASV-For | ATACCTCGGCACTGGAAGCGCTAGCGGACTACATCATCCA GCGTAATAAAGCAGCTAACGATGAAAACTACGCAGCATCT GTTTAAAATTAACCCTCACTAAAGGGCG (SEQ ID NO: 16) |
| GBisp2 | TATTTGGCAATATCAAAACTCATCAGGGGCCTATTAATAC TTATTGTTTATAATACGACTCACTATAGGGCTC (SEQ ID NO: 17) |
| ispTest1 | CAAGCCGAACAGCGCGTACAAATTC (SEQ ID NO: 18) |
| GBprimer2 | CGAGACTAGTGAGACGTGCTAC (SEQ ID NO: 19) |

TABLE 3

Strains

| Strain | Resistance | Description |
|---|---|---|
| MD08-97 | Chlor | BL21 DE3 with IspA-tmRNA tag |
| DW141 | Kan | BL21 DE3 with Ptrc-lower MVA pathway on MCM107 (control) |
| DW142 | Chlor/Kan | BL21 DE3 with IspA-tmRNA tag and Ptrc-lower MVA pathway on MCM107 |

TABLE 4

Intracellular metabolite concentrations. Metabolite values shown were corrected for $OD_{600}$

| Sample | FPP | GPP | IPP | DMAPP |
|---|---|---|---|---|
| DW141 (exp. 1) | 1.633 | 0.066 | 0.003 | 0.015 |
| DW142 (exp. 1) | 0.212 | 0.206 | 0.394 | 0.530 |
| DW141 (exp. 2) | 3.575 | 0.325 | 0.060 | 0.126 |
| DW142 (exp. 2) | 1.791 | 0.940 | 0.265 | 0.611 |

Example 3

Auto-Regulatory System for Controlling IspA Expression

Promoters which were temporally repressed during fermentation only in a strain over expressing MVA pathway enzymes and not in control strains either over expressing DXP pathway enzymes or wild type strains were identified based on gene expression data. Without being bound to theory, it is hypothesized that such promoters may be repressed due to increased accumulation of isoprenoid compounds. When such promoters are introduced to control the expression of ispA, ispA can be repressed at time periods which correspond to flux through the isoprenoid pathway. However, at time periods where the flux is low, the promoter remains induced and thereby permits expression of ispA. This signature activity profile will constitute an auto-regulatory ispA expression control system.

Method for RNA Purification and Transcription Analysis:

Strains used in this genome-wide transcription study are CMP457 and MCM1020. Strain MCM1020 was constructed by electroporating plasmids pTrcHis2B (Invitrogen, Carlsbad, Calif.) and pCL1920 (see U.S. Publication No. 2009/0203102, the contents of which is incorporated herein by reference) into strain CMP258 (see International Patent Application No. PCT/US2011/058188, the contents of which is incorporated herein by reference) and selecting a colony on LB+50 mg/L spectinomycin+50 mg/L carbenicillin.

Fermentation samples were quickly diluted 1:5 in RNALater (Qiagen, Valencia, Calif.) and frozen at −20° C. Cells were harvested and lysed in Trizol (Invitrogen) and incubated at room temperature for 5 minutes. Nucleic acids were isolated by extracting by adding 20% ice cold chloroform. The solution was mixed and incubated for 5 minutes at room temperature followed by centrifugation at 13,000 rpm at 4° C. for 15 minutes. The top water phase was isolated and an equal volume of ice cold ethanol was added. RNA was isolated using the RNEasy mini kit (Qiagen). Following the manufactures instructions, DNA was degraded during the procedure by adding a DNase solution (10 μL DNase I stock in 70 μL RDD buffer) (Qiagen) and incubating at room temperature for 30 minutes. RNA was eluted from the RNeasy column in nuclease-free water. A minimum of 20 μg of RNA was collected from each sample as measured using a Nanodrop instrument. RNA was further purified by precipitation by adding 1/10th volume if 3M sodium acetate. Glycogen (RNA grade from Fermentas) was added to a final concentration of 1 ug/uL followed by the addition of 2.5 volume of ice cold ethanol. The solution was incubated for 60 minutes at −80° C. and then centrifuged for 15 minutes at 10.000 rpm. The supernatant was discarded and the RNA pellet was washed briefly with ice cold 70% ethanol. The RNA pellet was air dried for 20 minutes and dissolved in nuclease-free water at a concentration of 1 µg/µL. Quality and concentration was measured using a Nanodrop instrument and by gel electrophoresis. Synthesis of cDNA, labeling and transcription analysis was performed by Roche NimbleGen (Iceland) using a 385K 4-plex microarray designed specifically for *E. coli* BL21. The resulting data was analyzed using the GenespringGX Version 11 (Agilent). Certain promoters and their arbitrary expression levels elucidated from late stage fermentation of the full MVA pathway strain CMP457 are shown in Table 5.

Mass.) as follows: 95° C./2 minutes; 30 cycles of 95° C./30 seconds, x° C./30 seconds, 72° C./60 seconds; and 72° C./(40 seconds/kb of product). The reaction was then cooled to 4° C. The annealing temperature of x° C. was chosen to be 3° C. lower than the lower melting temperature of the primer pair. The size of the resulting PCR fragment was determined on a pre-cast 0.8% E-Gel® (Invitrogen, Carlsbad, Calif.), using DNA Molecular Weight Marker X (75-12,216 bp)(Roche Diagnostics, Mannheim, Germany) as size marker.

For the insertion of IspA in the yhfS locus, three DNA pieces were generated by PCR. Piece 1 contains a 15 bp sequence allowing assembly by the seamless kit (Invitrogen) to a XbaI/EcoRI-digested vector pBBR1MCS5 (Kovach et al. 1995, *Gene* 166:175-176), a region homologous to the yhfS region of BL21, a kanamycin marker, and a 15 bp allowing assembly to the promoter of the xseB-ispA-dxs operon. Primers used to obtain that piece are CMP247 (5'-gcggtggcggc-cgctttgtcatcggttaacgctggaa-cacctgccgcgcgcaacgttgccagcaccctccttagttcctattccgaagttc-3' (SEQ ID NO: 20)) and CMP248 (5'-gctggagctgcttcgaagttcc-

TABLE 5

Promoters repressed late during fed batch fermentation of the isoprene producing MVA pathway strain CMP457. Gene name, Entrez ID and expression levels are shown for a number of time points during fermentation.

| Gene | EntrezID | Fermentation time point | | | | | | | | | |
|------|----------|------|------|------|------|------|------|------|------|------|------|
|      |          | 4 hr | 6 hr | 8 hr | 12 hr | 16 hr | 18 hr | 20 hr | 22 hr | 26 hr | 32 hr |
| efeO | 945603 | 2265.6 | 1921.8 | 1913.7 | 2146.7 | 587.8 | 423.2 | 253.9 | 601.5 | 228.9 | 282.6 |
| kpsC | 8115953 | 935.9 | 1261.5 | 1406.6 | 1399.9 | 436.0 | 196.8 | 91.3 | 107.3 | 71.9 | 77.0 |
| kpsD | 8115949 | 1042.0 | 1694.9 | 2659.1 | 2563.7 | 882.5 | 371.4 | 120.8 | 112.6 | 242.2 | 344.4 |
| kpsE | 8115950 | 964.5 | 1871.4 | 2764.1 | 2795.4 | 1136.1 | 446.0 | 132.2 | 109.0 | 139.0 | 98.1 |
| kpsF | 8116223 | 3805.1 | 5650.1 | 7092.4 | 6239.4 | 2154.3 | 888.0 | 145.3 | 97.4 | 171.6 | 76.6 |
| kpsS | 8115947 | 1611.2 | 1796.7 | 1955.0 | 1722.3 | 721.6 | 324.4 | 108.2 | 111.9 | 93.3 | 128.4 |
| kpsU | 8115948 | 857.7 | 1535.7 | 2244.5 | 1852.3 | 687.3 | 268.0 | 127.0 | 126.1 | 137.7 | 168.1 |
| nmpC | 946786 | 2734.3 | 2833.2 | 5446.5 | 2678.4 | 992.6 | 339.4 | 162.4 | 74.0 | 55.0 | 160.2 |
| sodA | 948403 | 7680.9 | 5697.5 | 5490.4 | 5380.3 | 1981.1 | 408.5 | 598.5 | 619.3 | 649.6 | 914.0 |
| ybl129 | 8112884 | 30513.2 | 35702.2 | 39585.4 | 37840.7 | 22014.0 | 10849.2 | 4727.3 | 4456.2 | 5097.4 | 3665.1 |
| ybl130 | 8116226 | 15322.6 | 21237.2 | 23730.5 | 17822.7 | 10629.7 | 4955.7 | 1510.8 | 1098.1 | 941.2 | 438.5 |
| ybl131 | 8116228 | 16061.5 | 22400.0 | 25088.1 | 19536.8 | 9890.3 | 3587.4 | 1031.4 | 734.6 | 349.4 | 229.5 |
| yddV | 945835 | 1712.2 | 1102.2 | 598.5 | 604.1 | 282.7 | 214.3 | 204.5 | 116.5 | 57.7 | 92.9 |
| ydiU | 946219 | 497.9 | 514.3 | 508.6 | 522.6 | 223.0 | 109.4 | 70.7 | 74.4 | 59.0 | 48.0 |

Figure 6:
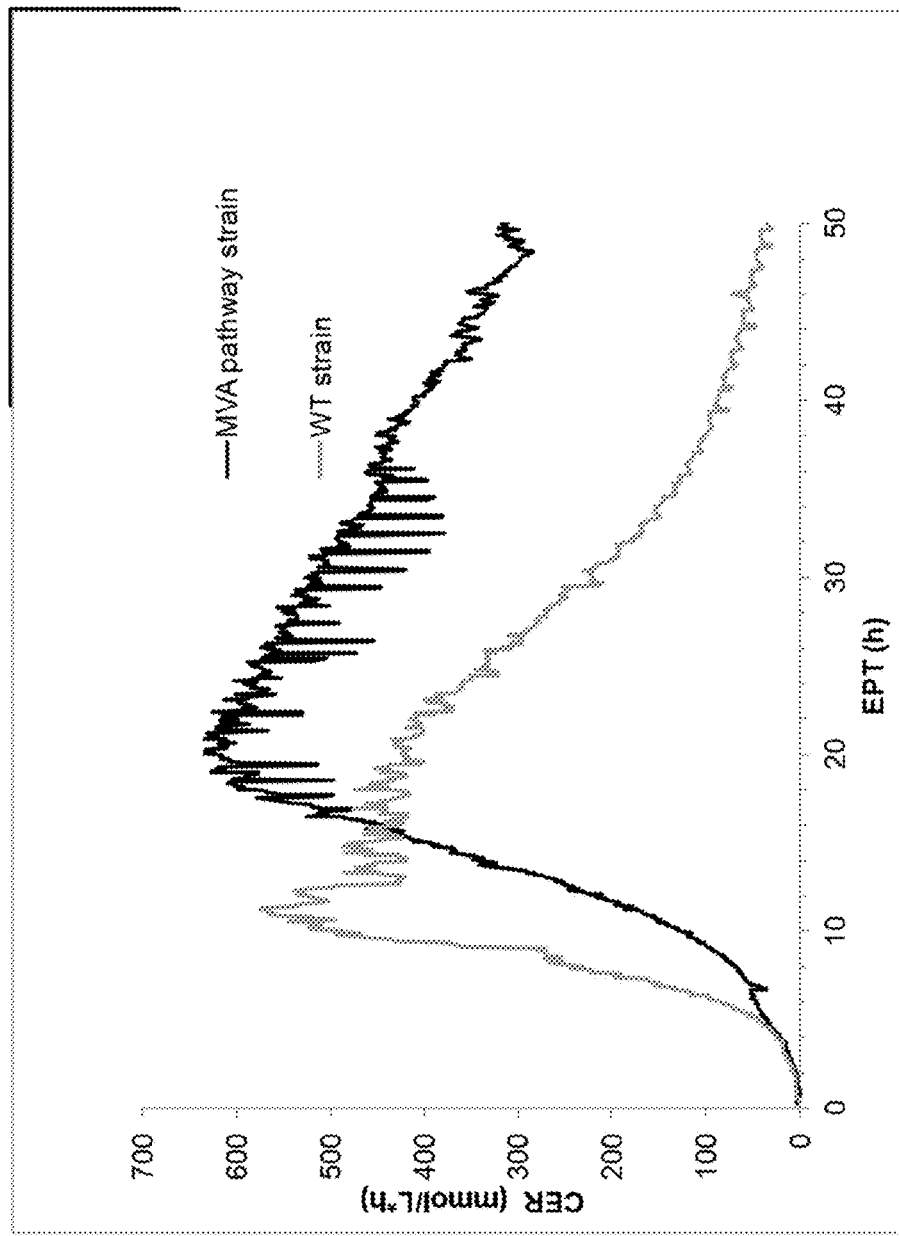
FIG. 6 depicts the respiration rate (CER) during fermentation of strains CMP457 and MCM1020.

An example of a promoter useful for the control of ispA expression is the one controlling the expression of yddV. This promoter is specifically repressed late during the fermentation in the MVA pathway strain. By contrast this promoter was not repressed in the wild type *E. coli* strain as shown in FIG. 5. The YddV protein binds heme, a compound that is likely to change concentration during high isoprenoid flux conditions. Respiration rates of the analyzed fermentations are shown in FIG. 6.

Example 4

Insertion of IspA in the yhfS Locus

Colony polymerase chain reaction (PCR) protocols were performed according to the following method. One bacterial colony was stirred in 30 µl H₂O and heated to 95° C. for 5 minutes. The resulting solution was spun down and 2 µl of the supernatant used as template in the following PCR reaction: 2 µl colony in H₂O, 10 µl Herculase® Buffer, 1 µl 100 mM dNTPs, 1.25 µl 10 µM Forward primer, 1.25 µl 10 µM Reverse primer, 1 µl of Herculase® Enhanced DNA Polymerase (Agilent Technologies, Stratagene Products Division, La Jolla, Calif.), and 33.5 µl diH₂O. The PCR reaction was cycled in a PCR Express Thermal Cycler (Thermo Hybaid, Franklin, 3' (SEQ ID NO: 21)), and template was pKD4 (Datsenko and Wanner, PNAS, 2000, 97(12), 6640-6645). Piece 2 contains the promoter of the xseB-ispA-dxs operon. Primers used to obtain that fragment are CMP249 (5'-cgaagcagctccagcgaa-caatttaatgataaacttcatggcg-3' (SEQ ID NO: 22)) and CMP250 (5'-AATGAATGTCTGACTCTCAATATTTTTCGC-3' (SEQ ID NO: 23), and template was chromosomal DNA of BL21 or a derivative thereof. Primers were designed to allow seamless assembly to piece 1 and piece 3. Piece 3 contains the *E. coli* ispA gene, and two sets of 15-bp allowing assembly with piece 2 and pBBR1MCS5 digested by XbaI and EcoRI. Primers used to obtain that fragment are CMP255 (5'-agtca-gacattcattatggactttccgcagcaactcg-3' (SEQ ID NO: 24)) and CMP256 (5'-ATAAGCTTGATATCGacctgtcggcact-gaagcaggtcgtcgacgagcaacaaccggatgcggcgTTATTTATTACG CTGGATGATGTAGTCC-3' (SEQ ID NO: 25)), and template was chromosomal DNA of BL21 or a derivative thereof.

Polymerase chain reactions (PCR) were all done using Herculase II Fusion according to the protocol recommended by the manufacturer (Agilent, Santa Clara, Calif.). They were purified using the PCR purification kit from Qiagen (Germantown, Md., USA). Piece 1, 2 and 3 were then assembled with EcoRI/XbaI-digested plasmid pBBR1-MCSS using the GeneArt seamless cloning and assembly kit (Invitrogen, Carlsbad, Calif.), according to the protocol recommended by the manufacturer. The reaction was transformed in *E. coli* Top10 cells (Invitrogen, Carlsbad, Calif.), and transformants were selected on LB+kanamycin 20 mg/L. Plasmid was isolated from one of those colonies, and named pCMP944. The presence of the right construct in the plasmid was confirmed by sequencing (Quintara Bio, Albany, Calif.). Plasmid pCMP944 was used as a template for a PCR reaction using primers CMP257 (5'-cattcgcgccgcattcacagccgattc-gagccaccttcatcaccgcatagttgtcatcggttaacgctggaacac-3' (SEQ ID NO: 26)) and CMP258 (5'-GGTTATTATTGAGCA-GATGGGGCTGACGCTTATTACTGT-TGATTTCAATGACCTGTCGG CACTGAAGCAGG-3' (SEQ ID NO: 27)). The PCR product was purified using the Qiagen PCR purification kit (Germantown, Md., USA) and digested with the restriction enzyme DpnI. After further purification, that PCR product was used in a recombineering reaction (Datsenko and Wanner, supra) with strain CMP451 (see U.S. patent application Ser. No. 13/283,564). Transformants were selected on LB+10 mg/L kanamycin. A colony found to be the correct size by PCR (using primers CMP267 (5'-cgattcgagccaccttcatcacc-3' (SEQ ID NO: 28)) and CMP268 (5'-CAG CGT CTT CTG GTG CAT GAC G-3' (SEQ ID NO: 29))) was named CMP981. The kanamycin marker was looped out with pCP20 (Datsenko and Wanner, supra) to make CMP992 which was then used for further modifications. To achieve loopout, a colony transformed with pCP20 (grown at 30° C. with 50 mg/L carbenicillin) was streaked on LB and grown at 42° C. overnight. The day after, colonies were picked and patched on LB and LB+10 mg/L kanamycin. A colony with the marker looped out grew on LB but not on LB+10 mg/L kanamycin.

Example 5

Knock Out of Endogenous IspA

For this reaction, three DNA pieces were generated by PCR. Polymerase chain reaction protocols were performed according to the method described in example 4. Piece 1 contains 289 bp of the thiI gene of BL21 and its promoter, flanked by 15 bp allowing seamless assembly (Invitrogen, Carlsbad, Calif.) to a XbaI/EcoRI-digested vector pBBR1-MCSS (Kovach et al., supra) and piece 2 described below. Primers used to obtain that piece were CMP236 (5'-Gcggtg-gcggccgctgaaccaacgctttctcgaaaatatcg-3' (SEQ ID NO: 30)) and CMP237 (5'-cagcctacacaatcgagcgatgttagtggtatacttccgc-3' (SEQ ID NO: 31)), and template was chromosomal DNA of *E. coli* BL21 or a derivative thereof. Piece 2 contains a FRT sites-flanked chloramphenicol cassette. Primers used to obtain that piece were CMP234 (5'-Cgattgtgtaggctggagct-gcttc-3' (SEQ ID NO: 32)) and CMP235 (5'-gtccatatgaatatc-ctccttagttc-3' (SEQ ID NO: 33)), and template was pKD3 (Datsenko and Wanner, supra). Piece 3 contains a fragment of DNA containing the promoter of the xseB-ispA-dxs operon and downstream DNA down to approximately the middle of the ispA gene. Primers used to obtain that piece were CMP238 (5'-gatattcatatggacttgctgcgcacatcaccttacc-3' (SEQ ID NO: 34)) and CMP239 (5'-ATAAGCTTGATATCG ccttc-cgcgtctaaatctagtgcc-3' (SEQ ID NO: 35)) and template was chromosomal DNA of *E. coli* BL21 or derivative.

Piece 1, 2 and 3 were then assembled with EcoRI/XbaI-digested plasmid pBBR1-MCSS using the GeneArt seamless cloning and assembly kit (Invitrogen, Carlsbad, Calif.), according to the protocol recommended by the manufacturer. The reaction was transformed in *E. coli* Top10 cells (Invitrogen, Carlsbdad, Calif.), and transformants were selected on LB+chloramphenicol 25 mg/L. The plasmid was isolated from one of those colonies and named pCMP935. The presence of the right construct in the plasmid was confirmed by sequencing (Quintara Bio, Albany, Calif.).

Plasmid pCMP935 was used as a template for a PCR reaction using primers CMP241 (5'-gaaccaacgctttctcgaaaatatcg-3' (SEQ ID NO: 36) and CMP242 (5'-ccttccgcgtctaaatctagt-gcc-3' (SEQ ID NO: 37). The PCR product was purified using the Qiagen PCR purification kit (Germantown, Md., USA) and digested with the restriction enzyme DpnI. After further purification, that PCR product was used in a recombineering reaction (Datsenko and Wanner, supra) with strain CMP451 (previously disclosed in U.S. patent application Ser. No. 13/283,564). Transformants were selected on LB+5 mg/L chloramphenicol. A colony found to be the correct size by PCR (using primers CMP265 (5'-cacgcgtacgcagaaggttttgc-3' (SEQ ID NO: 38)) and CMP266 (5'-CAGTGC-CAGGGTCGGGTATTTGG-3' (SEQ ID NO: 39))) was named CMP939. CMP939 had similar growth to its parent, CMP451.

Plasmid pCMP935 was subjected to a Quikchange reaction using the Quikchange $ kit according to the manufacturer (Agilent, Santa Clara, Calif.). Primer used were CMP245 (5'-cttttacaccggacaatgagtaatcgccccactgccctttcag-3' (SEQ ID NO: 40)) and CMP246 (5'-ctgaaagggcagtggggcgattactcat-tgtccggtgtaaaag-3' (SEQ ID NO: 41)). The plasmid thus obtained was named pCMP948 and does not encode ispA as the ATG and the 20 first amino acids of the gene were removed. Plasmid pCMP948 was used as a template for a PCR reaction using primers CMP241 (5'-gaaccaacgctttctc-gaaaatatcg-3' (SEQ ID NO: 42)) and CMP242 (5'-ccttc-cgcgtctaaatctagtgcc-3' (SEQ ID NO: 43)). The PCR product was purified using the Qiagen PCR purification kit (Germantown, Md., USA) and digested with the restriction enzyme DpnI. After further purification, that PCR product was used in a recombineering reaction (Datsenko and Wanner, supra) with strain CMP992. Transformants were selected on LB+5 mg/L chloramphenicol. A colony found to be the correct size by PCR (using primers CMP265 (5'-cacgcgtacgcagaag-gttttgc-3' (SEQ ID NO: 44)) and CMP266 (5'-CAGTGC-CAGGGTCGGGTATTTGG-3' (SEQ ID NO: 45))) was named CMP1018. The kanamycin marker was looped out with pCP20 (Datsenko and Wanner, supra) to make CMP1030 which was then used for further modifications. To achieve loopout, a colony transformed with pCP20 (grown at 30° C. with 50 mg/L carbenicillin) was streaked on LB and grown at 42° C. overnight. The day after, colonies were picked and patched on LB and LB+5 mg/L chloramphenicol. A colony with the marker looped out is growing on LB but not on LB+5 mg/L chloramphenicol. Plasmids MCM82 (see U.S. Pub. No. 2011/0159557) and pCHL243 (described previously in U.S. patent application Ser. No. 13/283,564) were electroporated concomitantly into CMP1030. A colony growing on LB+carbenicilin 50 mg/L and spectinomycin 50 mg/L was selected and named CMP1061.

Example 6

Introduction of PyddV-IspA at the yhfS Locus

Figure 10:
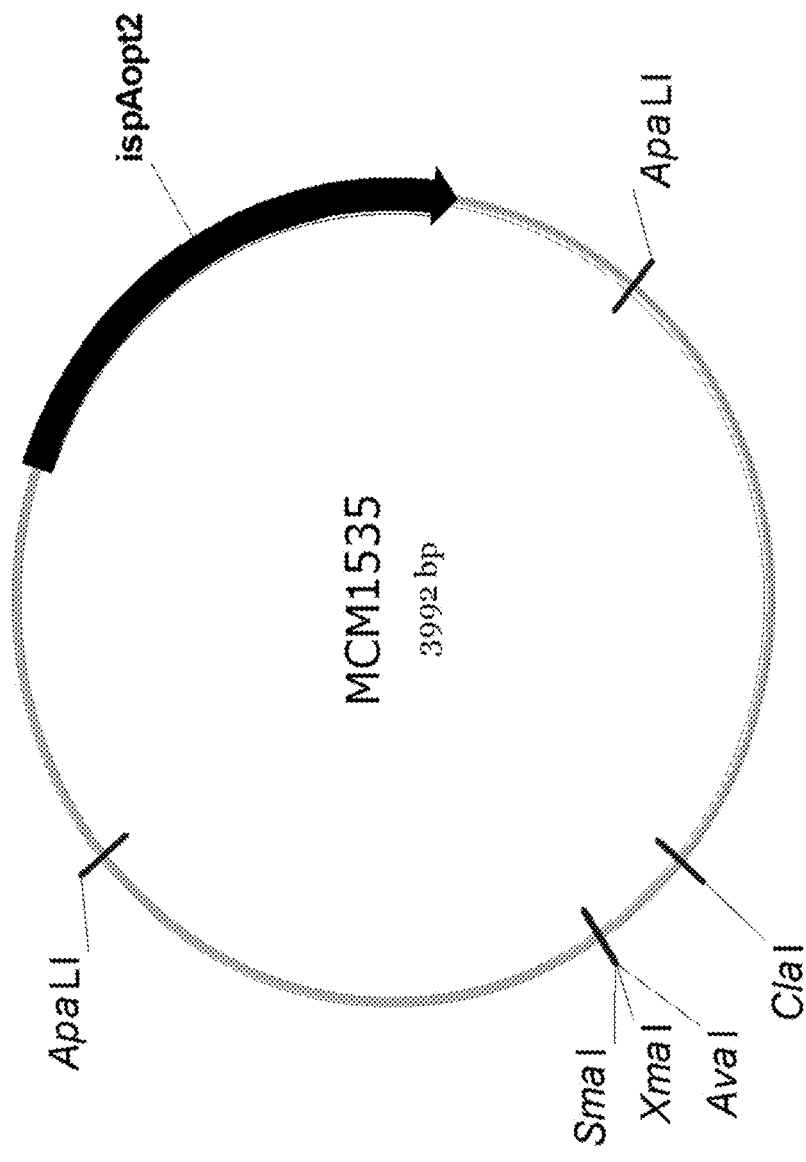
FIG. 10 depicts the plasmid construct of pMCM1535.

For this reaction, three DNA pieces were generated by PCR. Polymerase chain reaction protocols were performed according to the method described in example 4. Piece 1 contains a 15 bp sequence allowing assembly by the seamless kit (Invitrogen) to a XbaI/EcoRI-digested vector pBBR1MCS5 (Kovach et al., supra), a region homologous to the yhfS region of BL21, a kanamycin marker, and a 15 bp allowing assembly to the promoter of the xseB-ispA-dxs operon. Primers used to obtain that piece are CMP247 (5'-gcggtggcggccgctttgtcatcggt-taacgctggaacacctgccgcgcg-caacgttgccagcaccctccttagttcctattccgaagttc-3' (SEQ ID NO:46)) and CMP248 (5'-gctggagctgcttcgaagttcc-3' (SEQ ID NO:47)), and template is pKD4 (Datsenko and Wanner, supra). Piece 2 contains the promoter of the yddV gene. Primers used to obtain that fragment are CMP338 (5'-cgaag-cagctccagcgaactatcccactactaatcatgcttac-3' (SEQ ID NO:48)) and CMP339 (5'-ctgcggaaagtccatAATTCACACCCT-TATAAGGCTGGG-3' (SEQ ID NO:49)), and template is chromosomal DNA of BL21 or a derivative thereof. Primers were designed to allow seamless assembly to piece 1 and piece 3. Piece 3 contains the *E. coli* ispA gene whose codons have been altered by GeneOracle (FIG. 8), and two sets of 15-bp allowing assembly with piece 2 and pBBR1-MCSS digested by XbaI and EcoRI. Primers used to obtain that fragment are CMP340 (5'-ataagggtgtgaatt ATGGACTTTC-CGCAGCAACTCG-3' (SEQ ID NO:50)) and CMP256 (5'-ATAAGCTTGATATCGacctgtcggcact-gaagcaggtcgtcgacgagcaacaaccggatgcggcgTTATTTATTACG CTGGATGATGTAGTCC-3' (SEQ ID NO:51)), and template is plasmid pMCM1535 (FIGS. 9-10).

Polymerase chain reactions (PCR) were all done using Herculase II Fusion according to the protocol recommended by the manufacturer (Agilent, Santa Clara, Calif.). They were purified using the PCR purification kit from Qiagen (Germantown, Md., USA). Piece 1, 2 and 3 were then assembled with EcoRI/XbaI-digested plasmid pBBR1-MCSS using the GeneArt seamless cloning and assembly kit (Invitrogen, Carlsbad, Calif.), according to the protocol recommended by the manufacturer. The reaction was transformed in *E. coli* Top10 cells (Invitrogen, Carlsbdad, Calif.), and transformants were selected on LB+kanamycin 20 mg/L. Plasmid was isolated from one of those colonies, and named pCMP1046. The presence of the right construct in the plasmid was confirmed by sequencing (Quintara Bio, Albany, Calif.). Plasmid pCMP1046 was used as a template for a PCR reaction using primers CMP257 (5'-cattcgcgccgcattcacagc-cgattcgagccaccttcatcaccgcatagttgtcatcggttaacgctggaacac-3' (SEQ ID NO:52)) and CMP258 (5'-GGTTATTATTGAGCA-GATGGGGCTGACGCTTATTACTGT-TGATTTCAATGACCTGTCGG CACTGAAGCAGG-3' (SEQ ID NO:53)). The PCR product was purified using the Qiagen PCR purification kit (Germantown, Md., USA) and digested with the restriction enzyme DpnI. After further purification, that PCR product was used in a recombineering reaction (Datsenko and Wanner, supra) with strain CMP1018. Transformants were selected on LB+10 mg/L kanamycin. A colony found to be the correct size by PCR (using primers CMP267 (5'-cgattcgagccaccttcatcacc-3' (SEQ ID NO:54)) and CMP268 (5'-CAGCGTCTTCTGGTGCATGACG-3' (SEQ ID NO:55))) was named CMP1067. The kanamycin and chloramphenicol markers were looped out with pCP20 (Datsenko and Wanner, supra) to make CMP1075. To achieve loopout, a colony transformed with pCP20 (grown at 30° C. with 50 mg/L carbenicillin) was streaked on LB and grown at 42° C. overnight. The day after, colonies were picked and patched on LB, LB+10 mg/L kanamycin and LB+5 mg/L chloramphenicol. A colony with the marker looped out is growing on LB but not on LB+10 mg/L kanamycin or LB+5 mg/L chloramphenicol. Plasmids MCM82 (described previously) and pCHL243 were electroporated concomitantly into CMP1075. A colony growing on LB+carbenicilin 50 mg/L and spectinomycin 50 mg/L was selected and named CMP1082.

Example 7

Construction of Strain CMP1059 (ispA Linked to a Proteolytic Tag)

A PCR product containing a Kanamycin cassette flanked by FRT sites and regions homologous to upstream and downstream of ldhA was obtained using methods described above, a Keio strain JW1375 (Baba et al., 2006, *Mol Syst Biol.*, 2:1-11) which contains a deletion of ldhA, and primers ldhAseqF2 (5'-CTA ATG CAA TAC GTG TCC CGA GC-3' (SEQ ID NO:56)) and ldhAseqR (5'-ggcttaccgtttacgctttc-cagc-3' (SEQ ID NO:57)). This PCR product was used in a recombineering reaction (see protocol described above) with *E. coli* BL21 to form BL21 ldhA::Kan. A P1 lysate was prepared from the latter strain and was used to transduce CMP451. P1 lysates were prepared and used according to the method described in Ausubel, et al., *Current Protocols in Molecular Biology*, John Wiley and Sons, Inc. A colony was selected on LB+kanamycin 10 mg/L and named CMP596. The kanamycin marker was removed using the protocol recommended by the manufacturer (Gene Bridges, Heidelberg, Germany) to form strain CMP722.

Example 8

Isoprene Production in Strains Containing a Modification of ispA

Methods

TM3 Media Recipe (Per Liter Fermentation Media): K2HPO4 13.6 g, KH2PO4 13.6 g, MgSO4*7H2O 2 g, citric acid monohydrate 2 g, ferric ammonium citrate 0.3 g, (NH4) 2SO4 3.2 g, yeast extract 0.2 g, 1000× Trace Metals Solution 1 ml. All of the components are added together and dissolved in diH2O. The pH is adjusted to 6.8 with ammonium hydroxide (30%) and brought to volume. Media is filter-sterilized with a 0.22 micron filter. Glucose 10.0 g and antibiotics are added after pH adjustment and sterilization.

1000× Trace Metal Solution (Per Liter Fermentation Media): Citric Acid*H2O 40 g, MnSO4*H2O 30 g, NaCl 10 g, FeSO4*7H2O 1 g, CoCl2*6H2O 1 g, ZnSO4*7H2O 1 g, CuSO4*5H2O 100 mg, H3BO3 100 mg, NaMoO4*2H2O 100 mg. Each component is dissolved one at a time in diH2O. The pH is adjusted to 3.0 with HCl/NaOH, and then the solution is brought to volume and filter-sterilized with a 0.22 micron filter.

Cells are grown overnight in Luria-Bertani broth+antibiotics. The day after, they are diluted to an OD600 of 0.1 in 20 mL TM3 medium containing 50 µg/ml of spectinomycin and 50 µg/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay (see U.S. Publication No.: US 2005/0287655, the contents of which are incorporated herein by reference in its entirety). One hundred microliters of whole broth are placed in a sealed GC vial and incubated at 34° C. and 200 rpm for a fixed time of 30 minutes. Following a heat kill step, consisting of incubation at 70° C. for 7 minutes, the sample is loaded on the GC. The reported specific productivity is the amount of isoprene in µg/L read by the GC divided by the incubation time (30 min) and the measured OD600.

Results

Figure 7A:
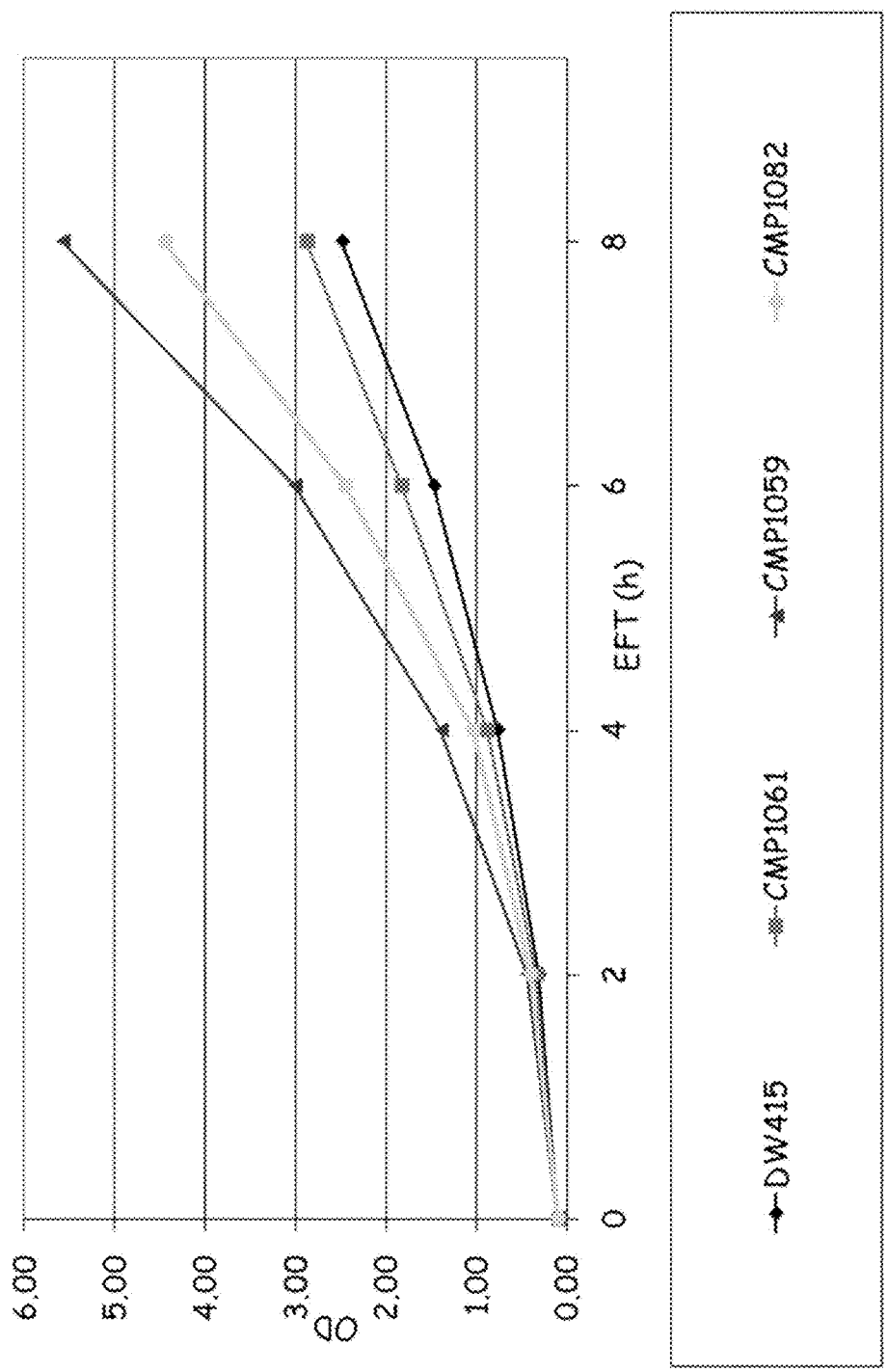
FIG. 7a depicts the growth curve of various engineered isoprene producing strains (average of duplicate runs).
Figure 7B:
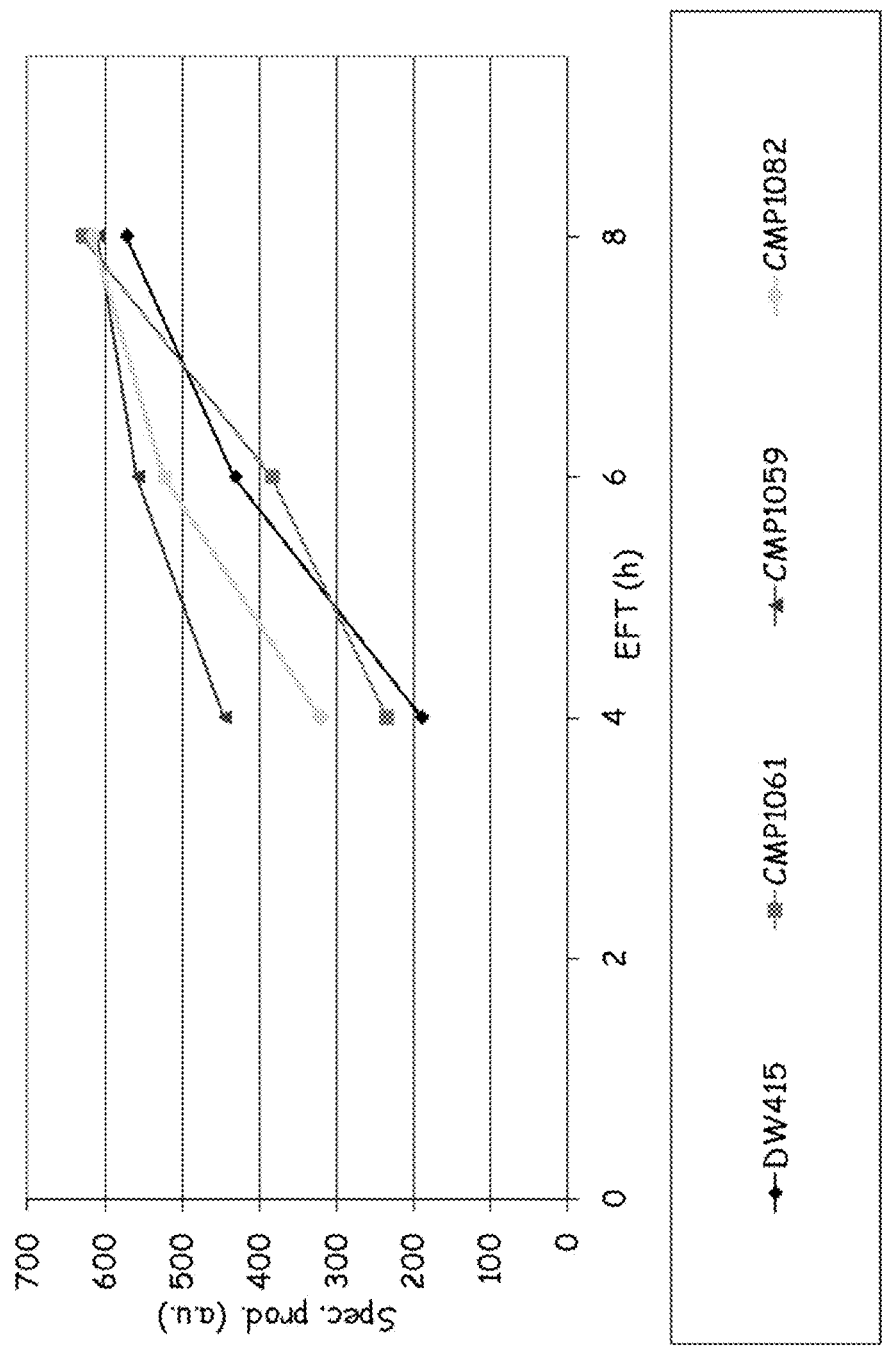
FIG. 7b depicts specific productivity (in arbitrary units) of various engineered isoprene producing strains (average of duplicate runs).

Strains with wild-type ispA, DW415 (described previously in U.S. patent application Ser. No. 13/283,564) or refactored ispA (CMP1061) grew slightly slower than the strains with a modified ispA expression (CMP1059 and CMP1082) (FIG. 7a). Specific productivity of all strains was very similar (FIG. 7b).

Example 9

Large Scale Fermentation of CMP1082

Fermentation runs were performed to test certain performance metrics (cumulative isoprene yield on glucose, isoprene productivity, peak specific productivity and cell productivity index) of strain CMP1082 (HMB GI1.2gltA, PyddVIspA_GO, truncIspA, MCM82, pCHL243) to that of a control strain CMP1043 (HMB GI1.2gltA, -MCM82, pCHL243) according to the following protocol.

Medium Recipe (Per Liter Fermentation Medium): K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di $H_2O$. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter): Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter): Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter): MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram): Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

Metabolite Analysis: Metabolite extraction from E. coli. was achieved by withdrawing approximately 3 mL of culture into a tube filled with 9 mL of dry ice-cold methanol. The resulting samples were weighed to calculate the amount of sampled broth and then stored at −80° C. until further analysis. For metabolite extraction and concentration, 0.5 mL aliquots of cell suspension (1 mL aliquot was used if cell density of the culture measured as $OD_{600}$ was below 50) were diluted with 2.5 mL of methanol/ammonium acetate buffer (5 mM, pH=8.0) mixture (6:1, v/v) and cell debris was pelleted by a 5 minute centrifugation. The supernatant was collected and loaded onto Strata-X-AW columns from Phenomenex (33 μm 30 mg/3 mL Polymeric Weak Anion Exchange). The cell pellet was extracted two more times, first with 3 mL of the methanol/ammonium acetate buffer (5 mM, pH=8.0) mixture (6:1 v/v), and then with 3 mL of methanol/ammonium acetate buffer (5 mM, pH=8.0) mixture (1:1 v/v). Both times the cells were pelleted by centrifugation, and the resulting supernatants were consecutively loaded onto the same Strata-X-AW columns. During the extraction-centrifugation, samples with cells were kept below 4° C. After washing the columns with 1 mL of water and 1 mL of methanol, metabolites of interest were eluted from the columns first with 0.3 mL of concentrated NH4OH/methanol (1:14, v/v) mixture and then with 0.3 mL of concentrated NH4OH/methanol/water (1:12:2, v/v/v) mixture. The resulting eluant was neutralized by adding 20 μL of glacial acetic acid, and then cleared by centrifugation.

Analysis of metabolites was carried out by mass spectrometry using a TSQ Quantum Access TSQ system (Thermo Scientific). All system control, data acquisition, and mass spectral data evaluation were performed using XCalibur and LCQuan software (Thermo Scientific). For the LC-ESI-MS/MS method, a chiral Nucleodex β-OH 5 μM HPLC column (100×2 mm, Macherey-Nagel, Germany) was used with a CC 8/4 Nucleodex beta-OH guard cartridge. A mobile phase gradient was applied in which mobile phase A was 100 mM ammonium acetate (SigmaUltra grade, Sigma) buffer (pH=8) in MilliQ-grade water, mobile phase B was MilliQ-grade water, and mobile phase C was LC-MS grade acetonitrile (Chromasolv, Riedel-de Haën). The column and sample tray temperatures were reduced to 5° C. and 4° C., respectively. The injection volume was 10 μL.

Mass detection was carried out using electrospray ionization in the negative mode (ESI spray voltage of 3.0 kV and ion transfer tube temperature of 390° C.). The following m/z values for precursor ions were selected to detect the metabolites of interest in SRM mode: 245.0 for IPP and DMAPP, 313.1 for GPP, 381.1 for FPP, 227.0 for MVP, and 307.1 for MVPP. Concentrations of metabolites were determined based on the integrated intensities of peaks generated by PO3— product ion (m/z=79.0). Calibration curves obtained by injection of standards were used to calculate concentrations of metabolites in cell extracts. IPP, DMAPP, GPP, and FPP standards were purchased from Echelon Biosciences Inc. and MVP and MVPP (R-forms) were purchased from Sigma-Aldrich. Intracellular concentrations of metabolites were determined based on the assumption that in 1 mL of the culture at $OD_{600}$=200 the integrated volume of all cells is 50 μL.

This experiment was carried at pH 7.0 and temperature 34° C. A frozen vial of the E. coli strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L. The batched media had glucose batched in at 9.7 g/L. Induction was achieved by adding isopropyl-beta-D-1-thiogalactopyranoside (IPTG) at a final concentration of 200 uM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 48 to 72 hrs elapsed fermentation time.

Isoprene is volatile and can be efficiently swept from the tank by the inlet gas. The isoprene level in the bioreactor off-gas was determined using an iSCAN (Hamilton Sundstrand) mass spectrometer. The inlet gas was a custom blend of oxygen and nitrogen (~9.3 vol % and 90.7 vol % respectively). The citrate, glucose, acetate, and mevalonate concentrations in the fermentor broth were determined in broth samples taken at 4 hour intervals by an HPLC analysis. Concentration in broth samples were determined by comparison of the refractive index response versus a previously generated calibration curve using standard of a known concentration.

Results

TABLE 6

Isoprene Productivity Metrics

| Strain description/ Run Number | EFT (hrs) | Isoprene Titer (g/L) | Isoprene Volumetric Productivity (g/L/hr) | Overall % Yield of Isoprene on glucose (g/g) | CPI (g Isoprene/ gDCW) | Peak Specific Productivity (mg isoprene/ L/hr/OD) |
|---|---|---|---|---|---|---|
| CMP1043 Control strain | 44 | 74.41 | 1.69 | 14.26 | 1.64 | 26.87 (at 16 hrs EFT) |
| CMP1082 PyddV-ispA strain | 44 | 83.95 | 1.91 | 16.03 | 1.79 | 30.31 (at 12 hrs EFT) |

Figure 13:
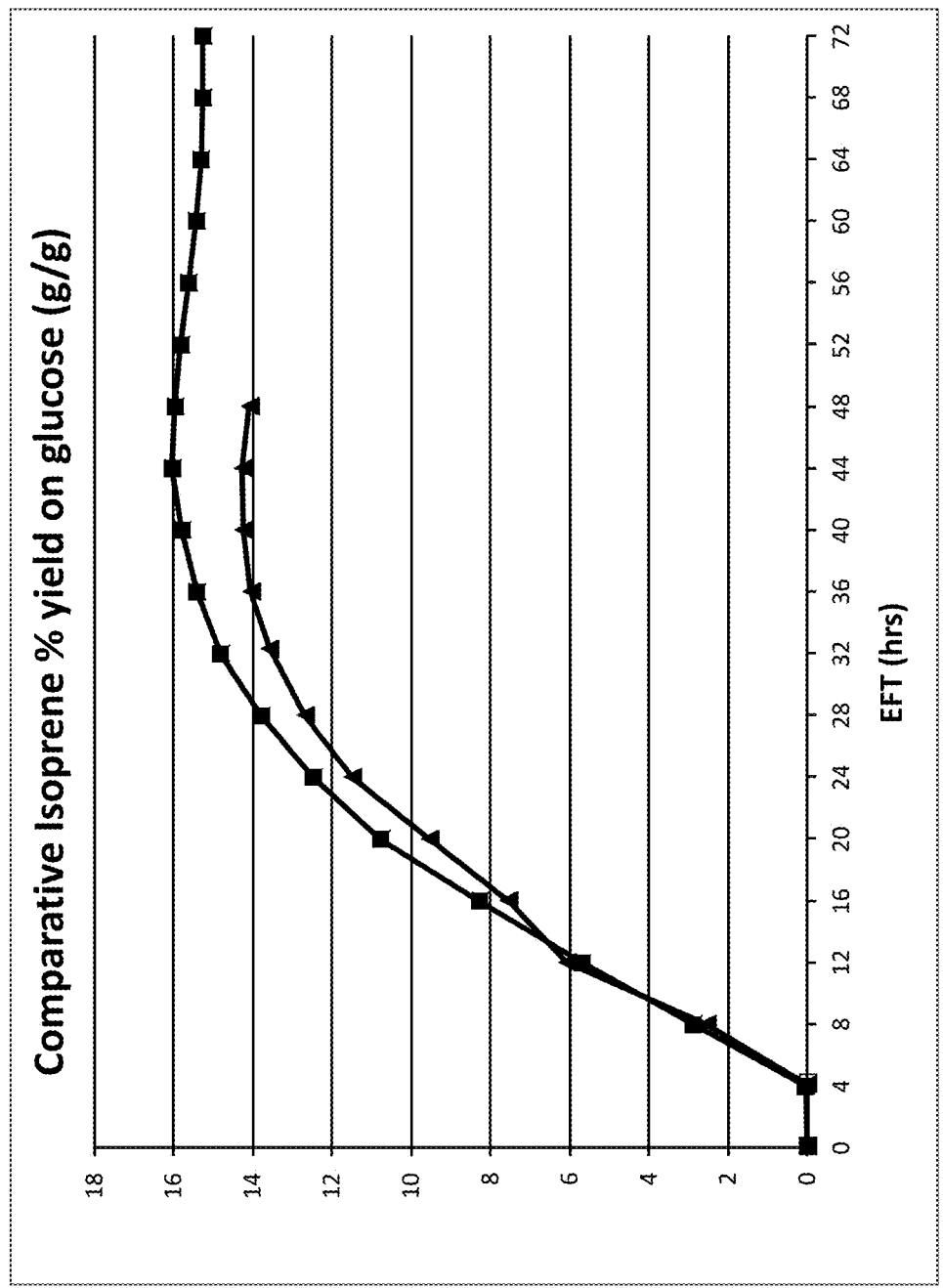
FIG. 13 depicts yield of isoprene on glucose achieved by the yddV-ispA strain CMP1082 (closed black squares), compared the control strain CMP1043 (closed triangles) in a 15-L fermentation over time.
Figure 14:
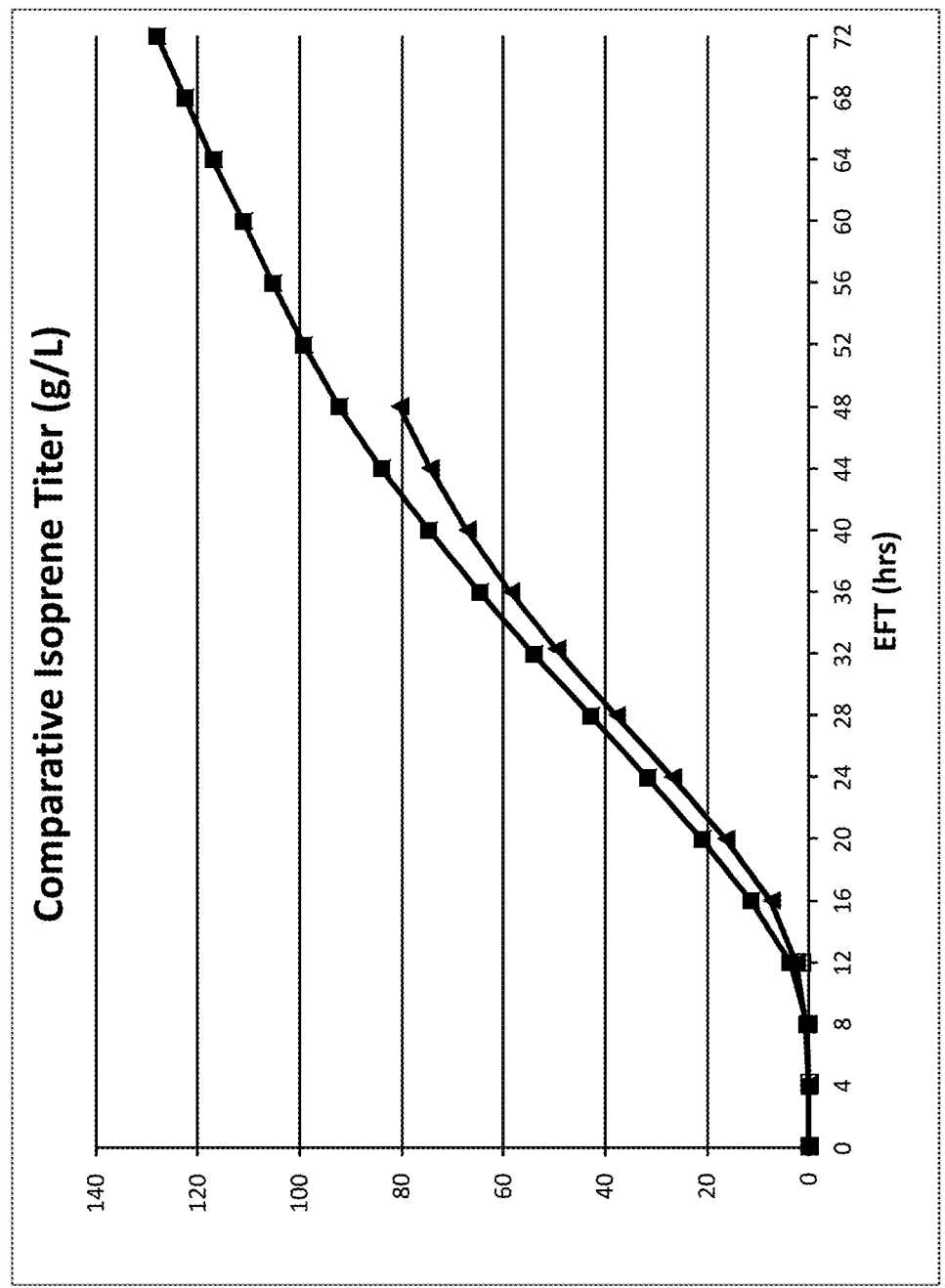
FIG. 14 depicts the isoprene titer achieved by the yddV-ispA strain CMP1082 (closed black and open squares), compared the control strain CMP1043 (closed triangles) in a 15-L fermentation over time.
Figure 15:
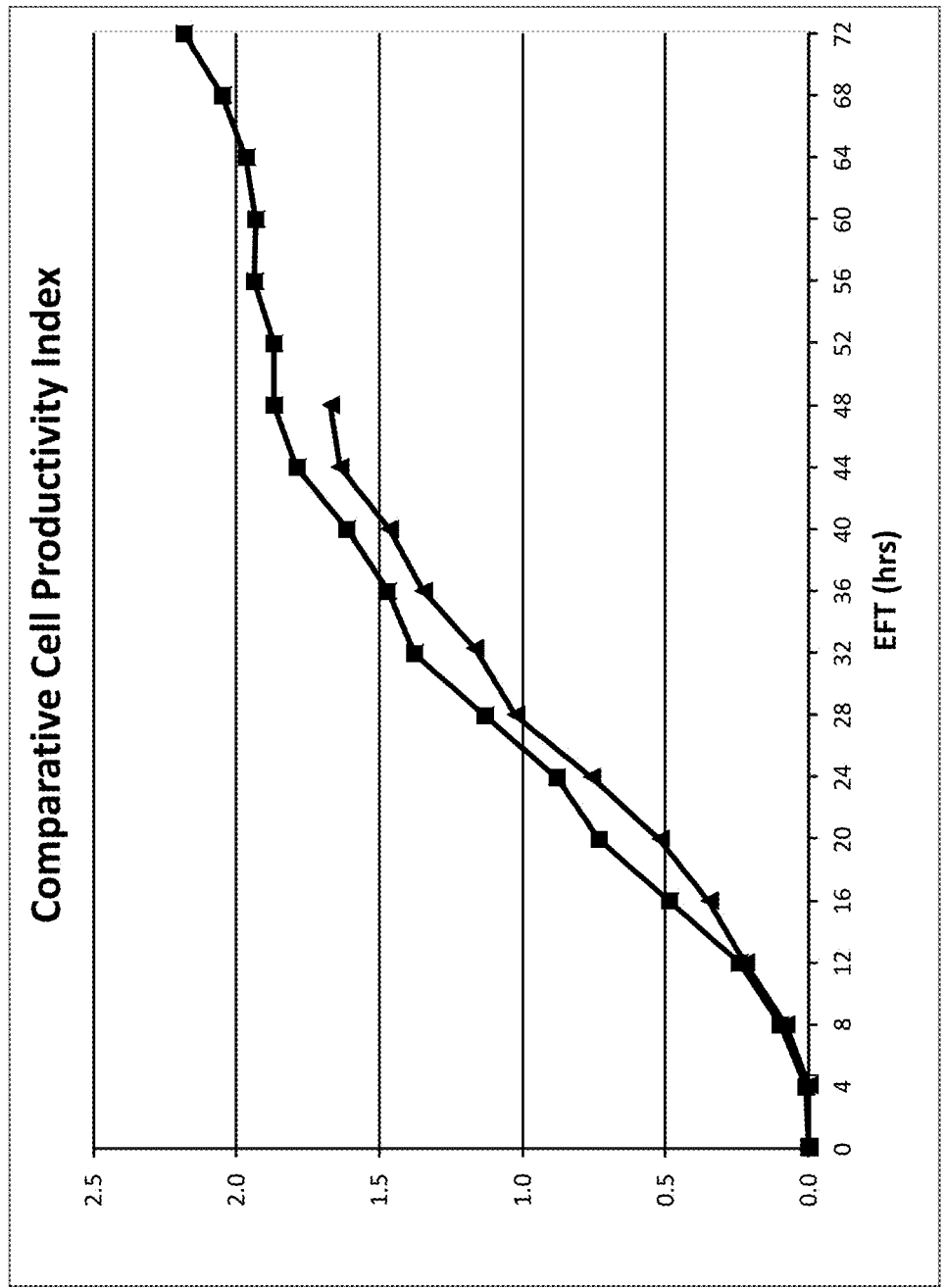
FIG. 15 depicts the Cell Productivity Index (CPI) achieved by the yddV-ispA strain CMP1082 (closed black squares), compared to the control strain CMP1043 (closed triangles) in a 15-L fermentation over time.
Figure 16:
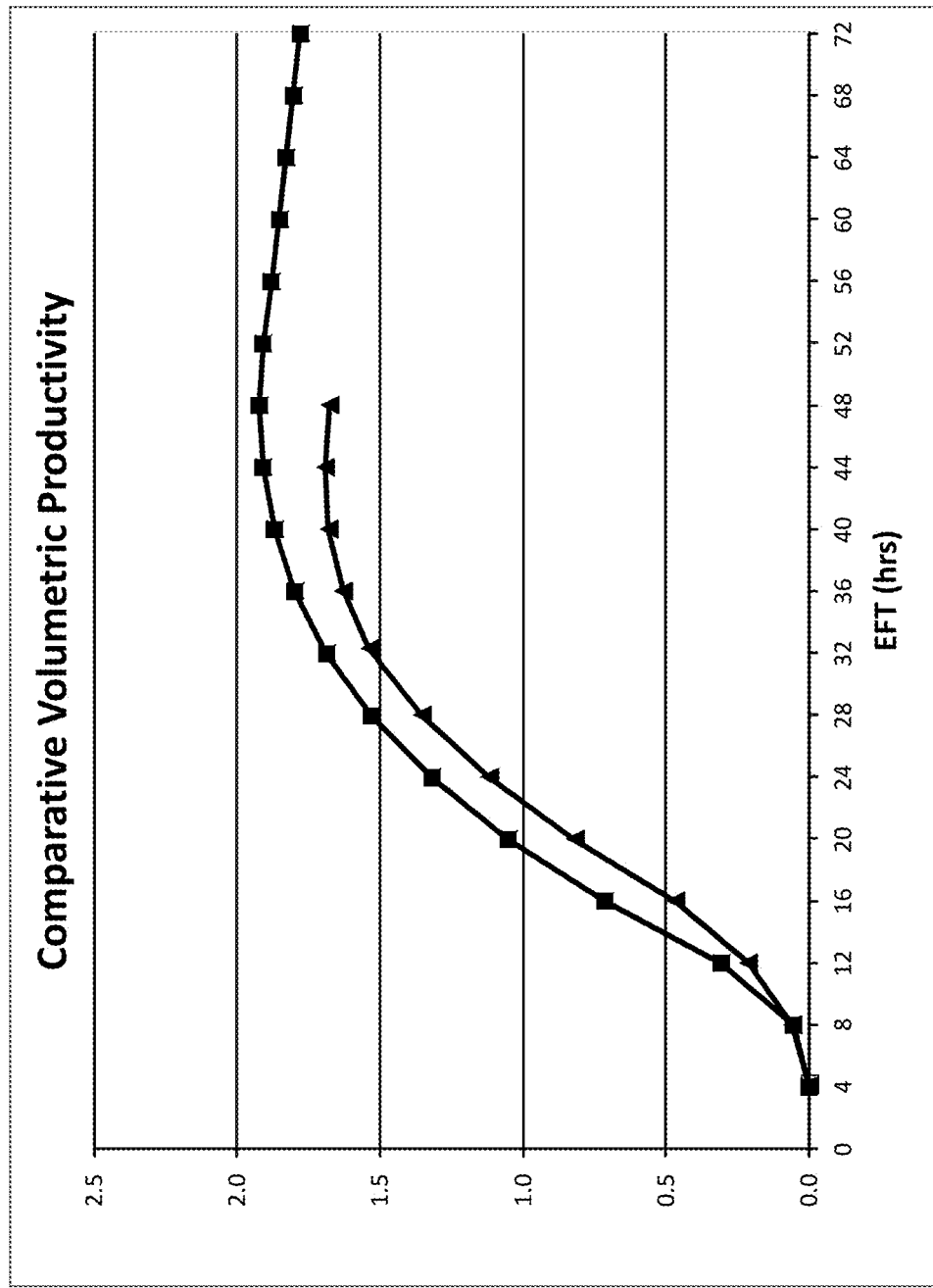
FIG. 16 depicts the volumetric productivity achieved by the yddV-ispA strain CMP1082 (closed black squares), compared the control strain CMP1043 (closed triangles) in a 15-L fermentation over time.
Figure 17:
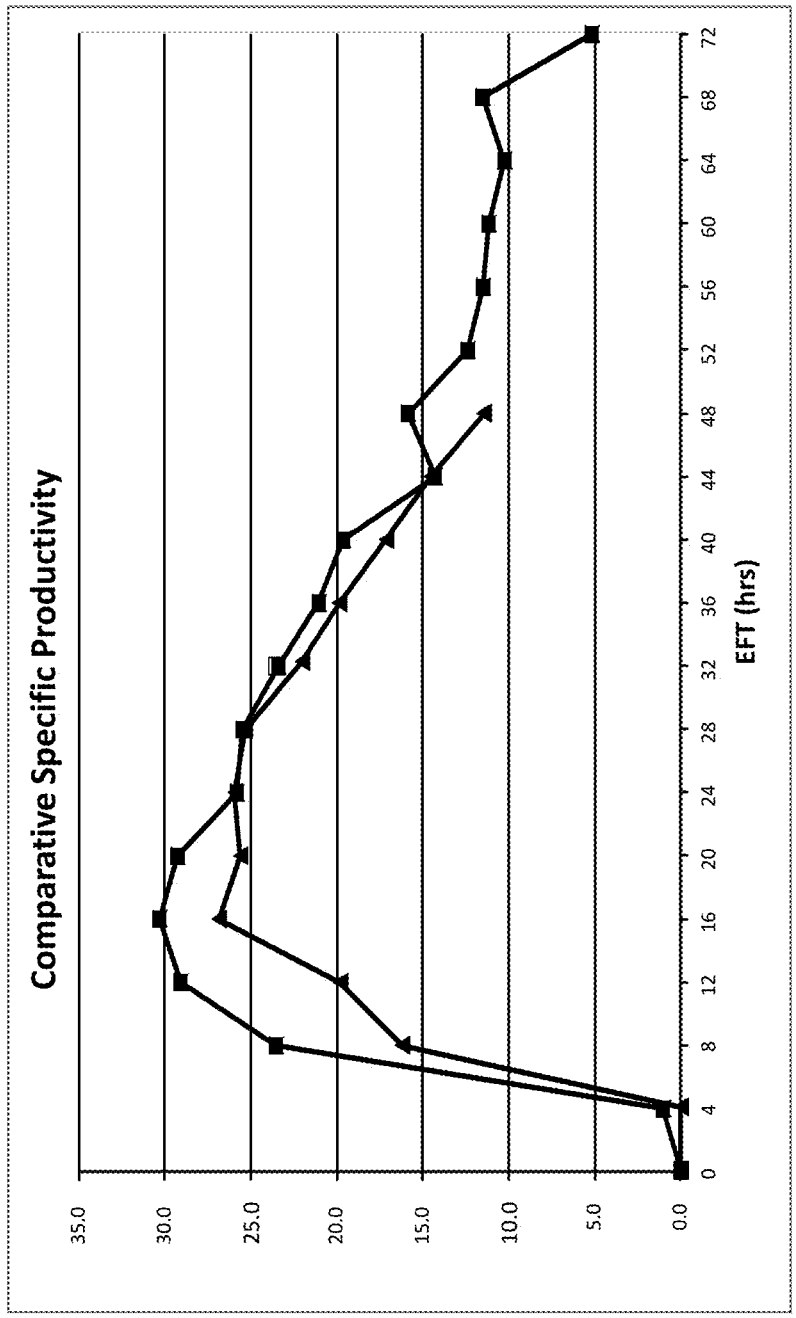
FIG. 17 depicts the specific productivity achieved by the yddV-ispA strain CMP1082 (closed black squares), compared the control strain CMP1043 (closed triangles) in a 15-L fermentation over time.

% wt Yield on glucose = Isoprene total (t)/[(Feed Wt(0) − Feed Wt(t) + 83.5) * 0.59)],
where 0.59 is the wt % of glucose in the glucose feed solution and 83.5 is the grams of this feed batched into the fermentor at t = 0. Each feed had its weight % measured independently.
Isoprene Titer (g/L) = Integrated isoprene evolution rate (mol/L) * molecular weight of isoprene (g/mol)
CPI = total grams Isoprene/total grams dry cell weight
Specific productivity (mg/L/hr/OD) = HgER * 68.117 g/mol/OD (HgER = isoprene evolution rate).
HgER is the Isoprene Evolution Rate in (mmol/L/hr).
OD = optical density = Absorbance at 550 nm * dilution factor in water Conclusions The fermentation with the modified ispA promoter strain (CMP1082) had a higher isoprene yield on glucose than the control strain (CMP1043) which uses a wild type ispA promoter, see FIG. 13 and Table 6. The fermentation with the modified ispA promoter strain (CMP1082) had a higher isoprene titer (see FIG. 14 and Table 6), a higher cell productivity index (see FIG. 15 and Table 6), a higher isoprene volumetric productivity (see FIG. 16 and Table 6), and a higher peak isoprene specific productivity (in the 12 hr range; see FIG. 17 and Table 6) than the control strain (CMP1043) which uses a wild type ispA promoter.

Example 10

Large Scale Fermentation of CMP1059

Polymerase chain reaction protocols were performed according to the method described in example 4. A P1 lysate was made from strain MD08-97 (described above) and used to transduce CMP722. A colony was selected on LB+chloramphenicol 5 mg/L and named CMP1024. CMP1024 was checked by PCR and sequenced to demonstrate presence of the proteolytic tag. The chloramphenicol marker was looped out using pCP20 (Datsenko and Wanner, supra) and a chloramphenicol sensitive colony was selected and named CMP1034. Plasmids MCM82 and pCHL243 were electroporated concomitantly into CMP1034. A colony growing on LB+carbenicilin 50 mg/L and spectinomycin 50 mg/L was selected and named CMP105.

Fermentation runs were performed to test certain performance metrics (cumulative isoprene yield on glucose, isoprene productivity, peak specific productivity and cell productivity index) of strain CMP1059 (HMB GI1.2gltA, ispA_prot_tag, MCM82, pCHL243) to that of a control strain CMP1043 (described previously) according to the following protocol:

Medium Recipe (Per Liter Fermentation Medium): K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000×Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000×Modified Trace Metal Solution (Per Liter): Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter): Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter): MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram): Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000×Modified Trace Metal Solution 0.82 ml.

This experiment was carried at pH 7.0 and temperature 34° C. A frozen vial of the E. coli strain was thawed and inoculated into a flask with tryptone-yeast extract medium and the appropriate antibiotics. After the inoculum grew to optical density 1.0, measured at 550 nm (OD550), 500 mL was used to inoculate a 15-L bioreactor and bring the initial tank volume to 5 L. The batched media had glucose batched in at 9.7 g/L. Induction was achieved by adding isopropyl-beta-D-1-thiogalactopyranoside (IPTG) at a final concentration of 200 μM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 48 to 72 hrs elapsed fermentation time.

The isoprene level in the bioreactor off-gas was determined using an iSCAN (Hamilton Sundstrand) mass spectrometer. The inlet gas was a custom blend of oxygen and nitrogen (~9.3 vol % and 90.7 vol % respectively). The citrate, glucose, acetate, and mevalonate concentrations in the fermentor broth were determined in broth samples taken at 4 hour intervals by an HPLC analysis. Concentration in broth samples were determined by comparison of the refractive index response versus a previously generated calibration curve using standard of a known concentration Results The fermentation with the proteolytic tag on ispA strain (CMP1059) had an 11% higher cell productivity index over the control strain (CMP1043) which uses the wild type ispA protein. Additionally, the fermentation with the proteolytic tag on ispA strain (CMP1059) had a 14% higher peak isoprene specific productivity (at 16 hrs EFT) versus the control strain (at 16 hrs EFT, CMP1043) which uses the wild type ispA protein.

Example 11

Metabolic Data in Strains Containing a Modification of ispA

Fermentation runs were performed to test metabolite accumulation in strains CMP1059 and CMP1082 as well as control strain CMP1043 according to the protocol described in Examples 9 and 10.

Metabolite Analysis: Metabolite extraction from *E. coli* was achieved by withdrawing approximately 3 mL of culture into a tube filled with 9 mL of dry ice-cold methanol. The resulting samples were weighed to calculate the amount of sampled broth and then stored at −80° C. until further analysis. For metabolite extraction and concentration, 0.5 mL aliquots of cell suspension (1 mL aliquot was used if cell density of the culture measured as $OD_{600}$ was below 50) were diluted with 2.5 mL of methanol/ammonium acetate buffer (5 mM, pH=8.0) mixture (6:1, v/v) and cell debris was pelleted by a 5 minute centrifugation. The supernatant was collected and loaded onto Strata-X-AW columns from Phenomenex (33 μm 30 mg/3 mL Polymeric Weak Anion Exchange). The cell pellet was extracted two more times, first with 3 mL of the methanol/ammonium acetate buffer (5 mM, pH=8.0) mixture (6:1 v/v), and then with 3 mL of methanol/ammonium acetate buffer (5 mM, pH=8.0) mixture (1:1 v/v). Both times the cells were pelleted by centrifugation, and the resulting supernatants were consecutively loaded onto the same Strata-X-AW columns. During the extraction-centrifugation, samples with cells were kept below 4° C. After washing the columns with 1 mL of water and 1 mL of methanol, metabolites of interest were eluted from the columns first with 0.3 mL of concentrated NH$_4$OH/methanol (1:14, v/v) mixture and then with 0.3 mL of concentrated NH$_4$OH/methanol/water (1:12:2, v/v/v) mixture. The resulting eluant was neutralized by adding 20 μL of glacial acetic acid, and then cleared by centrifugation.

Analysis of metabolites was carried out by mass spectrometry using a TSQ Quantum Access TSQ system (Thermo Scientific). All system control, data acquisition, and mass spectral data evaluation were performed using XCalibur and LCQuan software (Thermo Scientific). For the LC-ESI-MS/MS method, a chiral Nucleodex β-OH 5 μM HPLC column (100×2 mm, Macherey-Nagel, Germany) was used with a CC 8/4 Nucleodex beta-OH guard cartridge. A mobile phase gradient was applied in which mobile phase A was 100 mM ammonium acetate (SigmaUltra grade, Sigma) buffer (pH=8) in MilliQ-grade water, mobile phase B was MilliQ-grade water, and mobile phase C was LC-MS grade acetonitrile (Chromasolv, Riedel-de Haën). The column and sample tray temperatures were reduced to 5° C. and 4° C., respectively. The injection volume was 10 μL.

Mass detection was carried out using electrospray ionization in the negative mode (ESI spray voltage of 3.0 kV and ion transfer tube temperature of 390° C.). The following m/z values for precursor ions were selected to detect the metabolites of interest in SRM mode: 245.0 for IPP and DMAPP, 313.1 for GPP, and 381.1 for FPP. Concentrations of metabolites were determined based on the integrated intensities of peaks generated by PO$_3$—product ion (m/z=79.0). Calibration curves obtained by injection of standards were used to calculate concentrations of metabolites in cell extracts. IPP, DMAPP, GPP, and FPP standards were purchased from Echelon Biosciences Inc. Intracellular concentrations of metabolites were determined based on the assumption that in 1 mL of the culture at $OD_{600}$=200 the integrated volume of all cells is 50 μL.

Results

TABLE 7

Maximum amount of metabolites observed over the course of 48 hours. Metabolite values shown were corrected for $OD_{600}$

| Strain | FPP | GPP | IPP | DMAPP |
|---|---|---|---|---|
| Control strain CMP1043 | 3.675 | 2.648 | 16.747 | 51.543 |
| CMP1082 PyddV-ispA strain | 0.355 | 0.484 | 36.393 | 110.744 |
| CMP1059 - Prot tag | 0.318 | 0.546 | 13.356 | 16.280 |

Example 12

Replacement of *E. coli* Wild-Type Farnesyl Diphosphate Synthase by a Modified Avian Farnesyl Diphosphate Synthase In order to increase the carbon partition from DMAPP into isoprene rather than to lower isoprenoids, it may be useful to use a farnesyl diphosphate synthase with an increased Km value for DMAPP. Such enzymes are described in Fernandez, S. et al., 2000, Biochemistry, 39(50):15316-15321. Accordingly, the wild type *E. coli* farnesyl diphosphate synthase is replaced by the avian enzyme having the A116W or N144'W mutation.

To prepare such a strain, three DNA pieces were generated by PCR. Piece 1 contains a 15 bp sequence allowing assembly by the seamless kit (Invitrogen) to an XbaI/EcoRI-digested vector pBBR1MCS5 (Kovach et al. 1995. Gene 166:175-176), a region homologous to the yhfS region of BL21, a kanamycin marker, and a 15 bp allowing assembly to the promoter of the xseB-ispA-dxs operon. Primers used to obtain that piece are CMP247 (5'-gcggtggcggccgctttgtcatcggttaacgctggaacacctgccgcgcg-caacgttgccagcaccctccttagttcctattccgaagttc-3' (SEQ ID NO:58)) and CMP248 (5'-gctggagctgcttcgaagttcc-3' (SEQ ID NO:59)), and template is pKD4 (Datsenko and Wanner, supra). Piece 2 contains the promoter of the xseB-ispA-dxs operon. Primers used to obtain that fragment were CMP249 (5'-cgaagcagctccagcgaacaatttaatgataaacttcatggcg-3' (SEQ ID NO:60) and CMP250 (5'-AATGAATGTCTGACTCT-CAATATTTTTCGC-3' (SEQ ID NO:61)), and the template is chromosomal DNA of BL21 or a derivative thereof. Primers were designed to allow seamless assembly to piece 1 and piece 3. Piece 3 contains the avian farnesyl diphosphate synthase gene, allele A166W or N144'W, and two sets of 15-bp allowing assembly with piece 2 and pBBR1MCS5 digested by XbaI and EcoRI. Primers used to obtain that fragment are CMP343 (5'-ATAAGCTTGATATCGacctgtcggcact-gaagcaggtcgtcgacgagcaacaaccggatgcggcgTCATTTCTGGC GTTTGTAGATCTTC-3' (SEQ ID NO:62)) and CMP344 (5'-agtcagacattcattatgcataaatttactggtgtcaatg-3' (SEQ ID NO:63), and template is plasmid pA166W for the A166W allele and plasmid pN144'W for the N144'W allele (Fernandez, S. et al., supra).

Polymerase chain reactions (PCR) were all done using Herculase II Fusion according to the protocol recommended by the manufacturer (Agilent, Santa Clara, Calif.). They were purified using the PCR purification kit from Qiagen (Germantown, Md., USA).

Piece 1, 2 and 3 were then assembled with EcoRI/XbaI-digested plasmid pBBR1-MCSS using the GeneArt seamless cloning and assembly kit (Invitrogen, Carlsbad, Calif.), according to the protocol recommended by the manufacturer. The reaction was transformed in E. coli Top10 cells (Invitrogen, Carlsbdad, Calif.), and transformants were selected on LB+kanamycin 20 mg/L. Plasmid was isolated from one of those colonies, and named pCMP1093 for the A166W allele and pCMP1094 for the N144'W allele. The presence of the right construct in the plasmid was confirmed by sequencing (Quintara Bio, Albany, Calif.). Plasmids pCMP1093 and 1094 were used as a template for a PCR reaction using primers CMP257 (5'-cattcgcgccgcattcacagccgattc-gagccaccttcatcaccgcatagttgtcatcggttaacgctggaacac-3' (SEQ ID NO:64)) and CMP258 (5'-GGTTATTATTGAGCA-GATGGGGCTGACGCTTATTACTGT-TGATTTCAATGACCTGTCGG CACTGAAGCAGG-3' (SEQ ID NO: 65)). The PCR products were purified using the Qiagen PCR purification kit (Germantown, Md., USA) and digested with the restriction enzyme DpnI. After further purification, those PCR products were used in a recombineering reaction (Datsenko and Wanner, supra) with strain CMP1018. Transformants were selected on LB+10 mg/L kanamycin. Colonies found to be the correct size by PCR (using primers CMP267 (5'-cgattcgagccaccttcatcacc-3' (SEQ ID NO:66)) and CMP268 (5'-CAG CGTCTTCTGGTGCATGACG-3' (SEQ ID NO:67))) were named CMP1101 and CMP1102 respectively. The kanamycin marker was looped out with pCP20 (Datsenko and Wanner, supra) to make CMP1107 and CMP1108 respectively. To achieve loopout, a colony transformed with pCP20 (grown at 30° C. with 50 mg/L carbenicillin) was streaked on LB and grown at 42° C. overnight. The day after, colonies were picked and patched on LB and LB+10 mg/L kanamycin. A colony with the marker looped out is growing on LB but not on LB+10 mg/L kanamycin. Plasmids MCM82 and pCHL243 were electroporated concomitantly into CMP1107 and 1108. For each, a colony growing on LB+carbenicilin 50 mg/L and spectinomycin 50 mg/L was selected and named CMP1112 and CMP1113 respectively.

Example 13

Construction of Strains Harboring a Convergent Inducible Promoter Behind ispA

An alternate method to decrease the expression of ispA at a given time is to place a convergent inducible promoter downstream of the gene. This method has been applied successfully to decrease the expression of pykF (Krylov et al., 2010, J Mol Microbiol Biotechnol, 18:1-13).

In one embodiment, a Trc promoter is inserted downstream of ispA in strain CMP1018. Plasmids MCM82 (see U.S. Publ. No. 2011/0159557) and pCHL243 are electroporated concomitantly in the strain. A colony growing on LB+carbenicilin 50 mg/L and spectinomycin 50 mg/L is selected and named CMP1112 and CMP1113 respectively. Upon induction with IPTG, the Trc promoter is induced thereby decreasing expression of IspA.

Example 14

Utilization of Antisense RNA to Decrease IspA Expression

Antisense RNA technology presents methodology to obtain attenuation of a targeted gene. It has been used in E. coli, among other organisms, to reduce the production of acetate (Kim J. and Cha H.J., 2003, Biotech Bioeng., 283: 841-853) or to engineer a catalase knockout phenotype (Chan E. et al., 2010, J. Exp. Microbiol Immunol., 14:127-134).

Design of antisense constructs targeted to the ispA gene of E. coli can be prepared using methods described by Shao Y. et al., 2006, Nucleic Acids Res., 34:5660-5669. The antisense RNA molecules can be stabilized using paired termini (Nakashima N. et al., 2006, Nucleic Acids Res., 34:e138). These constructs are placed at the end of the operon in MCM82 or pCHL243. Use of these antisense RNA constructs will result in an increased yield of isoprene.

Example 15

Reduction of ispA Expression Via the Heterologous Repressor Protein HrcA

An alternate method to control expression of ispA is to utilize the previously identified transcriptional repressor HrcA of Caulobacter crescentus (Roberts et al., 1996, Journal of Bacteriology, 178(7):1829-1841; Susin et al., 2004, Journal of Bacteriology, 186(20):6759-6767). The gene encoding HrcA is not naturally found in many microorganisms (e.g., E. coli) and it is not believed that the CIRCE element, which is recognized by HrcA, is involved in governing gene expression in these microorganisms. Therefore, incorporating the CIRCE element within the regulatory sequence governing ispA expression will allow for HrcA-mediated repression of ispA. In addition, the heterologous hrcA gene can be introduced wherein its expression will be governed by at least one of a number of tightly regulated means. Such an engineered regulatory setup will result in the induction of hrcA expression at a defined period during the slow growth phase or high isoprene production phase of fermentation. To exemplify such methods, the following examples of tightly regulated gene expression control systems are described.

In order to eliminate downstream effects on the expression of the essential dxs gene, a two-step process is utilized. First, the 5' half of the ispA is removed from the endogenous locus using standard methods, such as GeneBridges technology (Heidelberg, Germany). This allows the normal expression of the linked genes xseB and dxs to remain intact at the native locus, which forms a three gene operon; xseB-ispA-dxs (see Ecocyc database, ecocyc.org). Second, promoter searches using the online SoftBerry tool BPROM-prediction of bacterial promoters (http://linux1.softberry.com/berry.phtml?topic=bprom&group=programs&subgroup=gfindb) predicts a sigma-70 dependent promoter governing dxs expression to be present in the 3' half of the ispA gene. This proposed ispA deletion occurs subsequent to the introduction of the randomized ispA HrcA-governed allele described directly below.

A sequence encoding a codon randomized version of ispA (see FIG. 8) obtained from Gene Oracle (Mountain View, Calif.) governed by a HrcA-regulated promoter is introduced into the chromosome of an isoprene producing *E. coli* strain using standard GeneBridges techniques. In order to optimize isoprene production, testing of two promoter options for isoprene production may be performed. The option which produces the same levels of ispA as with a wild type ispA locus strain during the growth phase is chosen for future use. The two promoter options include: promoter option 1) a portion of the regulatory sequence upstream of xseB putatively driving expression of the 3 gene operon with a CIRCE element introduced just 3' to the predicted start of transcription; and promoter option 2) a portion of the regulatory region upstream of ispA that encompasses part of the xseB coding sequence and is predicted by the online SoftBerry tool BPROM-prediction of bacterial promoters with a CIRCE element introduced just 3' to the predicted start of transcription. The CIRCE element sequence and placement within the promoter planned to govern ispA expression is derived from information provided in FIG. 10 of Baldini et al., 1998, *Journal of Bacteriology*, 180(7):1632-1641.

For promoter option 1), the bold base alone is the putative start of transcription, underlined sequence is the CIRCE element described in reference (Baldini et al., supra) where the bold underlined are the left and right arms of the CIRCE element inverted repeat, bold lowercase is the predicted RBS, and the lower case atg is the initiation codon.

```
                                            (SEQ ID NO: 68)
CTAACATCGCTTTGCTGTGCACATCACCTTACCATTGCGCGTTATTTGCT

ATTTGCCCTGAGTCCGTTACCATGACGGGCGGTTGGCACTCAATGGAGC

GACTGCTAACAAAAATATTGagagTCAGACATTCATTatg
(Promoter option 1).
```

For promoter option 2), bold base alone is the putative start of transcription, underlined sequence is the CIRCE element described in reference (Baldini et al., supra) where the bold underlined are the left and right arms of the CIRCE element inverted repeat, bold lowercase is the predicted RBS, and the lower case atg is the initiation codon.

```
                                            (SEQ ID NO: 69)
GAGTTCGAACGCGGCGTGC AGCTGGCACG TCAGGGGCAG

GCCAAATTAC AACAAGCCGA ACAGCGCGTACAAATTCTGC

TGTCGTTGGCACTCAATGGAGCGACTGCTAACTGACAA

TGAAGACGCC TCTCTAACCC CTTTTACACC ggacAATGAGTAatg (Promoter option 2)
```

A codon-optimized for expression in *E. coli* allele of hrcA may be obtained from Gene Oracle (Mountain View, Calif.), see FIG. 18 for nucleotide sequence. As discussed previously, the precise promoter governing expression of the HrcA repressor can be derived from a number of physiologically relevant attributes of an *E. coli* isoprene producing system. In one such instance, utilization of IPTG-regulated Tac promoter can be used to express PTac-hrcA from a plasmid vector derived from pK184 (Jobling et al., 1990, *Nucleic Acids Res.*, 18(17):5315-5316). The PTac-hrcA construct is moved into the ΔispA promoter option 1)-randomized ispA background and the ΔispA promoter option 2)-randomized ispA background via standard electroporation techniques and selected for on appropriate antibiotic plates, such as 50 ug/ml kanamycin LB media plates. A set of resulting kanamycin-resistant colonies are isolated and subjected to further assessment to evaluate potential benefits, such as enhanced isoprene production.

For the Tac promoter, bold lowercase is the predicted RBS and the lower case atg is the initiation codon.

```
                                            (SEQ ID NO: 70)
TGTTGACAATTAATCATCGGCTCGTATAATGTGTGGAATTGTGAGCGGAT

AACAATTTCACACAGGAAACAGATTACGGATCCCTggagTTTAAACAT atg (Tac Promoter).
```

Antibodies against IspA can be used to monitor IspA accumulation within liquid cultures. Optionally antibodies against HrcA may be used to monitor repressor levels in order to validate the functionality of this protein within the host. Successful expression and function of the HrcA repressor within an isoprene producing host cell along with the HrcA-repressibility of the designed promoter options 1) and 2) will be reflected by the levels of IspA subsequent to IPTG addition. If promoter options 1) and 2) can be repressed via HrcA binding to the CIRCE element then reduced accumulation of IspA will be observed. This observation will be inversely related to the levels of IPTG inducer added to the culture.

Cells can be monitored microscopically for any phenotypes associated with reduced IspA levels. Further, cell may be monitored for growth rate determination. Significantly reduced levels of IspA is expected to result in slower growth and sub-sufficient or loss of IspA accumulation is expected to arrest growth and reduce cell viability. In addition, qRT-PCR of ΔispA promoter option 1)-randomized ispA and ΔispA promoter option 2)-randomized ispA backgrounds may be performed to determine what levels of IspA and ispA mRNA are generated by each promoter option in the absence of HrcA expression. This information along with the growth and behavior of the strains will help guide which promoter provides optimal control of expression.

Example 16

Xylose Regulated Expression of ispA

As described herein, decreased expression of ispA can substantially increase the yield of isoprene produced from glucose by cells engineered to produce isoprene. Regulated gene expression mediated by carbon source availability is another scalable alternative to controlling ispA expression within the production host. Such a method offers the ability to provide relatively normal and/or sufficient levels of ispA expression required for healthy robust fast growing cells, allowing quick biomass placement. In addition, such a method offers the ability to restrict expression of ispA during the major window of glucose-supported isoprene production when IspA activity is believed to be detrimental to cell viability, resulting in reduced yield of isoprene produced from glucose. The use of carbon source regulated gene expression is economically feasible at large scale where chemical inducers such as IPTG can prove costly.

In one example, ispA expression in an isoprene-producing host strain is placed under the direct control of the xylA or xylF promoters endogenous to *E. coli* or under control of any promoter that is positively influence by D-xylose and negatively influenced by glucose within an *E. coli* isoprene-producing engineered cell. This is accomplished by deleting the endogenous ispA gene and substituting a heterologous ispA under the control of either the xylA or xylF D-xylose-responsive promoters. The divergent xylA-xylF promoters of *E. coli* and their positive regulation via D-xylose and the transcriptional activator XylR as well as their negative regulation by glucose and catabolite repression have been described (S. Song and C. Park, 1997, *J. Bacterial.* 179(22):7025-7032). In these cells, IspA activity is governed positively by the availability of xylose in the absence of glucose and negatively by the presence of glucose. The xylose-inducible ispA locus is present within the chromosome of the host, but, alternatively, may also be encoded on an extrachromosomal nucleotide sequence such as a plasmid. Construction of the xylose-inducible ispA construct and its introduction into the isoprene producing *E. coli* host can be performed using standard molecular and microbiology techniques (J. Sambrook, E. F. Fritsch, and T. Maniatis Cold Spring Harbor Laboratory Press, NY. 1989).

Growth of the isoprene-producing strain harboring either the xylA promoter-ispA or the xylF promoter-ispA as the only locus encoding IspA activity is performed initially in the presence of D-xylose as the sole carbon source. At the desired time into the fermentation run glucose is introduced into the fermentor, which effectively represses the expression of ispA and permits the rapid transition of respiration to be driven by glucose metabolism. Glucose remains the carbon source utilized for the production of isoprene for the remainder of the fermentation run. In the presence of glucose, the decreased transcription from the xylA promoter-ispA or the xylF promoter-ispA locus and the intrinsic half-life of the encoded IspA previously expressed in the absence of glucose results in the significant loss of IspA activity during the window of high level glucose-supported isoprene production, enhancing cell viability and allowing improved yield of isoprene generated from glucose by the isoprene producing host strain.

Example 17

Construction of Strain CMP1136 (-PGL)

A PCR product containing a Kanamycin cassette flanked by FRT sites and regions homologous to upstream and downstream of pgl (ybhE) was obtained, using the PCR method described in example 4, Keio strain JW0750 (Baba et al. 2006. *Mol. Syst. Biol.* 2:1-11) which contains a kanamycin cassette in the pgl locus, and primers pgl AmpF (5'-cagcaaat-agcaggtgtatccagc-3' (SEQ ID NO:71) and pgl AmpR (5'-GCA ACC GAC TGT TGA TAG AAC AAC-3' (SEQ ID NO:72)). This PCR product was used in a recombineering reaction (see protocol described above) with *E. coli* CMP1075 (supra). A colony was selected on LB+kanamycin 10 mg/L and named CMP1125. The kanamycin marker was removed using the protocol recommended by the manufacturer (Gene Bridges, Heidelberg, Germany) to form strain CMP1133.

CMP1133 was checked by PCR with primers pgl AmpF (supra) and pgl RecCheck (5'-GGT TAC AAA ATG ATT GGC GTA CGC-3' (SEQ ID NO:73)) to demonstrate deletion of the pgl gene. Plasmids MCM82 and pCHL243 were electroporated concomitantly into CMP1133. A colony growing on LB+carbenicilin 50 mg/L and spectinomycin 50 mg/L was selected and named CMP1136.

Example 18

Large Scale Fermentation of CMP1136

This experiment was performed to evaluate isoprene production from *E. coli*(BL21) expressing introduced genes from the mevalonate pathway and grown in fed-batch culture at the 15-L scale. An isoprene producing strain CMP1082 (HMB GI1.2gltA, PyddVIspA_GO, truncIspA, pMCM82, pDW72) was run in a standard isoprene production process, described below. The performance metrics (cumulative isoprene yield on glucose, instantaneous isoprene yield on glucose, volumetric productivity of isoprene, specific productivity and cell productivity index) are compared to an experimental strain CMP1136 (HMB GI1.2gltA, PyddVIspA_GO, truncIspA,pgl-, pMCM82, pDW72) that was run in the same conditions to see if any yield improvement can be attributed to the deletion of the pgl gene in CMP1136.

Medium Recipe (Per Liter Fermentation Medium): $K_2HPO_4$ 7.5 g, $MgSO_4*7H_2O$ 2 g, citric acid monohydrate 2 g, ferric ammonium citrate 0.3 g, yeast extract 0.5 g, 50% sulphuric acid 1.6 mL, 1000×Modified Trace Metal Solution 1 ml. All of the components were added together and dissolved in Di $H_2O$. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000×Modified Trace Metal Solution (Per Liter): Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component was dissolved one at a time in Di $H_2O$, pH was adjusted to 3.0 with HCl/NaOH, and then the solution was q.s. to volume and filter sterilized with a 0.22 micron filter.

Vitamin Solution (Per Liter): Thiamine hydrochloride 1.0 g, D-(+)-biotin 1.0 g, nicotinic acid 1.0 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Macro Salt Solution (Per Liter): $MgSO_4*7H_2O$ 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di $H_2O$ 0.393 kg, $K_2HPO_4$ 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000×Modified Trace Metal Solution 0.82 ml.

This experiment was carried out to monitor isoprene formation from glucose at the desired fermentation pH (7.0) and temperature (34° C.). A frozen vial of the *E. coli* strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L.

The batched media had glucose batched in at 9.7 g/L. Induction was achieved by adding isopropyl-beta-D-1-thiogalactopyranoside (IPTG). IPTG was added to the tank to bring the concentration to 200 uM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 68 to 72 hrs elapsed fermentation time.

Results

Figure 19:
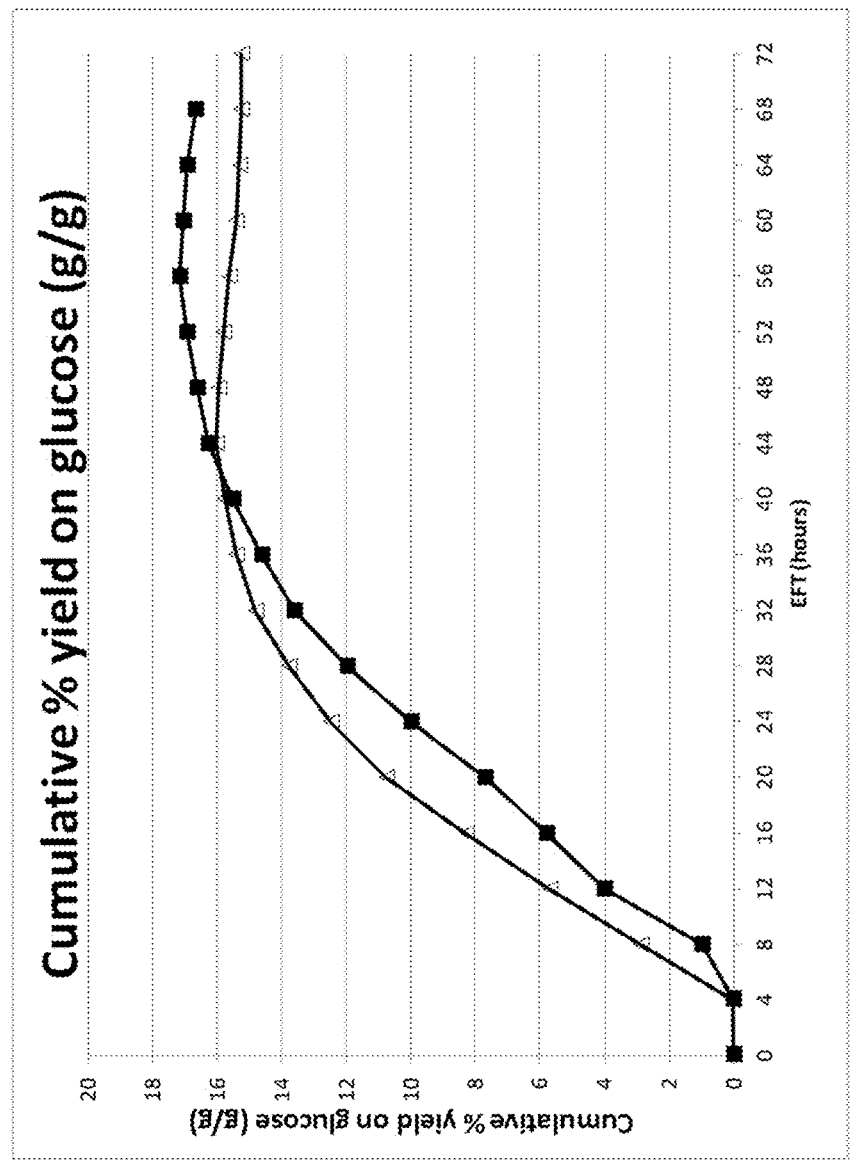
FIG. 19 depicts yield of isoprene on glucose achieved in each 15-L fermentation over time. CMP1082 (pgl+) is depicted by open triangles and CMP1136 (pgl−) is depicted by closed squares.
Figure 20:
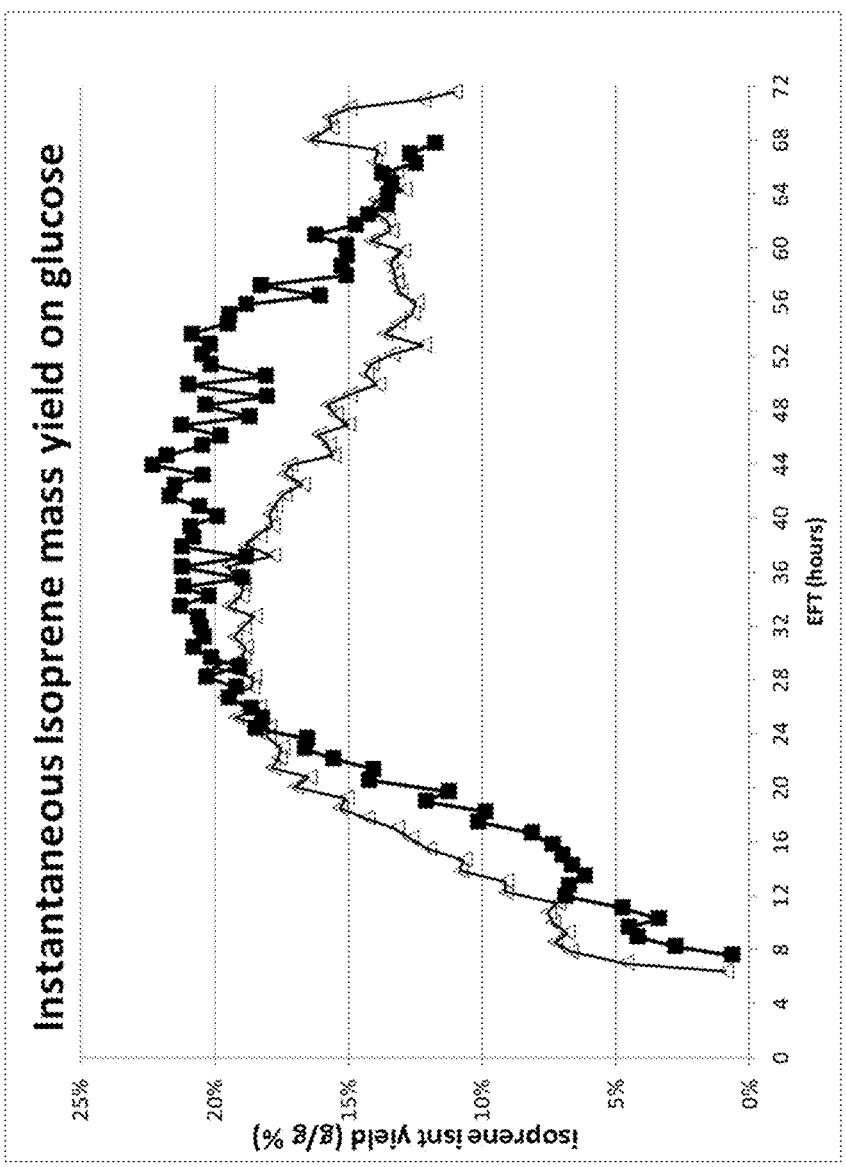
FIG. 20 depicts instantaneous yield of isoprene on glucose achieved in each 15-L fermentation over time. CMP1082 (pgl+) is depicted by open triangles and CMP1136 (pgl−) is depicted by closed squares.
Figure 21:
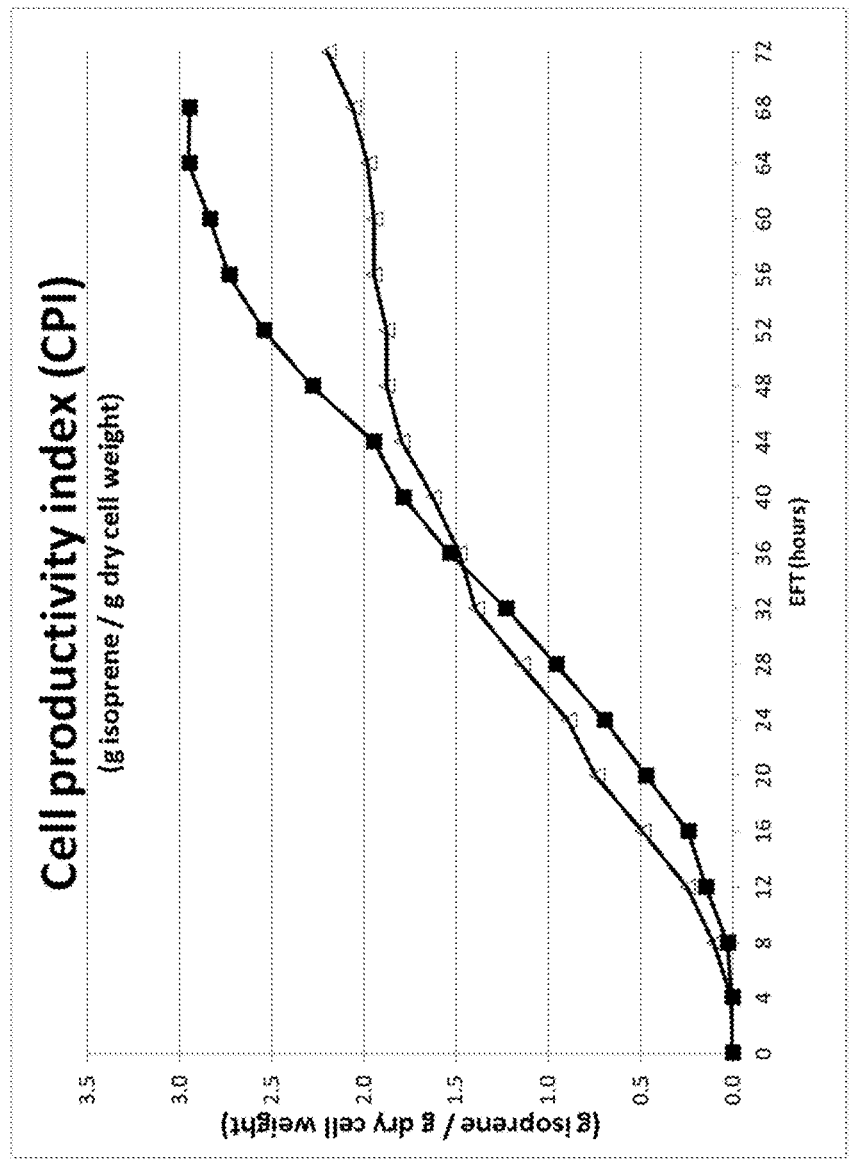
FIG. 21 depicts Cell Productivity Index (CPI) achieved in each 15-L fermentation over time. CMP1082 (pgl+) is depicted by open triangles and CMP1136 (pgl−) is depicted by closed squares.
Figure 22:
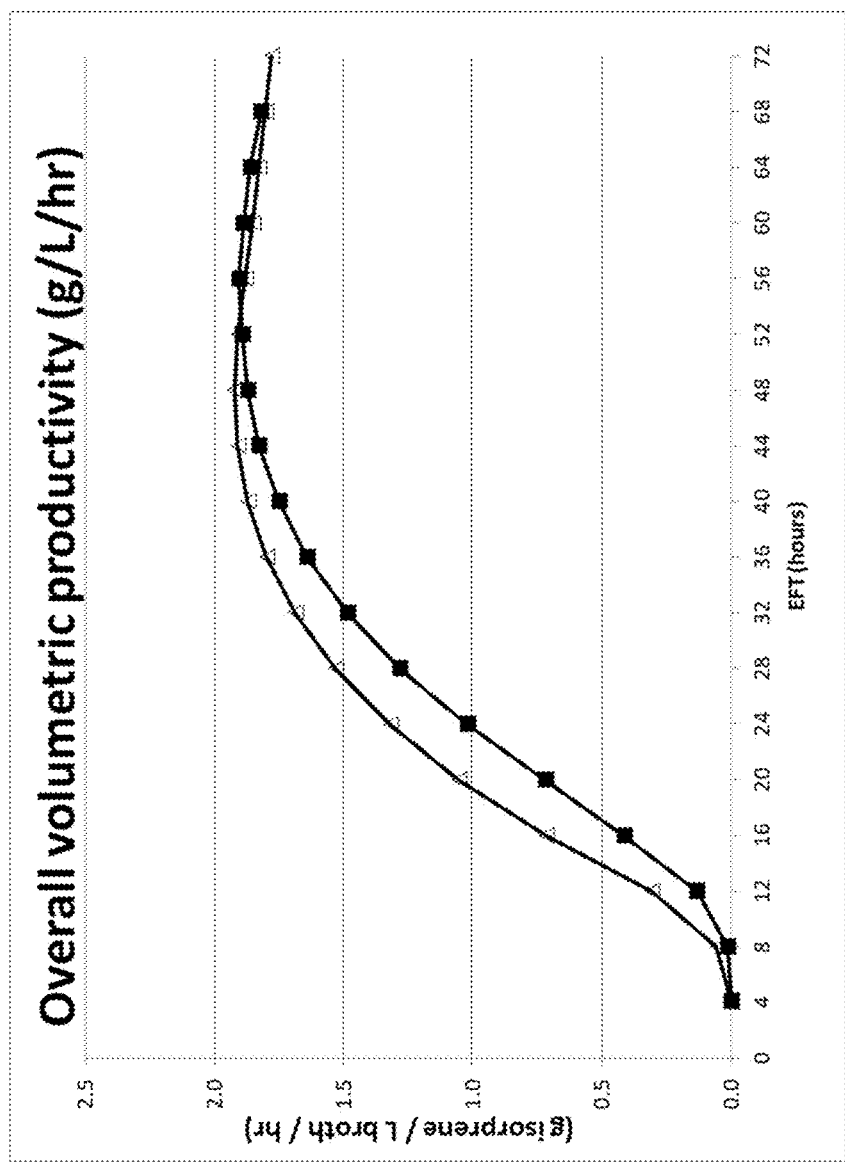
FIG. 22 depicts volumetric productivity achieved in each 15-L fermentation over time. CMP1082 (pgl+) is depicted by open triangles and CMP1136 (pgl−) is depicted by closed squares.
Figure 23:
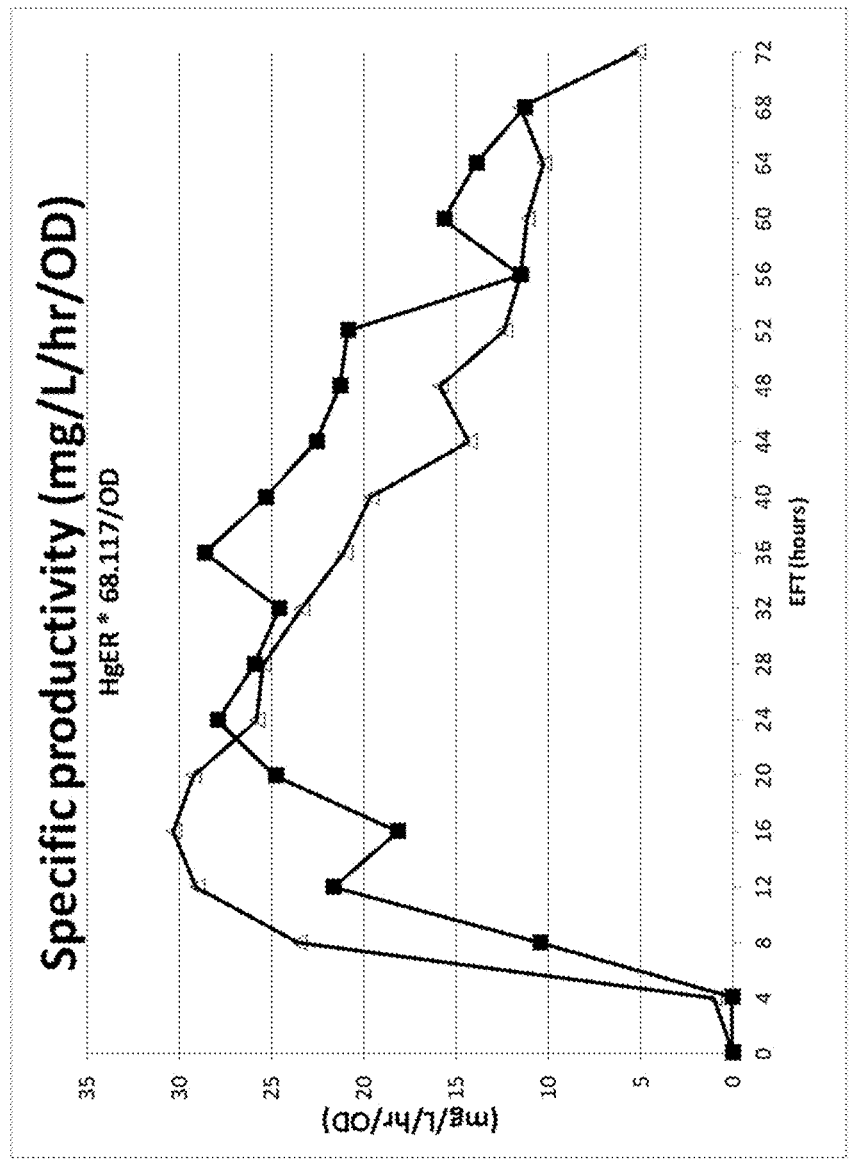
FIG. 23 depicts specific productivity achieved in each 15-L fermentation over time. CMP1082 (pgl+) is depicted by open triangles and CMP1136 (pgl−) is depicted by closed squares.

The pgl-strain (CMP1136) achieved a higher % yield of isoprene on glucose than the pgl+ strain (CMP1082). See Table 8 and FIG. 19. The pgl− strain (CMP1136) achieved a higher instantaneous % yield of isoprene on glucose than the pgl+ strain (CMP1082) and was able to maintain this high productivity for a longer period of time (~24 hrs at max for pgl− versus ~12 hrs at max for pgl+). See Table 8 and FIG. 20. The pgl− strain (CMP1136) achieved a higher cell productivity index than the pgl+ strain (CMP1082). At the end of fermentation 68 to 72 hrs, the pgl-strain had a much higher CPI. Also, at the time of maximum cumulative yield of isoprene on glucose (44 hrs for the pgl+ strain and 56 hrs for the pgl− strain) the CPI is higher in the pgl− strain. See Table 8 and FIG. 21. The pgl− strain (CMP1136) achieved about the same overall volumetric productivity as the pgl+ strain (CMP1082). See Table 8 and FIG. 22. The pgl− strain (CMP1136) achieved about the same peak specific productivity as the pgl+ strain (CMP1082). However, the pgl− strain (CMP1136) was able to maintain this high productivity for a longer period of time than the pgl+ strain (CMP1082) and was notably better late in the fermentation. See Table 8 and FIG. 23.

*E. faecalis* (strain DW709 and DW717), *E. casseliflavus* (DW718) or *E. gallinarum* (DW719, MCM2158 (BL21 t pgl, GI1.2gltA pgl-, yhfSFRTPyddVIspAyhfS thiFRTtruncIspA, FRT-PL.2-2cis-RBS10000-MVK(*burtonii*)-KDyI+ pTrcAlba-MVKde12+pCL-Ptrc-Upper_Egallinarum)).

(i) Materials and Methods

Strain Construction: Strains DW709, DW717, DW718, and DW719 were generated by co-transformation of a plasmid harboring an isoprene synthase (IspS) variant and one of four plasmids harboring different upper MVA pathways into a production host strain of *Escherichia coli*. Following standard molecular biology techniques, the host strain CMP1133 (BL21 Δpgl PL.2mKKDyI GI1.2gltA yhfSFRTPyddVIspAyhfS thiFRTtruncIspA) was electroporated with pDW240 (pTrc *P. alba* IspS MEA-mMVK (Carb50)), carrying an IspS variant, and either pMCM82 (U.S. Patent Application Publication No.: 2009/0203102), pCHL276 (pCLpTrc-Upper(*E. faecalis*)-leaderless), pCHL277 (pCLpTrc-Upper(*E. casseliflavus*)-leaderless), or pMCM1225 (pCL-Ptrc-Upper_*E. gallinarum*). Cells were recovered and plated on selective medium, and individual transformants, resistant to spectinomycin and carbenicillin, resulted in strains DW709, DW717, DW718, and DW719. These isoprene production strains expressed an IspS variant and either the upper MVA pathway from *Enterococcus faecalis*, the leaderless upper MVA pathway from *Enterococcus faecalis*, the upper MVA pathway from *Enterococcus casseliflavus*, or the upper MVA pathway from *Enterococcus gallinarum*, respectively (see Table 9).

TABLE 8

Isoprene productivity metrics

| Strain description/ Run Number | Inlet Oxygen Conc. (vol %) | Peak instantaneous % yield of isoprene on glucose (g/g %) | Overall Isoprene Volumetric Productivity (g/L/hr) at time of max overall isoprene yield | Max Overall % Yield of Isoprene on glucose (g/g) | CPI (g Isoprene/ gDCW) at time of max overall isoprene yield | Peak Specific Productivity (mg isoprene/ L/hr/OD) |
|---|---|---|---|---|---|---|
| CMP1082/ 20111110 | 9.3% | 20.1 | 1.91 | 16.3 | 1.81 | 30.31 |
| CMP1136/ 20111225 | 9.3% | 22.3 | 1.82 | 17.2 | 2.73 | 28.61 |

Example 19

Isoprene Production from *E. coli* Expressing Upper MVA Pathway Genes

This example evaluated isoprene production in *E. coli* (BL21) expressing introduced genes from the mevalonate pathway and grown in fed-batch culture at the 15-L scale. The genes for the upper MVA pathway enzymes came from either Strain MCM2065 was electroporated with plasmid pMCM2149 and transformants selected on LA carb50 plates at room temperature for three days. A single colony was grown to midlog in LB carb50, frozen and stored in 33% glycerol at −80 as MCM2152. MCM2152 was electroporated with plasmid pMCM1225 and transformants selected on LA carb50 spec50 plates. A single colony was grown to midlog in LB carb50 spec50, brought to 33% glycerol and frozen as MCM2158.

TABLE 9 isoprene-producing strains

| Strain name | genotype | Host parent | plasmids |
|---|---|---|---|
| DW709 | BL21 GI1.2gltA PL.2 MKKDyI t pgl pgl-, yhfSFRTPyddVIspAyhfS thiFRTtruncIspA, pTrc(IspS variant)_mMVK, pCLPtrcUpper_E.faecalis | CMP1133 | pDW240, pMCM82 |

TABLE 9-continued isoprene-producing strains

| Strain name | genotype | Host parent | plasmids |
|---|---|---|---|
| DW717 | BL21 GI1.2gltA PL.2 MKKDyI t pgl pgl-, yhfSFRTPyddVIspAyhfS thiFRTtruncIspA, pTrc(IspS variant)_mMVK, pCLPtrcUpper_E.faecalis_leaderless | CMP1133 | pDW240, pCHL276 |
| DW718 | BL21 GI1.2gltA PL.2 MKKDyI t pgl pgl-, yhfSFRTPyddVIspAyhfS thiFRTtruncIspA, pTrc(IspS variant)_mMVK, pCLPtrcUpper_E.casseliflavus | CMP1133 | pDW240, pCHL277 |
| DW719 | BL21 GI1.2gltA PL.2 MKKDyI t pgl pgl-, yhfSFRTPyddVIspAyhfS thiFRTtruncIspA, pTrc(IspS variant)_mMVK, pCLPtrcUpper_E.gallinarum | CMP1133 | pDW240, pMCM1225 |
| MCM2158 | BL21 t pgl, GI1.2gltA pgl-, yhfSFRTPyddVIspAyhfS thiFRTtruncIspA, FRT-PL.2-2cis-RBS10000-MVK(*burtonii*)-KDyI + pTrcAlba-MVKdel2 + pCL-Ptrc-Upper_Egallinarum | CMP1133 | pDW240 |

Medium Recipe (Per Liter Fermentation Medium): K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000×Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000×Modified Trace Metal Solution (Per Liter): Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter): Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter): MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram): Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000×Modified Trace Metal Solution 0.82 ml.

This experiment was carried out to monitor isoprene formation from glucose at the desired fermentation pH (7.0) and temperature (34° C.). A frozen vial of the *E. coli* strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L. The isoprene producing strains were run in a fed-batch fermentation process.

The batched media had glucose batched in at 9.7 g/L. Induction was achieved by adding isopropyl-beta-D-1-thiogalactopyranoside (IPTG). A shot of IPTG was added to the tank to bring the concentration to 200 uM when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 64 to 68 hrs elapsed fermentation time.

Analysis: Isoprene is volatile and can be efficiently swept from the tank by the inlet gas. The isoprene level in the bioreactor off-gas was determined using two mass spectrometers, an iSCAN (Hamilton Sundstrand), and a Hiden HPR20 (Hiden Analytical) mass spectrometer. Oxygen, Nitrogen, and CO2 levels in the offgas were determined by the same mass spec units. Dissolved Oxygen in the fermentation broth is measured by sanitary, sterilizable probe with an optical sensor provided Hamilton Company.

The citrate, glucose, acetate, and mevalonate concentrations in the fermentor broth was determined in broth samples taken at 4 hour intervals by an HPLC analysis. Concentration in broth samples were determined by comparison of the refractive index response versus a previously generated calibration curve using standard of a known concentration.

(ii) Results

TABLE 10

Isoprene productivity metrics

| Strain description/ Run Number | Overall Isoprene Volumetric Productivity (g/L/hr) (at peak yield) | Peak Overall % Yield of Isoprene on glucose (g/g) | Peak Specific Productivity (mg isoprene/ L/hr/OD) |
|---|---|---|---|
| DW709/ 20120108 | 1.89 | 16.35 | 26.0 |
| DW717/ 20120131 | 1.97 | 16.46 | 27.7 |

TABLE 10-continued

Isoprene productivity metrics

| Strain description/ Run Number | Overall Isoprene Volumetric Productivity (g/L/hr) (at peak yield) | Peak Overall % Yield of Isoprene on glucose (g/g) | Peak Specific Productivity (mg isoprene/ L/hr/OD) |
|---|---|---|---|
| DW718/ 20120132 | 2.44 | 17.54 | 37.6 |
| DW719/ 20120133 | 2.38 | 18.16 | 34.3 |
| MCM2158/ 20120409 | 2.11 | 17.35 | 38.6 |
| CMP1043 Control strain | 1.69 | 14.26 | 26.87 (at 16 hrs EFT) |

Figure 24:
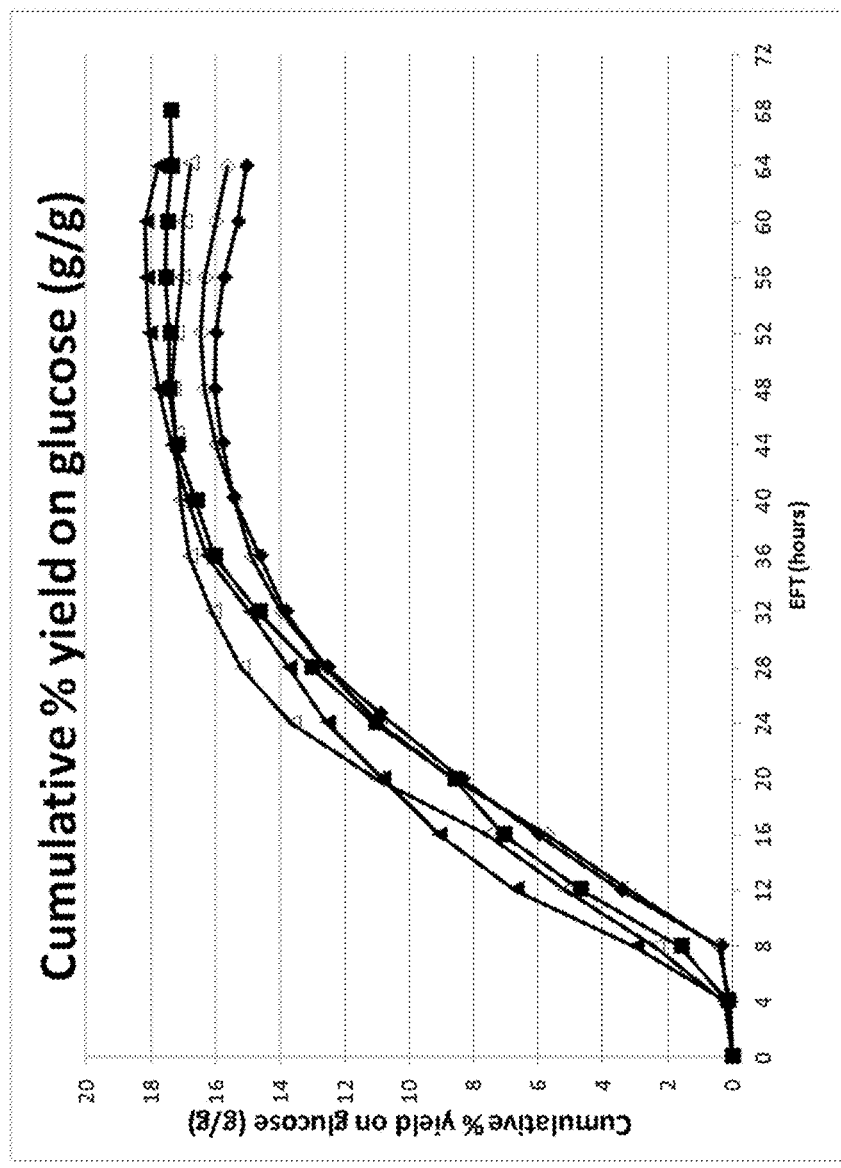
FIG. 24 depicts yield of isoprene on glucose achieved in each 15-L fermentation over time. All runs using the E. gallinarum or E. casseliflavus (triangles and squares, respectively) achieved a higher % yield of isoprene on glucose than the two runs using E. faecalis upper pathway enzymes (open and closed diamonds). % wt Yield on glucose calculated as isoprene total (t)/[(Feed Wt(0)−Feed Wt(t)+83.5)*0.59)], where 0.59 is the wt % of glucose in the glucose feed solution and 83.5 is the grams of this feed batched into the fermentor at t=0. Each feed had its weight % measured independently.
Figure 25:
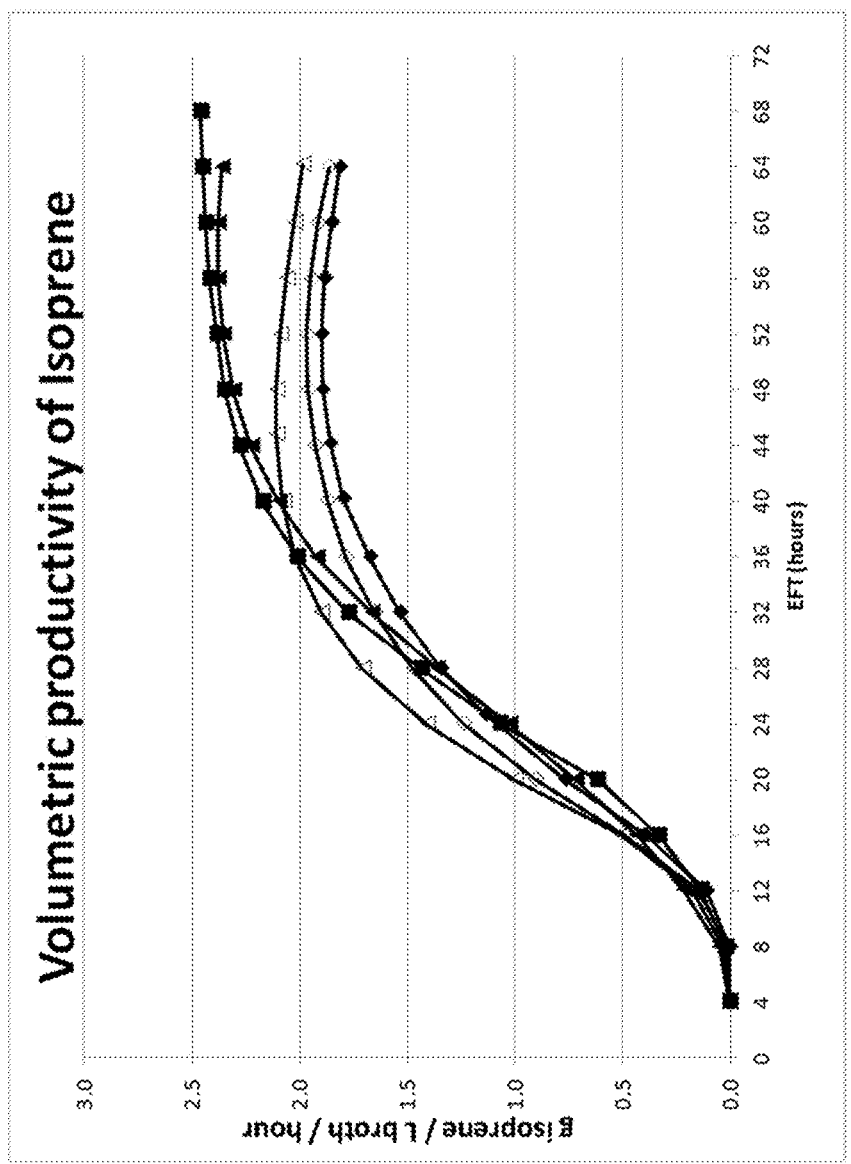
Figure 26:
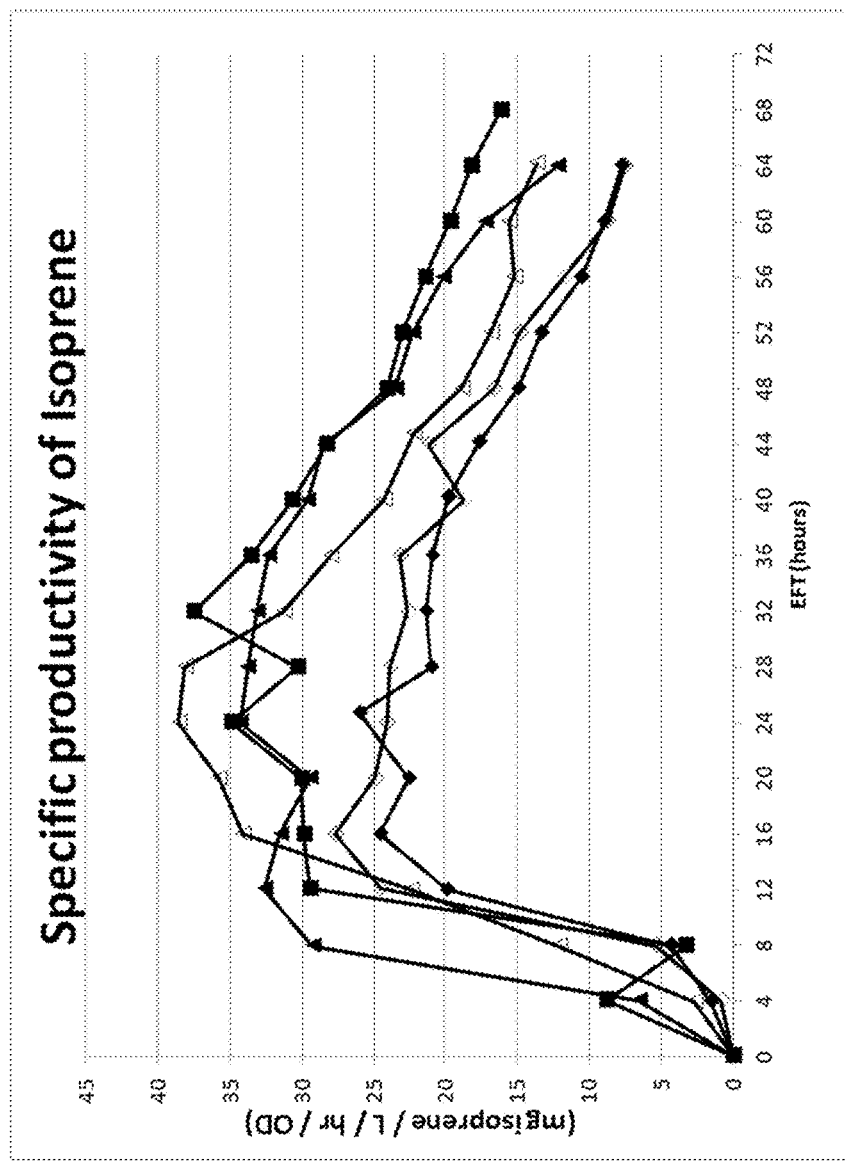
FIG. 26 depicts specific productivity achieved in each 15-L fermentation over time. All runs using the E. gallinarum or E. casseliflavus (triangles and squares, respectively) achieved a higher peak specific productivity than the two runs using E. faecalis upper pathway enzymes (open and closed diamonds). Specific Productivity was calculated using the following formula: Specific productivity (mg/L/hr/OD)=HgER*68.117 g/mol/OD. HgER is the Isoprene Evolution Rate in (mmol/L/hr). OD=optical density=Absorbance at 550 nm*dilution factor in water.

As summarized in Table 10, compared to fermentations using the upper MVA pathway of *E. faecalis*, fermentations using either *E. gallinarum* or *E. casseliflavus* upper MVA pathway enzymes exhibited overall higher mass yield (FIG. 24), higher peak volumetric productivity (FIG. 25), higher peak specific productivity (FIG. 26). Additionally, acetyl Co-A levels in the cells were lower when the strain harbored an *E. casseliflavus* or an *E. gallinarum* pathway (Table 11). This reduction is acetyl-CoA levels is indicative of increased carbon flux into the MVA pathway in cells.

TABLE 11

Acetyl-CoA levels (mM) at around 24 h of Elapsed Fermentation Time (EFT) in strains of identical background but with different Upper mevalonate pathway having upper MVA pathways from *E. gallinarum* or *E. casseliflavus*.

| Upper | *E. faecalis* (DW717) - 20 h | *E. casseliflavus* (DW718) - 24 h | *E. gallinarum* (DW719) - 24 h |
|---|---|---|---|
| Acetyl-CoA (mM) | 6.34 | 3.57 | 3.56 |

Example 20

Design of Ribosomal Binding Sites (RBSs) to Modify IspA Expression

RBS Calculator optimization software was used with RNA thermodynamic parameters calculated using the Vienna RNA Package v.1.8.4 (worldwide web.tbi.univie.ac.at/~ivo/RNA/, Andreas R. Gruber, Ronny Lorenz, Stephan H. Bernhart, Richard Neubock, and Ivo L. Hofacker (NAR, 2008)) and the Vienna RNA module for the RBS Calculator. RBSs were calculated on a Linux server running Python v.2.4.3.

(i) Materials and Methods

The transcriptional start site for PyddV is unknown, so sequences from the Pyddv-IspA construct including 40, 30 or 20 nt upstream of the IspA ORF and the first 50 nt of the ORF were analyzed for predicted RBS strength (see Table 12).

TABLE 12

Predicted RBS score.

| Upstream Nucleotides | RBS score |
|---|---|
| 40 | 74.5145721603 |
| 30 | 51.9851812562 |
| 20 | 219.445238073 |

75 was chosen as a target strength for design work. New RBSs were designed using the 5' UTR upstream of the RBS (27 nt, starting 40 nt upstream of the ORF) and 50 nt of ORF sequence. Multiple RBSs of a given target strength were calculated. RBSs of targeted strengths 8, 25, 225, and 675 (⅑×, ⅓×, 3×, and 9× the endogenous RBS score of 75) were designed using the upstream 5' UTR sequence tgattccgtct-gatttcccagccttat (SEQ ID NO:74) and downstream ORF sequence atggactttccgcaacaattggaggcgt-gcgtaaagcaagcaaatcaagc (SEQ ID NO:75).

(ii) Results

Through multiple rounds of computational design, two to three RBSs were designed for each target score (see Table 13).

TABLE 13

Designed RBSs.

| name | Target Score | RBS | score |
|---|---|---|---|
| PyddV-ispA_3A | 3 | ACTGTCAGGTCAACACTTACTTAAGAAAC (SEQ ID NO: 76) | 3.123885295 |
| PyddV-ispA_3B | 3 | TCGAGGGAGCCAAAAAAAACAAAACTTACTT (SEQ ID NO: 77) | 3.051627863 |
| PyddV-ispA_8A | 8 | CGAACATAAAGCAGACGTCAGCATTCGAAC (SEQ ID NO: 78) | 8.0960213 |
| PyddV-ispA_8B | 8 | TACCGGATACGAACGGAAGCCTATCGCAATT (SEQ ID NO: 79) | 7.267133647 |
| PyddV-ispA_8C | 8 | GGACAATTCTACTACACT (SEQ ID NO: 80) | 8.638070397 |
| PyddV-ispA_25A | 25 | TCTAGAGAAAGAGGGGAAACACTAG (SEQ ID NO: 81) | 23.12415389 |
| PyddV-ispA_25B | 25 | TCTAGAGAAAGAGGGGAAATACTAT (SEQ ID NO: 82) | 24.18861806 |

TABLE 13-continued

Designed RBSs.

| name | Target Score | RBS | score |
|---|---|---|---|
| PyddV-ispA_25C | 25 | TCTACGAGAAAAAGGGACTGACAAGA (SEQ ID NO: 83) | 27.83505607 |
| PyddV-ispA_225A | 225 | TCGAGAGATTAAACAGGCAGAAATACTAG (SEQ ID NO: 84) | 214.3693317 |
| PyddV-ispA_225B | 225 | GTCGTAGAGATTTAGTAAGGAGCCACTAT (SEQ ID NO: 85) | 240.1134974 |
| PyddV-ispA_225C | 225 | ATCTGGAGATTAAAGCAGAGAAATACTAG (SEQ ID NO: 86) | 222.2280211 |
| PyddV-ispA_675A | 675 | TCCAATAATTACAGCCAGGAGACAGACTAT (SEQ ID NO: 87) | 716.1008352 |
| PyddV-ispA_675B | 675 | TACAGAAATTAAAAGGAACAATATTAG (SEQ ID NO: 88) | 684.5875142 |
| PyddV-ispA_675C | 675 | TGCTGAGGTTAAAGAGGAAAATAATAT (SEQ ID NO: 89) | 710.9629141 |

Analysis of predicted RBS strength for these RBSs in the context of UTRs of different lengths showed less length dependence than with the endogenous RBS.

Example 21

Cloning/Expression of Various RBS Calculator Constructs

Plasmid pCMP1046 was submitted to a Quikchange reaction according to the manufacturer's protocol (Agilent, Santa Clara, Calif.) to get three altered RBSs. The primers that were used are listed in Table 14. After DpnI digest, the reaction was transformed in *E. coli* Top10 cells (Invitrogen, Carlsbdad, Calif.) and transformants were selected on LB+kanamycin 20 mg/L. Plasmids were isolated from 6 colonies per reaction and sent for sequencing. Plasmids containing the desired RBSs were named pCMP1249 (RBS 1/3), pCMP1258 (RBS 3) and pCMP1259 (RBS 9), respectively.

Plasmids pCMP1249, 1258 and 1259 were used as templates for PCR reactions using primers CMP257 (5'-cat-tcgcgccgcattcacagccgattcgagc-caccttcatcaccgcatagttgtcatcggttaacgctggaacac-3' (SEQ ID NO:90)) and CMP258 (5'-GGTTATTATTGAGCA-GATGGGGCTGACGCTTATTACTGT-TGATTTCAATGACCTGTCGG CACTGAAGCAGG-3' (SEQ ID NO:91)). The PCR products were purified using the Qiagen PCR purification kit (Germantown, Md., USA) and digested with the restriction enzyme DpnI. After further purification, the PCR products were used in a recombineering reaction (Datsenko and Wanner, supra) with strain CMP1133. Transformants were selected on LB+10 mg/L kanamycin. One colony for each transformation, found to be the correct size by PCR (using primers CMP267 (5'-cgattcgagccaccttcat-cacc-3' (SEQ ID NO:92)) and CMP268 (5'-CAGCGTCT-TCTGGTGCATGACG-3' (SEQ ID NO:93))) was named CMP1067. The kanamycin marker was looped out with pCP20 (Datsenko and Wanner, supra) to make CMP1262, CMP1266 and CMP1267, respectively (see Table 15). To achieve loopout, a colony transformed with pCP20 (grown at 30° C. with 50 mg/L carbenicillin) was streaked on LB and grown at 42° C. overnight. The following day, colonies were picked and patched on LB and LB+10 mg/L kanamycin. A colony with the marker looped out grows on LB but not on LB+10 mg/L kanamycin. Plasmids pMCM1225 and pDW240 were electroporated concomitantly into CMP1265, 1266 and 1267. For each transformation, a colony growing on LB+carbenicilin 50 mg/L and spectinomycin 50 mg/L was selected. They were named CMP1275, CMP1284 and CMP1286, respectively (see Table 15).

TABLE 14

Primers used to introduce altered RBSs in the PyddV-IspA construct.

| Primer name | Primer sequence |
|---|---|
| QCPyddV-ispA1/3F | Ctgatttcccagccttat TCTAGAGAAAGAGGGGAAACACTAGatgga ctttccgcaacaattg (SEQ ID NO: 94) |
| QCPyddV-ispA1/3R | CAA TTG TTG CGG AAA GTC CAT CTA GTG TTT CCC CTC TTT CTC TAG AAT AAG GCT GGG AAA TCA G (SEQ ID NO: 95) |
| QCPyddV-ispA3F | Ctgatttcccagccttat ATCTGGAGATTAAAGCAGAGAAATACTAGat ggactttccgcaacaattg (SEQ ID NO: 96) |
| QCPyddV-ispA3R | CAA TTG TTG CGG AAA GTC CAT CTA GTA TTT CTC TGC TTT AAT CTC CAG ATA TAA GGC TGG GAA ATC AG (SEQ ID NO: 97) |

TABLE 14-continued

Primers used to introduce altered RBSs in the PyddV-IspA construct.

| Primer name | Primer sequence |
|---|---|
| QCPyddV-ispA9F | CtgatttcccagccttatTACAGAAATTAAAAGGAACAATATTAGatg gactttccgcaacaattg (SEQ ID NO: 98) |
| QCPyddV-ispA9R | CAA TTG TTG CGG AAA GTC CAT CTA ATA TTG TTC CTT TTA ATT TCT GTA ATA AGG CTG GAA AAT CAG (SEQ ID NO: 99) |

TABLE 15

Strain descriptions.

| Strain name | Genotype | Parent | Plasmids |
|---|---|---|---|
| CMP1262 | BL21 t pgl, GI1.2gltA pgl-PL.2mKKDyI pgl yhfS-pKD4-PyddV(1/3rbs)ispA | CMP1133 | None |
| CMP1266 | BL21 t pgl, GI1.2gltA pgl-PL.2mKKDyI pgl yhfS-pKD4-PyddV(3rbs)ispA | CMP1133 | None |
| CMP1267 | BL21 t pgl, GI1.2gltA pgl-PL.2mKKDyI pgl yhfS-pKD4-PyddV(9rbs)ispA | CMP1133 | None |
| CMP1275 | BL21 t pgl, GI1.2gltA pgl-PL.2mKKDyI pgl yhfS-FRT-PyddV(1/3rbs)ispA, pCLPtrcUppergallinarum, pTrc(MEA variant) alba_mMVK | CMP1262 | pMCM1225, pDW240 |
| CMP1284 | BL21 t pgl, GI1.2gltA pgl-PL.2mKKDyI pgl yhfS-FRT-PyddV(3rbs)ispA, pCLPtrcUppergallinarum, pTrc(MEA variant) alba_mMVK | CMP1266 | pMCM1225, pDW240 |
| CMP1286 | BL21 t pgl, GI1.2gltA pgl-PL.2mKKDyIpgl yhfS-FRT-PyddV(9rbs)ispA, pCLPtrcUppergallinarum, pTrc(MEA variant) alba_mMVK | CMP1267 | pMCM1225, pDW240 |

Example 22

Farnesyl Diphosphate Synthase (IspA) Expression Analysis

A sandwich ELISA method was developed to quantify farnesyl diphosphate synthase (IspA) expression levels in *E. coli* cell lysate. Using this method, the concentration of IspA was analyzed for the strains described in Table 16.

TABLE 16

Strain descriptions.

| No | Strain # | Fermentation # | Genotype |
|---|---|---|---|
| 1 | BL21 | 20120607 | Wild type strain |
| 2 | CMP1286 | 20120571 | BL21 t pgl, GI1.2gltA pgl- PL.2mKKDyIpgl yhfS-FRT-PyddV(9rbs)ispA-go, pCLPtrcUppergallinarum, pTrc(MEA variant) alba mMVK double transformation |
| 3 | CMP1284 | 20120572 | BL21 t pgl, GI1.2gltA pgl- PL.2mKKDyI pgl yhfS-FRT-PyddV(3rbs)ispA-go, pCLPtrcUppergallinarum, pTrc(MEA variant) alba mMVK double transformation |
| 4 | DW719 | 20120565 | BL21 t pgl, GI1.2gltA pgl- PL.2mKKDyI BL21 t pgl, GI1.2gltA pgl- PL.2mKKDyI pgl-, *E. gallinarum* upper (pMCM1225), Ptrc-*P. alba* IspS (MEA variant)mMVK (pDW240) |
| 5 | CMP1275 | 20120566 | BL21 t pgl, GI1.2gltA pgl- PL.2mKKDyI pgl yhfS-FRT-PyddV(1/3rbs)ispA col2, pCLPtrcUppergallinarum, pTrc(MEA variant) alba mMVK |

(i) Materials and Methods

His-IspA enzyme was purified in-house. Affinity purified anti-IspA antibody and biotinylated anti-IspA antibody were prepared by ProSci Incorporated. High sensitivity streptavidin-HRP, SuperSignal ELISA Pico chemiluminescent substrate, black 96-well plates costar 3915, ELISA plate seals, and 10×PBS were purchased from Thermo Scientific. 4-(2-aminoethyl) benzenesulfonyl fluoride hydrochloride (AEBSF), deoxyribonuclease 1 from bovine pancreas, NaCl, imidazole, HEPES, $NaH_2PO_4$, EDTA, DTT, Tween-20, bovine serum albumin (BSA) and 200 mM isopropyl-beta-D-thiogalactoside (IPTG) were purchased from Sigma. Trap IMAC HP columns and Prep 26/10 desalting columns were purchased from HP. ELISA plate wash buffer (PBS-T) consisted of 1×PBS with 0.05% Tween-20. Blocking buffer was made up of 5% BSA in PBS-T. Nickel column wash buffer at pH 8 contained 50 mM $NaH_2PO_4$ and 300 mM NaCl. Nickel column elution buffer at pH 8 consisted of 20 mM imidazole, 50 mM $NaH_2PO_4$, 300 mM NaCl and 500 mM imidazole. The French Press was purchased from American Instrument Company.

IspA Purification: An overnight culture of MD08_67 (ispA-D227D-pET200D in BL21 (DE3)) was grown in LB media at 30° C. The day culture was started in fresh LB media by adding 10 mL of overnight inoculum to 1 L of fresh LB media at 34° C. Cells were induced with 200 µM IPTG and harvested 4 hrs post induction. The cell pellet was resuspended in nickel wash buffer with 1 mg/mL lysozyme, 0.1 mg/mL DNase and 0.5 mM AEBSF. The cell suspension was lysed using a French pressure cell at 14,000 psi. The lysate supernatant was passed through a nickel column and eluted using nickel elution buffer. Purified enzyme fractions were desalted with 1×PBS for further affinity purification and labeled antibody preparations. The purified enzyme concentration was determined by UV at 280 nm.

Cell Lysis Method for IspA Expression Analysis: For IspA expression analysis, fermentation sample cell pellets were resuspended in 2 mL of 1×PBS with 0.1% DNase and 0.5 mM AEBSF. The cell suspension was lysed using a French pressure cell at 14,000 psi. The lysate was then centrifuged at 15,000 rpm for 10 min at 4° C. in an Eppendorf 5804R centrifuge. The supernatant and pellet were separated, and the supernatant was used to quantify the IspA expression level.

Figure 27:
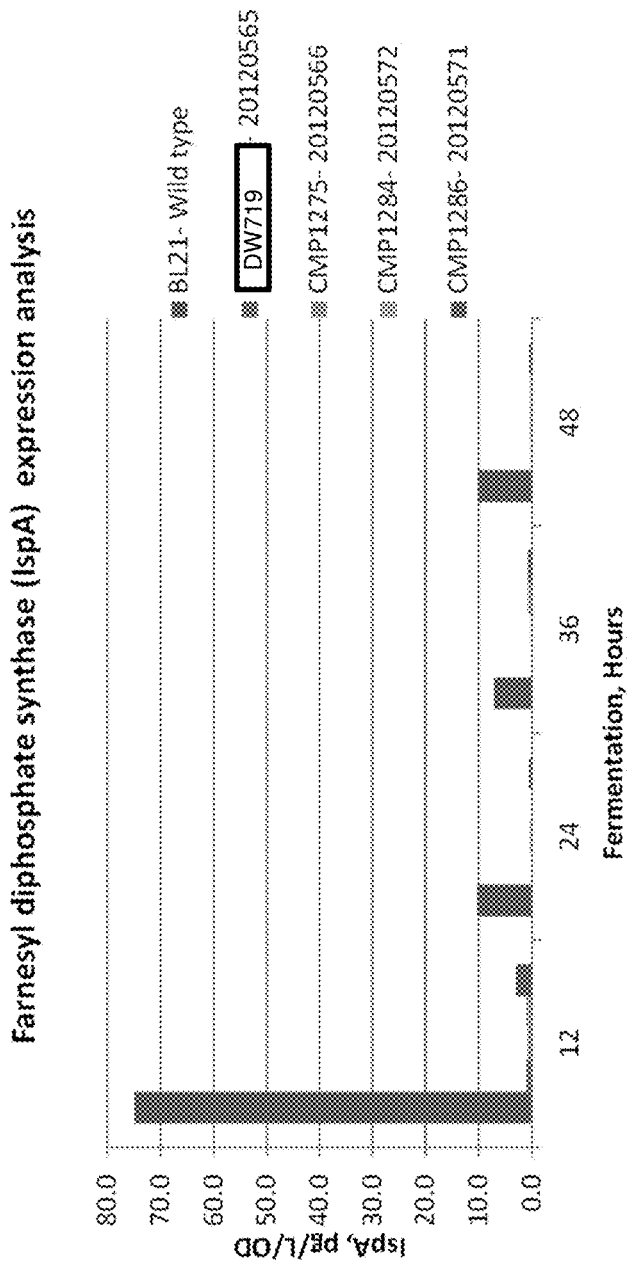
FIG. 27 depicts the concentration of IspA in the defined strains.

Sandwich ELISA Method: A black 96-well plate was coated with 5 μg/mL of capture antibody at 4° C. overnight. After ~24 hr, the plate was washed 3 times with PBS-T and blocked with 5% BSA in PBS-T for 2 hr at 37° C. After washing 3 times with PBS-T, the plate was coated with 100 μL of an unknown sample in PBS for 1 hr at 37° C., 2 μg/mL of biotinylated anti-IspA antibody in PBS-T for 1 hr at 34° C., and 1 μg/mL of streptavidin-HRP conjugate in PBS for 1 hr at 34° C. The plate was washed 3 times with PBS-T prior to each coating. Subsequently, 100 μL of luminescent substrate was added and the endpoint optical density was determined at 425 nm. Purified IspA was used to generate a standard curve to calculate the concentration of IspA in the samples (see Table 17 and FIG. 27).

TABLE 17

Concentration of IspA in the defined strains.

IspA expression in the fermentation samples, pg/L/OD

| EPT, Hours | BL21 BL21-Wildtype | DW719 PyddV ispA | CMP1275 PyddV(1/3rbs)ispA | CMP1284 PyddV(3rbs)ispA | CMP1286 PyddV(9rbs)ispA |
|---|---|---|---|---|---|
| 12 | 74.94 | 1.11 | 0.84 | 1.06 | 3.04 |
| 24 | 10.34 | 0.15 | 0.27 | 0.16 | 0.62 |
| 36 | 7.13 | 0.15 | 0.26 | 0.78 | 0.78 |
| 48 | 10.25 | 0.24 | 0.36 | 0.32 | 0.46 |

Results

As shown in Table 17, each of the *E. coli* strains engineered to have a decreased level of ispA expression displayed significantly lower ispA expression levels compared to the control strain (BL21) which possessed wild type ispA.

Example 23

Large Scale Fermentation Results

This experiment was performed to evaluate isoprene production from various modified *E. coli* (BL21) hosts (CMP1275, CMP1284, CMP1286) expressing introduced genes from the mevalonate/isoprene pathway and grown in fed-batch culture at the 15 L scale. The host modifications introduced into these strains were at the yddV promoter in front of IspA (see Table 18), and the modifications were designed in accordance with an RBS calculator in the hope of modifying the promoter strength and hence, the IspA expression level. These isoprene producing strains were run in a standard production process as described below. The performance metrics of a control strain (DW719) are compared here to the experimental strains CMP1275 (RBS1/3), CMP1284 (RBS3) and CMP1286 (RBS9). The goal of these experiments is to determine whether IspA expression can be modified in such a way as to allow minimal overflow into the potentially toxic intermediates FPP and GPP in order to maximize cell viability, and to increase isoprene yield on glucose or isoprene productivity. The experimental "RBS ladder" strains were run under the same conditions as the control (DW719) to determine if any yield or productivity improvement could be attributed to modified IspA expression. The model starts with a ribosome binding strength (RBS) of 1 and different RBS sequences gave values targeting predicted ribosome binding strengths of ⅓ (3-fold reduction), 3 (3-fold improvement) and 9 (9-fold improvement). However, actual expression levels of IspA were not measured in this experiment.

TABLE 18

List of strains.

| Strain Name | Host/yddV promoter modification | upper plasmid | lower plasmid | Run numbers |
|---|---|---|---|---|
| DW719 (Control) | BL21 t pgl, GI1.2gltA pgl-PL.2mKKDyI t pgl, GI1.2gltA pgl-PL.2mKKDyI pgl-(yddV promoter) | Ptrc-*P. alba* IspS (MEA variant)-mMVK, Carb50 ppm (pDW240) | *E. gallinarum* upper, Spec50 ppm (pMCM1225) | 20120526 20120565 |
| CMP1275 | BL21 t pgl, GI1.2gltA pgl-PL.2mKKDyI t pgl, GI1.2gltA pgl-PL.2mKKDyI pgl yhfS-FRT-PyddV(1/3rbs)ispA col2 | pDW240 | pMCM1225 | 20120566 |
| CMP1284 | BL21 t pgl, GI1.2gltA pgl-PL.2mKKDyI t pgl, GI1.2gltA pgl-PL.2mKKDyI pgl yhfS-FRT-PyddV(3rbs)ispA-go | pDW240 | pMCM1225 | 20120572 |

TABLE 18-continued

List of strains.

| Strain Name | Host/yddV promoter modification | upper plasmid | lower plasmid | Run numbers |
|---|---|---|---|---|
| CMP1286 | BL21 t pgl, GI1.2gltA pgl-PL.2mKKDyI t pgl, GI1.2gltA pgl-PL.2mKKDyI pgl yhfS-FRT-PyddV(9rbs)ispA-go | pDW240 | pMCM1225 | 20120571 |

In this experiment, DW719 (YddV promoter-IspA) was used as the baseline strain. Note that initial experiments under typical small-scale conditions using REM B7_26 (CMP1199 (HMB GI1.2gltA pg1–)+pDW240+pMCM1225) containing a wild-type IspA strain, were performed to determine the ability of that strain to produce isoprene as compared to DW719. DW719 showed better growth and specific productivity (18,276 μg/L/Hr/OD isoprene) compared to REM B7_26 (specific productivity was 10,184 μg/L/Hr/OD isoprene). Thus, the specific productivity of strain DW719 was almost 2-fold greater than that of the wild-type strain. Based upon the isoprene production of REM B7_26 at small scale, 15 L fermentations were not performed on this strain.

(i) Materials and Methods

Medium Recipe (per liter fermentation medium): K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000×Modified Trace Metal Solution 1 ml. All of the components were added together and dissolved in Di H2O. This solution was heat sterilized (123° C. for 20 min). The pH was adjusted to 7.0 with ammonium hydroxide (28%) and q.s. to volume. Glucose 10 g, Vitamin Solution 8 mL, and antibiotics were added after sterilization and pH adjustment.

1000×Modified Trace Metal Solution (Per Liter): Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter): Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter): MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram): Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 mL, Vitamin Solution 6.55 mL, 1000×Modified Trace Metal Solution 0.82 mL, 10 mg/mL IPTG solution (1.86 mL).

This experiment was carried out to monitor isoprene production from glucose at the desired fermentation pH (7.0) and temperature (34° C.). To start each experiment, the appropriate frozen vial of the *E. coli* (BL21) strain was thawed and inoculated into a flask with tryptone yeast extract (LB) medium and the appropriate antibiotics. After the inoculum grew to an optical density of approximately 1.0 as measured at 550 nm ($OD_{550}$), 500 mL was used to inoculate a 15 L bioreactor and bring the initial tank volume to 5 L.

The inlet gas used to maintain bioreactor backpressure at 0.7 bar gauge and to provide the oxygen to the production organisms was supplied by in-house facilities that dilute the inlet gas to a known concentration (7.7 to 9.5 vol % oxygen).

The batched media had glucose batched in at 9.7 g/L. Induction was achieved by adding IPTG. A shot of IPTG was added to the tank to bring the concentration to a specified level when the cells were at an $OD_{550}$ of 6. Once the glucose was consumed by the culture as signaled by a rise in pH, the glucose feed solution was fed to meet metabolic demands at rates less than or equal to 10 g/min. The fermentation was run long enough to determine the maximum cumulative isoprene mass yield on glucose, a total of 56 to 64 hr of elapsed fermentation time. The only variable in the process was the strain used to start the flask.

Oxygen, nitrogen, and carbon dioxide levels in the offgas were determined independently using the mass spectrometers iSCAN (Hamilton Sundstrand) and Hiden HPR20 (Hiden Analytical). Dissolved oxygen in the fermentation broth was measured by a sanitary, sterilizable probe with an optical sensor provided Hamilton Company.

The citrate, glucose, acetate, and mevalonate concentrations in the fermentor broth were determined in broth samples taken at 4 hr intervals by HPLC analysis. Concentrations in broth samples were determined by comparison of the refractive index response versus a previously generated calibration curve using standards of a known concentration. Relevant HPLC information is as follows: a) system: Waters Alliance 2695; b) column: BioRad—Aminex HPX-87H ion exclusion column, 300 mm×7.8 mm, catalog #125-0140; c) column temperature: 50° C.; d) guard column: BioRad—Microguard cation H refill, 30 mm×4.6 mm, catalog #125-0129; e) running buffer: 0.01 N $H_2SO_4$; f) running buffer flow rate: 0.6 mL/min; g) approximate running pressure: 1100-1200 psi; h) injection volume: 20 μL; i) detector: refractive index (Knauer K-2301); and j) runtime: 26 min.

(ii) Results

Figure 28:
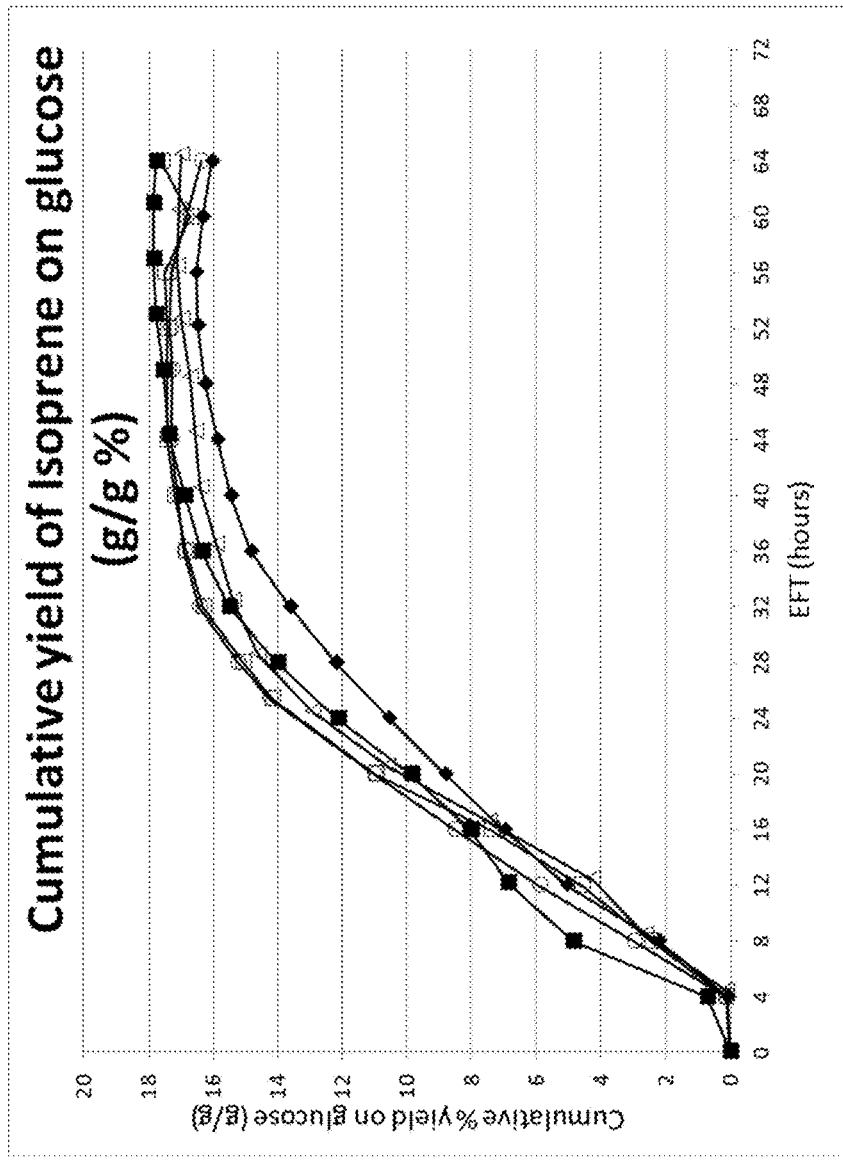
FIG. 28 depicts the yield of isoprene on glucose achieved in each 15 L fermentation over time. The strains with the modified RBS sites, namely CMP1286 (RBS9 yddV), CMP1284 (RBS3 yddV), and CMP1275 (RBS1/3 yddV) (open circles, open squares, and open triangles, respectively) achieved a cumulative % yield of isoprene on glucose that was similar to the control strain (DW719, runs 20120526 and 20120565, closed squares and closed diamonds, respectively). % wt Yield on glucose calculated as isoprene total (t)/[(Feed Wt(0)−Feed Wt(t)+83.5)*0.59)], where 0.59 is the wt % of glucose in the glucose feed solution and 83.5 is the grams of this feed batched into the fermentor at t=0. Each feed had its weight % measured independently.
Figure 29:
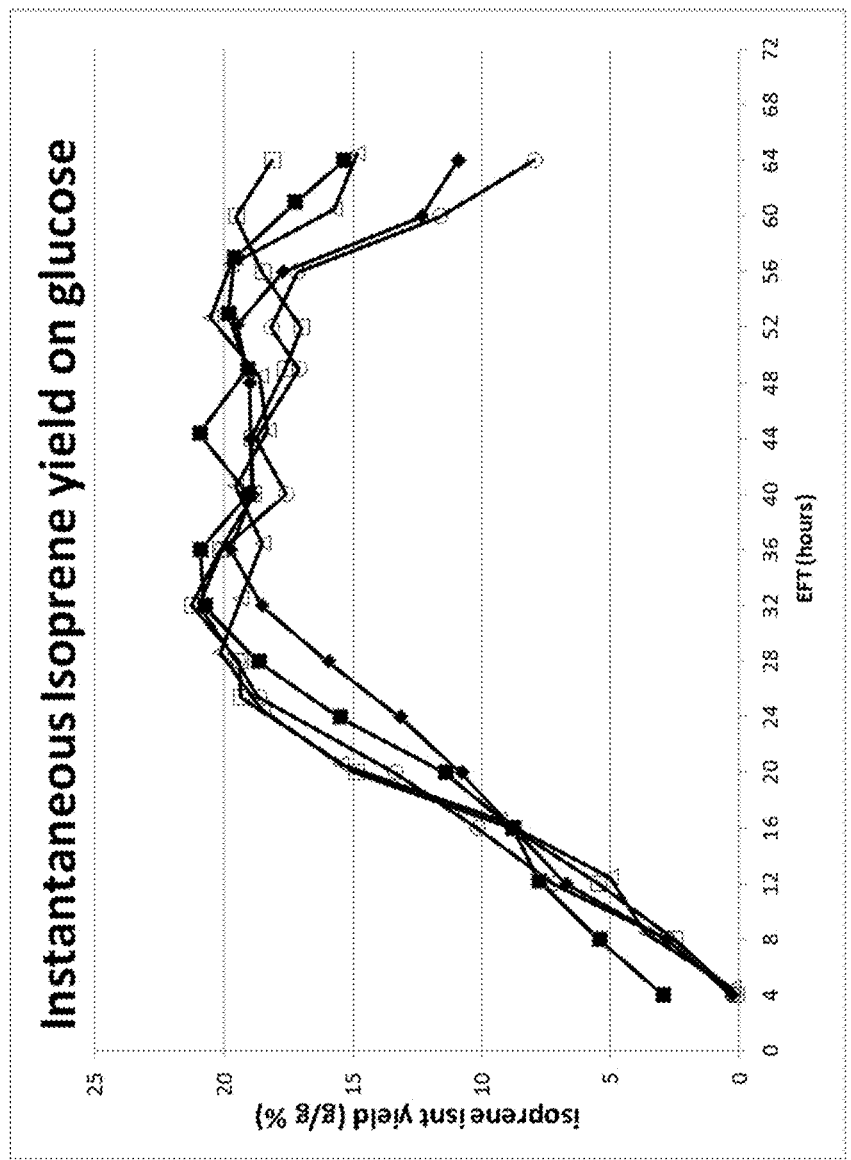
FIG. 29 depicts the instantaneous yield of isoprene on glucose achieved in each 15 L fermentation over time. The strains with the modified RBS sites, namely CMP1286 (RBS9 yddV), CMP1284 (RBS3 yddV), and CMP1275 (RBS1/3 yddV) (open circles, open squares, and open triangles, respectively) achieved similar peak instantaneous yields of isoprene on glucose that were similar to the control strain (DW719, runs 20120526 and 20120565, closed squares and closed diamonds, respectively). All the modified strains achieved higher instantaneous yield values early in the run and strain CMP1284 had the most robust performance at the end of the run (56 to 64 hrs EFT). Isoprene instantaneous yield (g/g %) calculated as isoprene produced $(t_1-t_0)$/consumed glucose $(t_1-t_0)$*100.
Figure 30:
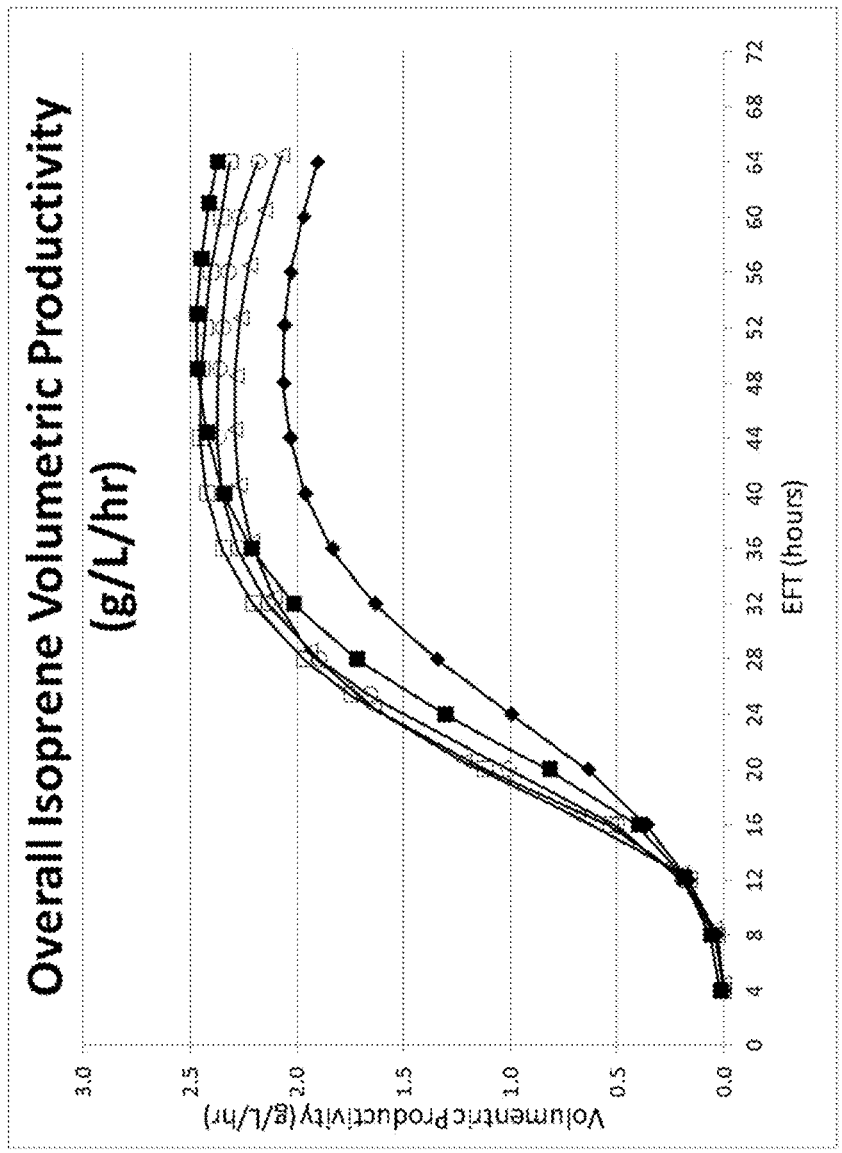
Figure 31:
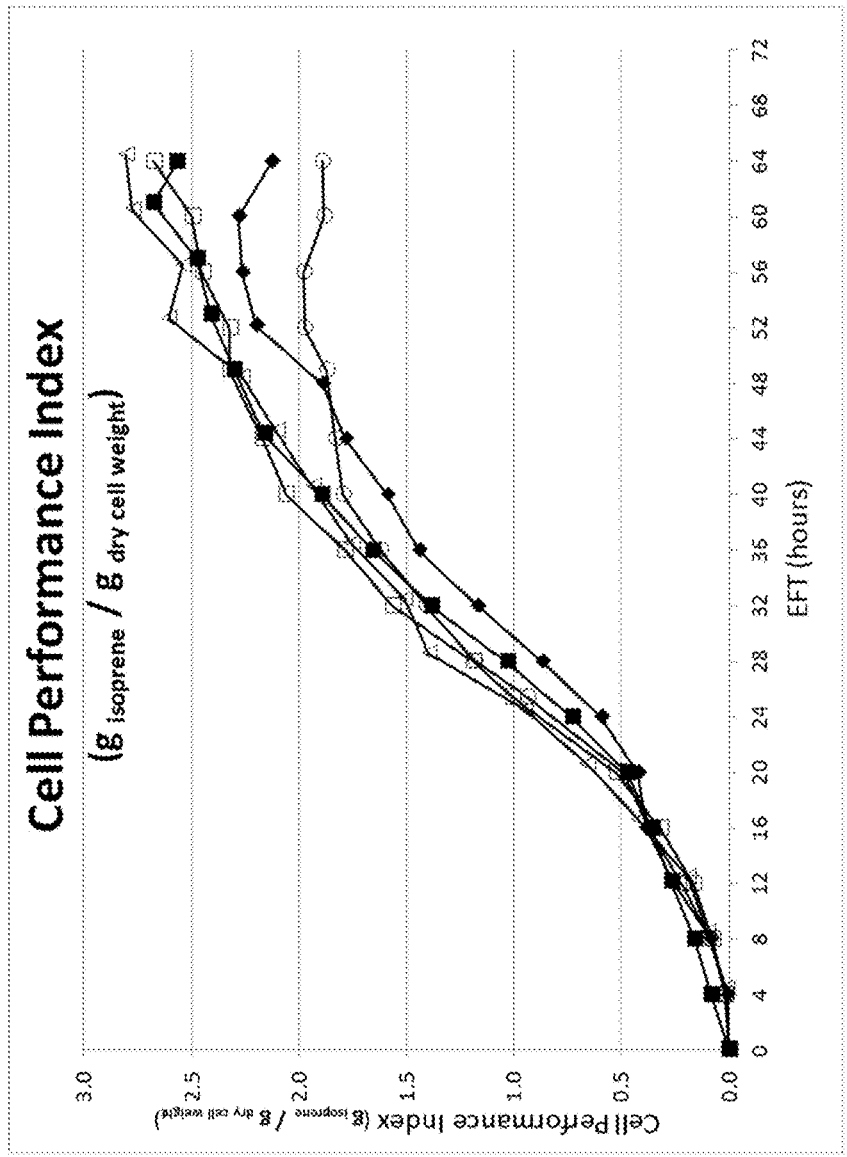
FIG. 31 depicts the Cell Productivity Index (CPI) achieved in each 15 L fermentation over time. The strains with the modified RBS sites, namely CMP1286 (RBS9 yddV), CMP1284 (RBS3 yddV), and CMP1275 (RBS1/3 yddV) (open circles, open squares, and open triangles, respectively) achieved a CPI that was similar to the control strain (DW719, runs 20120526 and 20120565, closed squares and closed diamonds, respectively). The Cell Productivity Index (CPI) was calculated using the following formula: CPI=total grams isoprene/total grams dry cell weight.
Figure 32:
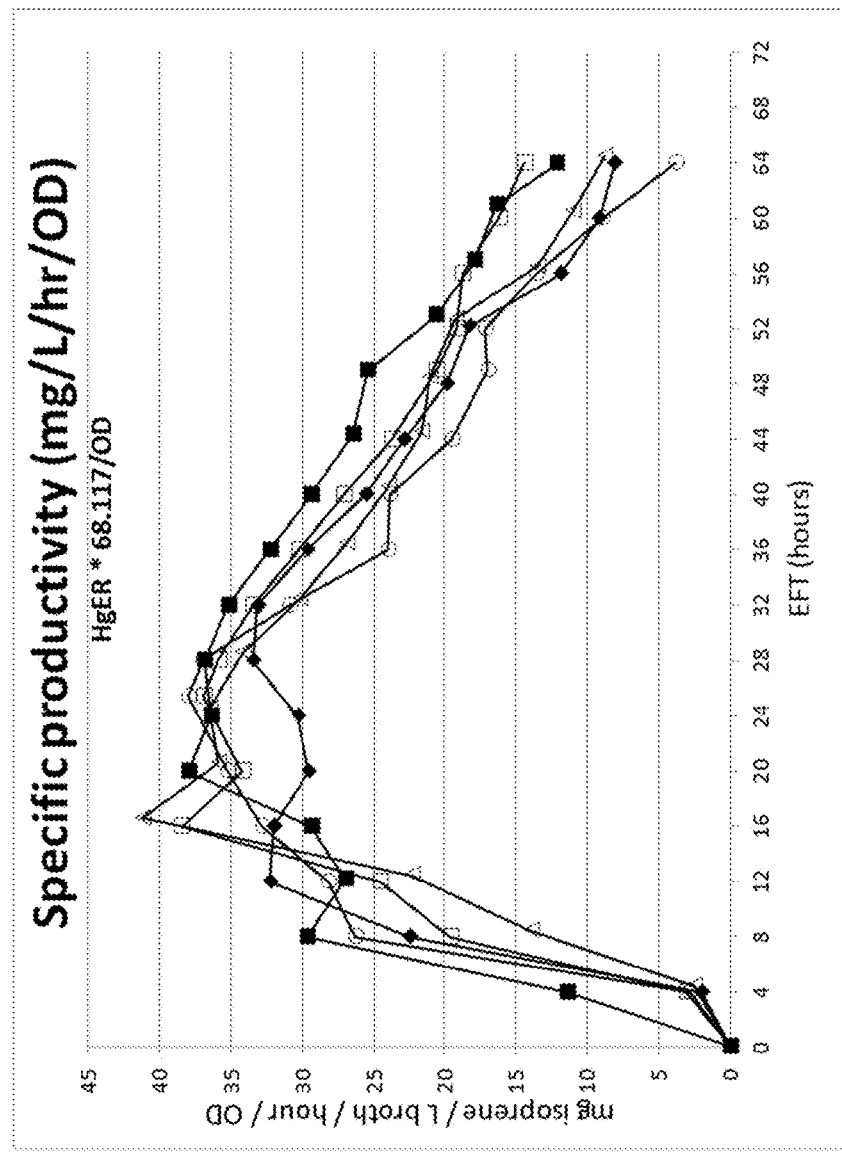
FIG. 32 depicts specific productivity achieved in each 15 L fermentation over time. The strains with the modified RBS sites, namely CMP1286 (RBS9 yddV), CMP1284 (RBS3 yddV), and CMP1275 (RBS1/3 yddV) (open circles, open squares, and open triangles, respectively), achieved a specific productivity of isoprene that was similar to the control strain (DW719, runs 20120526 and 20120565, closed squares and closed diamonds, respectively). Specific productivity was calculated using the following formula: specific productivity (mg/L/hr/OD)=HgER*68.117 g/mol/OD. HgER is the Isoprene Evolution Rate in (mmol/L/hr). OD=optical density=Absorbance at 550 nm* dilution factor in water.
Figure 33:
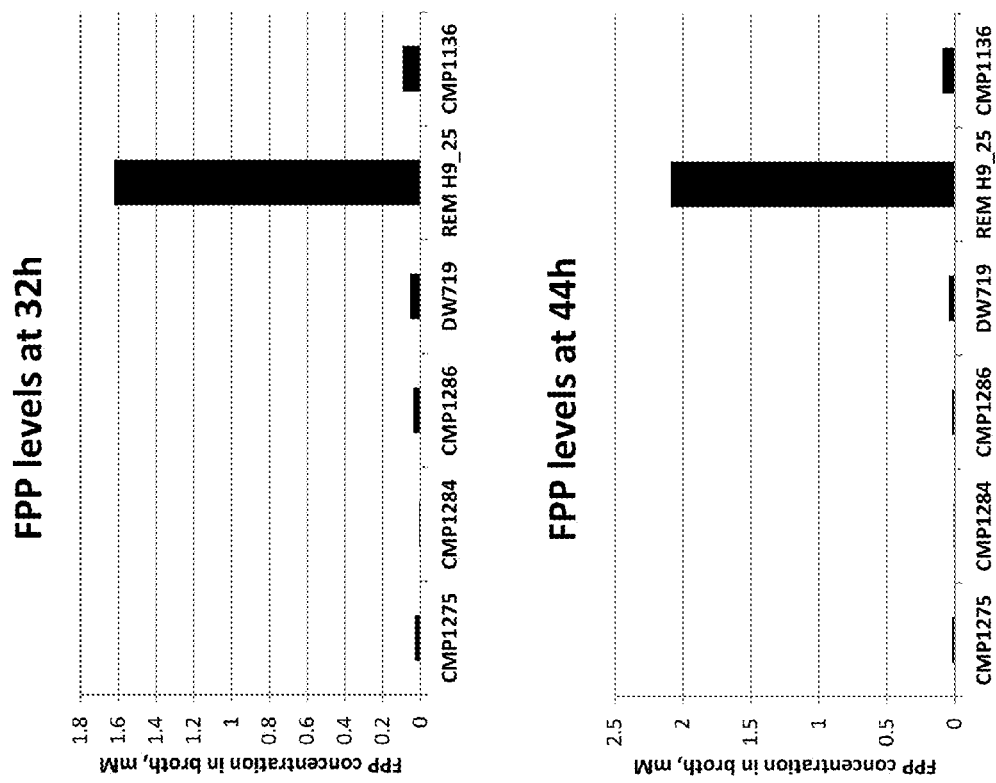
FIG. 33 depicts FPP levels measured after 32 and 44 hours of fermentation.
Figure 34:
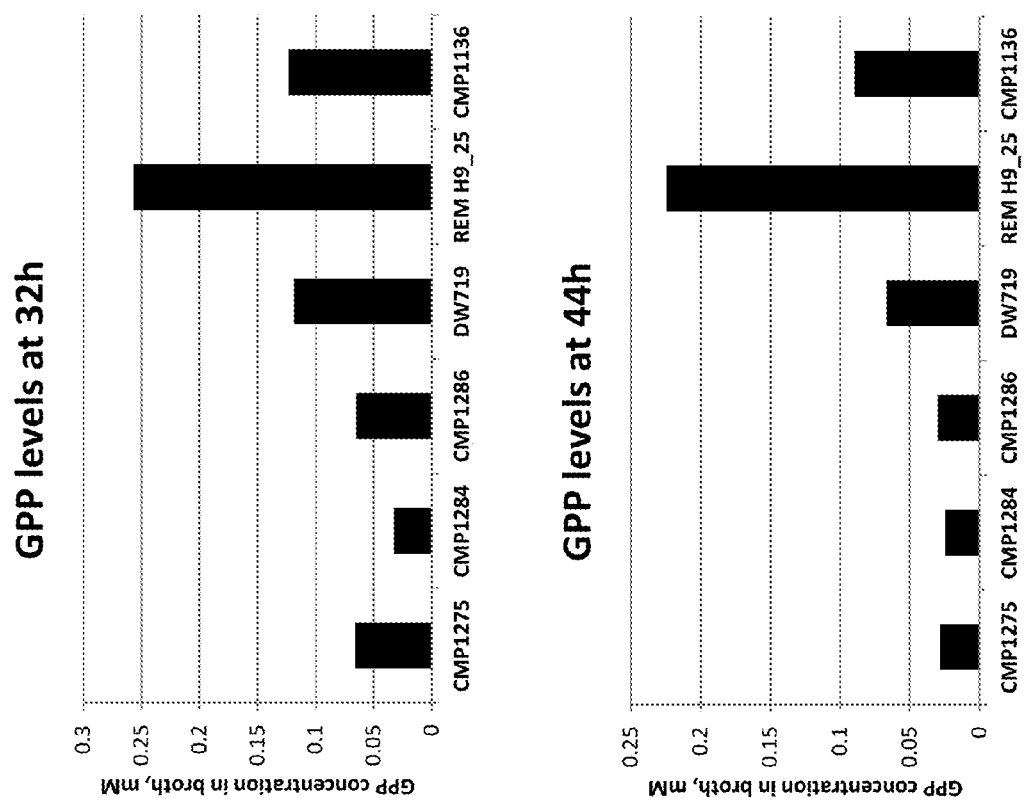
FIG. 34 depicts GPP levels measured after 32 and 44 hours of fermentation.
Figure 35:
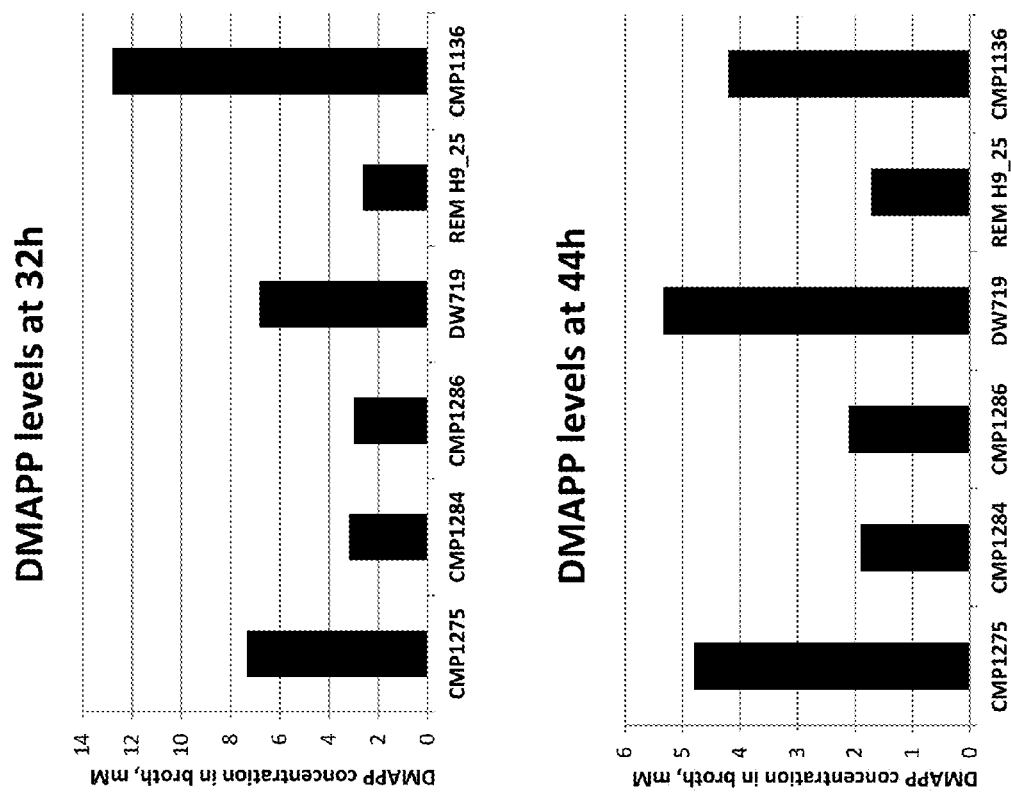
FIG. 35 depicts DMAPP levels measured after 32 and 44 hours of fermentation.
Figure 36:
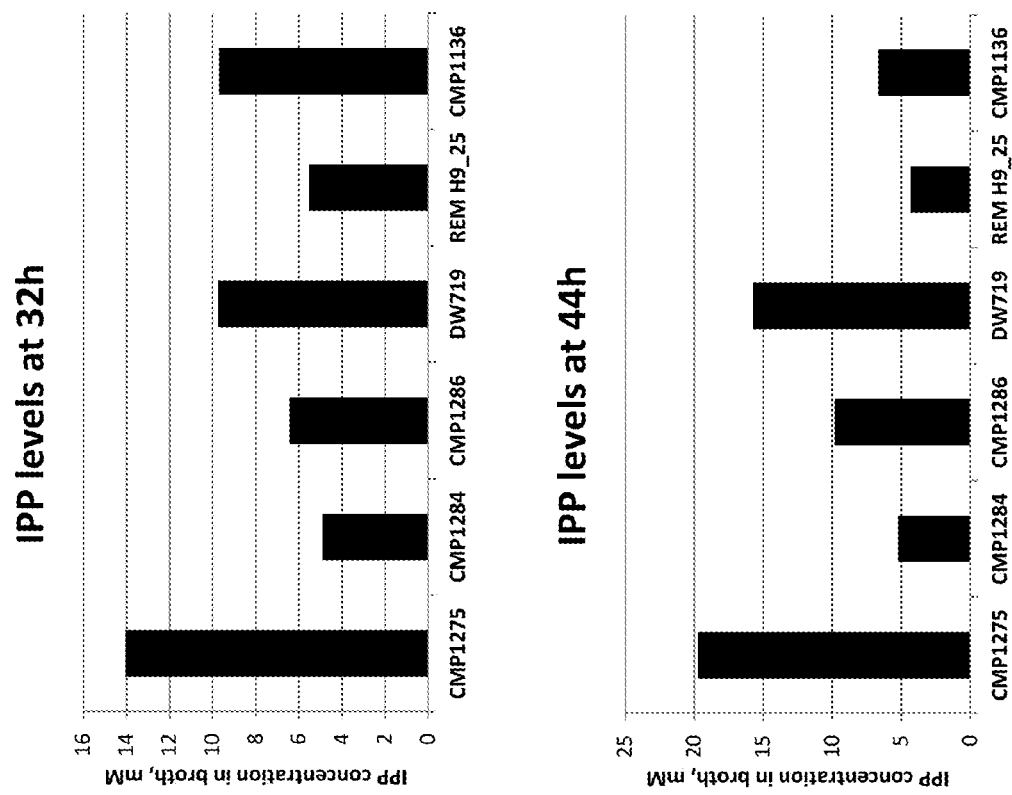
FIG. 36 depicts IPP levels measured after 32 and 44 hours of fermentation.

Isoprene productivity metrics are summarized in Table 19. Overall, the performance of the strain with the modified RBS sites was similar to the control strain (DW719, run 20120526 and 20120565). The strains with the modified RBS sites achieved a cumulative % yield of isoprene on glucose that was similar to the control strain (DW719, runs 20120526 and 20120565) (see FIG. 28). The strains with the modified RBS sites achieved similar peak instantaneous yields of isoprene on glucose that were similar to the control strain (DW719, runs 20120526 and 20120565) (see FIG. 29). The modified strains achieved higher instantaneous yield values early in the run and strain CMP1284 had the most robust performance at the end of the run (56 to 64 hr EFT), as well as the lowest FPP levels. The strains with the modified RBS sites achieved a volumetric productivity of isoprene that was similar to the control strain (DW719, runs 20120526 and 20120565) (see FIG. 30). The strains with the modified RBS sites achieved a CPI of isoprene that was similar to the control strain (DW719, runs 20120526 and 20120565) (see FIG. 31). However, after 40 hr of fermentation time, the CMP1286 (RBS9) strain showed continued cell growth and lower instantaneous yield of isoprene on glucose. It may be that the increased expression of IspA allowed greater flux to isoprenoid precursors, thereby allowing more growth. It could be that this IspA expression level represents a top end to the desirable expression level. In contrast, the ⅓RBS strain had the lowest overall cell mass and the highest CPI at the end of the run. This may represent a low end to the desirable IspA expression level as it also had the lowest volumetric productivity of the 3 RBS ladder strains examined. The strains with the modified RBS sites achieved a specific productivity of isoprene that was similar to the control strain (DW719, runs 20120526 and 20120565) (see FIG. 32).

extraction and concentration, 0.25 mL aliquots of cell suspension (0.4 mL was used if the cell density of the culture measured at $OD_{600}$ was below 50) were diluted with 1.5 mL of a methanol/ammonium acetate buffer (5 mM, pH 8.0) mixture (6:1, v/v), and cell debris was pelleted by a 4 min centrifugation. The supernatant was collected and loaded onto Strata-X-AW columns from Phenomenex (33 μm 30 mg/well, 96-well polymeric weak anion exchange). The cell pellet was extracted two more times, first with 1.5 mL of the methanol/ammonium acetate buffer (5 mM, pH 8.0) mixture (6:1 v/v), and then with 1.5 mL of a methanol/ammonium acetate buffer (5 mM, pH 8.0) mixture (1:1 v/v). Both times the cells were pelleted by centrifugation, and the resulting supernatants were consecutively loaded onto the same Strata-X-AW columns. During the extraction-centrifugation, samples with cells were kept below 4° C. After washing the columns with 1 mL of water and 1 mL of methanol, metabolites of interest were eluted from the columns first with 0.3 mL of a concentrated $NH_4OH$/methanol mixture (1:14, v/v), and then with 0.3 mL of a concentrated $NH_4OH$/methanol/water mixture (1:12:2, v/v/v). The resulting eluent was neutralized by adding 20 μL of glacial acetic acid and then cleared by centrifugation.

Metabolite Quantification. Analysis of metabolites was carried out by mass spectrometry using a TSQ Quantum Access system (Thermo Scientific). All system control, data acquisition, and mass spectral data evaluation were per-

TABLE 19

Isoprene productivity metrics.

| Strain Name/ Run Number/ (RBS) | Inlet Oxygen Conc. (vol %) | Max Overall % Yield of Isoprene on glucose (g/g %) | Peak instantaneous % yield of isoprene on glucose (g/g %) | Overall Isoprene Volumetric Productivity (g/L/hr) at time of max overall isoprene yield | CPI (g Isoprene/ gDCW) at time of max overall isoprene yield | Peak Specific Productivity (mg isoprene/ L/hr/OD) |
|---|---|---|---|---|---|---|
| DW719/ 20120526 | 8.61 | 17.84 | 20.41 (+/−0.91) | 2.45 | 2.48 | 38.01 |
| DW719/ 20120565 | 8.85 | 16.53 | 19.22 (+/−0.38) | 2.03 | 2.27 | 33.48 |
| CM1275/ 20120566/ (RBS 1/3) | 8.86 | 17.12 | 19.28 (+/−0.85) | 2.22 | 2.54 | 41.21 |
| CMP1284/ 20120572/ (RBS3) | 8.71 | 17.49 | 19.37 (+/−1.28) | 2.41 | 2.45 | 36.97 |
| CMP1286/ 20120571/ (RBS9) | 8.73 | 17.32 | 19.71 (+/−0.99) | 2.35 | 1.97 | 38.01 |
| CMP1043 Control strain | — | 14.26 | — | 1.69 | 1.64 | 26.87 (at 16 hrs EFT) |

Example 24

Metabolite Analysis for IspA Variants

This Examples measured metabolites from IspA expression variants in *E. coli*.

(i) Materials and Methods

Metabolite Extraction from *E. coli*. The metabolism of bacterial cells grown in fermenters was rapidly inactivated by withdrawing approximately 3 mL of culture into a tube filled with 9 mL of dry ice-cold methanol. The resulting samples were weighed to calculate the amount of sampled broth and then stored at −80° C. until further analysis. For metabolite formed using XCalibur and LCQuan software (Thermo Scientific). For the LC-ESI-MS/MS method, a chiral Nucleodex β-OH 5 μM HPLC column (100×2 mm, Macherey-Nagel, Germany) was used with a CC 8/4 Nucleodex beta-OH guard cartridge. A mobile phase gradient was applied as described in Table 20 in which mobile phase A was 100 mM ammonium bicarbonate buffer (BioUltra grade, Fluka, pH 7) in MilliQ-grade water, mobile phase B was MilliQ-grade water, and mobile phase C was acetonitrile (Honeywell B&J Brand, LC-MS grade). The column and sample tray temperatures were reduced to 5° C. and 4° C., respectively. The injection volume was 10 μL.

TABLE 20

HPLC gradient used to elute metabolites in the MVA pathway.

| Time | Solvent A | Solvent B | Solvent C | Flow rate |
|---|---|---|---|---|
| 0.0 min | 20% | 0% | 80% | 0.4 mL/min |
| 0.5 min | 20% | 0% | 80% | 0.4 mL/min |
| 5.5 min | 60% | 0% | 40% | 0.4 mL/min |
| 6.5 min | 60% | 0% | 40% | 0.4 mL/min |
| 7.0 min | 0.5% | 59.5% | 40% | 0.5 mL/min |
| 13.0 min | 0.1% | 34.9% | 65% | 0.5 mL/min |
| 13.5 min | 20% | 0% | 80% | 0.5 mL/min |
| 14.5 min | 20% | 0% | 80% | 0.5 mL/min |

Mass detection was carried out using electrospray ionization in the negative mode (ESI spray voltage of 3.5 kV and ion transfer tube temperature of 350° C.). The following m/z values for precursor ions were selected to detect the metabolites of interest in SRM mode: 245.1 for IPP and DMAPP, 313.1 for GPP, 381.0 for FPP, 227.1 for MVP, and 307.1 for MVPP. To account for small variations in sensitivity while running the mass spectrometer, uniformly labeled $^{13}C_{10}$-ADP was also added in equal amounts (final concentration of 19.6 μM) to both samples and calibrants as an internal standard ($^{13}C_{10}$-ADP was prepared enzymatically from $^{13}C_{10}$-ATP obtained from Isotec, Sigma-Aldrich; m/z=436.1). Concentrations of metabolites were determined based on the sample/internal standard response ratio of integrated intensities of peaks generated by the $PO_3^-$ product ion (m/z=79.0), or in the case of labeled ADP, the diphosphate product ion (m/z=159.0). Calibration curves obtained by the injection of standards were used to calculate concentrations of metabolites in cell extracts. IPP, DMAPP, GPP, and FPP standards were purchased from Echelon Biosciences Inc., and MVP and MVPP were purchased from Sigma Aldrich.

(ii) Results

Concentrations of IPP, DMAPP, GPP, and FPP after 32 and 44 hr of fermentation are presented in Tables 21 and 22, and FIGS. 33-36.

TABLE 21

Concentrations of FPP, GPP, DMAPP, and IPP after 32 hr of fermentation.

| | 32 h | | | |
|---|---|---|---|---|
| | FPP (mM) | GPP (mM) | DMAPP (mM) | IPP (mM) |
| CMP1275 | 0.030 | 0.066 | 7.346 | 14.038 |
| CMP1284 | 0.007 | 0.032 | 3.180 | 4.899 |
| CMP1286 | 0.039 | 0.065 | 2.995 | 6.423 |
| DW719 | 0.054 | 0.119 | 6.844 | 9.736 |
| REM H9_25 | 1.622 | 0.257 | 2.635 | 5.534 |
| CMP1136 | 0.093 | 0.124 | 12.792 | 9.696 |

TABLE 22

Concentrations of FPP, GPP, DMAPP, and IPP after 44 hr of fermentation.

| | 44 h | | | |
|---|---|---|---|---|
| | FPP (mM) | GPP (mM) | DMAPP (mM) | IPP (mM) |
| CMP1275 | 0.020 | 0.028 | 4.801 | 19.732 |
| CMP1284 | 0.008 | 0.024 | 1.903 | 5.236 |
| CMP1286 | 0.020 | 0.030 | 2.112 | 9.830 |
| DW719 | 0.042 | 0.067 | 5.334 | 15.749 |
| REM H9_25 | 2.091 | 0.224 | 1.724 | 4.313 |
| CMP1136 | 0.090 | 0.089 | 4.202 | 6.656 |

Example 25

Constitutive Isoprene Synthase in Refactored IspA Host Strain

Isoprene synthase, IspS and IspS_mMVK, were expressed constitutively without the repressor lacIq.

(i) Materials and Methods

Figure 37:
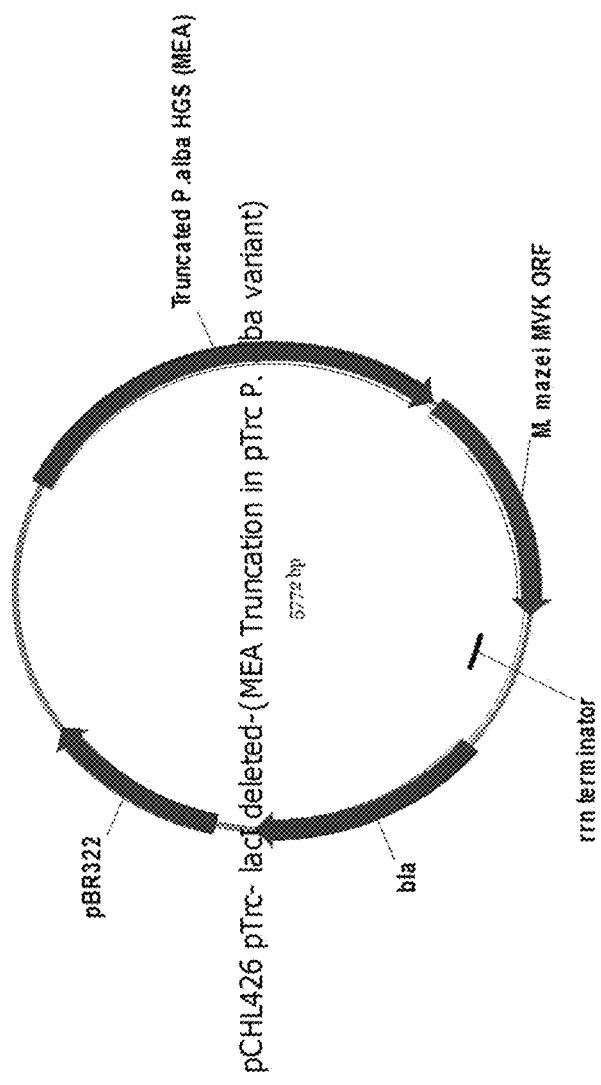
FIG. 37 depicts the plasmid construct of pCHL426.
Figure 38:
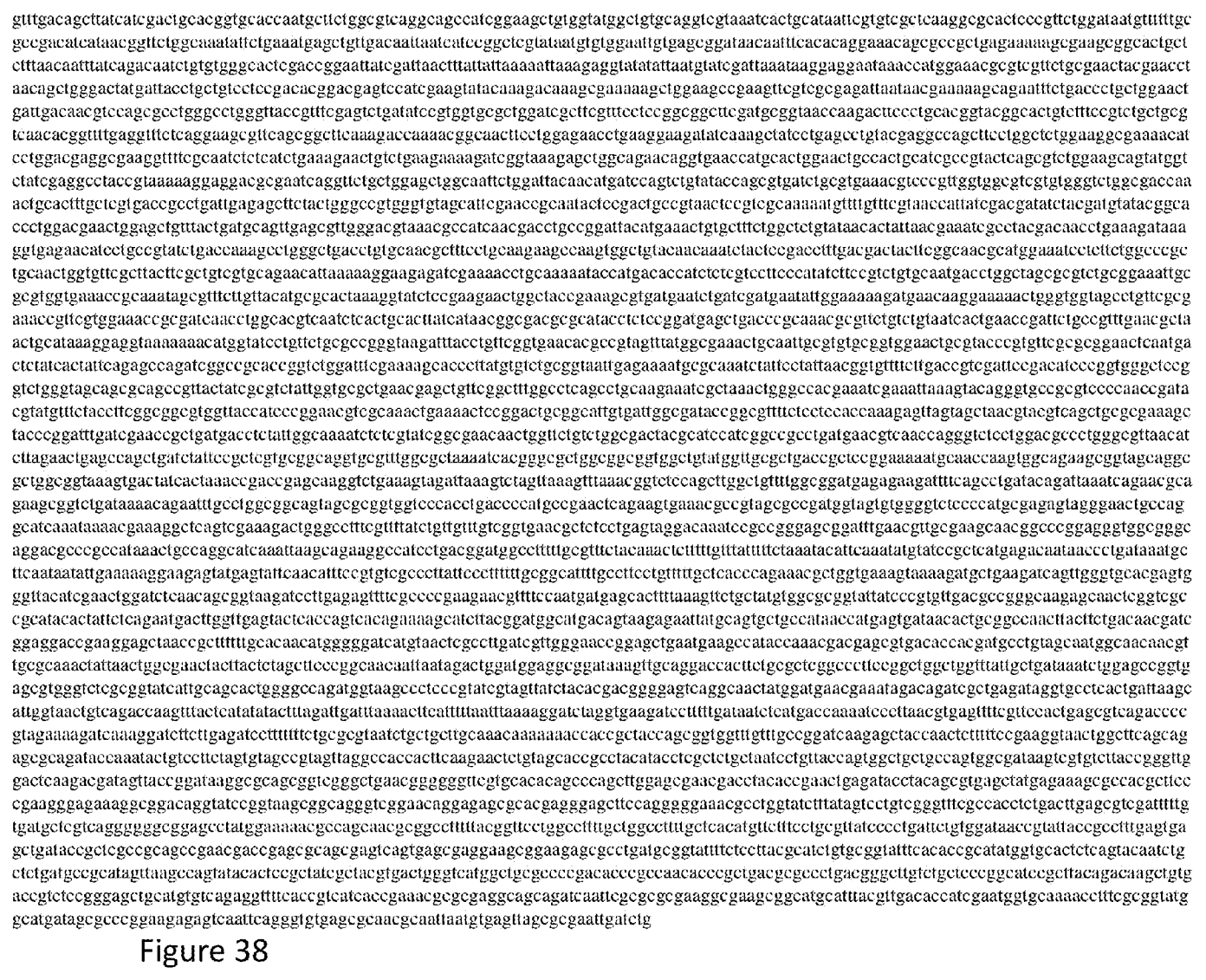

Construction of pCHL426, pTrc(lacI deleted)_pTrc-IspS (variant)_ mMVK. The repressor gene lacIq was deleted from plasmid pDW240 by using the following primers: CL449F (5'-attcagggtgtgagcgcaacgcaattaatgt-3' (SEQ ID NO:100)) and CL45OR (5'-GTTGCGCTCACACCCT-GAATTGACTCTCTTC-3' (SEQ ID NO:101)). The PCR reaction consisted of template DNA, pDW240 (100 ng), 50 μM of each forward (CL449F) and reverse primer (CL450R), 1 μL of 10 mM dNTPs (Roche), 5 uL of 10×pfuII reaction buffer (Agilent), 1 μL of pfu II fusion enzyme (Agilent), and 40 μL of water. 18 cycles were performed with a temperature profile of 50 seconds at 95° C., 50 seconds at 60° C., 4 min at 68° C., and an additional 10 min extension at 68° C. in a Bio-Rad thermocycler. Following completion of the PCR reaction, 1 μL of DpnI was added and the mixture was incubated at 37° C. for 2 hr to remove the template DNA. An additional 1 μL of DpnI was added and the mixture was incubated at 37° C. overnight. Next, 2 μL of the reaction was transformed into TOP10F' cells (Invitrogen) and plated on LA+carbenicillin 50 mg/L. In alternative embodiments, 2 μL of the reaction can be transformed into TOP10F' cells (Invitrogen) and plated on LB+carbenicillin 50 mg/L. The correct clone was confirmed by sequencing. The plasmid map and sequence are shown in FIGS. 37 and 38.

Figure 39:
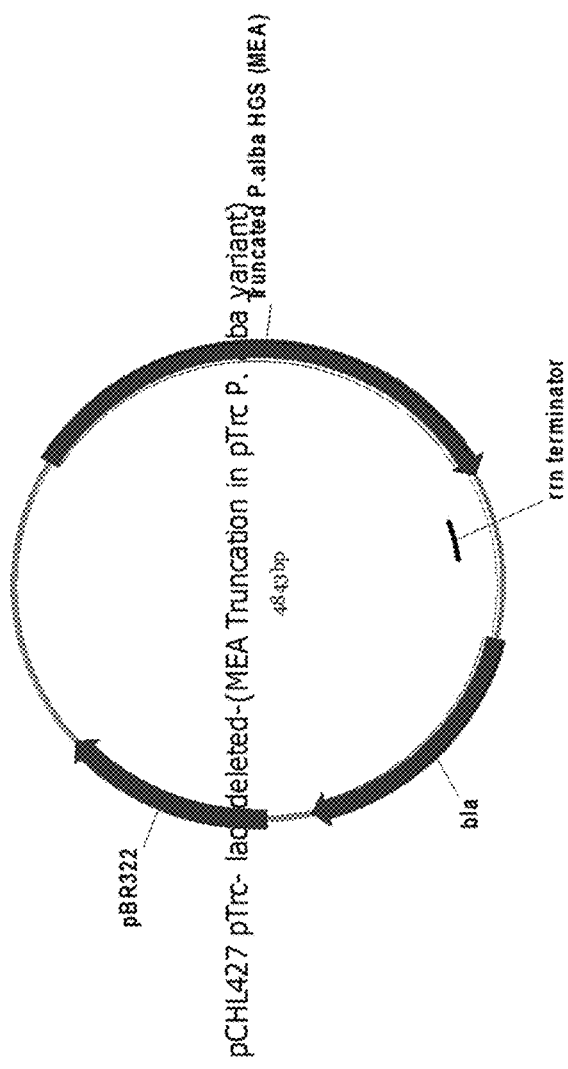
FIG. 39 depicts the plasmid construct of pCHL427.
Figure 40:
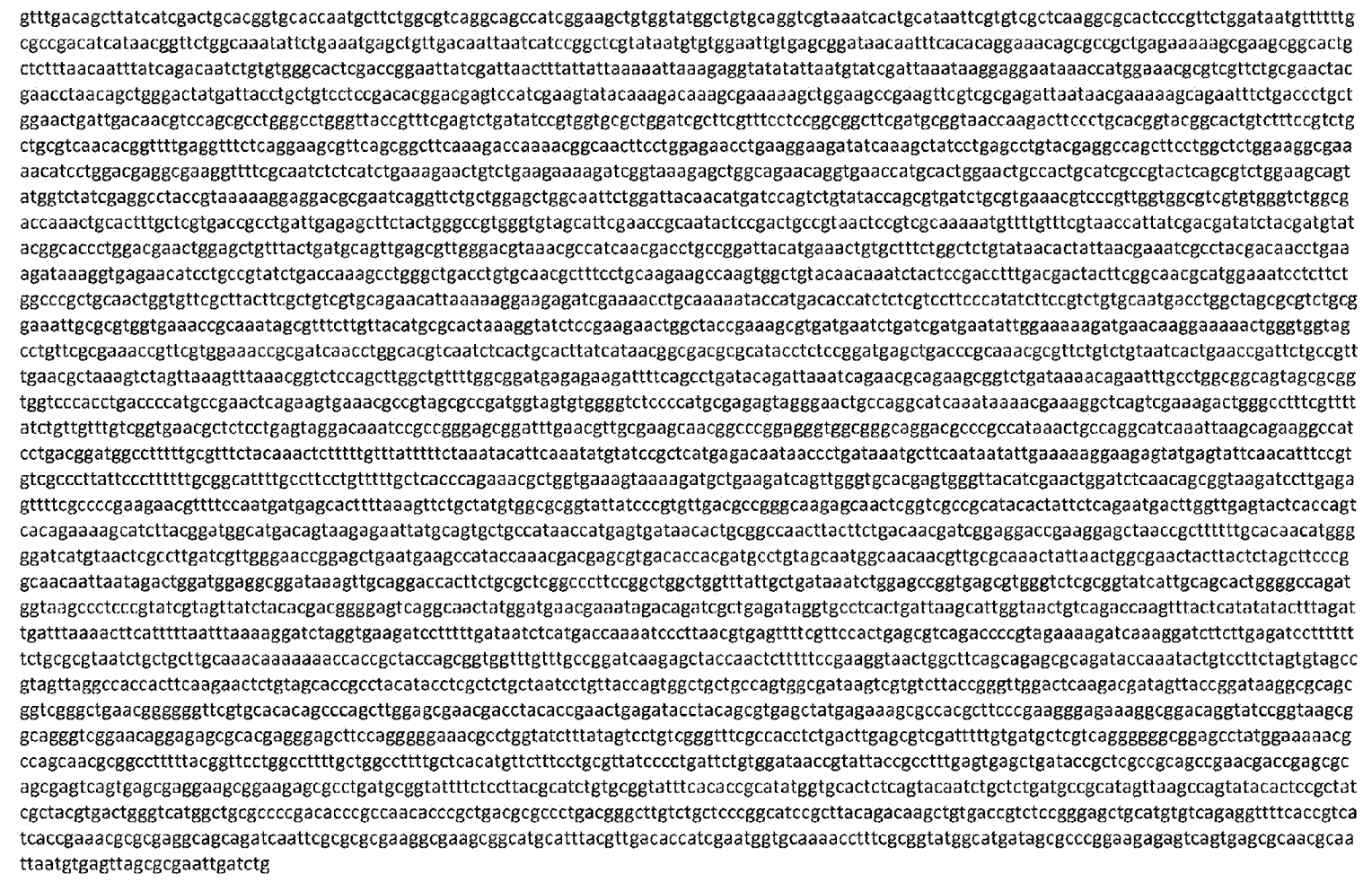

Construction of pCHL427, pTrc(lacI deleted)_pTrc-IspS (variant). The repressor gene lacIq was deleted from plasmid pMCM2149 by using the following primers: CL449F (5'-attcagggtgtgagcgcaacgcaattaatgt-3' (SEQ ID NO:102)) and CL45OR (5'-GTTGCGCTCACACCCTGAAT-TGACTCTCTTC-3' (SEQ ID NO:103)). The PCR reaction consisted of template DNA, pMCM2149 (100 ng), 50 μM of each forward (CL449F) and reverse primer (CL450R), 1 μL of 10 mM dNTPs (Roche), 5 μL of 10×pfuII reaction buffer (Agilent), 1 μL of pfu II fusion enzyme (Agilent), and 40 μL of water. 18 cycles were performed with a temperature profile of 50 seconds at 95° C., 50 seconds at 60° C., 4 min at 68° C., and an additional 10 min extension at 68° C. in a Bio-Rad thermocycler. Upon completion of the PCR reaction, 1 μL of DpnI was added and the reaction mixture was incubated at 37° C. for two hr to remove the template DNA. An additional 1 μL of DpnI was added and the mixture was incubated at 37° C. overnight. Next, 2 μL of the reaction was transformed into TOP1OF' cell (Invitrogen) and plate on LA+carbenicillin 50 mg/L. In alternative embodiments, 2 μL of the reaction can be transformed into TOP1OF' cells (Invitrogen) and plated on LB+carbenicillin 50 mg/L. The correct clone was confirmed by sequencing. The plasmid map and sequence are shown in FIGS. 39 and 40.

Figure 41:
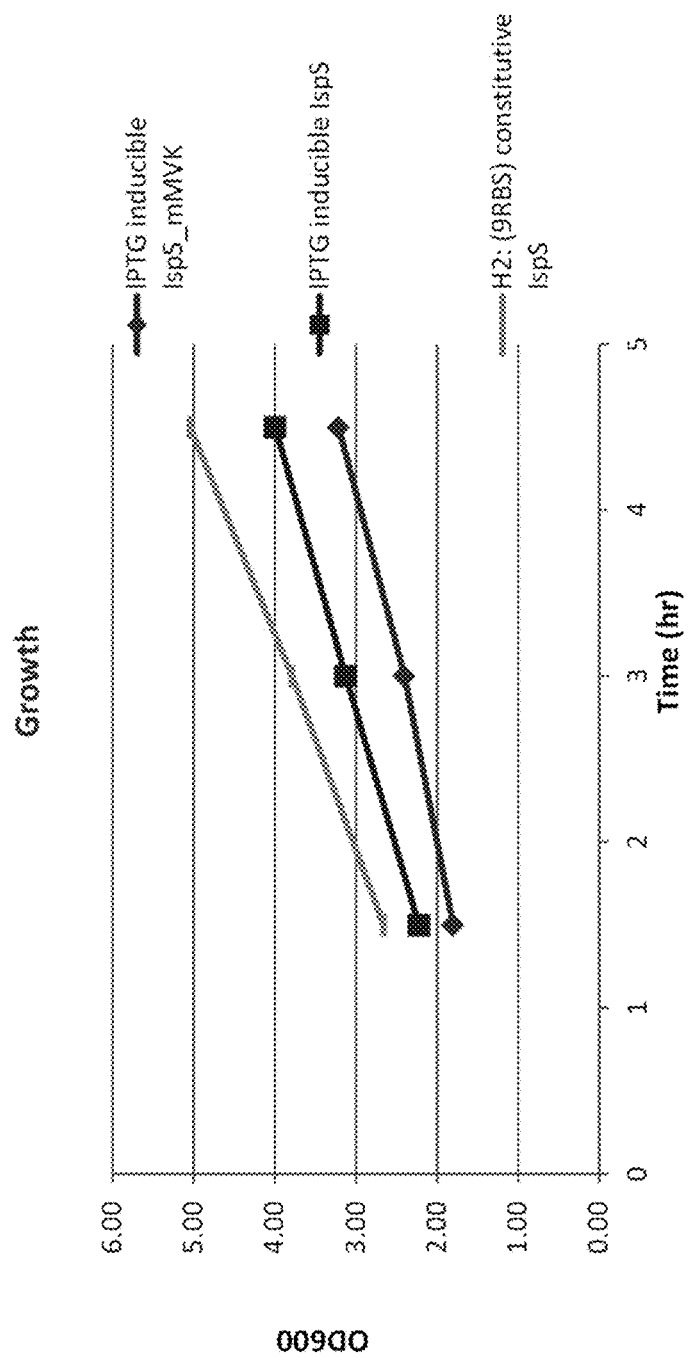
FIG. 41 depicts the growth of a host cell comprising a constitutively expressed isoprene synthase variant as compared to host cells comprising an inducible isoprene synthase variant.
Figure 42:
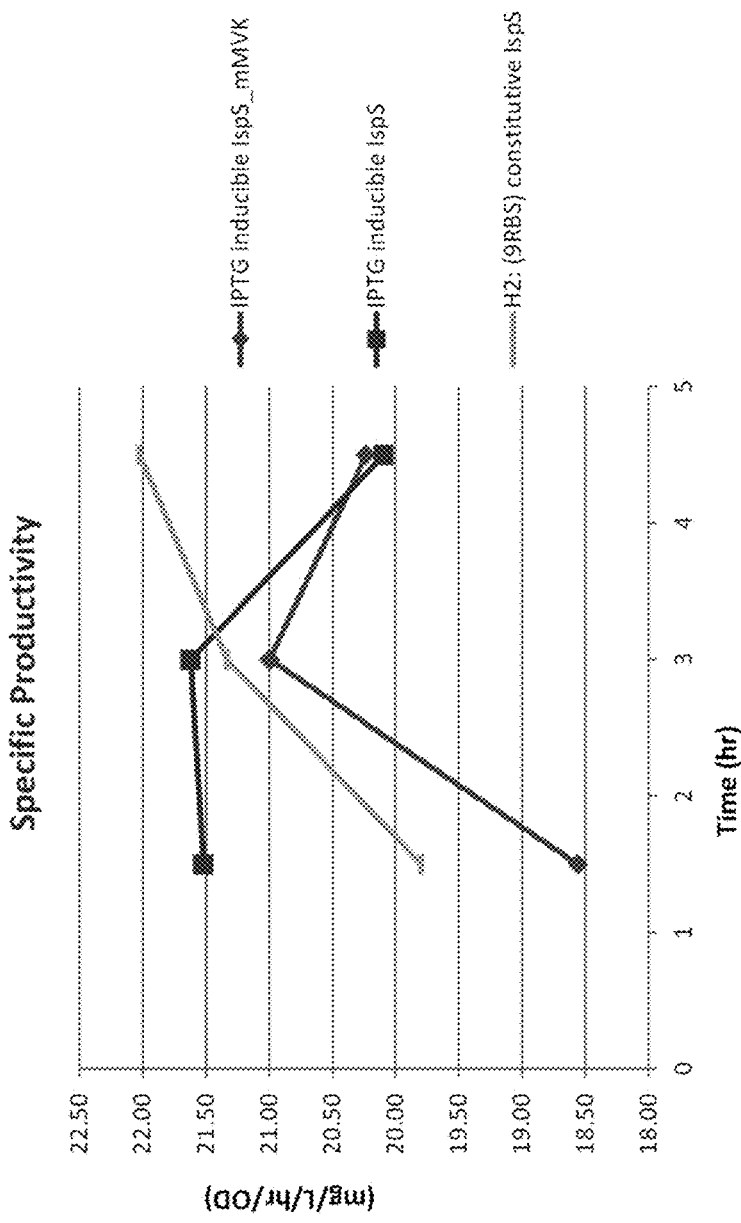
FIG. 42 depicts the specific productivity of isoprene from a host cell comprising a constitutively expressed isoprene synthase variant as compared to host cells comprising an inducible isoprene synthase variant.

Construction of a Constitutive Isoprene Production Strain. pCHL426 and pCHL427 were transformed by electroporation into the strains listed in Table 23. Various RBSs with differential IspA expression level hosts were capable of accommodating constitutively expressed IspS variants. In particular, constitutively expressed isoprene synthase variants expressed in the CMP1281 host background exhibited similar or better cell growth and isoprene specific productivity than the IPTG control strains (FIGS. 41 and 42).

TABLE 23

Strains used for transformation.

| | |
|---|---|
| CMP1133 | HMB GI1.2gltA yhfSFRTPyddVIspAyhfS thiFRTtruncIspA pgl ML |
| CMP1279 | BL21 t pgl, GI1.2gltA pgl- PL.2mKKDyI pgl yhfS-FRT-PyddV(1/3rbs)ispA-go |
| CMP1280 | BL21 t pgl, GI1.2gltA pgl- PL.2mKKDyI pgl yhfS-FRT-PyddV(3rbs)ispA-go |
| CMP1281 | BL21 t pgl, GI1.2gltA pgl- PL.2mKKDyI pgl yhfS-FRT-PyddV(9rbs)ispA-go |

Example 26

Construction of a *Saccharomyces cerevisiae* Strain Containing the Gene Coding For Farnesyl Pyrophosphate Synthetase (ERG20)

A. Insertion of ERG2OP or an Alternate Promoter, and ERG20 at a Different Locus

Colony polymerase chain reaction (PCR) protocols are performed according to the following method. The template is chromosomal DNA of a *Saccharomyces cerevisiae* strain. The template is used in the following PCR reaction: 100 ng template DNA in 1 µl, 10 µl Herculase Buffer, 1 µl 100 mM dNTPs, 1.25 µl 10 m M Forward primer, 1.25 µl 10 m M Reverse primer, 1 µl of Herculase Fusion II DNA Polymerase (Agilent Technologies, Stratagene Products Division, La Jolla, Calif.), and 34.5 µl diH2O. The PCR reaction is cycled in a PCR Express Thermal Cycler (Thermo Hybaid, Franklin, Mass.) as follows: 95° C./2 minutes; 30 cycles of 95° C./20 seconds, x° C. (annealing temperature)/20 seconds, and 72° C./(40 seconds/kb of product). The reaction is cooled to 4° C. The annealing temperature of x° C. is chosen to be 3° C. lower than the lower melting temperature of the primer pair. The size of the resulting PCR fragment is determined on a pre-cast 0.8% E-gel®(Invitrogen, Carlsbad, Calif.), using DNA Molecular Weight Marker X (75-12,216 bp) (Roche Diagnostics, Mannheim, Germany) as size marker.

For the insertion of ERG20 in an exogenous locus (e.g. PDC6), three DNA pieces are generated by PCR. Piece 1 contains a 15 bp sequence allowing assembly by the seamless kit (Life Technologies, Carlsbad, Calif.) to a XbaI/EcoRI-digested vector pBBR1MCS5 (Kovach et al. 1995. *Gene* 166: 175-176), a region (around 50 bp) homologous to the PDC6 region of *Saccharomyces cerevisiae*, a URA3 marker and its promoter flanked by loxP sites, and a 15 bp allowing assembly to the promoter of ERG20 or any other chosen promoter (other promoters can be chosen on the basis of their expression signature as determined by microarray experiments of a *S. cerevisiae* strain producing isoprene). The aim of the other chosen promoters is to get a promoter which provides lower expression of the ispA enzyme than the endogenous ERG20 promoter at all times or, in the alternative, during the production period of a fermentation run (or when isoprenoid molecules begin to accumulate). Template is a plasmid containing the URA3 gene between loxP sites. Piece 2 contains the promoter of the ERG20 gene or one of the other chosen promoters. Template for that piece is chromosomal DNA of a *Saccharomyces cerevisiae* strain. Primers are designed to allow seamless assembly to piece 1 and piece 3. Piece 3 contains the *S. cerevisiae* ERG20 gene amplified from chromosomal DNA or a codon-redesigned allele, a homology region to recombine at the PDC6 locus (around 50 bp, incorporated in the primer) and two sets of 15-bp allowing assembly with piece 2 and pBBR1MCS5 digested by XbaI and EcoRI. Template for this piece is chromosomal DNA of a *Saccharomyces cerevisiae*, or a plasmid containing a codon-altered version of the gene, designed and synthesized by DNA2.0 (Menlo Park, Calif.).

All Polymerase chain reactions (PCR) are done using Herculase II Fusion according to the protocol recommended by the manufacturer (Agilent Technologies, Stratagene Products Division, La Jolla, Calif.). The reaction products are purified using the PCR purification kit from Qiagen (Germantown, Md., USA). Piece 1, 2 and 3 are then assembled with EcoRI/XbaI-digested plasmid pBBR1-MCSS using the GeneArt seamless cloning and assembly kit (Life Technologies, Carlsbad, Calif.), according to the protocol recommended by the manufacturer. The reaction is transformed in *E. coli* Top10 cells (Invitrogen, Carlsbad, Calif.), and transformants are selected on LB+gentamycin 5 mg/L. Plasmid is isolated from one of those colonies, and named pCPN100 for ERG20 promoter, and pCPN110, 120, 130 for three alternate promoters. The presence of the right construct in the plasmid is confirmed by sequencing (Quintara Bio, Albany, Calif.). Plasmids pCPN101, pCNP100, 110, 120 and 130 are used as a template for a PCR reaction using primers which amplify the whole constructed cassette. The PCR products are purified using the Qiagen PCR purification kit (Germantown, Md., USA). After further purification, that PCR product is transformed in a URA3, HIS3 minus version of *S. cerevisiae* using the Sigma yeast transformation kit according to the manufacturer's protocol (Sigma-Aldrich, St Louis, Mo., USA). Transformants are selected on Yeast Nitrogen Base without amino acids (Difco Yeast Nitrogen Base without Amino Acids) supplemented with Formedium drop out (Kaiser, DSCK162), histidine and 10 g/L glucose or ethanol. After re-streaking a colony one more time on the same plates, the presence of the right insert is verified by PCR using chromosomal DNA of a colony growing on those plates. The URA3 marker is looped out with a plasmid expressing an inducible Cre recombinase and a HIS3 gene, which is introduced by transformation (Sigma yeast transformation kit) and selection on Yeast Nitrogen Base without amino acids (Difco Yeast Nitrogen Base without Amino Acids) supplemented with Formedium drop out (Kaiser, DSCK162), uracil and 10 g/L glucose or ethanol. Colonies thus obtained were named CPN101, 111, 121 and 131 respectively and were used for further modifications.

B. Knock Out of Endogenous IspA

For this example, one piece of DNA is generated by PCR. Polymerase chain reaction protocols are performed according to the method described in Example 26(A), above. Template is a plasmid containing a URA3 gene and its promoter flanked by loxP site (see Example 26(A), above), and the forward primer contained 50 bp homology to upstream of ERG20 followed by 25 bp allowing annealing to loxP-URA3-loxP cassette, while the reverse primer contained 50 bp homology to downstream of ERG20 (in reverse orientation to forward primer) followed by 25 bp allowing annealing to loxP-URA3-loxP cassette.

The PCR product thus obtained is transformed in CPN101, 111, 121 and 131 using the Sigma yeast transformation kit according to the manufacturer's protocol (Sigma-Aldrich, St Louis, Mo., USA). Transformants are selected on Yeast Nitrogen Base without amino acids (Difco Yeast Nitrogen Base without Amino Acids) supplemented with Formedium drop out (Kaiser, DSCK162), histidine and 10 g/L glucose or ethanol. After restreaking a colony one more time on the same plates, the presence of the right insert is verified by PCR using chromosomal DNA of a colony growing on those plates. The URA3 marker is looped out as described in Example 26(A), above, and one colony coming from each CPN101, 111, 121 and 131 is checked by PCR and, if correct, named CPN102, 112, 122 and 132.

C. Construction of *S. cerevisiae* CPN103, 113, 123 and 133 which Contain ERG20 Behind its Endogenous Promoter or Alternate Promoter, and which can Produce Isoprene Two plasmids, one expressing the URA3 gene, the other expressing the HIS3 gene, and together expressing one or more of the MVA pathway polypeptides needed for producing isoprene from acetyl-CoA, are transformed in CPN102, 112, 122 and 132 using the Sigma yeast transformation kit. Colonies are selected on Yeast Nitrogen Base without amino acids (Difco Yeast Nitrogen Base without Amino Acids) supplemented with Formedium drop out (Kaiser, DSCK162) and 10 g/L glucose or ethanol. One colony of each was picked, named CPN103, 113, 123 and 133 respectively, and tested for production of isoprene.

What is claimed is:

1. Recombinant microbial cells capable of producing isoprene, wherein said cells comprise
   (i) a geranyltranstransferase or farnesyl diphosphate synthase (ispA) gene having decreased functional activity and
   (ii) one or more nucleic acids encoding: (a) an isoprene synthase polypeptide, wherein the isoprene synthase polypeptide is encoded by a heterologous nucleic acid; and (b) one or more mevalonate (MVA) pathway polypeptides, and (c) a polypeptide having phosphoketolase activity, wherein culturing of said recombinant cells in a suitable media provides for the production of said polypeptides and synthesis of isoprene.

2. A composition comprising the cells of claim 1.

3. A method of producing isoprene comprising: (a) culturing said recombinant cells of claim 1 in suitable conditions which provide for production of isoprene; and (b) producing isoprene.

4. The recombinant cells of claim 1, wherein the functional activity of the ispA gene is decreased by:
   (i) deleting the ispA gene;
   (ii) decreasing ispA gene expression;
   (iii) decreasing ispA protein activity;
   (iv) decreasing ispA protein expression; or
   (v) temporally modulating ispA expression.

5. The recombinant cells of claim 4, wherein ispA gene expression is decreased by placing the ispA gene under the control of a weak promoter.

6. The recombinant cells of claim 4, wherein ispA gene expression is decreased by placing the ispA gene under the control of an auto-regulatory promoter.

7. The recombinant cells of claim 4, wherein ispA protein activity is decreased by translational fusion of the ispA protein with a proteolytic tag.

8. The recombinant cells of claim 4, wherein ispA protein activity is decreased by use of antisense RNA.

9. The recombinant cells of claim 4, wherein ispA protein activity is decreased by introducing one or more mutations into a ribosomal binding site located in the ispA mRNA molecule.

10. The recombinant cells of claim 4, wherein ispA gene expression is decreased by a heterologous repressor (HrcA) transcriptional repressor protein.

11. The recombinant cells of claim 4, wherein ispA protein activity is decreased by replacing the endogenous ispA gene with a gene encoding a polypeptide comprising an increased Km for dimethylallyl diphosphate (DMAPP) in comparison to the Km of the polypeptide encoded by the endogenous ispA gene.

12. The recombinant cells of claim 4, wherein ispA protein activity is decreased by replacing the endogenous ispA gene with another gene comprising a different temperature optimum.

13. The recombinant cells of claim 12, wherein the isoprene synthase polypeptide is a plant isoprene synthase polypeptide or variant thereof.

14. The recombinant cells of claim 13, wherein the isoprene synthase polypeptide is a polypeptide from *Pueraria* or *Populus* or a hybrid, *Populus alba*×*Populus tremula* or variant thereof.

15. The recombinant cells of claim 14, wherein the isoprene synthase polypeptide is selected from the group consisting of *Pueraria montana*, *Pueraria lobata*, *Populus tremuloides*, *Populus alba*, *Populus nigra*, *Populus trichocarpa* and variants thereof.

16. The recombinant cells of claim 13, wherein the plant isoprene synthase polypeptide is a kudzu isoprene synthase polypeptide or variant thereof.

17. The recombinant cells of claim 13, wherein the plant isoprene synthase polypeptide is a Eucalyptus isoprene synthase polypeptide or variant thereof.

18. The recombinant cells of claim 1, wherein said one or more nucleic acids encoding one or more MVA pathway polypeptides of (b) is a heterologous nucleic acid.

19. The recombinant cells of claim 18, wherein said cells comprise one or more nucleic acids encoding MVA pathway polypeptides are from the upper MVA pathway, wherein the upper MVA pathway nucleic acids are selected from the group consisting of acetyl-CoA acetyltransferase (AA-CoA thiolase) or acetoacetyl-CoA synthase, 3-hydroxy-3-methylglutaryl Co-A (HMG-CoA) synthase, and HMG-CoA reductase nucleic acids.

20. The recombinant cells of claim 18, wherein said cells comprise one or more nucleic acids encoding MVA pathway polypeptides are from the lower MVA pathway, wherein the lower MVA pathway nucleic acids are selected from the group consisting of mevalonate kinase (MVK), phosphomevalonate kinase (PMK), and diphosphomevalonte decarboxylase (MVD) nucleic acids.

21. The recombinant cells of claim 18, wherein said cells comprise one or more nucleic acids encoding MVA pathway polypeptides of the complete MVA pathway.

22. The cells of claim 1, further comprising one or more nucleic acids encoding an isopentenyl-diphosphate delta-isomerase (IDI) polypeptide.

23. The recombinant cells of claim 1, further comprising a 1-Deoxyxlulose-5-phosphate synthase (DXS) polypeptide.

24. The recombinant cells of claim 23, wherein said one or more nucleic acids encoding a DXS polypeptide is a heterologous nucleic acid encoding a DXS polypeptide.

25. The recombinant cells of claim 23, wherein said one or more nucleic acids encoding a DXS polypeptide is a copy of an endogenous nucleic acid encoding a DXS polypeptide.

26. The recombinant cells of claim 1, wherein the one or more heterologous nucleic acids is placed under an inducible promoter or a constitutive promoter.

27. The recombinant cells of claim 1, wherein the one or more heterologous nucleic acids is cloned into a multicopy plasmid.

28. The recombinant cells of claim 1, wherein the one or more heterologous nucleic acids is integrated into a chromosome of the cells.

29. The recombinant cells of claim 1, wherein the cells are bacterial, algal, fungal or yeast cells.

30. The recombinant cells of claim 29, wherein the cells are bacterial cells.

31. The bacterial cells of claim 30, wherein the bacterial cells are gram-positive bacterial cells or gram-negative bacterial cells.

32. The bacterial cells of claim 31, wherein the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp.,*Corynebacterium* sp., and *P. alcaligenes* cells.

33. The bacterial cells of claim 31, wherein the bacterial cells are *E. coli* cells.

34. The recombinant cells of claim 29, wherein the cells are algal cells.

35. The algal cells of claim 34, wherein the algal cells are from the group consisting of green algae, red algae, glaucophytes, chlorarachniophytes, euglenids, chromista, or dinoflagellates.

36. The recombinant cells of claim 29, wherein the cells are fungal cells.

37. The fungal cells of claim 36, wherein the fungal cells are filamentous fungi.

38. The recombinant cells of claim 29, wherein the cells are yeast cells.

39. The yeast cells of claim 38, wherein the yeast cells are is selected from the group consisting of *Saccharomyces* sp., *Schizosaccharomyces* sp., *Pichia* sp., and *Candida* sp.

40. The yeast cells of claim 39, wherein the yeast cells are *Saccharomyces cerevisiae* cells.

41. The recombinant cells of claim 1, wherein the one or more nucleic acids encoding a polypeptide having phosphoketolase activity is isolated from *Lactobacillus reuteri, Bifidobacterium longum, Ferrimonas balearica, Pedobactor saltans, Streptomyces griseus, Nocardiopsis dassonvillei, Enterococcus gallinarum, Nostoc* sp., or *Pantoea* sp.

42. The recombinant cells of claim 1, wherein the polypeptide having phosphoketolase activity is capable of catalyzing the conversion of xylulose 5-phosphate to glyceraldehyde 3-phosphate and acetyl phosphate.

43. The recombinant cells of claim 1, wherein the polypeptide having phosphoketolase activity is capable of catalyzing the conversion of fructose 6-phosphate to erythrose 4-phosphate and acetyl phosphate.

* * * * *

SEQUENCE LISTING

```
<160> NUMBER OF SEQ ID NOS: 105

<210> SEQ ID NO 1
<211> LENGTH: 329
<212> TYPE: PRT
<213> ORGANISM: Artificial Sequence
<220> FEATURE:
<223> OTHER INFORMATION: Synthetic Construct

<400> SEQUENCE: 1

Met Thr Asp Val Arg Phe Arg Ile Ile Gly Thr Gly Ala Tyr Val Pro
 1               5                  10                  15

Glu Arg Ile Val Ser Asn Asp Glu Val Gly Ala Pro Ala Gly Val Asp
                20                  25                  30

Asp Asp Trp Ile Thr Arg Lys Thr Gly Ile Arg Gln Arg Arg Trp Ala
            35                  40                  45

Ala Asp Asp Gln Ala Thr Ser Asp Leu Ala Thr Ala Ala Gly Arg Ala
        50                  55                  60

Ala Leu Lys Ala Ala Gly Ile Thr Pro Glu Gln Leu Thr Val Ile Ala
 65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Ala Phe Asp Val Asn
                100                 105                 110

Ala Val Cys Ser Gly Thr Val Phe Ala Leu Ser Ser Val Ala Gly Thr
            115                 120                 125

Leu Val Tyr Arg Gly Gly Tyr Ala Leu Val Ile Gly Ala Asp Leu Tyr
        130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
                180                 185                 190

Leu Ile Arg Val Pro Ala Gly Gly Ser Arg Gln Pro Leu Asp Thr Asp
            195                 200                 205

Gly Leu Asp Ala Gly Leu Gln Tyr Phe Ala Met Asp Gly Arg Glu Val
        210                 215                 220

Arg Arg Phe Val Thr Glu His Leu Pro Gln Leu Ile Lys Gly Phe Leu
225                 230                 235                 240

His Glu Ala Gly Val Asp Ala Ala Asp Ile Ser His Phe Val Pro His
                245                 250                 255

Gln Ala Asn Gly Val Met Leu Asp Glu Val Phe Gly Glu Leu His Leu
```

```
                260              265              270
Pro Arg Ala Thr Met His Arg Thr Val Glu Thr Tyr Gly Asn Thr Gly
        275              280              285

Ala Ala Ser Ile Pro Ile Thr Met Asp Ala Ala Val Arg Ala Gly Ser
        290              295              300

Phe Arg Pro Gly Glu Leu Val Leu Leu Ala Gly Phe Gly Gly Gly Met
305              310              315              320

Ala Ala Ser Phe Ala Leu Ile Glu Trp
                325

<210> SEQ ID NO 2
<211> LENGTH: 2439
<212> TYPE: DNA
<213> ORGANISM: Listeria grayi DSM 20601 mvaE

<400> SEQUENCE: 2
atggttaaag acattgtaat aattgatgcc ctccgtactc ccatcggtaa gtaccgcggt      60
cagctctcaa agatgacggc ggtggaattg ggaaccgcag ttacaaaggc tctgttcgag     120
aagaacgacc aggtcaaaga ccatgtagaa caagtcattt ttggcaacgt tttacaggca     180
gggaacggcc agaatcccgc ccgtcagatc gcccttaatt ctggcctgtc cgcagagata     240
ccggcttcga ctattaacca ggtgtgtggt tctggcctga agcaataag catggcgcgc      300 caacagatcc tactcggaga agcggaagta atagtagcag gaggtatcga atccatgacg     360
aatgcgccga gtattacata ttataataaa gaagaagaca ccctctcaaa gcctgttcct     420
acgatgacct cgatggtct gaccgacgcg tttagcggaa agattatggg tttaacagcc      480
gaaaatgttg ccgaacagta cggcgtatca cgtgaggccc aggacgcctt gcgtatgga      540 tcgcagatga aagcagcaaa ggcccaagaa cagggcattt cgcagctga atactgcct      600 cttgaaatag ggacgaagt tattactcag gacgaggggg ttcgtcaaga gaccaccctc     660
gaaaaattaa gtctgcttcg gaccattttt aaagaagatg gtactgttac agcgggcaac     720
gcctcaacga tcaatgatgg cgcctcagcc gtgatcattg catcaaagga gtttgctgag     780
acaaaccaga ttccctacct tgcgatcgta catgatatta cagagatagg cattgatcca     840
tcaataatgg gcattgctcc cgtgagtgcg atcaataaac tgatcgatcg taaccaaatt     900
agcatggaag aaatcgatct cttttgaaatt aatgaggcat tgcagcatc ctcggtggta     960 gttcaaaaag agttaagcat tcccgatgaa aagatcaata ttggcggttc cggtattgca    1020
ctaggccatc ctcttggcgc cacaggagcg gcattgtaa ccaccctagc gcaccagttg     1080
aaacgtacac acggacgcta tggtattgcc tccctgtgca ttggcggtgg ccttggccta    1140
gcaatattaa tagaagtgcc tcaggaagat cagccggtta aaaatttta tcaattggcc    1200 cgtgaggacc gtctggctag acttcaggag caagccgtga tcagcccagc tacaaaacat    1260
gtactggcag aaatgacact tcctgaagat attgccgaca atctgatcga aaatcaaata    1320
tctgaaatgg aaatccctct ggtgtggct ttgaatctga gggtcaatga taagagttat     1380
accatcccac tagcaactga ggaaccgagt gtaatcgctg cctgtaataa tggtgcaaaa    1440
atggcaaacc acctgggcgg ttttcagtca gaattaaaag atggtttcct gcgtgggcaa    1500
attgtactta tgaacgtcaa agaacccgca actatcgagc atacgatcac ggcagagaaa    1560
gcggcaattt ttcgtgccgc agcgcagtca catccatcga ttgtgaaacg aggtgggggt    1620
ctaaaagaga tagtagtgcg tacgttcgat gatgatccga cgttcctgtc tattgatctg    1680
atagttgata ctaaagacgc aatgggcgct aacatcatta caccattct cgagggtgta    1740
```

-continued

```
gccggctttc tgagggaaat ccttaccgaa gaaattctgt tctctatttt atctaattac    1800
gcaaccgaat caattgtgac cgccagctgt cgcataccttt acgaagcact gagtaaaaaa    1860
ggtgatggta acgaatcgc tgaaaaagtg gctgctgcat ctaaatttgc ccagttagat    1920
ccttatcgag ctgcaaccca caacaaaggt attatgaatg gtattgaggc cgtcgttttg    1980
gcctcaggaa atgacacacg gcggtcgcg gcagccgcac atgcgtatgc ttcacgcgat    2040
cagcactatc ggggcttaag ccagtggcag gttcagaag gcgcgttaca cggggagatc    2100
agtctaccac ttgcactcgg cagcgttggc ggtgcaattg aggtcttgcc taaagcgaag    2160
gcggcattcg aaatcatggg gatcacagag gcgaaggagc tggcagaagt cacagctgcg    2220
gtagggctgg cgcaaaacct ggcggcgtta agagcgcttg ttagtgaagg aatacagcaa    2280
ggtcacatgt cgctccaggc tcgctctctt gcattatcgg taggtgctac aggcaaggaa    2340
gttgaaatcc tggccgaaaa attacagggc tctcgtatga atcaggcgaa cgctcagacc    2400
atactcgcag agatcagatc gcaaaaagtt gaattgtga                           2439
```

<210> SEQ ID NO 3
<211> LENGTH: 1158
<212> TYPE: DNA
<213> ORGANISM: Enterococcus faecium mvaE

<400> SEQUENCE: 3

```
atgaccatga acgttggaat cgataaaatg tcattctttg ttccaccttta ctttgtggac     60
atgactgatc tggcagtagc acgggatgtc gatcccaata gtttctgat tggtattggc    120
caggaccaga tggcagttaa tccgaaaacg caggatattg tgacatttgc cacaaatgct    180
gccaaaaaca tactgtcagc tgaggacctt gataaaattg atatggtcat agtcggcacc    240
gagagtggaa tcgatgaatc caaagcgagt gccgtagtgc ttcacaggtt gctcggtatc    300
cagaagtttg ctcgctcctt tgaaatcaaa gaagcctgtt atgggggtac cgcggcttta    360
cagttcgctg taaaccacat taggaatcat cctgaatcaa aggttcttgt agttgcatca    420
gatatcgcga atacggcct ggcttctgga ggtgaaccaa cgcaaggtgc aggcgctgtg    480
gctatgctcg tctcaactga ccctaagatc attgctttca cgacgatag cctcgcgctt    540
acacaagata tctatgactt ctggcgacca gttggacatg actatcctat ggtcgacggg    600
cctcttagta cagagaccta catccagtca tttcagaccg tatggcagga atacacaaaa    660
cggtcgcagc atgcactggc agactttgct gcccttagct ttcatatccc gtatactaaa    720
atgggcaaaa aggcgctgct tgcaatcctt gaaggcgaat cagaggaggc tcagaaccgt    780
atactagcaa aatatgaaaa gagtatagcc tactccagaa aggcgggtaa cctgtatacc    840
ggtagcctgt atctaggact tatttcactt ctggaaaatg cagaagacct taaagctggt    900
gatttaatag gcctcttttc ttacggttcc ggtgctgttg cggagttttt ctcaggaagg    960
ctggttgagg actatcagga acagctactt aaaacaaaac atgccgaaca gctggccat   1020
agaaagcaac tgacaatcga ggagtacgaa acgatgttct ccgatcgctt ggacgtggac   1080
aaagacgccg aatacgaaga cacattagct tatagcattt cgtcagtccg aaacaccgta   1140
cgtgagtaca ggagttga                                                 1158
```

<210> SEQ ID NO 4
<211> LENGTH: 2442
<212> TYPE: DNA
<213> ORGANISM: Enterococcus gallinarum EG2 mvaE

<400> SEQUENCE: 4

```
atgaaagaag tggttatgat tgatgcggct cgcacaccca ttgggaaata cagaggtagt      60
cttagtcctt ttacagcggt ggagctgggg acactggtca cgaaagggct gctggataaa     120
acaaagctta agaaagacaa gatagaccaa gtgatattcg gcaatgtgct tcaggcagga     180
aacggacaaa acgttgcaag acaaatagcc ctgaacagtg gcttaccagt tgacgtgccg     240
gcgatgacta ttaacgaagt ttgcgggtcc ggaatgaaag cggtgatttt agcccgccag     300
ttaatacagt taggggaggc agagttggtc attgcagggg gtacggagtc aatgtcacaa     360
gcacccatgc tgaaaccttta ccagtcagag accaacgaat acggagagcc gatatcatca     420
atggttaatg acgggctgac ggatgcgttt tccaatgctc acatgggtct tactgccgaa     480
aaggtggcga cccagttttc agtgtcgcgc gaggaacaag accggtacgc attgtccagc     540
caattgaaag cagcgcacgc ggttgaagcc ggggtgttct cagaagagat tattccggtt     600
aagattagcg acgaggatgt cttgagtgaa gacgaggcag taagaggcaa cagcactttg     660
gaaaaactgg gcaccttgcg gacggtgttt tctgaagagg gcacggttac cgctggcaat     720
gcttcaccgc tgaatgacgg cgctagtgtc gtgattcttg catcaaaaga atacgcggaa     780
aacaataatc tgccttacct ggcgacgata aaggaggttg cggaagttgg tatcgatcct     840
tctatcatgg gtattgcccc aataaaggcc attcaaaagt taacagatcg gtcgggcatg     900
aacctgtcca cgattgatct gttcgaaatt aatgaagcat tcgcggcatc tagcattgtt     960
gtttctcaag agctgcaatt ggacgaagaa aaagtgaata tctatggcgg ggcgatagct    1020
ttaggccatc caatcggcgc aagcggagcc cggatactga caaccttagc atacggcctc    1080
ctgcgtgagc aaaagcgtta tggtattgcg tcattatgta tcggcggtgg tcttggtctg    1140
gccgtgctgt tagaagctaa tatggagcag acccacaaag acgttcagaa gaaaaagttt    1200
taccagctta cccctccga gcggagatcg cagcttatcg agaagaacgt tctgactcaa    1260
gaaacggcac ttattttcca ggagcagacg ttgtccgaag aactgtccga tcacatgatt    1320
gagaatcagg tctccgaagt ggaaattcca atgggaattg cacaaaattt tcagattaat    1380
ggcaagaaaa aatggattcc tatggcgact gaagaacctt cagtaatagc ggcagcatcg    1440
aacggcgcca aaatctgcgg gaacatttgc gcggaaacgc ctcagcggct tatgcgcggg    1500
cagattgtcc tgtctggcaa atcagaatat caagccgtga taaatgccgt gaatcatcgc    1560
aaagaagaac tgattctttg cgcaaacgag tcgtacccga gtattgttaa acgcggggga    1620
ggtgttcagg atatttctac gcgggagttt atgggttctt ttcacgcgta tttatcaatc    1680
gactttctgg tggacgtcaa ggacgcaatg ggggcaaaca tgatcaactc tattctcgaa    1740
agcgttgcaa ataaactgcg tgaatggttc ccggaagagg aaatactgtt ctccatcctg    1800
tcaaacttcg ctacggagtc cctggcatct gcatgttgcg agattccttt tgaaagactt    1860
ggtcgtaaca agaaattggg tgaacagatc gccaagaaaa ttcaacaggc agggaatat    1920
gctaagcttg acccttaccg cgcggcaacc ataacaagg ggattatgaa cggtatcgaa    1980
gccgtcgttg ccgcaacggg aaacgacaca cgggctgttt ccgcttctat tcacgcatac    2040
gccgcccgta atgccttgta ccaaggttta acgattggc agatcaaggg cgataaactg    2100
gttggtaaat taacagtccc actggctgtg gcgactgtcg gtggcgcgtc gaacatatta    2160
ccaaaagcca aagcttccct cgccatgctg gatattgatt ccgcaaaaga actggcccaa    2220
gtgatcgccg cggtaggttt agcacagaat ctggcggcgt tacgtgcatt agtgacagaa    2280
ggcattcaga aaggacacat gggcttgcaa gcacgttctt tagcgatttc gataggtgcc    2340
```

| | |
|---|---|
| atcggtgagg agatagagca agtcgcgaaa aaactgcgtg aagctgaaaa aatgaatcag | 2400 |
| caaacggcaa tacagatttt agaaaaaatt cgcgagaaat ga | 2442 |

<210> SEQ ID NO 5
<211> LENGTH: 1155
<212> TYPE: DNA
<213> ORGANISM: Enterococcus casseliflavus mvaE

<400> SEQUENCE: 5

| | |
|---|---|
| atgaaaatcg gtattgaccg tctgtccttc ttcatcccga atttgtattt ggacatgact | 60 |
| gagctggcag aatcacgcgg ggatgatcca gctaaatatc atattggaat cggacaagat | 120 |
| cagatggcag tgaatcgcgc aaacgaggac atcataacac tgggtgcaaa cgctgcgagt | 180 |
| aagatcgtga cagagaaaga ccgcgagttg attgatatgg taatcgttgg cacggaatca | 240 |
| ggaattgacc actccaaagc aagcgccgtg attattcacc atctccttaa aattcagtcg | 300 |
| ttcgcccgtt ctttcgaggt aaaagaagct tgctatggcg aactgctgcc cctgcacatg | 360 |
| gcgaaggagt atgtcaaaaa tcatccggag cgtaaggtct tggtaattgc gtcagacatc | 420 |
| gcgcgttatg gttggccag cggaggagaa gttactcaag cgtggggc cgtagccatg | 480 |
| atgattacac aaaaccccg gattctttcg attgaagacg atagtgtttt tctcacagag | 540 |
| gatatctatg atttctggcg gcctgattac tccgagttcc ctgtagtgga cgggccccttt | 600 |
| tcaaactcaa cgtatataga gagttttcag aaagtttgga accggcacaa ggaattgtcc | 660 |
| ggaagagggc tggaagatta tcaagctatt gcttttcaca taccctatac gaagatgggt | 720 |
| aagaaagcgc tccagagtgt tttagaccaa accgatgaag ataaccagga gcgcttaatg | 780 |
| gctagatatg aggagtctat cgctatagc cggagaattg gtaacctgta cacaggcagc | 840 |
| ttgtaccttg gtcttacaag cttgttggaa aactctaaaa gtttacaacc gggagatcgg | 900 |
| atcggcctct ttcctatgg cagtggtgcg gtgtccgagt tctttaccgg gtatttagaa | 960 |
| gaaaattacc aagagtacct gttcgctcaa agccatcaag aaatgctgga tagccggact | 1020 |
| cggattacgg tcgatgaata cgagaccatc ttttcagaga ctctgccaga acatggtgaa | 1080 |
| tgcgccgaat atacgagcga cgtccccttt tctataacca agattgagaa cgacattcgt | 1140 |
| tattataaaa tctga | 1155 |

<210> SEQ ID NO 6
<211> LENGTH: 2448
<212> TYPE: DNA
<213> ORGANISM: Listeria grayi DSM 20601 mvaS

<400> SEQUENCE: 6

| | |
|---|---|
| atggaagaag tggtaattat agatgcacgt cggactccga ttggtaaata tcacgggtcg | 60 |
| ttgaagaagt tttcagcggt ggcgctgggg acggccgtgg ctaaagacat gttcgaacgc | 120 |
| aaccagaaaa tcaaagagga gatcgcgcag gtcataattg gtaatgtctt gcaggcagga | 180 |
| aatggccaga accccgcgcg gcaagttgct cttcaatcag ggttgtccgt tgacattccc | 240 |
| gcttctacaa ttaacgaggt ttgtgggtct ggtttgaaag ctatcttgat gggcatggaa | 300 |
| caaatccaac tcggcaaagc gcaagtagtg ctggcaggcg gcattgaatc aatgacaaat | 360 |
| gcgccaagcc tgtcccacta taacaaggcg gaggatacgt atagtgtccc agtgtcgagc | 420 |
| atgacactgg atggtctgac agacgcattt tctagtaaac ctatgggatt aacagcggaa | 480 |
| aacgtcgcac agcgctacgg tatctcccgt gaggcgcaag atcaattcgc atatcaatct | 540 |

| | |
|---|---|
| cagatgaaag cagcaaaagc gcaggcagaa acaaattcg ctaaggaaat tgtgccactg | 600 |
| gcgggtgaaa ctaaaaccat cacagctgac gaagggatca gatcccaaac aacgatggag | 660 |
| aaactggcaa gtctcaaacc tgttttaaa accgatggca ctgtaaccgc agggaatgct | 720 |
| agcaccatta atgacggggc cgccttgtg ctgcttgcta gcaaaactta ctgcgaaact | 780 |
| aatgacatac cgtaccttgc gacaatcaaa gaaattgttg aagttggaat cgatccggag | 840 |
| attatgggca tctctccgat aaaagcgata caaacattgt tacaaaatca aaagttagc | 900 |
| ctcgaagata ttggagtttt tgaaataaat gaagcctttg ccgcaagtag catagtggtt | 960 |
| gaatctgagt tgggattaga tccggctaaa gttaaccgtt atgggggtgg tatatcctta | 1020 |
| ggtcatgcaa ttggggcaac cggcgctcgc ctggccactt cactggtgta tcaaatgcag | 1080 |
| gagatacaag cacgttatgg tattgcgagc ctgtgcgttg gtggtggact tggactggca | 1140 |
| atgcttttag aacgtccaac tattgagaag gctaaaccga cagacaaaaa gttctatgaa | 1200 |
| ttgtcaccag ctgaacggtt gcaagagctg gaaaatcaac agaaaatcag ttctgaaact | 1260 |
| aaacagcagt tatctcagat gatgcttgcc gaggacactg caaaccattt gatagaaaat | 1320 |
| caaatatcag agattgaact cccaatgggc gtcgggatga acctgaaggt tgatgggaaa | 1380 |
| gcctatgttg tgccaatggc gacgaagag ccgtccgtca tcgcggccat gtctaatggt | 1440 |
| gccaaaatgg ccggcgaaat tcacactcag tcgaaagaac ggctgctcag aggtcagatt | 1500 |
| gttttcagcg cgaagaatcc gaatgaaatc gaacagagaa tagctgagaa ccaagctttg | 1560 |
| attttcgaac gtgccgaaca gtcctatcct tccattgtga aaagagaggg aggtctccgc | 1620 |
| cgcattgcac ttcgtcattt tcctgccgat tctcagcagg agtctgcgga ccagtccaca | 1680 |
| ttttatcag tggaccttt tgtagatgtg aaagacgcga tgggggcaaa tatcataaat | 1740 |
| gcaatacttg agggcgtcgc agccctgttt cgcgaatggt tccccaatga ggaaattctt | 1800 |
| ttttctattc tctcgaactt ggctacggag agcttagtca cggctgtttg tgaagtccca | 1860 |
| tttagtgcac ttagcaagag aggtggtgca acggtggccc agaaaattgt gcaggcgtcg | 1920 |
| ctcttcgcaa agacagaccc ataccgcgca gtgacccaca caaagggat tatgaacggt | 1980 |
| gtagaggctg ttatgcttgc cacaggcaac gacacgcgcg cagtctcagc cgcttgtcat | 2040 |
| ggatacgcag cgcgcaccgg tagctatcag ggtctgacta actggacgat tgagtcggat | 2100 |
| cgcctggtag gcgagataac actgccgctg gccatcgcta cagttggagg cgctaccaaa | 2160 |
| gtgttgccca agctcaagc ggcactggag attagtgatg ttcactcttc tcaagagctt | 2220 |
| gcagccttag cggcgtcagt aggtttagta caaaatctcg cggccctgcg cgcactggtt | 2280 |
| tccgaaggta tacaaaaagg gcacatgtcc atgcaagccc ggtctctcgc aatcgcggtc | 2340 |
| ggtgctgaaa aagccgagat cgagcaggtc gccgaaaagt gcggcagaa cccgccaatg | 2400 |
| aatcagcagc aggcgctccg tttcttggc gagatccgcg aacaatga | 2448 |

<210> SEQ ID NO 7
<211> LENGTH: 1155
<212> TYPE: DNA
<213> ORGANISM: Enterococcus faecium mvaS

<400> SEQUENCE: 7

| | |
|---|---|
| atgaacgtcg gcattgacaa aattaatttt ttcgttccac cgtattatct ggatatggtc | 60 |
| gacctggccc acgcacgcga agtggacccg aacaaattta caattggaat tggacaggat | 120 |
| cagatggctg tgagcaaaaa gacgcacgat atcgtaacat tcgcggctag tgccgcgaag | 180 |
| gaaattttag aacctgagga cttgcaagct atagacatgg ttatagttgg taccgaatcg | 240 |

```
ggcattgacg agagcaaagc atccgcggtc gttttacatc gtttgttggg cgtacaacct    300
ttcgctcgca gttttgaaat taaagaagcc tgttacgggg caaccgcagg cattcagttt    360
gccaagactc atatacaagc gaacccggag agcaaggtcc tggtaattgc aagcgatata    420
gctcggtatg tcttcggtc aggtggagag cccacacaag gcgcagggc agttgctatg      480 cttctcacgg caaatcccag aatcctgacc ttcgaaaacg acaatctgat gttaacgcag    540
gatatttatg acttctggag accacttggt cacgcttacc ctatggtaga tggccacctt    600
tccaatcaag tctatattga cagttttaag aaggtctggc aagcacattg cgaacgcaat    660
caagcttcta tatccgacta tgccgcgatt agttttcata ttccgtatac aaaaatgggt    720
aagaaagccc tgctcgctgt ttttgcagat gaagtggaaa ctgaacagga acgcgttatg    780
gcacggtatg aagagtctat cgtatattca cgccggatcg gcaacttgta tacgggatca    840
ttgtacctgg ggctgatatc cttattggaa acagttctc acctgtcggc gggcgaccgg    900
ataggattgt ttagttatgg gagtggcgct gtcagcgaat ttttctccgg tcgtttagtg    960
gcaggctatg aaaatcaatt gaacaaagag gcgcataccc agctcctgga tcagcgtcag   1020
aagctttcca tcgaagagta tgaggcgatt tttacagatt ccttagaaat tgatcaggat   1080
gcagcgttct cggatgacct gccatattcc atccgcgaga taaaaacac gattcggtac   1140 tataaggaga gctga                                                     1155

<210> SEQ ID NO 8
<211> LENGTH: 2475
<212> TYPE: DNA
<213> ORGANISM: Enterococcus gallinarum EG2 mvaS

<400> SEQUENCE: 8
atggaagaag ttgtcatcat tgacgcactg cgtactccaa taggaaagta ccacggttcg     60
ctgaaagatt acacagctgt tgaactgggg acagtagcag caaaggcgtt gctggcacga    120
aatcagcaag caaaagaaca catagcgcaa gttattattg gcaacgtcct gcaagccgga    180
agtgggcaga atccaggccg acaagtcagt ttacagtcag gattgtcttc tgatatcccc    240
gctagcacga tcaatgaagt gtgtggctcg ggtatgaaag cgattctgat gggtatggag    300
caaattcagc tgaacaaagc ctctgtggtc ttaacaggcg gaattgaaag catgaccaac    360
gcgccgctgt ttagttatta caacaaggct gaggatcaat attcggcgcc ggttagcaca    420
atgatgcacg atggtctaac agatgctttc agttccaaac caatgggctt aaccgcagag    480
accgtcgctg agagatatgg aattacgcgt aaggaacaag atgaatttgc ttatcactct    540
caaatgaagg cggccaaagc ccaggcggcg aaaaagtttg atcaggaaat tgtacccctg    600
acggaaaaat ccgaacggt tctccaggac gaaggcatca gagccgcgac aacagtcgag    660
aagctagctg agcttaaaac ggtgttcaaa aagacggaa cagttacagc gggtaacgcc    720
tctacgataa atgatggcgc tgctatggta ttaatagcat caaatctta ttgcgaagaa    780 caccagattc cttatctggc cgttataaag gagatcgttg aggtgggttt tgccccgaa    840 ataatgggta tttcccccat taaggctata gacaccctgc tgaaaaatca agcactgacc    900
atagaggata taggaatatt tgagattaat gaagcctttg ctgcgagttc gattgtggta   960
gaacgcgagt tgggcctgga ccccaaaaaa gttaatcgct atggcggtgg tatatcactc   1020
ggccacgcaa ttgggcgac gggagctcgc attgcgacga ccgttgctta tcagctgaaa   1080
gatacccagg agcgctacgg tatagcttcc ttatgcgttg tgggggtct tggattggcg   1140
```

```
atgcttctgg aaaacccatc ggccactgcc tcacaaacta attttgatga ggaatctgct    1200
tccgaaaaaa ctgagaagaa gaagttttat gcgctagctc ctaacgaacg cttagcgttt    1260
ttggaagccc aaggcgctat taccgctgct gaaaccctgg tcttccagga gatgacctta    1320
aacaaagaga cagccaatca cttaatcgaa accaaatca gcgaagttga aattccttta     1380
ggcgtgggcc tgaacttaca ggtgaatggg aaagcgtata atgttcctct ggccacggag    1440
gaaccgtccg ttatcgctgc gatgtcgaat ggcgccaaaa tggctggtcc tattacaaca    1500
acaagtcagg agaggctgtt acggggtcag attgtcttca tggacgtaca ggacccagaa    1560
gcaatattag cgaaagttga atccgagcaa gctaccattt tcgcggtggc aaatgaaaca    1620
tacccgtcta tcgtgaaaag aggaggaggt ctgcgtagag tcattggcag gaatttcagt    1680
ccggccgaaa gtgacttagc cacggcgtat gtatcaattg acctgatggt agatgttaag    1740
gatgcaatgg gtgctaatat catcaatagt atcctagaag gtgttgcgga attgtttaga    1800
aaatggttcc cagaagaaga aatcctgttc tcaattctct ccaatctcgc gacagaaagt    1860
ctggtaacgg cgacgtgctc agttccgttt gataaattgt ccaaaactgg gaatggtcga    1920
caagtagctg gtaaaatagt gcacgcggcg gactttgcta agatagatcc atacagagct    1980
gccacacaca ataaaggtat tatgaatggc gttgaagcgt taatcttagc caccggtaat    2040
gacacccgtg cggtgtcggc tgcatgccac ggttacgcgg cacgcaatgg gcgaatgcaa    2100
gggcttacct cttggacgat tatcgaagat cggctgatag gctctatcac attacctttg    2160
gctattgcga cagtgggggg tgccacaaaa atcttgccaa aagcacaggc cgccctggcg    2220
ctaactggcg ttgagacggc gtcggaactg gccagcctgg cggcgagtgt gggattagtt    2280
caaaatttgg ccgctttacg agcactagtg agcgagggca ttcagcaagg gcacatgagt    2340
atgcaagcta gatccctggc cattagcgta ggtgcgaaag gtactgaaat agagcaacta    2400
gctgcgaagc tgagggcagc gacgcaaatg aatcaggagc aggctcgtaa atttctgacc    2460
gaaataagaa attaa                                                     2475
```

<210> SEQ ID NO 9
<211> LENGTH: 1161
<212> TYPE: DNA
<213> ORGANISM: Enterococcus casseliflavus mvaS

<400> SEQUENCE: 9

```
atgaacgttg gaattgataa aatcaatttt ttcgttccgc cctatttcat tgatatggtg     60
gatctcgctc atgcaagaga agttgacccc aacaagttca ctataggaat aggccaagat    120
cagatggcag taaacaagaa aacgcaagat atcgtaacgt tcgcgatgca cgccgcgaag    180
gatattctga ctaaggaaga tttacaggcc atagatatgg taatagtggg gactgagtct    240
gggatcgacg agagcaaggc aagtgctgtc gtattgcatc ggcttttagg tattcagcct    300
tttgcgcgct cctttgaaat taaggaggca tgctatgggg ccactgccgg ccttcagttt    360
gcaaaagctc atgtgcaggc taatccccag agcaaggtcc tggtggtagc ttccgatata    420
gcacgctacg gactggcatc cggaggagaa ccgactcaag gtgtaggtgc tgtggcaatg    480
ttgatttccg ctgatccagc tatcttgcag ttagaaaatg ataatctcat gttgacccaa    540
gatatatacg attttggcg cccggtcggg catcaatatc ctatggtaga cggccatctg    600
tctaatgccg tctatataga cagctttaaa caagtctggc aagcacattg cgagaaaaac    660
caacggactc taaagatta tgctgcattg tcgttccata ttccgtacac gaaaatgggt    720
aagaaagctc tgttagcggt ttttgcggag gaagatgaga cagaacaaaa gcggttaatg    780
```

```
gcacgttatg aagaatcaat tgtatacagt cgtcggactg gaaatctgta tactggctca      840
ctctatctgg gcctgatttc cttactggag aatagtagca gtttacaggc gaacgatcgc      900
ataggtctgt ttagctatgg ttcagggcc  gttgcggaat ttttcagtgg cctcttggta      960
ccgggttacg agaaacaatt agcgcaagct gcccatcaag ctcttctgga cgaccggcaa     1020
aaactgacta tcgcagagta cgaagccatg tttaatgaaa ccattgatat tgatcaggac     1080
cagtcatttg aggatgactt actgtactcc atcagagaga tcaaaaacac tattcgctac     1140
tataacgagg agaatgaata a                                               1161
```

<210> SEQ ID NO 10
<211> LENGTH: 900
<212> TYPE: DNA
<213> ORGANISM: Artificial Sequence
<220> FEATURE:
<223> OTHER INFORMATION: Synthetic Construct

<400> SEQUENCE: 10

```
atggactttc cgcaacaatt ggaggcgtgc gtaaagcaag caaatcaagc cctgtctcgc       60
tttattgcgc cacttccgtt tcaaaacacg cctgtggtcg aaaccatgca atacggggct      120
ctcctgggag ggaagcggtt gagaccattc ttagtgtacg ctaccggtca tatgtttggc      180
gtaagtacca acactctgga tgcgcctgct gctgccgtgg aatgcatcca tgcgtacagt      240
ttaattcatg acgatctgcc tgcgatggat gatgatgatc tgcgtagagg cttacctaca      300
tgtcacgtaa aatttggcga agctaacgca atacttgcgg gcgatgctct ccagacgctg      360
gctttctcta tcctgtctga tgcggatatg cccgaagtga gcgaccggga tcggattagt      420
atgatttcag aattagcctc tgcgagtgga attgcaggca tgtgcggggg acaagcactg      480
gatttggatg cagagggcaa acatgtacca ttagatgcat tggaacgcat acatcggcac      540
aaaaccgggg ctttaattag agctgccgtt cggttaggag ccttgtctgc cggtgataaa      600
gggcgtcgtg cgttgcctgt attagataaa tatgccgaga gtatcggtct ggcttttcaa      660
gtgcaggacg atatcctgga tgtcgtagga gataccgcaa cactgggtaa acgccagggt      720
gcagatcaac agctgggtaa atccacatac ccagctcttc ttggtctgga acaagcccgt      780
aaaaaggcaa gagacctgat cgacgacgcg cgccagtccc tgaaacagtt agcggaacag      840
tctttggata ctagtgcttt agaggccttg gcagattata ttatacagcg taataagtaa      900
```

<210> SEQ ID NO 11
<211> LENGTH: 3992
<212> TYPE: DNA
<213> ORGANISM: Artificial Sequence
<220> FEATURE:
<223> OTHER INFORMATION: Synthetic Construct

<400> SEQUENCE: 11

```
gcgcccaata cgcaaaccgc ctctccccgc gcgttggccg attcattaat gcagctggca       60
cgacaggttt cccgactgga aagcgggcag tgagcgcaac gcaattaatg tgagttagct      120
cactcattag gcaccccagg ctttacactt tatgcttccg gctcgtatgt tgtgtggaat      180
tgtgagcggc cagcccctca gcatggactt tccgcaacaa ttggaggcgt gcgtaaagca      240
agcaaatcaa gccctgtctc gctttattgc gccacttccg tttcaaaaca cgcctgtggt      300
cgaaaccatg caatacgggg ctctcctggg agggaagcgg ttgagaccat tcttagtgta      360
cgctaccggt catatgtttg gcgtaagtac caacactctg gatgcgcctg ctgctgccgt      420
```

```
ggaatgcatc catgcgtaca gtttaattca tgacgatctg cctgcgatgg atgatgatga    480
tctgcgtaga ggcttaccta catgtcacgt aaaatttggc gaagctaacg caatacttgc    540
gggcgatgct ctccagacgc tggctttctc tatcctgtct gatgcggata tgcccgaagt    600
gagcgaccgg gatcggatta gtatgatttc agaattagcc tctgcgagtg gaattgcagg    660
catgtgcggg ggacaagcac tggatttgga tgcagagggc aaacatgtac cattagatgc    720
attggaacgc atacatcggc acaaaaccgg ggctttaatt agagctgccg ttcggttagg    780
agccttgtct gccggtgata agggcgtcg tgcgttgcct gtattagata aatatgccga     840
gagtatcggt ctggcttttc aagtgcagga cgatatcctg gatgtcgtag agataccgc     900
aacactgggt aaacgccagg gtgcagatca acagctgggt aaatccacat acccagctct    960
tcttggtctg gaacaagccc gtaaaaaggc aagagacctg atcgacgacg cgcgccagtc    1020
cctgaaacag ttagcggaac agtctttgga tactagtgct ttagaggcct tggcagatta    1080
tattatacag cgtaataagt aagctgaggg gctggcaagt gtagcggtca cgctgcgcgt    1140
aaccaccaca cccgccgcgc ttaatgcgcc gctacagggc gcgtcaggtg gcacttttcg    1200
gggaaatgtg cgcggaaccc ctatttgttt attttttctaa atacattcaa atatgtatcc   1260
gctcatgaga caataaccct gataaatgct tcaataatat tgaaaaagga gagtatgag    1320
tattcaacat ttccgtgtcg cccttattcc cttttttgcg gcattttgcc ttcctgtttt    1380
tgctcaccca gaaacgctgg tgaaagtaaa agatgctgaa gatcagttgg gtgcacgagt    1440
gggttacatc gaactggatc tcaacagcgg taagatcctt gagagttttc gccccgaaga    1500
acgttttcca atgatgagca cttttaaagt tctgctatgt ggcgcggtat tatcccgtat    1560
tgacgccggg caagagcaac tcggtcgccg catacactat tctcagaatg acttggttga    1620
gtactcacca gtcacagaaa agcatcttac ggatggcatg acagtaagag aattatgcag   1680
tgctgccata accatgagtg ataacactgc ggccaactta cttctgacaa cgatcggagg    1740
accgaaggag ctaaccgctt ttttgcacaa catgggggat catgtaactc gccttgatcg    1800
ttgggaaccg gagctgaatg aagccatacc aaacgacgag cgtgacacca cgatgcctgt    1860
agcaatggca acaacgttgc gcaaactatt aactggcgaa ctacttactc tagcttcccg    1920
gcaacaatta atagactgga tggaggcgga taaagttgca ggaccacttc tgcgctcggc    1980
ccttccggct ggctggttta ttgctgataa atctggagcc ggtgagcgtg ggtctcgcgg    2040
tatcattgca gcactggggc cagatggtaa gccctcccgt atcgtagtta tctacacgac    2100
ggggagtcag gcaactatgg atgaacgaaa tagacagatc gctgagatag gtgcctcact    2160
gattaagcat tggtaactgt cagaccaagt ttactcatat atactttaga ttgatttaaa    2220
acttcatttt taatttaaaa ggatctaggt gaagatcctt tttgataatc tcatgaacaa    2280
taaaactgtc tgcttacata aacagtaata caaggggtgt tatgagccat attcaacggg    2340
aaacgtcttg ctctaggccg cgattaaatt ccaacatgga tgctgattta tatgggtata    2400
aatgggctcg cgataatgtc gggcaatcag gtgcgacaat ctatcgattg tatgggaagc    2460
ccgatgcgcc agagttgttt ctgaaacatg gcaaaggtag cgttgccaat gatgttacag    2520
atgagatggt cagactaaac tggctgacgg aatttatgcc tcttccgacc atcaagcatt    2580
ttatccgtac tcctgatgat gcatggttac tcaccactgc gatccccggg aaaacagcat    2640
tccaggtatt agaagaatat cctgattcag gtgaaaatat tgttgatgcg ctggcagtgt    2700
tcctgcgccg gttgcattcg attcctgttt gtaattgtcc ttttaacagc gatcgcgtat    2760
ttcgtctcgc tcaggcgcaa tcacgaatga ataacggttt ggttgatgcg agtgattttg    2820
```

```
atgacgagcg taatggctgg cctgttgaac aagtctggaa agaaatgcat aaacttttgc    2880
cattctcacc ggattcagtc gtcactcatg gtgatttctc acttgataac cttattttg    2940 acgagggaa attaataggt tgtattgatg ttggacgagt cggaatcgca gaccgatacc    3000
aggatcttgc catcctatgg aactgcctcg gtgagttttc tccttcatta cagaaacggc    3060
tttttcaaaa atatggtatt gataatcctg atatgaataa attgcagttt catttgatgc    3120
tcgatgagtt tttctaagaa ttaattcatg accaaaatcc cttaacgtga gttttcgttc    3180
cactgagcgt cagaccccgt agaaaagatc aaggatcttc ttgagatcc tttttttctg    3240 ccgtaatct gctgcttgca acaaaaaaa ccaccgctac cagcggtggt ttgtttgccg    3300
gatcaagagc taccaactct ttttccgaag gtaactggct tcagcagagc gcagatacca    3360
aatactgtcc ttctagtgta gccgtagtta ggccaccact tcaagaactc tgtagcaccg    3420
cctacatacc tcgctctgct aatcctgtta ccagtggctg ctgccagtgg cgataagtcg    3480
tgtcttaccg ggttggactc aagacgatag ttaccggata aggcgcagcg gtcgggctga    3540
acggggggtt cgtgcacaca gcccagcttg gagcgaacga cctacaccga actgagatac    3600
ctacagcgtg agctatgaga aagcgccacg cttcccgaag ggagaaaggc ggacaggtat    3660
ccggtaagcg gcagggtcgg aacaggagag cgcacgaggg agcttccagg gggaaacgcc    3720
tggtatcttt atagtcctgt cgggtttcgc cacctctgac ttgagcgtcg attttgtga    3780 tgctcgtcag ggggggggag cctatggaaa aacgccagca acgcggcctt tttacggttc    3840
ctggcctttt gctggccttt tgctcacatg ttctttcctg cgttatcccc tgattctgtg    3900
gataaccgta ttaccgcctt tgagtgagct gataccgctc gccgcagccg aacgaccgag    3960
cgcagcgagt cagtgagcga ggaagcggaa ga                                 3992
```

<210> SEQ ID NO 12
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 12

```
atgcataaat ttactggtgt caatgccaag tttcagcaac ccgcgttgag gaacctcagc      60
cccgtggtgg ttgagaggga gagggaggag ttcgtggggt tcttcccgca gatcgtccgc     120
gatctgaccg aggacggcat cggacacccg gaggtgggcg acgctgtggc gcggctgaag     180
gaggtgctgc aatacaacgc tcccggtggg aaatgcaacc gtgggctgac ggtggtggct     240
gcgtaccggg agctgtcggg gccggggcag aaggatgctg agagcctgcg gtgcgcgctg     300
gccgtgggtt ggtgcatcga gttgttccag gccttcttcc tggtgtggga tgacatcatg     360
gatcagtccc tcacgcgccg ggggcagctg tgttggtata agaaggaggg ggtcggtttg     420
gatgccatca cgactccttc ctcctcgag tcctctgtgt acagagtgct gaagaagtac     480
tgcaggcagc ggccgtatta cgtgcatctg ttggagctct tcctgcagac cgcctaccag     540
actgagctcg gcagatgct ggacctcatc acagctcccg tctccaaagt ggatttgagt     600
cacttcagtg aggagaggta caaagccatc gttaagtaca agactgcctt ctactccttc     660
tacctacccg tggctgctgc catgtatatg gttgggatcg acagtaagga agaacacgag     720
aatgccaaag ccatcctgct ggagatgggg gaatacttcc agatccagga tgattacctg     780
gactgctttg gggacccggc gctcacgggg aaggtgggca ccgacatcca ggacaataaa     840
```

```
tgcagctggc tcgtggtgca gtgcctgcag cgcgtcacgc cggagcagcg gcagctcctg    900
gaggacaact acggccgtaa ggagcccgag aaggtggcga aggtgaagga gctgtatgag    960
gccgtgggga tgagggctgc gttccagcag tacgaggaga gcagctaccg gcgcctgcag   1020
gaactgatag agaagcactc gaaccgcctc ccgaaggaga tcttcctcgg cctggcacag   1080
aagatctaca aacgccagaa atga                                          1104
```

<210> SEQ ID NO 13
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 13

```
atgcataaat ttactggtgt caatgccaag tttcagcaac ccgcgttgag gaacctcagc     60
cccgtggtgg ttgagaggga gagggaggag ttcgtggggt tcttcccgca gatcgtccgc    120
gatctgaccg aggacggcat cggacaccca gaggtgggcg acgctgtggc gcggctgaag    180
gaggtgctgc aatacaacgc tcccggtggg aaatgcaacc gtgggctgac ggtggtggct    240
gcgtaccggg agctgtcggg gccggggcag aaggatgctg agagcctgcg gtgcgcgctg    300
gccgtgggtt ggtgcatcga gttgttccag gccttcttcc tggtggctga tgatatcatg    360
gatcagtccc tcacgcgccg ggggcagctg tgttggtata agaaggaggg ggtcggtttg    420
gatgccatgt gggactcctt cctcctggaa tcctctgtgt acagagtgct gaagaagtac    480
tgcaggcagc ggccgtatta cgtgcatctg ttggagctct tcctgcagac cgcctaccag    540
actgagctcg gcagatgct ggacctcatc acagctcccg tctccaaagt ggatttgagt    600
cacttcagtg aggagaggta caaagccatc gttaagtaca agactgcctt ctactccttc    660
tacctacccg tggctgctgc catgtatatg gttgggatcg acagtaagga agaacacgag    720
aatgccaaag ccatcctgct ggagatgggg gaatacttcc agatccagga tgattacctg    780
gactgctttg ggacccggc gctcacgggg aaggtgggca ccgacatcca ggacaataaa    840
tgcagctggc tcgtggtgca gtgcctgcag cgcgtcacgc cggagcagcg gcagctcctg    900
gaggacaact acggccgtaa ggagcccgag aaggtggcga aggtgaagga gctgtatgag    960
gccgtgggga tgagggctgc gttccagcag tacgaggaga gcagctaccg gcgcctgcag   1020
gaactgatag agaagcactc gaaccgcctc ccgaaggaga tcttcctcgg cctggcacag   1080
aagatctaca aacgccagaa atga                                          1104
```

<210> SEQ ID NO 14
<211> LENGTH: 1077
<212> TYPE: DNA
<213> ORGANISM: E. coli

<400> SEQUENCE: 14

```
atgactcaac ttttccccgg tcccatagtt cggacgccag gacttgcaga actcgatgcg     60
cgggctcgcg acatattcag acgtgtcgta gaatcttatc tggagaccgg tgaaccagtg    120
ggctctcgca cgattagcaa aggtggtgta gcactcagcc ctgcgtcaat ccgcaataca    180
atgcaggact ggcccagtt ggggttactt gacgcacctc ataccagtgc cggccgtatg    240
ccgacacacg ctggtttaag aatgtttgta gacgggttcc tggaagttgg cgacgtggcg    300
gagcaagaga agcgggctat tgaagcacgg ctggcagtga agggacgttc ctttgaagaa    360
gcccttgcgg aggcaagctc tattttaagc ggtctggctg gcggagcggg cattgtcgtc    420
```

```
actccggtac gggaaggcgg ggtcaaacat gttgagtttg tgccgctggg aggtggtcag    480
gttctggctg tgatggtctt tgaagatggc caagtagaaa accgcttaat gcgccaggcc    540
cccggcgtca cccccttctgc tctacaggaa gcctcgaatt tcttgaatgc ccgtttacgt   600
ggacggacac tcacggaagc ccgtaccgaa atgggaggtg aacttgatgc ggctcgccgc    660
cagcttaatg aaacagctgc tcggctggtg gaagatggac tggcagcatg gtcaggtgga    720
gaaggagacg cccgcagctt gatcgttcgc ggacaggcga accttcttgc cgatgctcgt    780
gcacgcgagg atatagaccg cgttcgtcag ttgttcgatg atttgagtcg ccgtgcgcaa    840
ctcatcgggc tcctcgatga tgtccggac gcggaaggtg tgcgcattta tattggagct     900
gaaacccgcc tgttctcact ttctggaagc tcggtgatcg ctgccccgta catgacaggc    960
cgtcaaaagg tattgggcgc catagggggtt atcggacctg cccgcttgaa ttacgctcgc  1020
gttatcccac tcgtggatta tacggcacgc gttttgggcc gtatgatgga cggttga      1077
```

```
<210> SEQ ID NO 15
<211> LENGTH: 125
<212> TYPE: DNA
<213> ORGANISM: Enterobacteria phage Lambda

<400> SEQUENCE: 15
aattcatata aaaaacatac agataaccat ctgcggtgat aaattatctc tggcggtgtt     60
gacataaata ccactggcgg tgatactgag cacatcagca ggacgcactg accaccatga    120
aggtg                                                                125

<210> SEQ ID NO 16
<211> LENGTH: 108
<212> TYPE: DNA
<213> ORGANISM: Artificial Sequence
<220> FEATURE:
<223> OTHER INFORMATION: Synthetic Construct

<400> SEQUENCE: 16
atacctcggc actggaagcg ctagcggact acatcatcca gcgtaataaa gcagctaacg     60
atgaaaacta cgcagcatct gtttaaaatt aaccctcact aaagggcg                 108

<210> SEQ ID NO 17
<211> LENGTH: 73
<212> TYPE: DNA
<213> ORGANISM: Artificial Sequence
<220> FEATURE:
<223> OTHER INFORMATION: Synthetic Construct

<400> SEQUENCE: 17
tatttggcaa tatcaaaact catcagggc ctattaatac ttattgttta taatacgact      60
cactataggg ctc                                                       73

<210> SEQ ID NO 18
<211> LENGTH: 25
<212> TYPE: DNA
<213> ORGANISM: Artificial Sequence
<220> FEATURE:
<223> OTHER INFORMATION: Synthetic Construct

<400> SEQUENCE: 18
caagccgaac agcgcgtaca aattc                                           25

<210> SEQ ID NO 19
```

```
<211> LENGTH: 22
<212> TYPE: DNA
<213> ORGANISM: Artificial Sequence
<220> FEATURE:
<223> OTHER INFORMATION: Synthetic Construct

<400> SEQUENCE: 19
cgagactagt gagacgtgct ac                                              22

<210> SEQ ID NO 20
<211> LENGTH: 91
<212> TYPE: DNA
<213> ORGANISM: Artificial Sequence
<220> FEATURE:
<223> OTHER INFORMATION: Synthetic Construct

<400> SEQUENCE: 20
gcggtggcgg ccgctttgtc atcggttaac gctggaacac ctgccgcgcg caacgttgcc     60
agcaccctcc ttagttccta ttccgaagtt c                                    91

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
gctggagctg cttcgaagtt cc                                              22

<210> SEQ ID NO 22
<211> LENGTH: 43
<212> TYPE: DNA
<213> ORGANISM: Artificial Sequence
<220> FEATURE:
<223> OTHER INFORMATION: Synthetic Construct

<400> SEQUENCE: 22
cgaagcagct ccagcgaaca atttaatgat aaacttcatg gcg                       43

<210> SEQ ID NO 23
<211> LENGTH: 30
<212> TYPE: DNA
<213> ORGANISM: Artificial Sequence
<220> FEATURE:
<223> OTHER INFORMATION: Synthetic Construct

<400> SEQUENCE: 23
aatgaatgtc tgactctcaa tattttcgc                                       30

<210> SEQ ID NO 24
<211> LENGTH: 37
<212> TYPE: DNA
<213> ORGANISM: Artificial Sequence
<220> FEATURE:
<223> OTHER INFORMATION: Synthetic Construct

<400> SEQUENCE: 24
agtcagacat tcattatgga ctttccgcag caactcg                              37

<210> SEQ ID NO 25
<211> LENGTH: 93
<212> TYPE: DNA
<213> ORGANISM: Artificial Sequence
<220> FEATURE:
<223> OTHER INFORMATION: Synthetic Construct
```

<400> SEQUENCE: 25
ataagcttga tatcgacctg tcggcactga agcaggtcgt cgacgagcaa caaccggatg    60
cggcgttatt tattacgctg gatgatgtag tcc                                 93

<210> SEQ ID NO 26
<211> LENGTH: 75
<212> TYPE: DNA
<213> ORGANISM: Artificial Sequence
<220> FEATURE:
<223> OTHER INFORMATION: Synthetic Construct

<400> SEQUENCE: 26
cattcgcgcc gcattcacag ccgattcgag ccaccttcat caccgcatag ttgtcatcgg    60
ttaacgctgg aacac                                                     75

<210> SEQ ID NO 27
<211> LENGTH: 71
<212> TYPE: DNA
<213> ORGANISM: Artificial Sequence
<220> FEATURE:
<223> OTHER INFORMATION: Synthetic Construct

<400> SEQUENCE: 27
ggttattatt gagcagatgg ggctgacgct tattactgtt gatttcaatg acctgtcggc    60
actgaagcag g                                                         71

<210> SEQ ID NO 28
<211> LENGTH: 23
<212> TYPE: DNA
<213> ORGANISM: Artificial Sequence
<220> FEATURE:
<223> OTHER INFORMATION: Synthetic Construct

<400> SEQUENCE: 28
cgattcgagc caccttcatc acc                                            23

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
cagcgtcttc tggtgcatga cg                                             22

<210> SEQ ID NO 30
<211> LENGTH: 41
<212> TYPE: DNA
<213> ORGANISM: Artificial Sequence
<220> FEATURE:
<223> OTHER INFORMATION: Synthetic Construct

<400> SEQUENCE: 30
gcggtggcgg ccgctgaacc aacgctttct cgaaaatatc g                        41

<210> SEQ ID NO 31
<211> LENGTH: 40
<212> TYPE: DNA
<213> ORGANISM: Artificial Sequence
<220> FEATURE:
<223> OTHER INFORMATION: Synthetic Construct

<400> SEQUENCE: 31
cagcctacac aatcgagcga tgttagtggt atacttccgc        40

<210> SEQ ID NO 32
<211> LENGTH: 25
<212> TYPE: DNA
<213> ORGANISM: Artificial Sequence
<220> FEATURE:
<223> OTHER INFORMATION: Synthetic Construct

<400> SEQUENCE: 32
cgattgtgta ggctggagct gcttc        25

<210> SEQ ID NO 33
<211> LENGTH: 26
<212> TYPE: DNA
<213> ORGANISM: Artificial Sequence
<220> FEATURE:
<223> OTHER INFORMATION: Synthetic Construct

<400> SEQUENCE: 33
gtccatatga atatcctcct tagttc        26

<210> SEQ ID NO 34
<211> LENGTH: 37
<212> TYPE: DNA
<213> ORGANISM: Artificial Sequence
<220> FEATURE:
<223> OTHER INFORMATION: Synthetic Construct

<400> SEQUENCE: 34
gatattcata tggacttgct gcgcacatca ccttacc        37

<210> SEQ ID NO 35
<211> LENGTH: 39
<212> TYPE: DNA
<213> ORGANISM: Artificial Sequence
<220> FEATURE:
<223> OTHER INFORMATION: Synthetic Construct

<400> SEQUENCE: 35
ataagcttga tatcgccttc cgcgtctaaa tctagtgcc        39

<210> SEQ ID NO 36
<211> LENGTH: 26
<212> TYPE: DNA
<213> ORGANISM: Artificial Sequence
<220> FEATURE:
<223> OTHER INFORMATION: Synthetic Construct

<400> SEQUENCE: 36
gaaccaacgc tttctcgaaa atatcg        26

<210> SEQ ID NO 37
<211> LENGTH: 24
<212> TYPE: DNA
<213> ORGANISM: Artificial Sequence
<220> FEATURE:
<223> OTHER INFORMATION: Synthetic Construct

<400> SEQUENCE: 37
ccttccgcgt ctaaatctag tgcc        24

<210> SEQ ID NO 38
<211> LENGTH: 23

```
<212> TYPE: DNA
<213> ORGANISM: Artificial Sequence
<220> FEATURE:
<223> OTHER INFORMATION: Synthetic Construct

<400> SEQUENCE: 38
cacgcgtacg cagaaggttt tgc                                              23

<210> SEQ ID NO 39
<211> LENGTH: 23
<212> TYPE: DNA
<213> ORGANISM: Artificial Sequence
<220> FEATURE:
<223> OTHER INFORMATION: Synthetic Construct

<400> SEQUENCE: 39
cagtgccagg gtcgggtatt tgg                                              23

<210> SEQ ID NO 40
<211> LENGTH: 43
<212> TYPE: DNA
<213> ORGANISM: Artificial Sequence
<220> FEATURE:
<223> OTHER INFORMATION: Synthetic Construct

<400> SEQUENCE: 40
cttttacacc ggacaatgag taatcgcccc actgcccttt cag                        43

<210> SEQ ID NO 41
<211> LENGTH: 43
<212> TYPE: DNA
<213> ORGANISM: Artificial Sequence
<220> FEATURE:
<223> OTHER INFORMATION: Synthetic Construct

<400> SEQUENCE: 41
ctgaaagggc agtggggcga ttactcattg tccggtgtaa aag                        43

<210> SEQ ID NO 42
<211> LENGTH: 26
<212> TYPE: DNA
<213> ORGANISM: Artificial Sequence
<220> FEATURE:
<223> OTHER INFORMATION: Synthetic Construct

<400> SEQUENCE: 42
gaaccaacgc tttctcgaaa atatcg                                           26

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43
ccttccgcgt ctaaatctag tgcc                                             24

<210> SEQ ID NO 44
<211> LENGTH: 23
<212> TYPE: DNA
<213> ORGANISM: Artificial Sequence
<220> FEATURE:
<223> OTHER INFORMATION: Synthetic Construct

<400> SEQUENCE: 44
```
cacgcgtacg cagaaggttt tgc                                           23

<210> SEQ ID NO 45
<211> LENGTH: 23
<212> TYPE: DNA
<213> ORGANISM: Artificial Sequence
<220> FEATURE:
<223> OTHER INFORMATION: Synthetic Construct

<400> SEQUENCE: 45
cagtgccagg gtcgggtatt tgg                                           23

<210> SEQ ID NO 46
<211> LENGTH: 91
<212> TYPE: DNA
<213> ORGANISM: Artificial Sequence
<220> FEATURE:
<223> OTHER INFORMATION: Synthetic Construct

<400> SEQUENCE: 46
gcggtggcgg ccgctttgtc atcggttaac gctggaacac ctgccgcgcg caacgttgcc    60
agcaccctcc ttagttccta ttccgaagtt c                                  91

<210> SEQ ID NO 47
<211> LENGTH: 22
<212> TYPE: DNA
<213> ORGANISM: Artificial Sequence
<220> FEATURE:
<223> OTHER INFORMATION: Synthetic Construct

<400> SEQUENCE: 47
gctggagctg cttcgaagtt cc                                            22

<210> SEQ ID NO 48
<211> LENGTH: 43
<212> TYPE: DNA
<213> ORGANISM: Artificial Sequence
<220> FEATURE:
<223> OTHER INFORMATION: Synthetic Construct

<400> SEQUENCE: 48
cgaagcagct ccagcgaact atcccactac taatcatgct tac                     43

<210> SEQ ID NO 49
<211> LENGTH: 39
<212> TYPE: DNA
<213> ORGANISM: Artificial Sequence
<220> FEATURE:
<223> OTHER INFORMATION: Synthetic Construct

<400> SEQUENCE: 49
ctgcggaaag tccataattc acacccttat aaggctggg                          39

<210> SEQ ID NO 50
<211> LENGTH: 37
<212> TYPE: DNA
<213> ORGANISM: Artificial Sequence
<220> FEATURE:
<223> OTHER INFORMATION: Synthetic Construct

<400> SEQUENCE: 50
ataagggtgt gaattatgga ctttccgcag caactcg                            37

<210> SEQ ID NO 51
<211> LENGTH: 93

```
<212> TYPE: DNA
<213> ORGANISM: Artificial Sequence
<220> FEATURE:
<223> OTHER INFORMATION: Synthetic Construct

<400> SEQUENCE: 51
ataagcttga tatcgacctg tcggcactga agcaggtcgt cgacgagcaa caaccggatg    60
cggcgttatt tattacgctg gatgatgtag tcc                                 93

<210> SEQ ID NO 52
<211> LENGTH: 75
<212> TYPE: DNA
<213> ORGANISM: Artificial Sequence
<220> FEATURE:
<223> OTHER INFORMATION: Synthetic Construct

<400> SEQUENCE: 52
cattcgcgcc gcattcacag ccgattcgag ccaccttcat caccgcatag ttgtcatcgg    60
ttaacgctgg aacac                                                     75

<210> SEQ ID NO 53
<211> LENGTH: 71
<212> TYPE: DNA
<213> ORGANISM: Artificial Sequence
<220> FEATURE:
<223> OTHER INFORMATION: Synthetic Construct

<400> SEQUENCE: 53
ggttattatt gagcagatgg ggctgacgct tattactgtt gatttcaatg acctgtcggc    60
actgaagcag g                                                         71

<210> SEQ ID NO 54
<211> LENGTH: 23
<212> TYPE: DNA
<213> ORGANISM: Artificial Sequence
<220> FEATURE:
<223> OTHER INFORMATION: Synthetic Construct

<400> SEQUENCE: 54
cgattcgagc caccttcatc acc                                            23

<210> SEQ ID NO 55
<211> LENGTH: 22
<212> TYPE: DNA
<213> ORGANISM: Artificial Sequence
<220> FEATURE:
<223> OTHER INFORMATION: Synthetic Construct

<400> SEQUENCE: 55
cagcgtcttc tggtgcatga cg                                             22

<210> SEQ ID NO 56
<211> LENGTH: 23
<212> TYPE: DNA
<213> ORGANISM: Artificial Sequence
<220> FEATURE:
<223> OTHER INFORMATION: Synthetic Construct

<400> SEQUENCE: 56
ctaatgcaat acgtgtcccg agc                                            23

<210> SEQ ID NO 57
<211> LENGTH: 24
<212> TYPE: DNA
```

<213> ORGANISM: Artificial Sequence
<220> FEATURE:
<223> OTHER INFORMATION: Synthetic Construct

<400> SEQUENCE: 57
ggcttaccgt ttacgctttc cagc                                                24

<210> SEQ ID NO 58
<211> LENGTH: 91
<212> TYPE: DNA
<213> ORGANISM: Artificial Sequence
<220> FEATURE:
<223> OTHER INFORMATION: Synthetic Construct

<400> SEQUENCE: 58
gcggtggcgg ccgctttgtc atcggttaac gctggaacac ctgccgcgcg caacgttgcc      60
agcaccctcc ttagttccta ttccgaagtt c                                      91

<210> SEQ ID NO 59
<211> LENGTH: 22
<212> TYPE: DNA
<213> ORGANISM: Artificial Sequence
<220> FEATURE:
<223> OTHER INFORMATION: Synthetic Construct

<400> SEQUENCE: 59
gctggagctg cttcgaagtt cc                                                22

<210> SEQ ID NO 60
<211> LENGTH: 43
<212> TYPE: DNA
<213> ORGANISM: Artificial Sequence
<220> FEATURE:
<223> OTHER INFORMATION: Synthetic Construct

<400> SEQUENCE: 60
cgaagcagct ccagcgaaca atttaatgat aaacttcatg gcg                         43

<210> SEQ ID NO 61
<211> LENGTH: 30
<212> TYPE: DNA
<213> ORGANISM: Artificial Sequence
<220> FEATURE:
<223> OTHER INFORMATION: Synthetic Construct

<400> SEQUENCE: 61
aatgaatgtc tgactctcaa tattttcgc                                         30

<210> SEQ ID NO 62
<211> LENGTH: 90
<212> TYPE: DNA
<213> ORGANISM: Artificial Sequence
<220> FEATURE:
<223> OTHER INFORMATION: Synthetic Construct

<400> SEQUENCE: 62
ataagcttga tatcgacctg tcggcactga agcaggtcgt cgacgagcaa caaccggatg      60
cggcgtcatt tctggcgttt gtagatcttc                                        90

<210> SEQ ID NO 63
<211> LENGTH: 40
<212> TYPE: DNA
<213> ORGANISM: Artificial Sequence
<220> FEATURE:
<223> OTHER INFORMATION: Synthetic Construct

<400> SEQUENCE: 63
agtcagacat tcattatgca taaatttact ggtgtcaatg                              40

<210> SEQ ID NO 64
<211> LENGTH: 75
<212> TYPE: DNA
<213> ORGANISM: Artificial Sequence
<220> FEATURE:
<223> OTHER INFORMATION: Synthetic Construct

<400> SEQUENCE: 64
cattcgcgcc gcattcacag ccgattcgag ccaccttcat caccgcatag ttgtcatcgg        60
ttaacgctgg aacac                                                        75

<210> SEQ ID NO 65
<211> LENGTH: 71
<212> TYPE: DNA
<213> ORGANISM: Artificial Sequence
<220> FEATURE:
<223> OTHER INFORMATION: Synthetic Construct

<400> SEQUENCE: 65
ggttattatt gagcagatgg ggctgacgct tattactgtt gatttcaatg acctgtcggc        60
actgaagcag g                                                            71

<210> SEQ ID NO 66
<211> LENGTH: 23
<212> TYPE: DNA
<213> ORGANISM: Artificial Sequence
<220> FEATURE:
<223> OTHER INFORMATION: Synthetic Construct

<400> SEQUENCE: 66
cgattcgagc caccttcatc acc                                               23

<210> SEQ ID NO 67
<211> LENGTH: 22
<212> TYPE: DNA
<213> ORGANISM: Artificial Sequence
<220> FEATURE:
<223> OTHER INFORMATION: Synthetic Construct

<400> SEQUENCE: 67
cagcgtcttc tggtgcatga cg                                                22

<210> SEQ ID NO 68
<211> LENGTH: 140
<212> TYPE: DNA
<213> ORGANISM: Artificial Sequence
<220> FEATURE:
<223> OTHER INFORMATION: Synthetic Construct

<400> SEQUENCE: 68
ctaacatcgc tttgctgtgc acatcacctt accattgcgc gttatttgct atttgccctg        60
agtccgttac catgacgggg cggttggcac tcaatggagc gactgctaac aaaaatattg       120
agagtcagac attcattatg                                                  140

<210> SEQ ID NO 69
<211> LENGTH: 162
<212> TYPE: DNA
<213> ORGANISM: Artificial Sequence
<220> FEATURE:

<223> OTHER INFORMATION: Synthetic Construct

<400> SEQUENCE: 69
gagttcgaac gcggcgtgca gctggcacgt caggggcagg ccaaattaca acaagccgaa    60
cagcgcgtac aaattctgct gtcgttggca ctcaatggag cgactgctaa ctgacaatga   120
agacgcctct ctaaccccct tttacaccgga caatgagtaa tg   162

<210> SEQ ID NO 70
<211> LENGTH: 101
<212> TYPE: DNA
<213> ORGANISM: Artificial Sequence
<220> FEATURE:
<223> OTHER INFORMATION: Synthetic Construct

<400> SEQUENCE: 70
tgttgacaat taatcatcgg ctcgtataat gtgtggaatt gtgagcggat aacaatttca    60
cacaggaaac agattacgga tccctggagt ttaaacatat g   101

<210> SEQ ID NO 71
<211> LENGTH: 24
<212> TYPE: DNA
<213> ORGANISM: Artificial Sequence
<220> FEATURE:
<223> OTHER INFORMATION: Synthetic Construct

<400> SEQUENCE: 71
cagcaaatag caggtgtatc cagc    24

<210> SEQ ID NO 72
<211> LENGTH: 24
<212> TYPE: DNA
<213> ORGANISM: Artificial Sequence
<220> FEATURE:
<223> OTHER INFORMATION: Synthetic Construct

<400> SEQUENCE: 72
gcaaccgact gttgatagaa caac    24

<210> SEQ ID NO 73
<211> LENGTH: 24
<212> TYPE: DNA
<213> ORGANISM: Artificial Sequence
<220> FEATURE:
<223> OTHER INFORMATION: Synthetic Construct

<400> SEQUENCE: 73
ggttacaaaa tgattggcgt acgc    24

<210> SEQ ID NO 74
<211> LENGTH: 27
<212> TYPE: DNA
<213> ORGANISM: Artificial Sequence
<220> FEATURE:
<223> OTHER INFORMATION: Synthetic Construct

<400> SEQUENCE: 74
tgattccgtc tgatttccca gccttat    27

<210> SEQ ID NO 75
<211> LENGTH: 50
<212> TYPE: DNA
<213> ORGANISM: Artificial Sequence
<220> FEATURE:
<223> OTHER INFORMATION: Synthetic Construct

```
<400> SEQUENCE: 75
atggactttc cgcaacaatt ggaggcgtgc gtaaagcaag caaatcaagc          50

<210> SEQ ID NO 76
<211> LENGTH: 29
<212> TYPE: DNA
<213> ORGANISM: Artificial Sequence
<220> FEATURE:
<223> OTHER INFORMATION: Synthetic Construct

<400> SEQUENCE: 76
actgtcaggt caacacttac ttaagaaac                                 29

<210> SEQ ID NO 77
<211> LENGTH: 31
<212> TYPE: DNA
<213> ORGANISM: Artificial Sequence
<220> FEATURE:
<223> OTHER INFORMATION: Synthetic Construct

<400> SEQUENCE: 77
tcgagggagc caaaaaaaac aaaacttact t                              31

<210> SEQ ID NO 78
<211> LENGTH: 30
<212> TYPE: DNA
<213> ORGANISM: Artificial Sequence
<220> FEATURE:
<223> OTHER INFORMATION: Synthetic Construct

<400> SEQUENCE: 78
cgaacataaa gcagacgtca gcattcgaac                                30

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
taccggatac gaacggaagc ctatcgcaat t                              31

<210> SEQ ID NO 80
<211> LENGTH: 18
<212> TYPE: DNA
<213> ORGANISM: Artificial Sequence
<220> FEATURE:
<223> OTHER INFORMATION: Synthetic Construct

<400> SEQUENCE: 80
ggacaattct actacact                                             18

<210> SEQ ID NO 81
<211> LENGTH: 25
<212> TYPE: DNA
<213> ORGANISM: Artificial Sequence
<220> FEATURE:
<223> OTHER INFORMATION: Synthetic Construct

<400> SEQUENCE: 81
tctagagaaa gagggggaaac actag                                    25

<210> SEQ ID NO 82
```

```
<211> LENGTH: 25
<212> TYPE: DNA
<213> ORGANISM: Artificial Sequence
<220> FEATURE:
<223> OTHER INFORMATION: Synthetic Construct

<400> SEQUENCE: 82
tctagagaaa gagggggaaat actat                                              25

<210> SEQ ID NO 83
<211> LENGTH: 26
<212> TYPE: DNA
<213> ORGANISM: Artificial Sequence
<220> FEATURE:
<223> OTHER INFORMATION: Synthetic Construct

<400> SEQUENCE: 83
tctacgagaa aagggactg acaaga                                               26

<210> SEQ ID NO 84
<211> LENGTH: 29
<212> TYPE: DNA
<213> ORGANISM: Artificial Sequence
<220> FEATURE:
<223> OTHER INFORMATION: Synthetic Construct

<400> SEQUENCE: 84
tcgagagatt aaacaggcag aaatactag                                           29

<210> SEQ ID NO 85
<211> LENGTH: 29
<212> TYPE: DNA
<213> ORGANISM: Artificial Sequence
<220> FEATURE:
<223> OTHER INFORMATION: Synthetic Construct

<400> SEQUENCE: 85
gtcgtagaga tttagtaagg agccactat                                           29

<210> SEQ ID NO 86
<211> LENGTH: 29
<212> TYPE: DNA
<213> ORGANISM: Artificial Sequence
<220> FEATURE:
<223> OTHER INFORMATION: Synthetic Construct

<400> SEQUENCE: 86
atctggagat taaagcagag aaatactag                                           29

<210> SEQ ID NO 87
<211> LENGTH: 30
<212> TYPE: DNA
<213> ORGANISM: Artificial Sequence
<220> FEATURE:
<223> OTHER INFORMATION: Synthetic Construct

<400> SEQUENCE: 87
tccaataatt acagccagga gacagactat                                          30

<210> SEQ ID NO 88
<211> LENGTH: 27
<212> TYPE: DNA
<213> ORGANISM: Artificial Sequence
<220> FEATURE:
<223> OTHER INFORMATION: Synthetic Construct

<400> SEQUENCE: 88
```

```
tacagaaatt aaaaggaaca atattag                                              27

<210> SEQ ID NO 89
<211> LENGTH: 27
<212> TYPE: DNA
<213> ORGANISM: Artificial Sequence
<220> FEATURE:
<223> OTHER INFORMATION: Synthetic Construct

<400> SEQUENCE: 89
tgctgaggtt aaagaggaaa ataatat                                              27

<210> SEQ ID NO 90
<211> LENGTH: 75
<212> TYPE: DNA
<213> ORGANISM: Artificial Sequence
<220> FEATURE:
<223> OTHER INFORMATION: Synthetic Construct

<400> SEQUENCE: 90
cattcgcgcc gcattcacag ccgattcgag ccaccttcat caccgcatag ttgtcatcgg          60
ttaacgctgg aacac                                                           75

<210> SEQ ID NO 91
<211> LENGTH: 71
<212> TYPE: DNA
<213> ORGANISM: Artificial Sequence
<220> FEATURE:
<223> OTHER INFORMATION: Synthetic Construct

<400> SEQUENCE: 91
ggttattatt gagcagatgg ggctgacgct tattactgtt gatttcaatg acctgtcggc          60
actgaagcag g                                                               71

<210> SEQ ID NO 92
<211> LENGTH: 23
<212> TYPE: DNA
<213> ORGANISM: Artificial Sequence
<220> FEATURE:
<223> OTHER INFORMATION: Synthetic Construct

<400> SEQUENCE: 92
cgattcgagc caccttcatc acc                                                  23

<210> SEQ ID NO 93
<211> LENGTH: 22
<212> TYPE: DNA
<213> ORGANISM: Artificial Sequence
<220> FEATURE:
<223> OTHER INFORMATION: Synthetic Construct

<400> SEQUENCE: 93
cagcgtcttc tggtgcatga cg                                                   22

<210> SEQ ID NO 94
<211> LENGTH: 64
<212> TYPE: DNA
<213> ORGANISM: Artificial Sequence
<220> FEATURE:
<223> OTHER INFORMATION: Synthetic Construct

<400> SEQUENCE: 94
ctgatttccc agccttattc tagagaaaga ggggaaacac tagatggact ttccgcaaca          60
```

```
attg                                                               64

<210> SEQ ID NO 95
<211> LENGTH: 64
<212> TYPE: DNA
<213> ORGANISM: Artificial Sequence
<220> FEATURE:
<223> OTHER INFORMATION: Synthetic Construct

<400> SEQUENCE: 95
caattgttgc ggaaagtcca tctagtgttt cccctctttc tctagaataa ggctgggaaa    60
tcag                                                               64

<210> SEQ ID NO 96
<211> LENGTH: 68
<212> TYPE: DNA
<213> ORGANISM: Artificial Sequence
<220> FEATURE:
<223> OTHER INFORMATION: Synthetic Construct

<400> SEQUENCE: 96
ctgatttccc agccttatat ctggagatta agcagagaa atactagatg gactttccgc     60
aacaattg                                                           68

<210> SEQ ID NO 97
<211> LENGTH: 68
<212> TYPE: DNA
<213> ORGANISM: Artificial Sequence
<220> FEATURE:
<223> OTHER INFORMATION: Synthetic Construct

<400> SEQUENCE: 97
caattgttgc ggaaagtcca tctagtattt ctctgcttta atctccagat ataaggctgg    60
gaaatcag                                                           68

<210> SEQ ID NO 98
<211> LENGTH: 66
<212> TYPE: DNA
<213> ORGANISM: Artificial Sequence
<220> FEATURE:
<223> OTHER INFORMATION: Synthetic Construct

<400> SEQUENCE: 98
ctgatttccc agccttatta cagaaattaa aggaacaat attagatgga ctttccgcaa     60
caattg                                                             66

<210> SEQ ID NO 99
<211> LENGTH: 66
<212> TYPE: DNA
<213> ORGANISM: Artificial Sequence
<220> FEATURE:
<223> OTHER INFORMATION: Synthetic Construct

<400> SEQUENCE: 99
caattgttgc ggaaagtcca tctaatattg ttccttttaa tttctgtaat aaggctggga    60
aatcag                                                             66

<210> SEQ ID NO 100
<211> LENGTH: 31
<212> TYPE: DNA
<213> ORGANISM: Artificial Sequence
<220> FEATURE:
<223> OTHER INFORMATION: Synthetic Construct
```

<400> SEQUENCE: 100
attcagggtg tgagcgcaac gcaattaatg t                                   31

<210> SEQ ID NO 101
<211> LENGTH: 31
<212> TYPE: DNA
<213> ORGANISM: Artificial Sequence
<220> FEATURE:
<223> OTHER INFORMATION: Synthetic Construct

<400> SEQUENCE: 101
gttgcgctca caccctgaat tgactctctt c                                   31

<210> SEQ ID NO 102
<211> LENGTH: 31
<212> TYPE: DNA
<213> ORGANISM: Artificial Sequence
<220> FEATURE:
<223> OTHER INFORMATION: Synthetic Construct

<400> SEQUENCE: 102
attcagggtg tgagcgcaac gcaattaatg t                                   31

<210> SEQ ID NO 103
<211> LENGTH: 31
<212> TYPE: DNA
<213> ORGANISM: Artificial Sequence
<220> FEATURE:
<223> OTHER INFORMATION: Synthetic Construct

<400> SEQUENCE: 103
gttgcgctca caccctgaat tgactctctt c                                   31

<210> SEQ ID NO 104
<211> LENGTH: 5772
<212> TYPE: DNA
<213> ORGANISM: Artificial Sequence
<220> FEATURE:
<223> OTHER INFORMATION: Synthetic Construct

<400> SEQUENCE: 104
gtttgacagc ttatcatcga ctgcacggtg caccaatgct tctggcgtca ggcagccatc      60
ggaagctgtg gtatggctgt gcaggtcgta atcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggaaac     420
gcgtcgttct gcgaactacg aacctaacag ctgggactat gattacctgc tgtcctccga     480
cacggacgag tccatcgaag tatacaaaga caaagcgaaa aagctggaag ccgaagttcg     540
tcgcgagatt aataacgaaa aagcagaatt tctgacccctg ctggaactga ttgacaacgt     600
ccagcgcctg ggcctgggtt accgtttcga gtctgatatc cgtggtgcgc tggatcgctt     660
cgtttcctcc ggcggcttcg atgcggtaac caagacttcc ctgcacggta cggcactgtc     720
tttccgtctg ctgcgtcaac acggttttga ggtttctcag gaagcgttca gcggcttcaa     780
agaccaaaac ggcaacttcc tggagaacct gaaggaagat atcaaagcta tcctgagcct     840

```
gtacgaggcc agcttcctgg ctctggaagg cgaaaacatc ctggacgagg cgaaggtttt    900
cgcaatctct catctgaaag aactgtctga agaaaagatc ggtaaagagc tggcagaaca    960
ggtgaaccat gcactggaac tgccactgca tcgccgtact cagcgtctgg aagcagtatg   1020
gtctatcgag gcctaccgta aaaggagga cgcgaatcag gttctgctgg agctggcaat    1080
tctggattac aacatgatcc agtctgtata ccagcgtgat ctgcgtgaaa cgtcccgttg   1140
gtggcgtcgt gtgggtctgg cgaccaaact gcactttgct cgtgaccgcc tgattgagag   1200
cttctactgg gccgtgggtg tagcattcga accgcaatac tccgactgcc gtaactccgt   1260
cgcaaaaatg ttttgtttcg taaccattat cgacgatatc tacgatgtat acggcaccct   1320
ggacgaactg gagctgttta ctgatgcagt tgagcgttgg gacgtaaacg ccatcaacga   1380
cctgccggat tacatgaaac tgtgcttcct ggctctgtat aacactatta acgaaatcgc   1440
ctacgacaac ctgaaagata aggtgagaa catcctgccg tatctgacca agcctgggc    1500 tgacctgtgc aacgctttcc tgcaagaagc caagtggctg tacaacaaat ctactccgac   1560 cttttgacgac tacttcggca acgcatggaa atcctcttct ggcccgctgc aactggtgtt   1620
cgcttacttc gctgtcgtgc agaacattaa aaaggaagag atcgaaaacc tgcaaaaata   1680
ccatgacacc atctctcgtc cttcccatat cttccgtctg tgcaatgacc tggctagcgc   1740
gtctgcggaa attgcgcgtg gtgaaaccgc aaatagcgtt tcttgttaca tgcgcactaa   1800
aggtatctcc gaagaactgg ctaccgaaag cgtgatgaat ctgatcgatg aatattggaa   1860
aaagatgaac aaggaaaaac tgggtggtag cctgttcgcg aaaccgttcg tggaaaccgc   1920
gatcaacctg gcacgtcaat ctcactgcac ttatcataac ggcgacgcgc atacctctcc   1980
ggatgagctg acccgcaaac gcgttctgtc tgtaatcact gaaccgattc tgccgtttga   2040
acgctaactg cataaaggag gtaaaaaaac atggtatcct gttctgcgcc gggtaagatt   2100
tacctgttcg gtgaacacgc cgtagtttat ggcgaaactg caattgcgtg tgcggtggaa   2160
ctgcgtaccc gtgttcgcgc ggaactcaat gactctatca ctattcagag ccagatcggc   2220
cgcaccggtc tggatttcga aaagcaccct tatgtgtctg cggtaattga aaaatgcgc    2280 aaatctattc ctattaacgg tgttttcttg accgtcgatt ccgacatccc ggtgggctcc   2340
ggtctgggta gcagcgcagc cgttactatc gcgtctattg gtgcgctgaa cgagctgttc   2400
ggctttggcc tcagcctgca agaaatcgct aaactgggcc acgaaatcga attaaagta    2460 cagggtgccg cgtccccaac cgatacgtat gtttctacct tcggcggcgt ggttaccatc   2520
ccggaacgtc gcaaactgaa aactccggac tgcggcattg tgattggcga taccggcgtt   2580
ttctcctcca ccaaagagtt agtagctaac gtacgtcagc tgcgcgaaag ctacccggat   2640
ttgatcgaac cgctgatgac ctctattggc aaaatctctc gtatcggcga caactggtt    2700 ctgtctggcg actacgcatc catcggccgc ctgatgaacg tcaaccaggg tctcctggac   2760
gccctgggcg ttaacatctt agaactgagc cagctgatct attccgctcg tgcggcaggt   2820
gcgtttggcg ctaaaatcac gggcgctggc ggcggtggct gtatggttgc gctgaccgct   2880
ccggaaaaat gcaaccaagt ggcagaagcg gtagcaggcg ctggcggtaa agtgactatc   2940
actaaaccga ccgagcaagg tctgaaagta gattaaagtc tagttaaagt ttaaacggtc   3000
tccagcttgg ctgttttggc ggatgagaga agattttcag cctgatacag attaaatcag   3060
aacgcagaag cggtctgata aaacagaatt tgcctggcgg cagtagcgcg gtggtcccac   3120
ctgaccccat gccgaactca gaagtgaaac gccgtagcgc cgatggtagt gtggggtctc   3180
cccatgcgag agtagggaac tgccaggcat caaataaaac gaaaggctca gtcgaaagac   3240
```

```
tgggcctttc gttttatctg ttgtttgtcg gtgaacgctc tcctgagtag gacaaatccg   3300
ccgggagcgg atttgaacgt tgcgaagcaa cggcccggag ggtggcgggc aggacgcccg   3360
ccataaactg ccaggcatca aattaagcag aaggccatcc tgacggatgg ccttttttgcg  3420 tttctacaaa ctcttttttgt ttattttttct aaatacattc aaatatgtat ccgctcatga  3480
gacaataacc ctgataaatg cttcaataat attgaaaaag gaagagtatg agtattcaac   3540
atttccgtgt cgcccttatt cccttttttg cggcattttg ccttcctgtt tttgctcacc   3600
cagaaacgct ggtgaaagta aaagatgctg aagatcagtt gggtgcacga gtgggttaca   3660
tcgaactgga tctcaacagc ggtaagatcc ttgagagttt tcgccccgaa gaacgttttc    3720
caatgatgag cacttttaaa gttctgctat gtggcgcggt attatcccgt gttgacgccg   3780
ggcaagagca actcggtcgc cgcatacact attctcagaa tgacttggtt gagtactcac   3840
cagtcacaga aaagcatctt acggatggca tgacagtaag agaattatgc agtgctgcca   3900
taaccatgag tgataacact gcggccaact tacttctgac aacgatcgga ggaccgaagg   3960
agctaaccgc ttttttgcac aacatggggg atcatgtaac tcgccttgat cgttgggaac   4020
cggagctgaa tgaagccata ccaaacgacg agcgtgacac cacgatgcct gtagcaatgg   4080
caacaacgtt gcgcaaacta ttaactggcg aactacttac tctagcttcc cggcaacaat   4140
taatagactg gatggaggcg gataaagttg caggaccact tctgcgctcg gcccttccgg   4200
ctggctggtt tattgctgat aaatctggag ccggtgagcg tgggtctcgc ggtatcattg   4260
cagcactggg gccagatggt aagccctccc gtatcgtagt tatctacacg acggggagtc   4320
aggcaactat ggatgaacga aatagacaga tcgctgagat aggtgcctca ctgattaagc   4380
attggtaact gtcagaccaa gtttactcat atatacttta gattgattta aaacttcatt   4440
tttaatttaa aaggatctag gtgaagatcc tttttgataa tctcatgacc aaaatccctt   4500
aacgtgagtt ttcgttccac tgagcgtcag accccgtaga aaagatcaaa ggatcttctt   4560
gagatccttt ttttctgcgc gtaatctgct gcttgcaaac aaaaaaacca ccgctaccag   4620
cggtggtttg tttgccggat caagagctac caactctttt tccgaaggta actggcttca   4680
gcagagcgca gataccaaat actgtccttc tagtgtagcc gtagttaggc caccacttca   4740
agaactctgt agcaccgcct acatacctcg ctctgctaat cctgttacca gtggctgctg   4800
ccagtggcga taagtcgtgt cttaccgggt tggactcaag acgatagtta ccggataagg   4860
cgcagcggtc gggctgaacg gggggttcgt gcacacagcc cagcttggag cgaacgacct   4920
acaccgaact gagataccta cagcgtgagc tatgagaaag cgccacgctt cccgaaggga   4980
gaaaggcgga caggtatccg gtaagcggca gggtcggaac aggagagcgc acgagggagc   5040
ttccaggggg aaacgcctgg tatctttata gtcctgtcgg gtttcgccac ctctgacttg   5100
agcgtcgatt tttgtgatgc tcgtcagggg ggcggagcct atggaaaaac gccagcaacg   5160
cggccttttt acgttcctg gccttttgct ggccttttgc tcacatgttc tttcctgcgt    5220
tatcccctga ttctgtggat aaccgtatta ccgcctttga gtgagctgat accgctcgcc   5280
gcagccgaac gaccgagcgc agcgagtcag tgagcgagga agcggaagag cgcctgatgc   5340
ggtattttct ccttacgcat ctgtgcggta tttcacaccg catatggtgc actctcagta   5400
caatctgctc tgatgccgca tagttaagcc agtatacact ccgctatcgc tacgtgactg   5460
ggtcatggct gcgccccgac acccgccaac cccgctgac gcgccctgac gggcttgtct   5520
gctcccggca tccgcttaca gacaagctgt gaccgtctcc gggagctgca tgtgtcagag   5580
```

| | |
|---|---|
| gttttcaccg tcatcaccga aacgcgcgag gcagcagatc aattcgcgcg cgaaggcgaa | 5640 |
| gcggcatgca tttacgttga caccatcgaa tggtgcaaaa cctttcgcgg tatggcatga | 5700 |
| tagcgcccgg aagagagtca attcaggggtg tgagcgcaac gcaattaatg tgagttagcg | 5760 |
| cgaattgatc tg | 5772 |

<210> SEQ ID NO 105
<211> LENGTH: 4834
<212> TYPE: DNA
<213> ORGANISM: Artificial Sequence
<220> FEATURE:
<223> OTHER INFORMATION: Synthetic Construct

<400> SEQUENCE: 105

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggaaac | 420 |
| gcgtcgttct gcgaactacg aacctaacag ctgggactat gattacctgc tgtcctccga | 480 |
| cacggacgag tccatcgaag tatacaaaga caaagcgaaa aagctggaag ccgaagttcg | 540 |
| tcgcgagatt aataacgaaa aagcagaatt tctgaccctg ctggaactga ttgacaacgt | 600 |
| ccagcgcctg ggcctgggtt accgtttcga gtctgatatc cgtggtgcgc tggatcgctt | 660 |
| cgtttcctcc ggcggcttcg atgcggtaac caagacttcc ctgcacggta cggcactgtc | 720 |
| tttccgtctg ctgcgtcaac acggtttttga ggtttctcag gaagcgttca gcggcttcaa | 780 |
| agaccaaaac ggcaacttcc tggagaacct gaaggaagat atcaaagcta tcctgagcct | 840 |
| gtacgaggcc agcttcctgg ctctggaagg cgaaaacatc ctggacgagg cgaaggtttt | 900 |
| cgcaatctct catctgaaag aactgtctga agaaaagatc ggtaaagagc tggcagaaca | 960 |
| ggtgaaccat gcactggaac tgccactgca tcgccgtact cagcgtctgg aagcagtatg | 1020 |
| gtctatcgag gcctaccgta aaaggagga cgcgaatcag ttctgctgg agctggcaat | 1080 |
| tctggattac aacatgatcc agtctgtata ccagcgtgat ctgcgtgaaa cgtcccgttg | 1140 |
| gtggcgtcgt gtgggtctgg cgaccaaact gcactttgct cgtgaccgcc tgattgagag | 1200 |
| cttctactgg gccgtgggtg tagcattcga accgcaatac tccgactgcc gtaactccgt | 1260 |
| cgcaaaaatg ttttgtttcg taaccattat cgacgatatc tacgatgtat acggcaccct | 1320 |
| ggacgaactg gagctgtttta ctgatgcagt tgagcgttgg gacgtaaacg ccatcaacga | 1380 |
| cctgccggat tacatgaaac tgtgctttct ggctctgtat aacactatta cgaaatcgc | 1440 |
| ctacgacaac ctgaaagata aggtgagaa catcctgccg tatctgacca agcctgggc | 1500 |
| tgacctgtgc aacgctttcc tgcaagaagc caagtggctg tacaacaaat ctactccgac | 1560 |
| ctttgacgac tacttcggca acgcatgaa atcctcttct ggcccgctgc aactggtgtt | 1620 |
| cgcttacttc gctgtcgtgc agaacattaa aaaggaagag atcgaaaacc tgcaaaaata | 1680 |
| ccatgacacc atctctcgtc cttcccatat cttccgtctg tgcaatgacc tggctagcgc | 1740 |
| gtctgcggaa attgcgcgtg gtgaaaccgc aaatagcgtt tccttgttaca tgcgcactaa | 1800 |
| aggtatctcc gaagaactgg ctaccgaaag cgtgatgaat ctgatcgatg aatattggaa | 1860 |

```
aaagatgaac aaggaaaaac tgggtggtag cctgttcgcg aaaccgttcg tggaaaccgc    1920
gatcaacctg gcacgtcaat ctcactgcac ttatcataac ggcgacgcgc atacctctcc    1980
ggatgagctg acccgcaaac gcgttctgtc tgtaatcact gaaccgattc tgccgtttga    2040
acgctaaagt ctagttaaag tttaaacggt ctccagcttg gctgttttgg cggatgagag    2100
aagattttca gcctgataca gattaaatca gaacgcagaa gcggtctgat aaaacagaat    2160
ttgcctggcg gcagtagcgc ggtggtccca cctgacccca tgccgaactc agaagtgaaa    2220
cgccgtagcg ccgatggtag tgtggggtct ccccatgcga gagtagggaa ctgccaggca    2280
tcaaataaaa cgaaaggctc agtcgaaaga ctgggccttt cgttttatct gttgtttgtc    2340
ggtgaacgct ctcctgagta ggacaaatcc gccgggagcg gatttgaacg ttgcgaagca    2400
acggcccgga gggtggcggg caggacgccc gccataaact gccaggcatc aaattaagca    2460
gaaggccatc ctgacggatg ccttttttgc gtttctacaa actcttttcg tttattttc    2520 taaatacatt caaatatgta tccgctcatg agacaataac cctgataaat gcttcaataa    2580
tattgaaaaa ggaagagtat gagtattcaa catttccgtg tcgcccttat ccctttttt    2640 gcggcatttt gccttcctgt ttttgctcac ccagaaacgc tggtgaaagt aaaagatgct    2700
gaagatcagt tgggtgcacg agtgggttac atcgaactgg atctcaacag cggtaagatc    2760
cttgagagtt ttcgccccga agaacgtttt ccaatgatga gcacttttaa agttctgcta    2820
tgtggcgcgg tattatcccg tgttgacgcc gggcaagagc aactcggtcg ccgcatacac    2880
tattctcaga atgacttggt tgagtactca ccagtcacag aaaagcatct tacgatggc    2940 atgacagtaa gagaattatg cagtgctgcc ataaccatga gtgataacac tgcggccaac    3000
ttacttctga caacgatcgg aggaccgaag gagctaaccg cttttttgca caacatgggg    3060
gatcatgtaa ctcgccttga tcgttgggaa ccggagctga atgaagccat accaaacgac    3120
gagcgtgaca ccacgatgcc tgtagcaatg gcaacaacgt tgcgcaaact attaactggc    3180
gaactactta ctctagcttc ccggcaacaa ttaatagact ggatggaggc ggataaagtt    3240
gcaggaccac ttctgcgctc ggcccttccg gctggctggt ttattgctga taaatctgga    3300
gccggtgagc gtgggtctcg cggtatcatt gcagcactgg ggccagatgg taagccctcc    3360
cgtatcgtag ttatctacac gacggggagt caggcaacta tggatgaacg aaatagacag    3420
atcgctgaga taggtgcctc actgattaag cattggtaac tgtcagacca agtttactca    3480
tatatacttt agattgattt aaaacttcat ttttaattta aaaggatcta ggtgaagatc    3540
ctttttgata atctcatgac caaaatccct taacgtgagt tttcgttcca ctgagcgtca    3600
gaccccgtag aaaagatcaa aggatcttct tgagatcctt ttttttctgcg cgtaatctgc    3660 tgcttgcaaa caaaaaaacc accgctacca gcggtggttt gtttgccgga tcaagagcta    3720
ccaactcttt ttccgaaggt aactggcttc agcagagcgc agataccaaa tactgtcctt    3780
ctagtgtagc cgtagttagg ccaccacttc aagaactctg tagcaccgcc tacatacctc    3840
gctctgctaa tcctgttacc agtggctgct gccagtggcg ataagtcgtg tcttaccggg    3900
ttggactcaa gacgatagtt accggataag gcgcagcggt cgggctgaac ggggggttcg    3960
tgcacacagc ccagcttgga gcgaacgacc tacaccgaac tgagatacct acagcgtgag    4020
ctatgagaaa gcgccacgct tcccgaaggg agaaaggcgg acaggtatcc ggtaagcggc    4080
agggtcggaa caggagagcg cacgagggag cttccagggg gaaacgcctg gtatctttat    4140
agtcctgtcg ggtttcgcca cctctgactt gagcgtcgat ttttgtgatg ctcgtcaggg    4200
```

```
gggcggagcc tatggaaaaa cgccagcaac gcggcctttt tacggttcct ggccttttgc    4260
tggccttttg ctcacatgtt ctttcctgcg ttatcccctg attctgtgga taaccgtatt    4320
accgcctttg agtgagctga taccgctcgc cgcagccgaa cgaccgagcg cagcgagtca    4380
gtgagcgagg aagcggaaga gcgcctgatg cggtattttc tccttacgca tctgtgcggt    4440
atttcacacc gcatatggtg cactctcagt acaatctgct ctgatgccgc atagttaagc    4500
cagtatacac tccgctatcg ctacgtgact gggtcatggc tgcgcccga cacccgccaa    4560 cacccgctga cgcgccctga cgggcttgtc tgctcccggc atccgcttac agacaagctg    4620
tgaccgtctc cgggagctgc atgtgtcaga ggttttcacc gtcatcaccg aaacgcgcga    4680
ggcagcagat caattcgcgc gcgaaggcga agcggcatgc atttacgttg acaccatcga    4740
atggtgcaaa acctttcgcg gtatggcatg atagcgcccg gaagagagtc agtgagcgca    4800
acgcaattaa tgtgagttag cgcgaattga tctg                               4834
```